(12) United States Patent
Jamieson et al.

(10) Patent No.: US 11,478,500 B2
(45) Date of Patent: Oct. 25, 2022

(54) ANTICANCER COMPOSITIONS AND METHODS FOR MAKING AND USING THEM

(71) Applicant: The Regents of the University of California, Oakland, CA (US)

(72) Inventors: Catriona Jamieson, San Diego, CA (US); Raymond Diep, San Diego, CA (US); Jane Isquith, San Diego, CA (US); Qingfei Jiang, San Diego, CA (US); Jessica Pham, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 16/543,167

(22) Filed: Aug. 16, 2019

(65) Prior Publication Data

US 2020/0054666 A1     Feb. 20, 2020

Related U.S. Application Data

(60) Provisional application No. 62/863,778, filed on Jun. 19, 2019, provisional application No. 62/718,997, filed on Aug. 16, 2018.

(51) Int. Cl.
    *A61K 31/7105*     (2006.01)
    *C12Q 1/68*     (2018.01)

(52) U.S. Cl.
    CPC ............................ *A61K 31/7105* (2013.01)

(58) Field of Classification Search
None
See application file for complete search history.

(56) References Cited

U.S. PATENT DOCUMENTS

| | | | |
|---|---|---|---|
| 2008/0081791 A1* | 4/2008 | Huang | C12N 15/111 514/44 A |
| 2009/0163435 A1* | 6/2009 | Bader | A61K 9/00 514/44 R |
| 2019/0359980 A1* | 11/2019 | Rodman | A61P 35/00 |

OTHER PUBLICATIONS

Zipeto et al., Cell vol. 19:177-191, Aug. 4, 2016.*
Jiang et al., PNAS vol. 110(3):1041-1046, Jan. 15, 2013.*
Jiang et al., "Hyper-Editing of Cell-Cycle Regulatory and Tumor Suppressor RNA Promotes Malignant Progenitor Propagation" Cancer Cell, 2019, v 35, p. 81-94.
Jiang et al., "Inflammation-driven deaminase deregulation fuels human pre-leukemia stem cell evolution" Cell Reports, 2021, v 34.
Zipeto et al., "ADAR1 Activation Drives Leukemia Stem Cell Self-Renewal by Impairing Let-7 Biogenesis" Cell Stem Cell, 2016, v 19, p. 177-191.
Bayraktar et al., "miR-155 in cancer drug resistance and as target for miRNA-based therapeutics" Cancer and Metastasis Reviews, 2018, v 37, p. 33-44.
Han et al., "The Genomic Landscape and Clinical Relevance of A-to-I RNA Editing in Human Cancers" Cancer Cell, 2015, v 28, p. 515-528.
Hartner et al., "ADAR1 is essential for the maintenance of hematopoiesis and suppression of interferon signaling" Nature Immunology, 2009, v 10, n 1, p. 109-115.
Nishikura, "Functions and Regulation of RNA Editing by ADAR Deaminases" Annu. Rev. Biochem., 2010, v 79, p. 321-349.
Nishikura, "A-to-I editing of coding and non-coding RNAs by ADARs" Nature Reviews | Molecular Cell Biology, 2016, v 17, p. 83-96.
Peng et al., "A-to-I RNA Editing Contributes to Proteomic Diversity in Cancer" Cancer Cell, 2018, v 33, p. 817-828.
Qin et al., "Adenosine-to-Inosine RNA Editing Mediated by ADARs in Esophageal Squamous Cell Carcinoma" Cancer Res, 2014, v 74, n 3, p. 840-851.
Shao et al., "The value of miR-155 as a biomarker for the diagnosis and prognosis of lung cancer: a systematic review with meta-analysis" BMC Cancer, 2019, v 19, p. 1-10.
Yang et al., "Modulation of microRNA processing and expression through RNA editing by ADAR deaminases" Nature Structural & Molecular Biology, 2006, v 13, n 1, p. 13-21.
Zhang et al., "Altered RNA editing in 3' UTR perturbs microRNA-mediated regulation of oncogenes and tumor-suppressors" Scientific Reports, 2016, p. 1-13.
Zipeto et al., "RNA rewriting, recoding, and rewiring in human disease" Trends in Molecular Medicine, 2015, v 15, n 9, p. 549-559.

\* cited by examiner

*Primary Examiner* — Sean McGarry
(74) *Attorney, Agent, or Firm* — Greer, Burns & Crain, Ltd.; Gregory P. Einhorn

(57) ABSTRACT

In alternative embodiments, provided are compositions, including products of manufacture and kits, and methods, for treating or ameliorating a cancer by inhibiting expression or activity of Mouse Double Minute 2 homolog (MDM2), an APOBEC3G (A3G) protein, message (mRNA) or gene, and/or an ADAR1p150 protein, message (mRNA) or gene, e.g., by increasing the presence of in a cell or adding to a cell a molecule inhibitory to MDM2, APOBEC3G and/or ADAR1p150 expression, such as an miRNA that binds to MDM2, APOBEC3G and/or ADAR1p150 transcripts, or any molecule that can inhibit or destabilize the transcripts, resulting in decreased MDM2, APOBEC3G and/or ADAR1p150 expression, to treat a cancer such as leukemia, e.g., by inhibiting the propagation of a cancer cell, a leukemia cell, a leukemia stem cell (LSC) or a pre-leukemia cell stem cell (pre-LSC).

19 Claims, 129 Drawing Sheets
Specification includes a Sequence Listing.

FIG. 1D
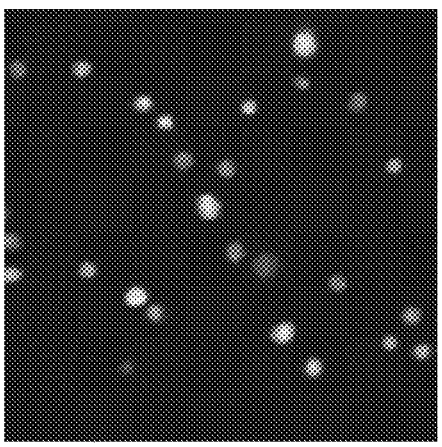 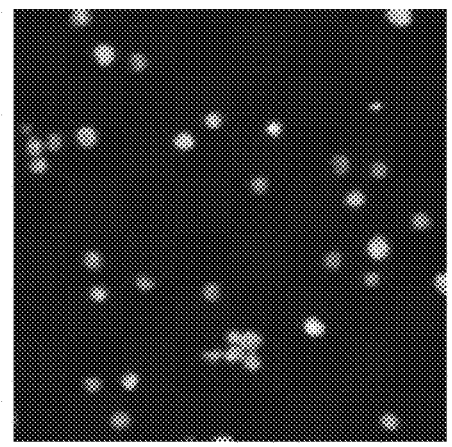
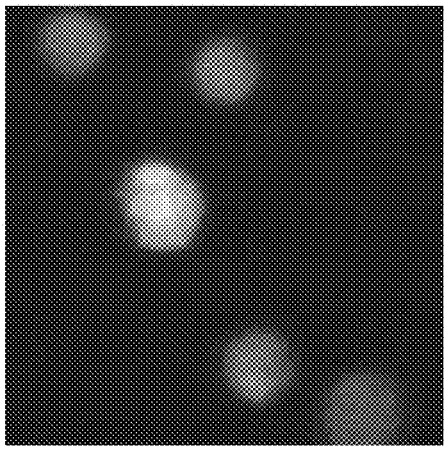 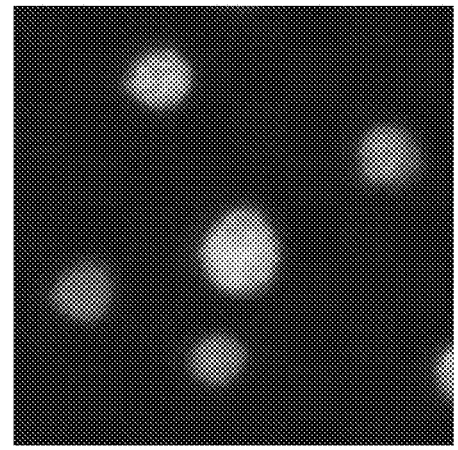
DAPI/Ki67

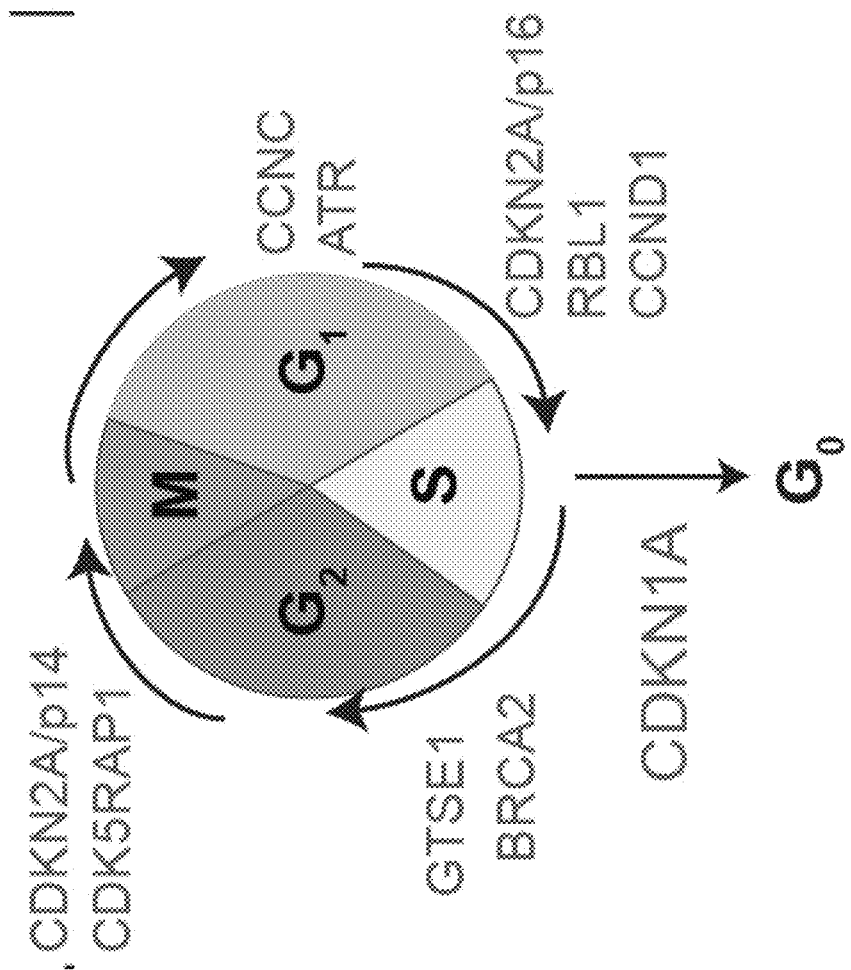

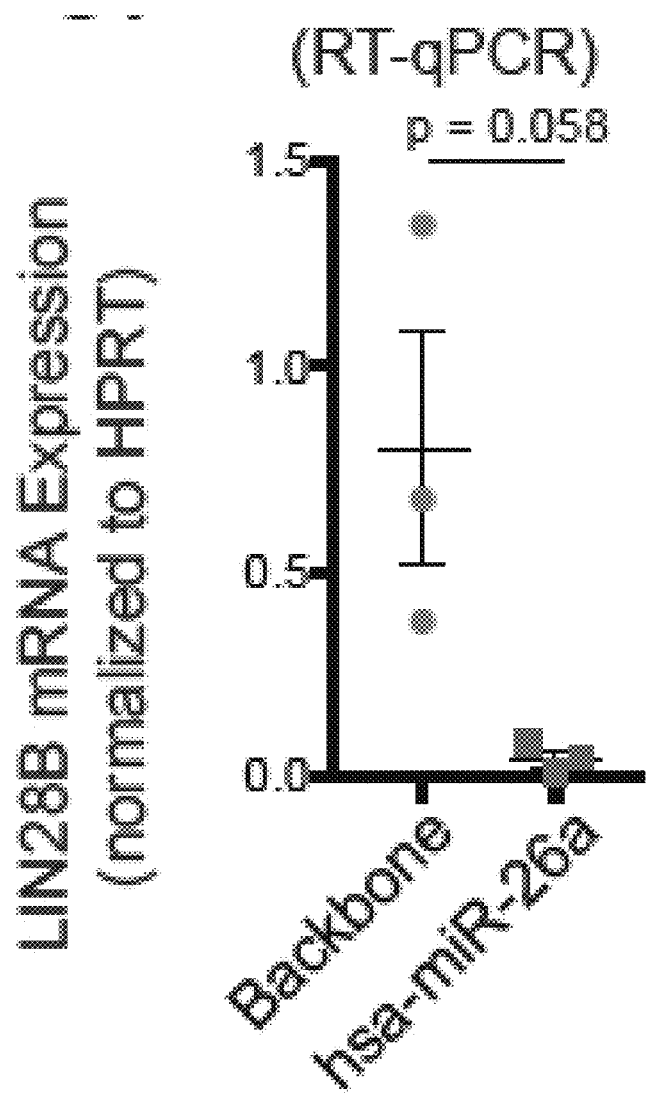

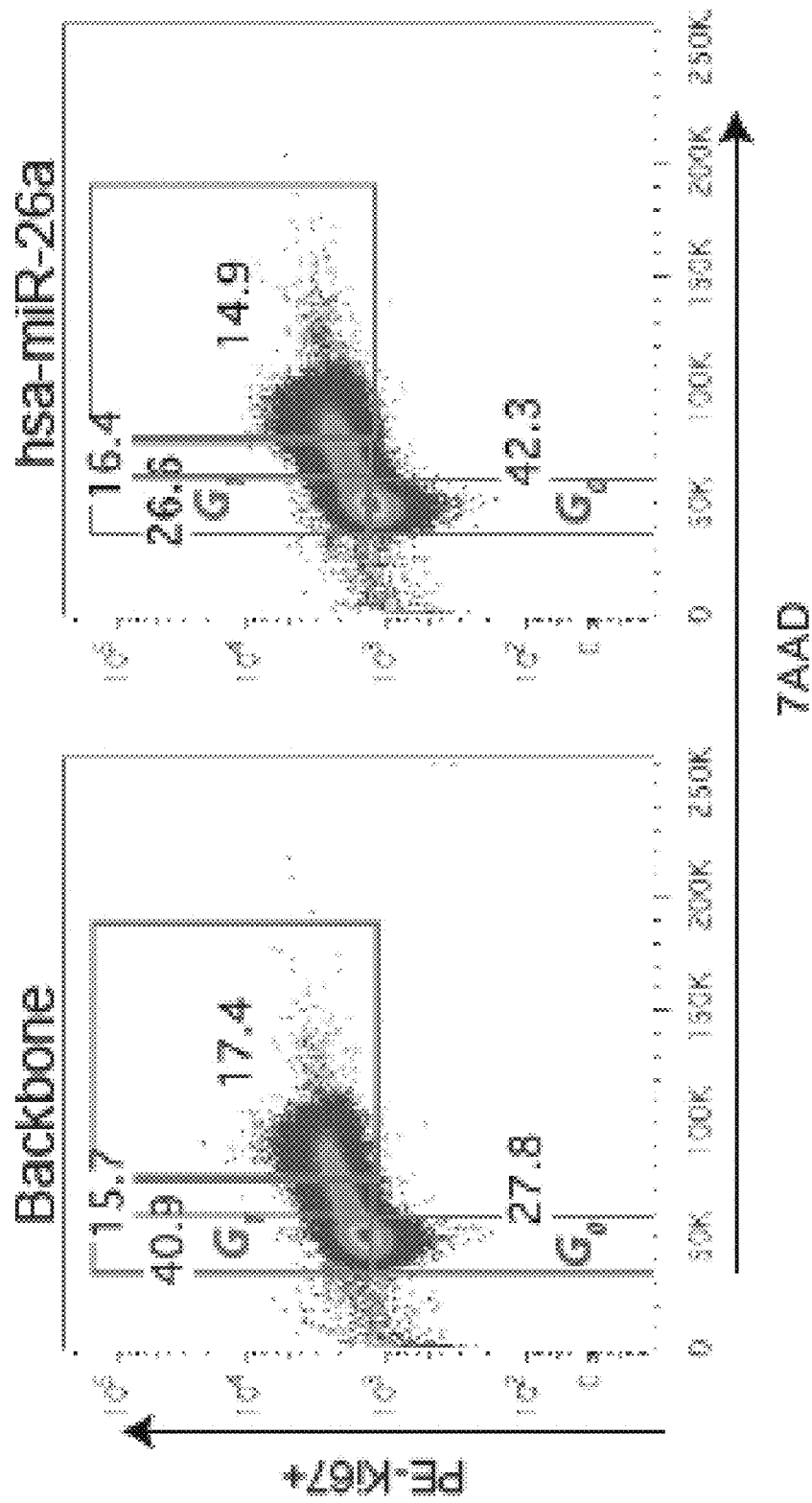

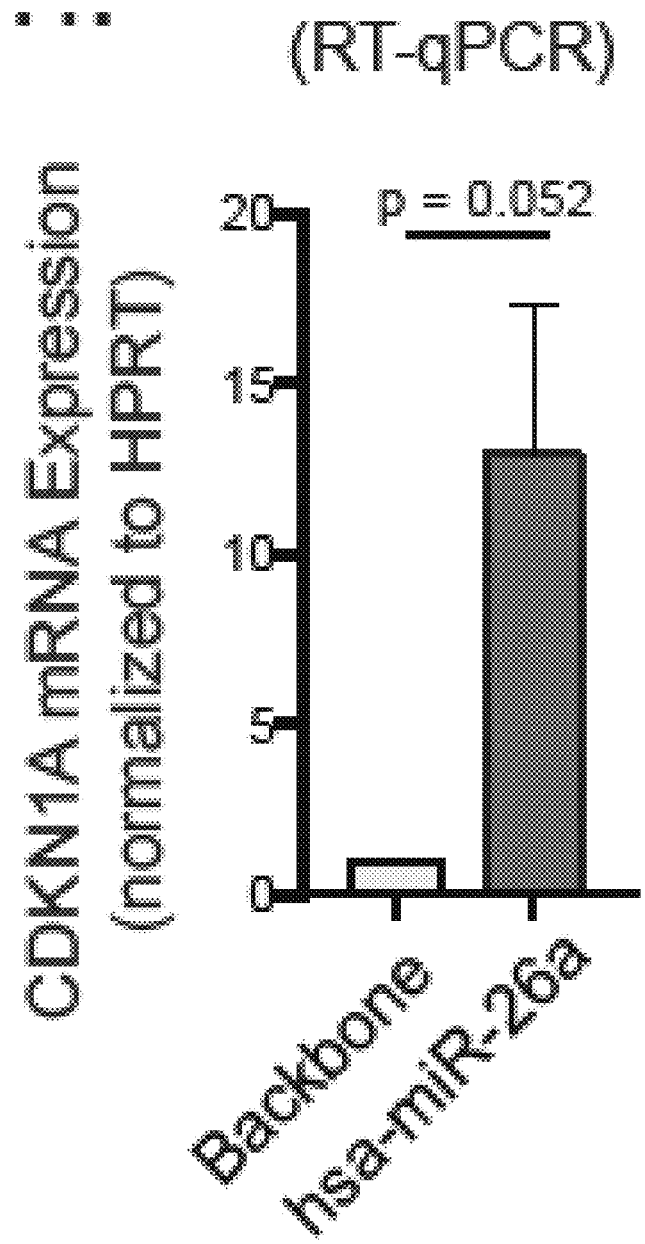

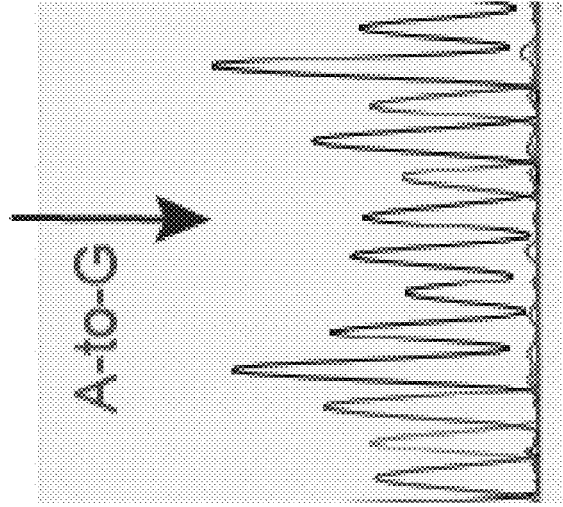
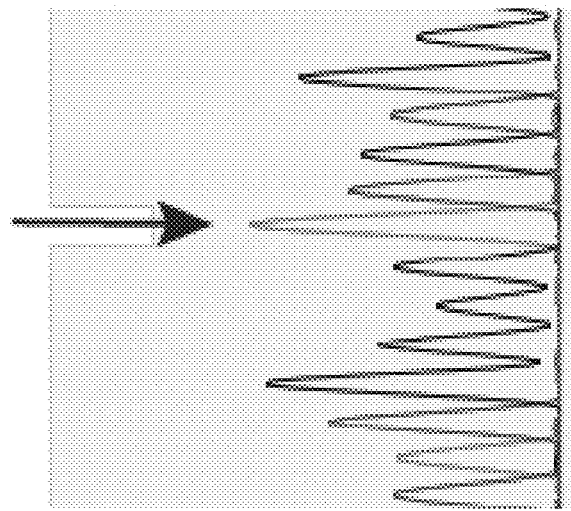
FIG. 3N

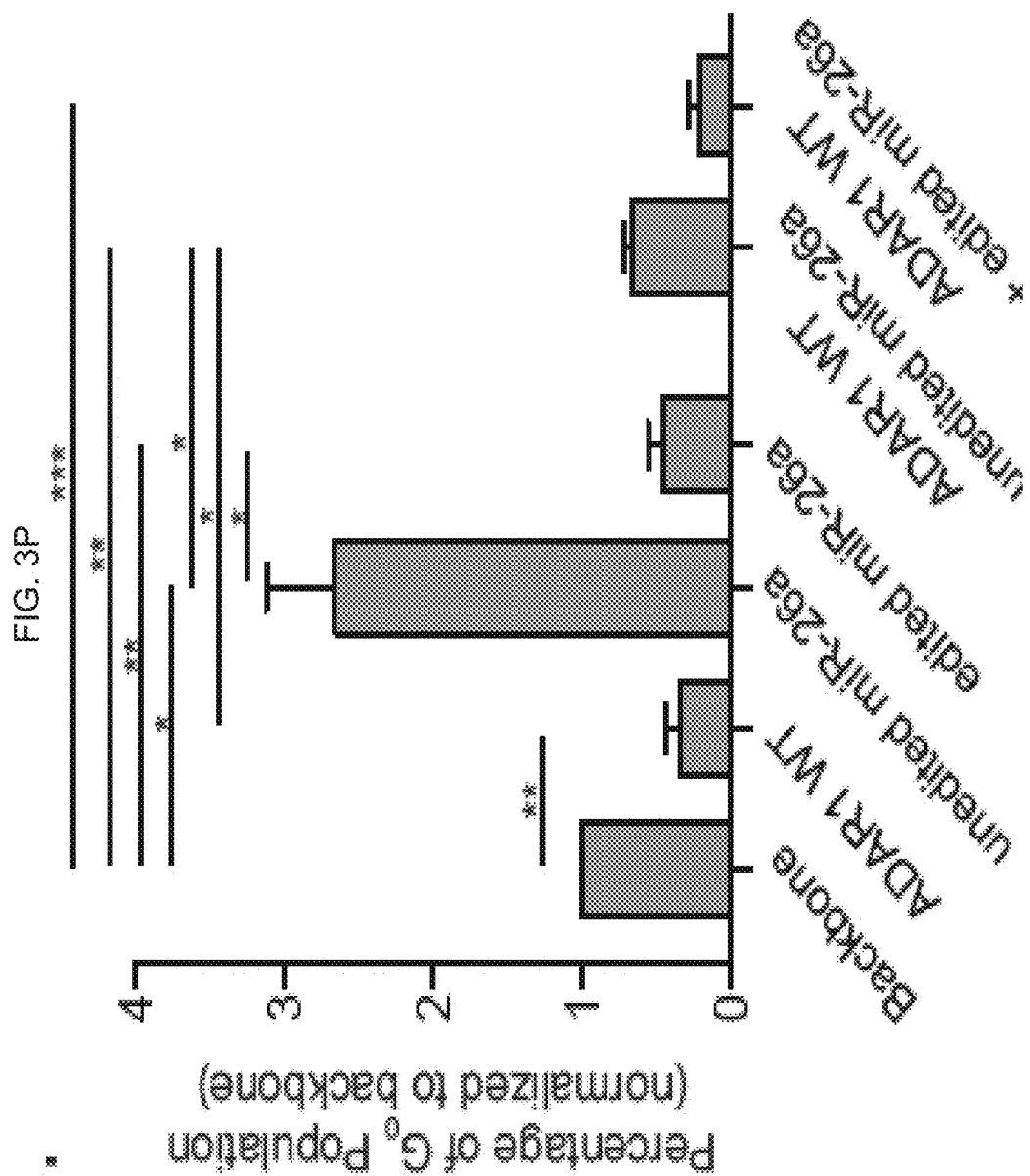

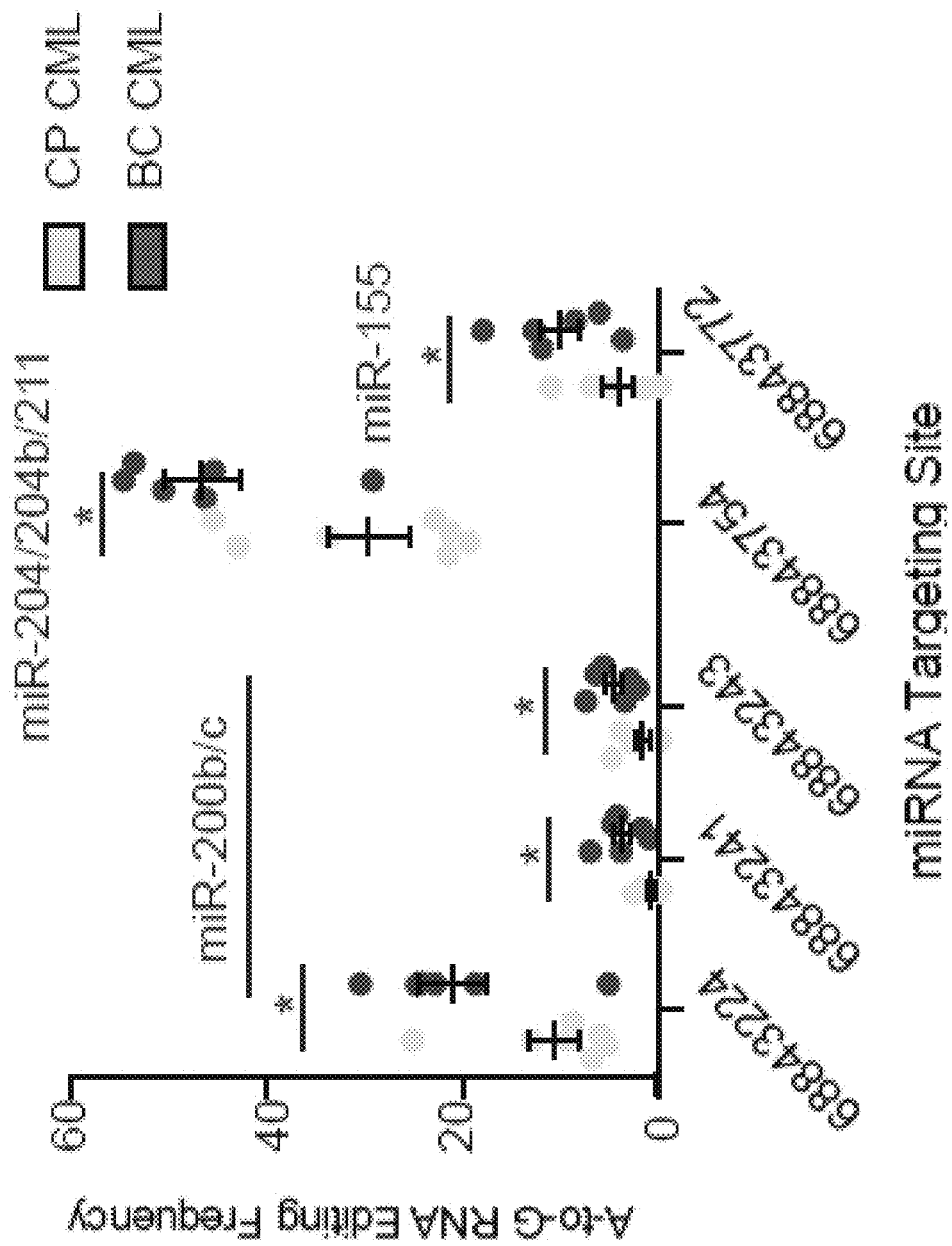

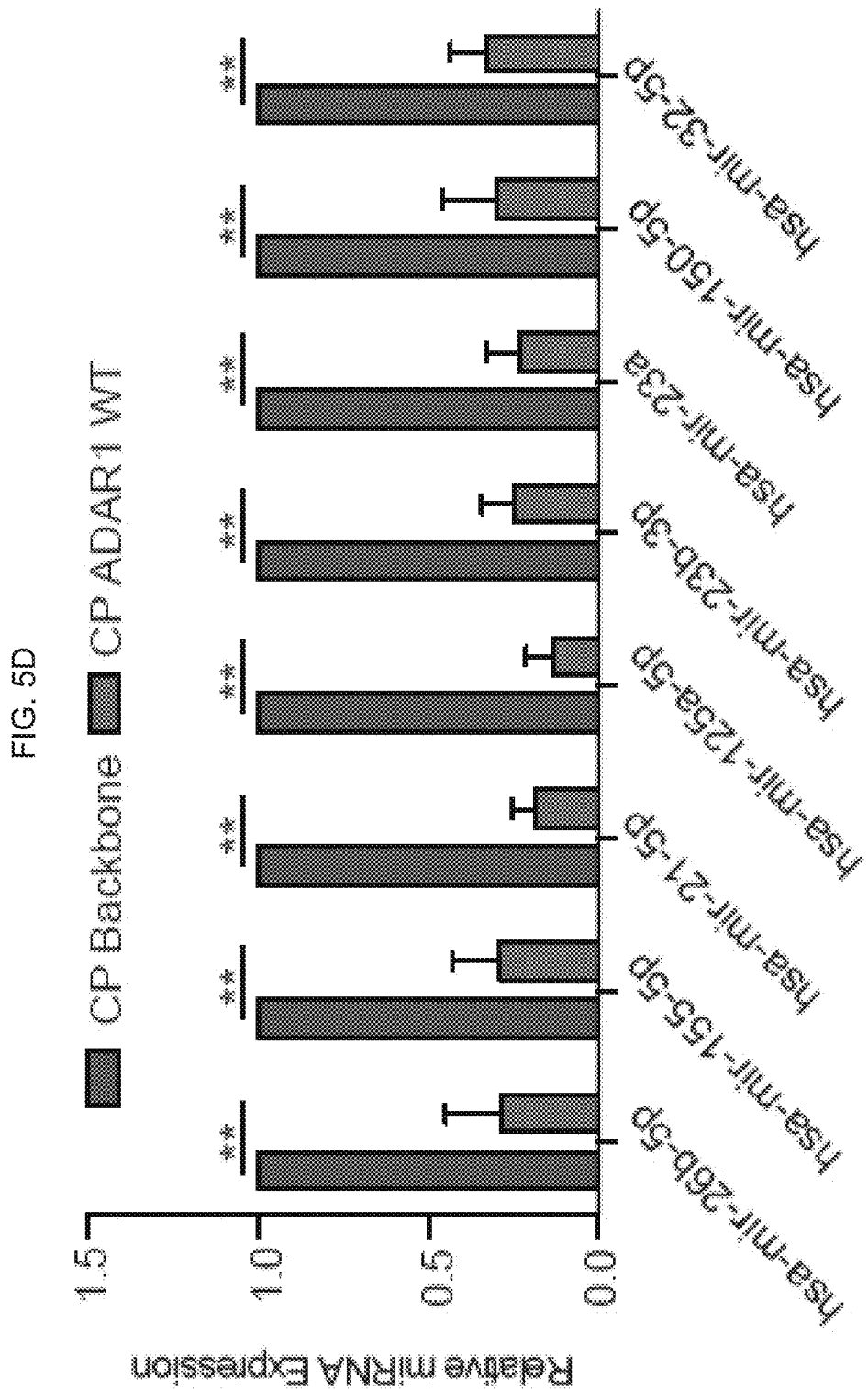

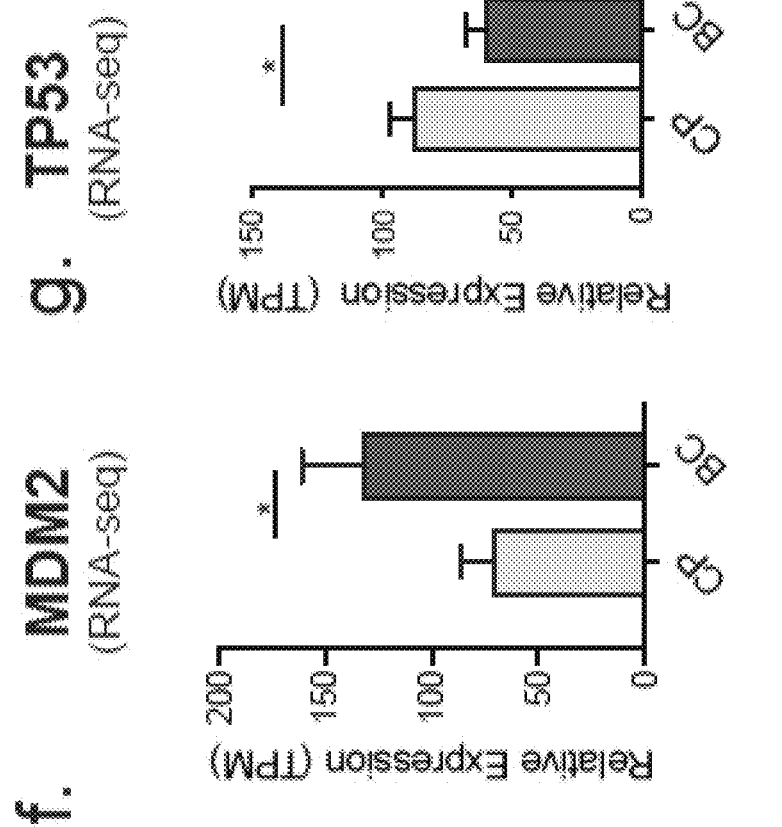
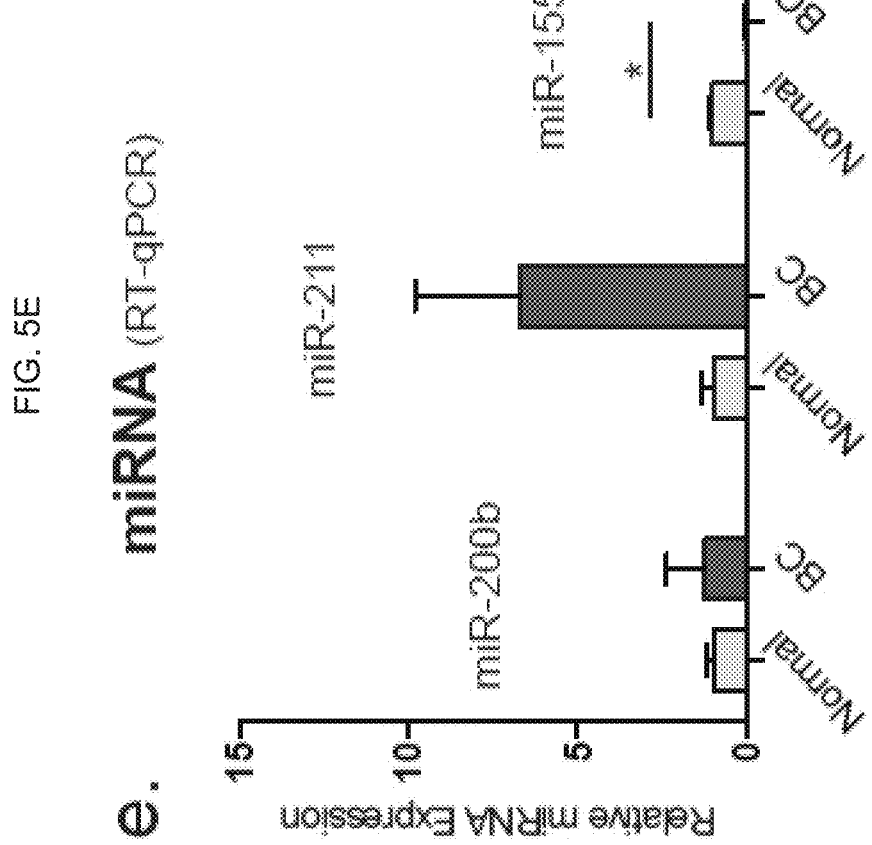
FIG. 5E, FIG. 5F, FIG. 5G

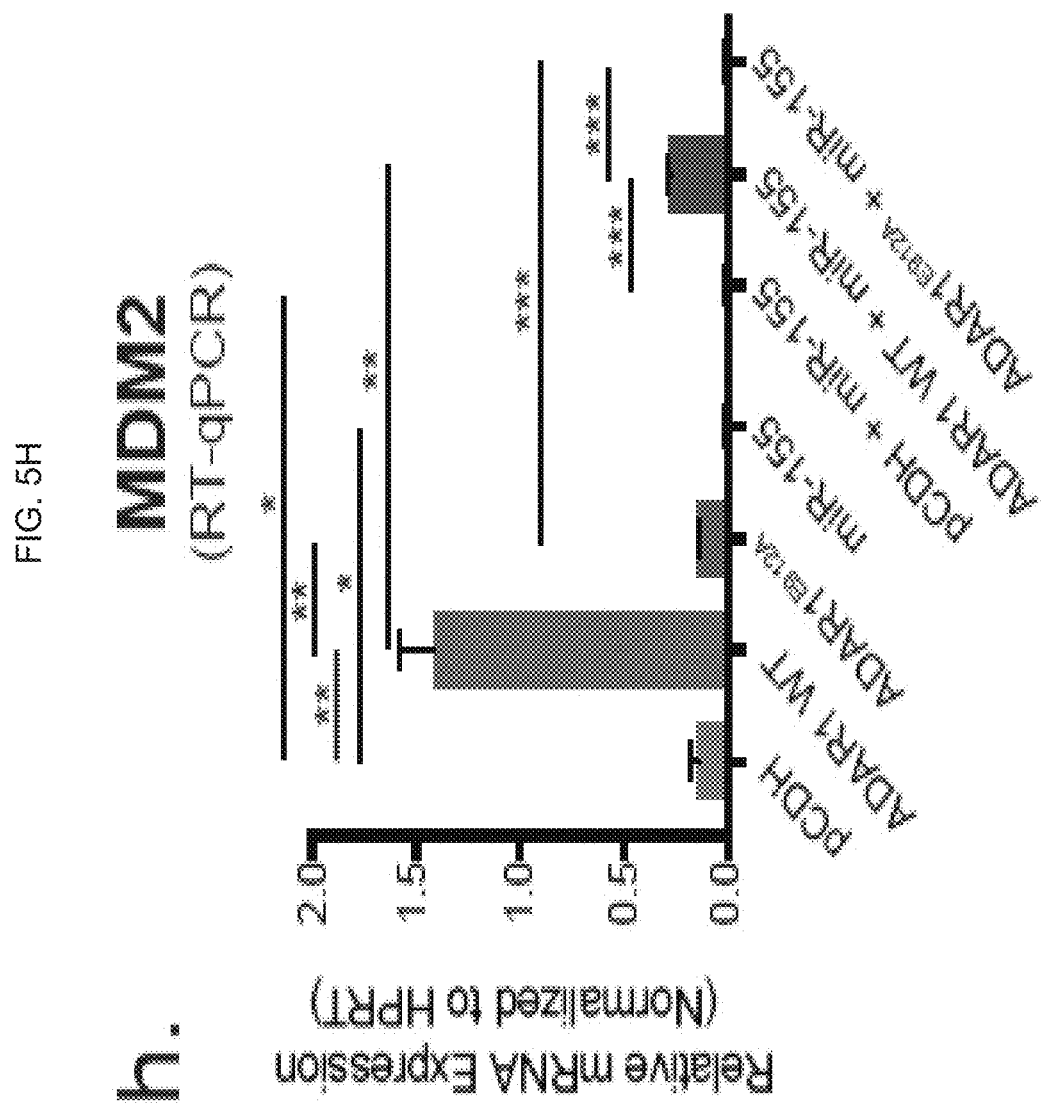

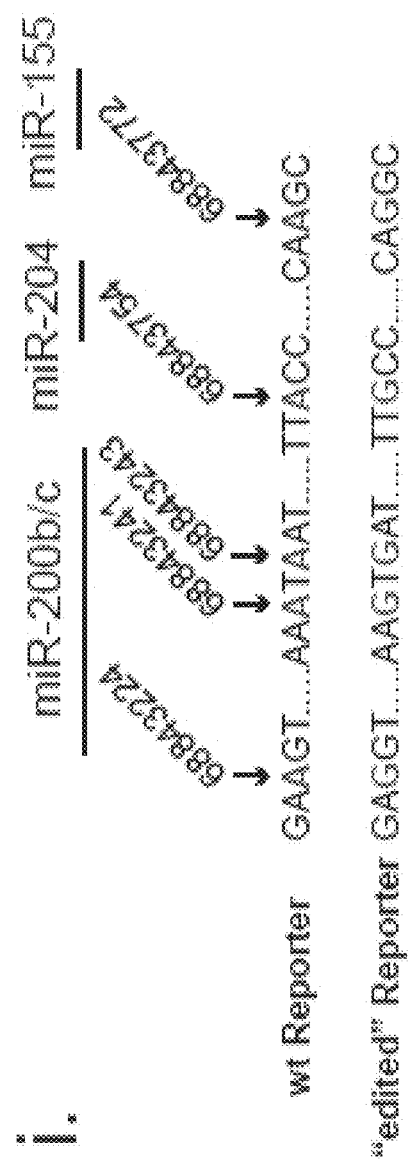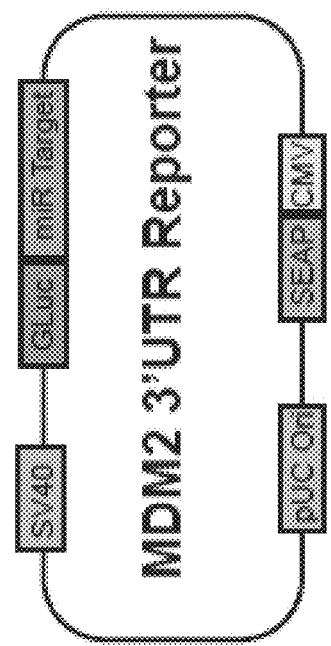
FIG. 51

FIG. 7B
Stem Cells (CD34+CD38-Lin-)
Backbone ADAR1 WT
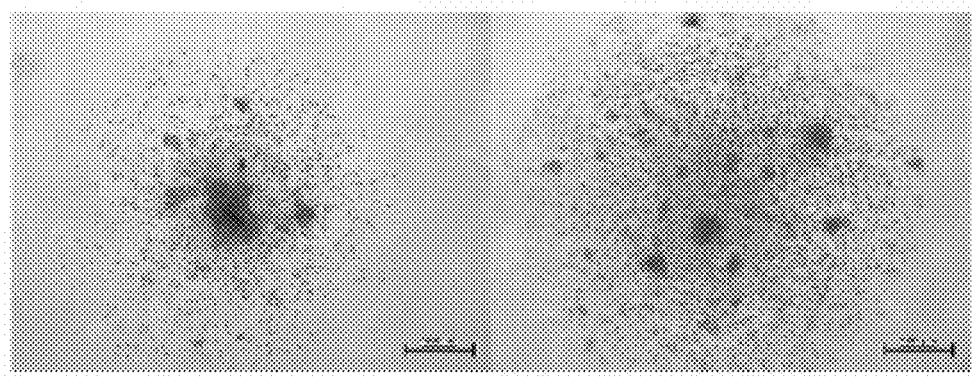
Progenitors (CD34+CD38+Lin-)
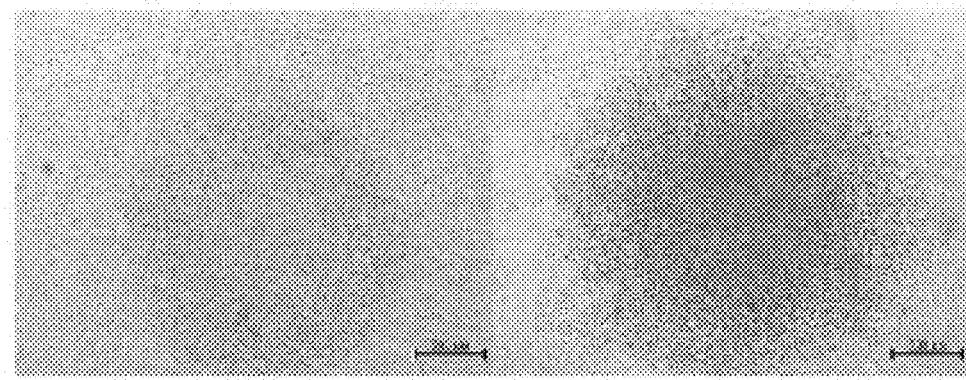

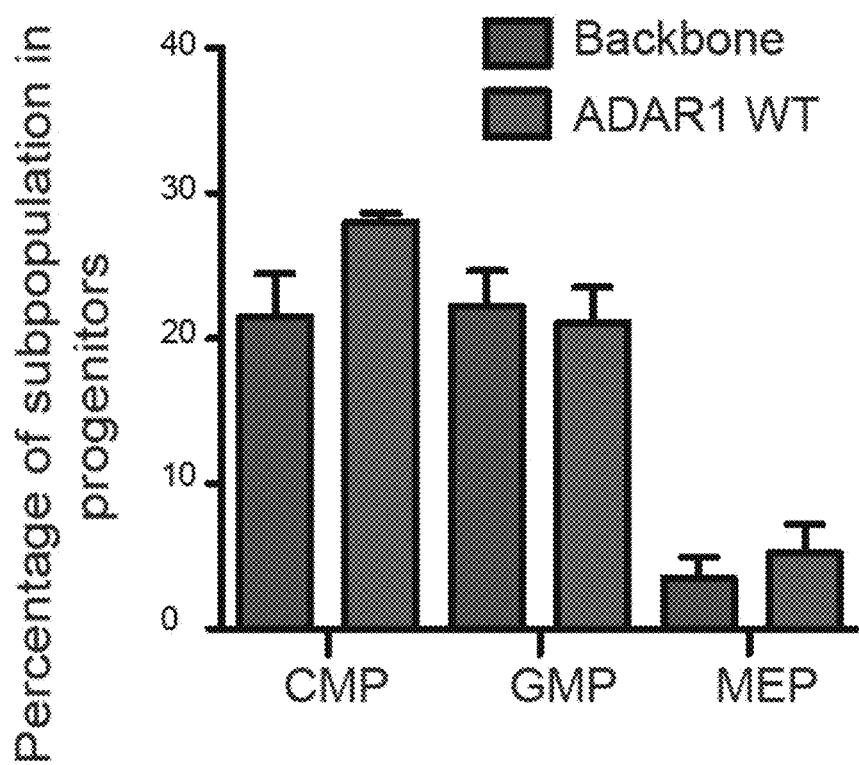

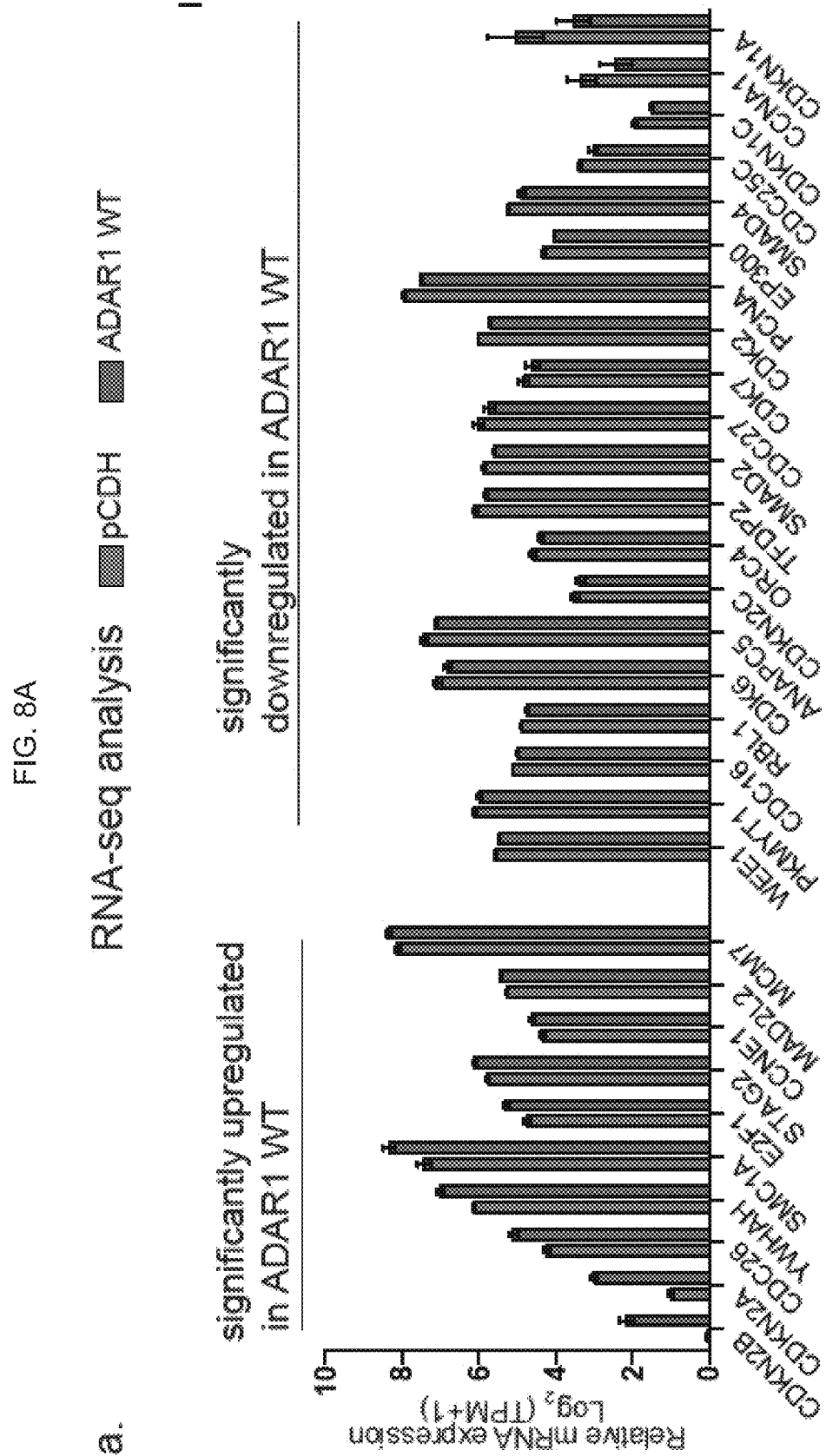

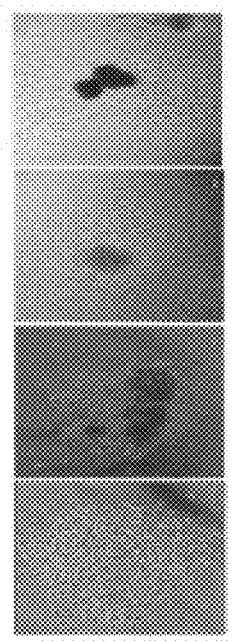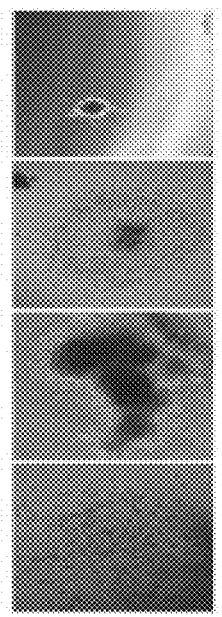
FIG. 9A

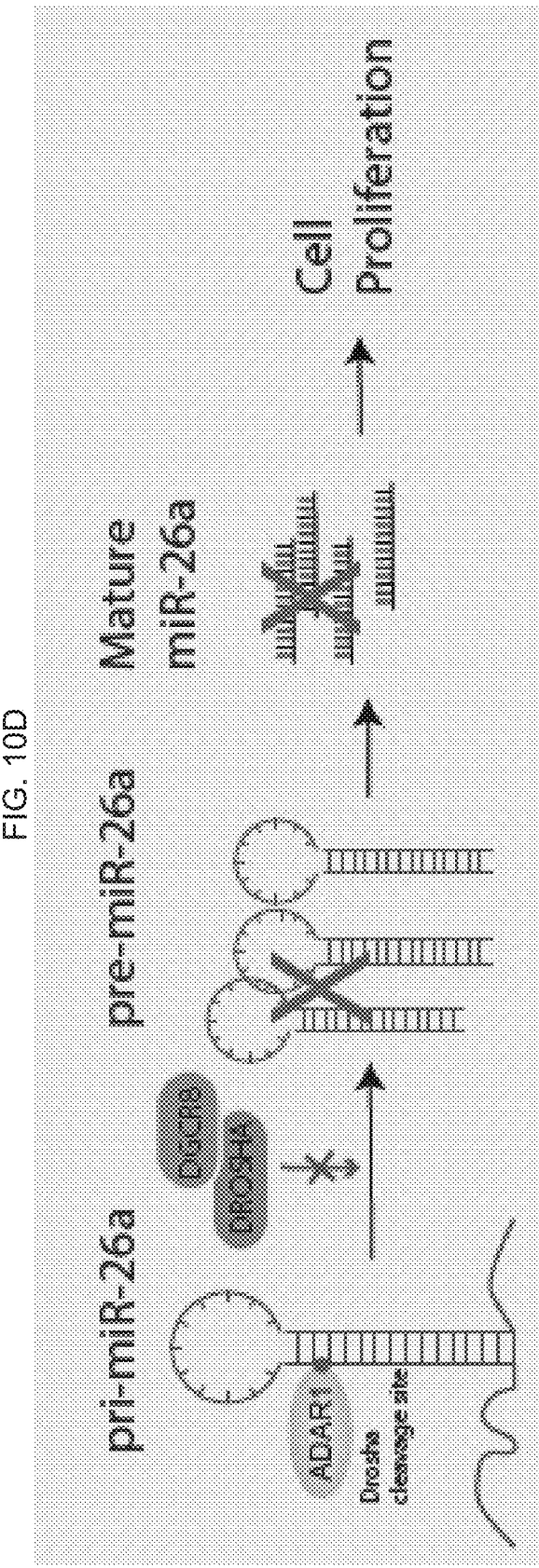

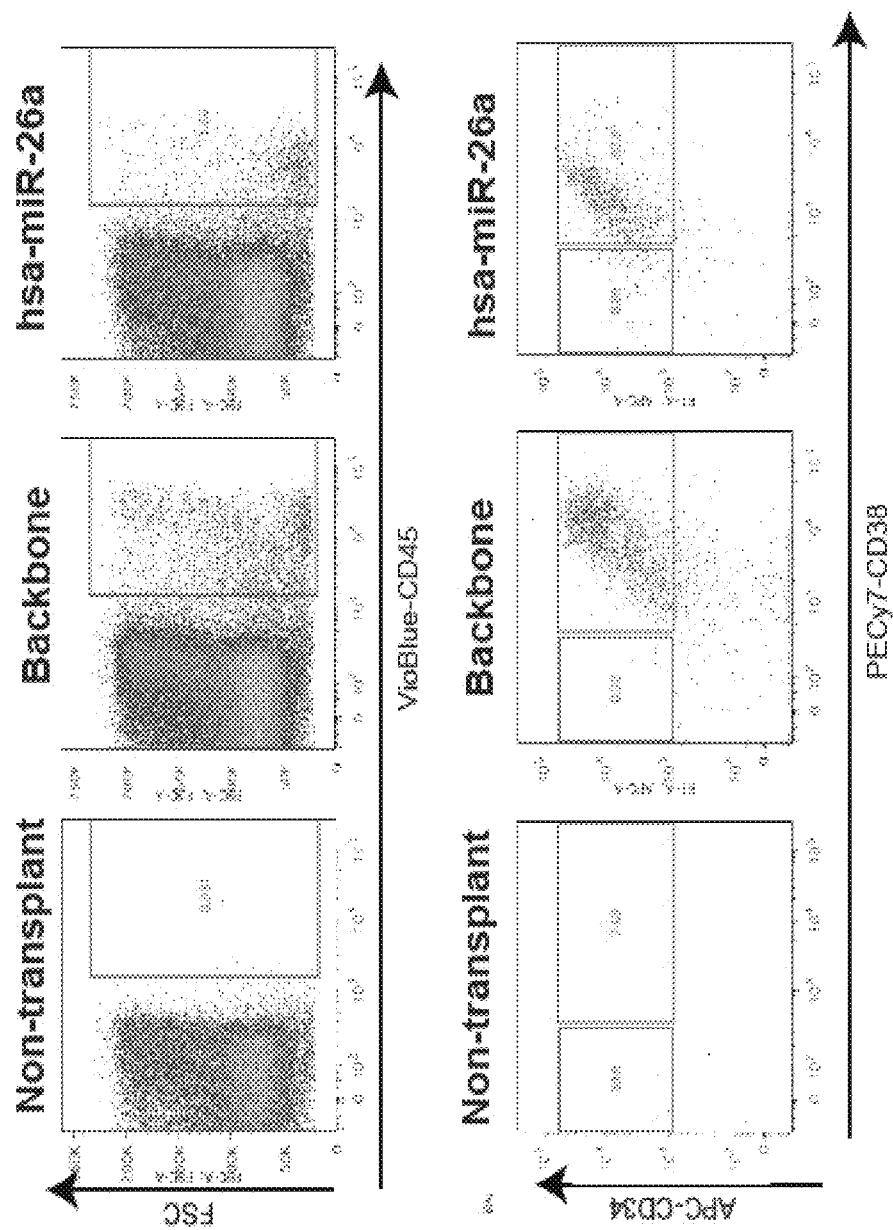

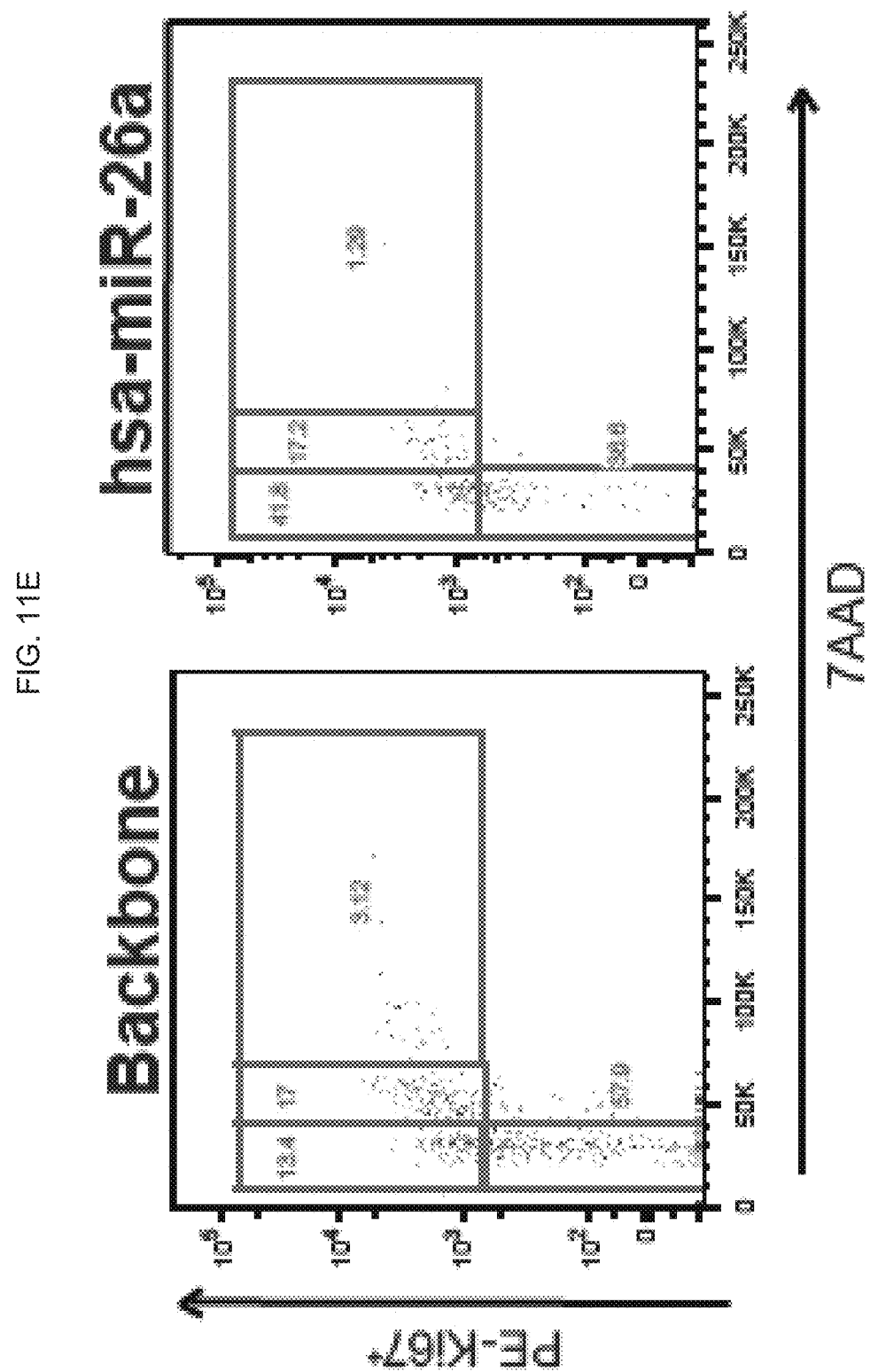

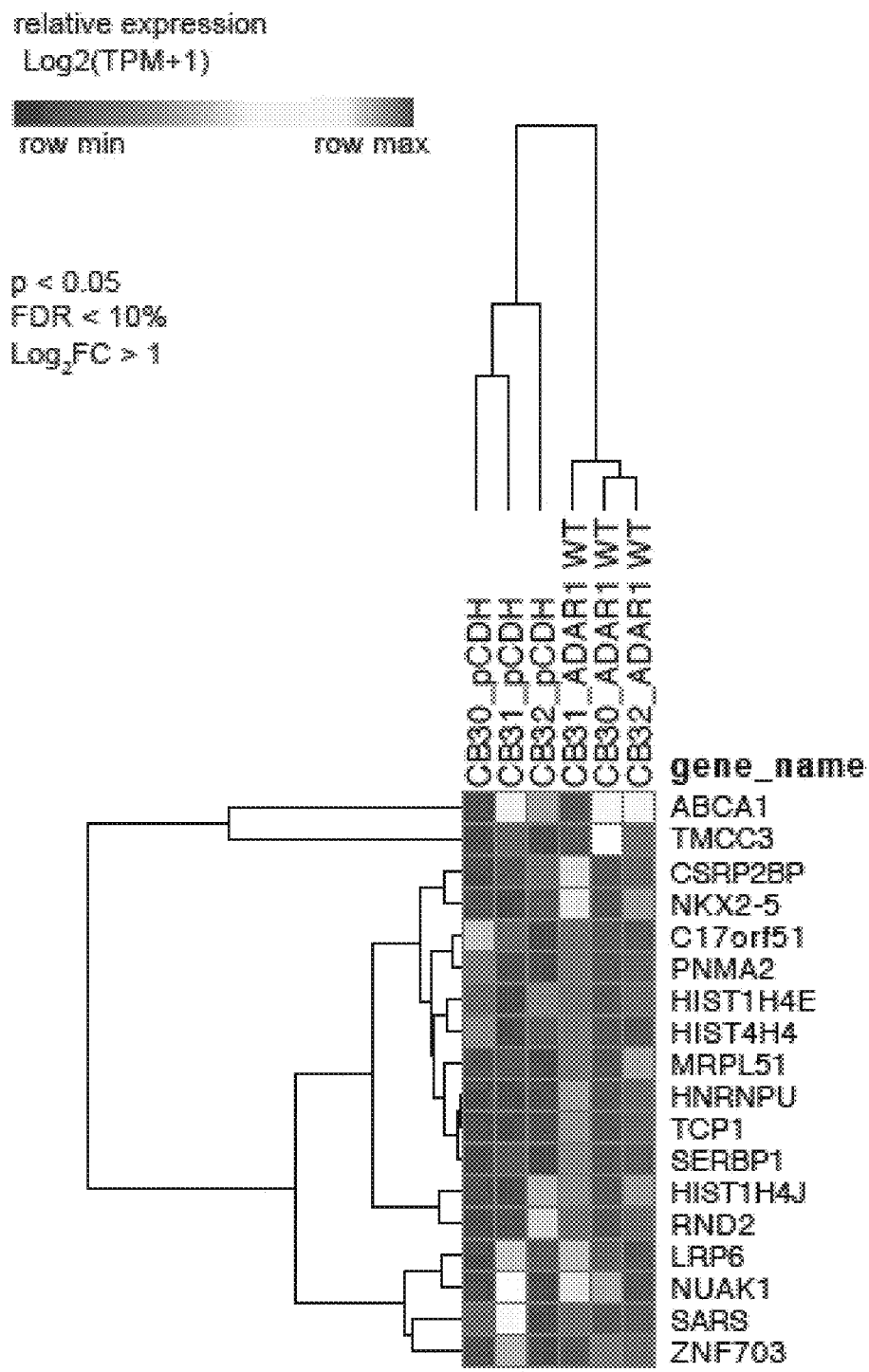

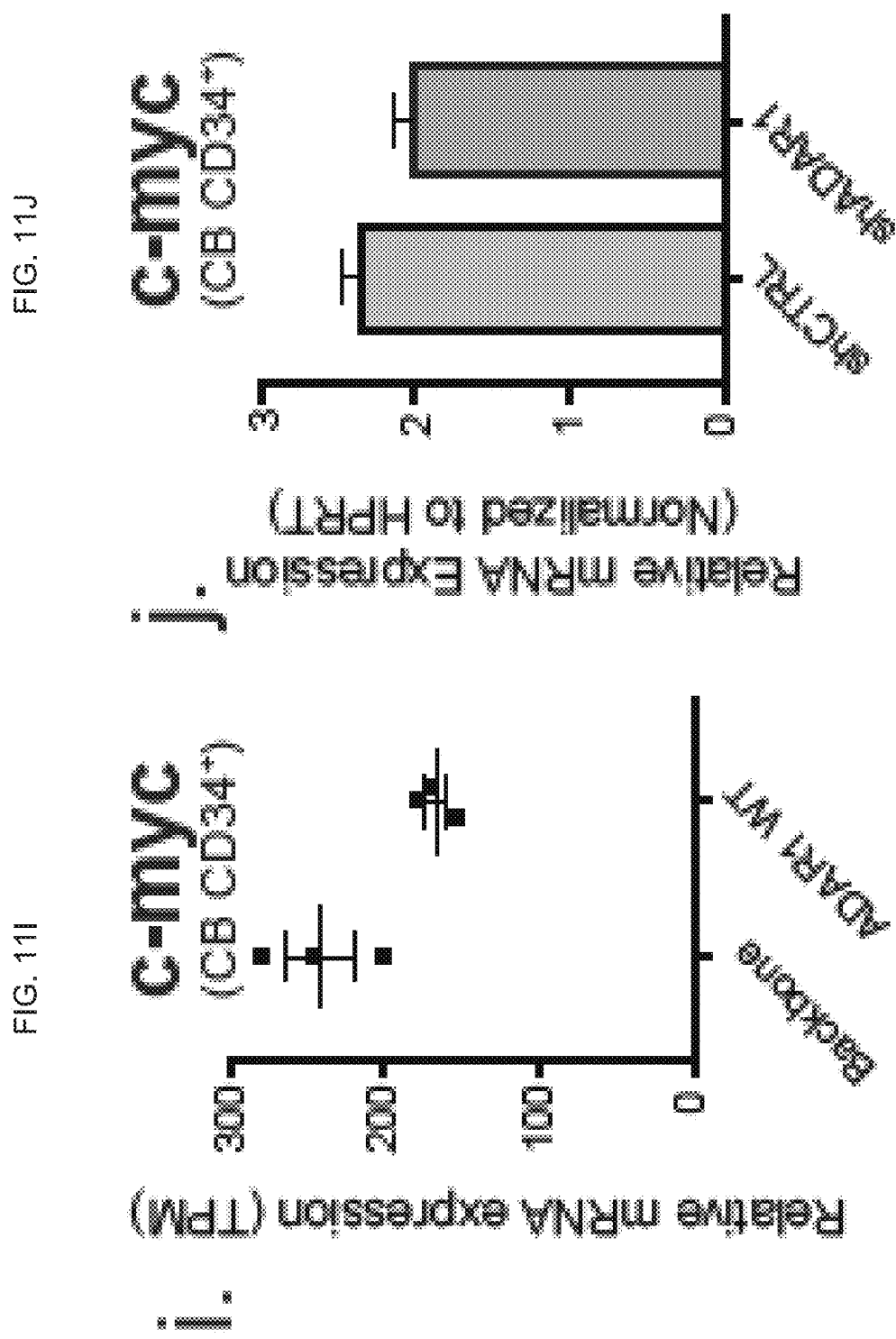

FIG. 15D

| A-To-I RNA editing Region | YMML P.Val | ET P.Val | PV P.Val | MF P.Val | CML P.Val | AML P.Val |
|---|---|---|---|---|---|---|
| IGR | 0.30 | 0d+00 | 1.0E-05 | 1.57E-11 | 1.0e+000 | 0.23 |
| Intron | 0.74 | 8.6E-23 | 1.4E-4m | 7.0E-0mm | 1.0e+01 | 1.e+00 |
| Synonymous | 0.77 | 0.21 | 1.24E-03 | 1.24E-04 | 1.0E-04 | 0.37 |
| Utr 01R | 0.34 | 0.64 | 0.12 | 0mis | 0.30 | 0mis |
| UTR | 0.84 | 1.0E-04 | 8.4E-11 | 1.e-04 | 4.0E-0 | 3.1E-02 |
| UTR | 0.22 | 0mis | 0.051 | 0mis | 0mis | 0mis |
| Nonsyn. | 0.81 | 7.1E-02 | 1.e-m | 7.1E-03 | 0mis | 0.51 |
| ncRNA | 0.65 | 2.6E-02 | 1.6E-02 | 1.2E-04 | 0.14 | 1.e+00 |
| Silent | 0.71 | 0.45 | 0.21 | 1.e-11 | 0.37 | 0mis |

FIG. 15F
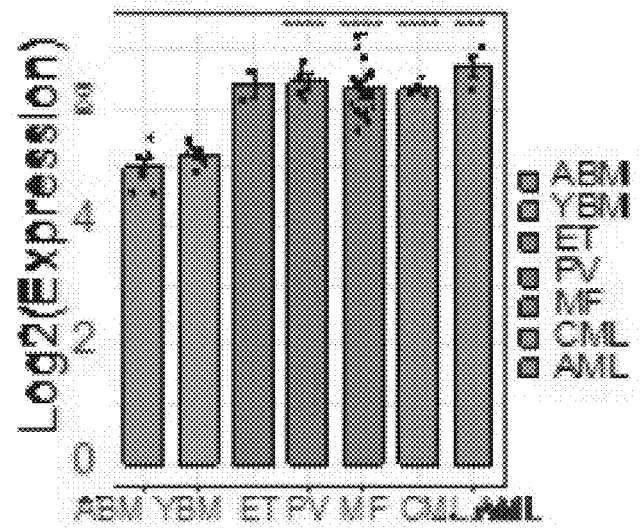
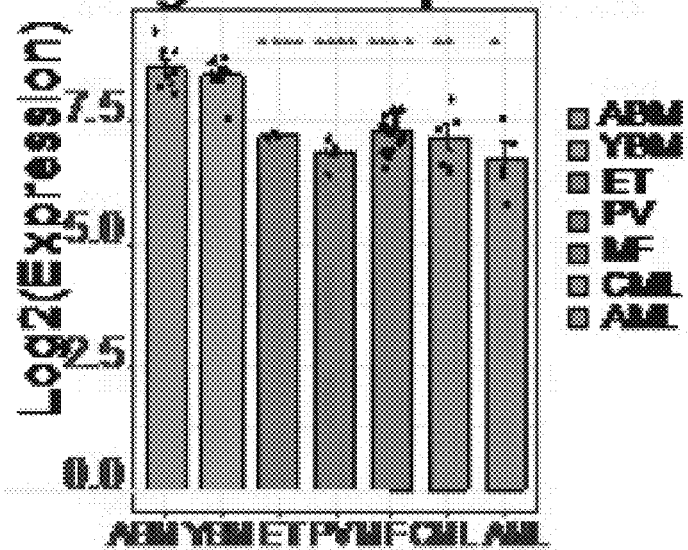

B  Significantly Enriched STRING Interactome from Differentially Edited Genes
MF vs ABM (Progenitor Cells)

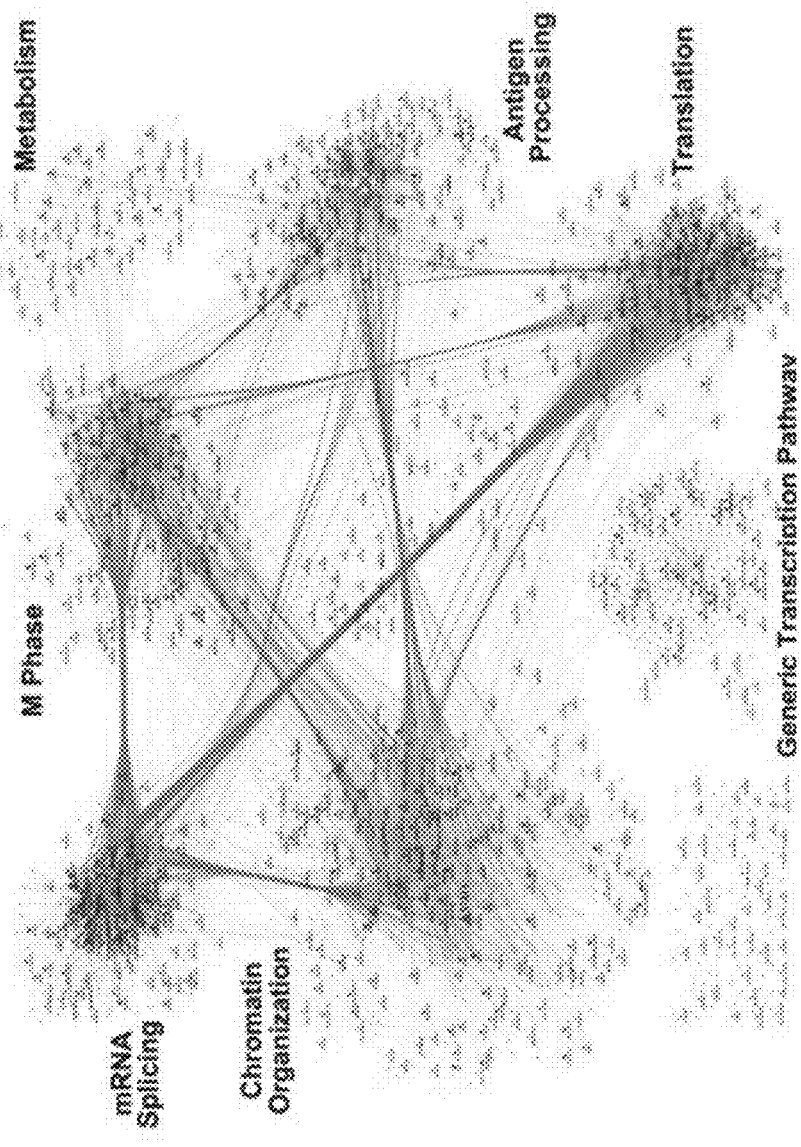

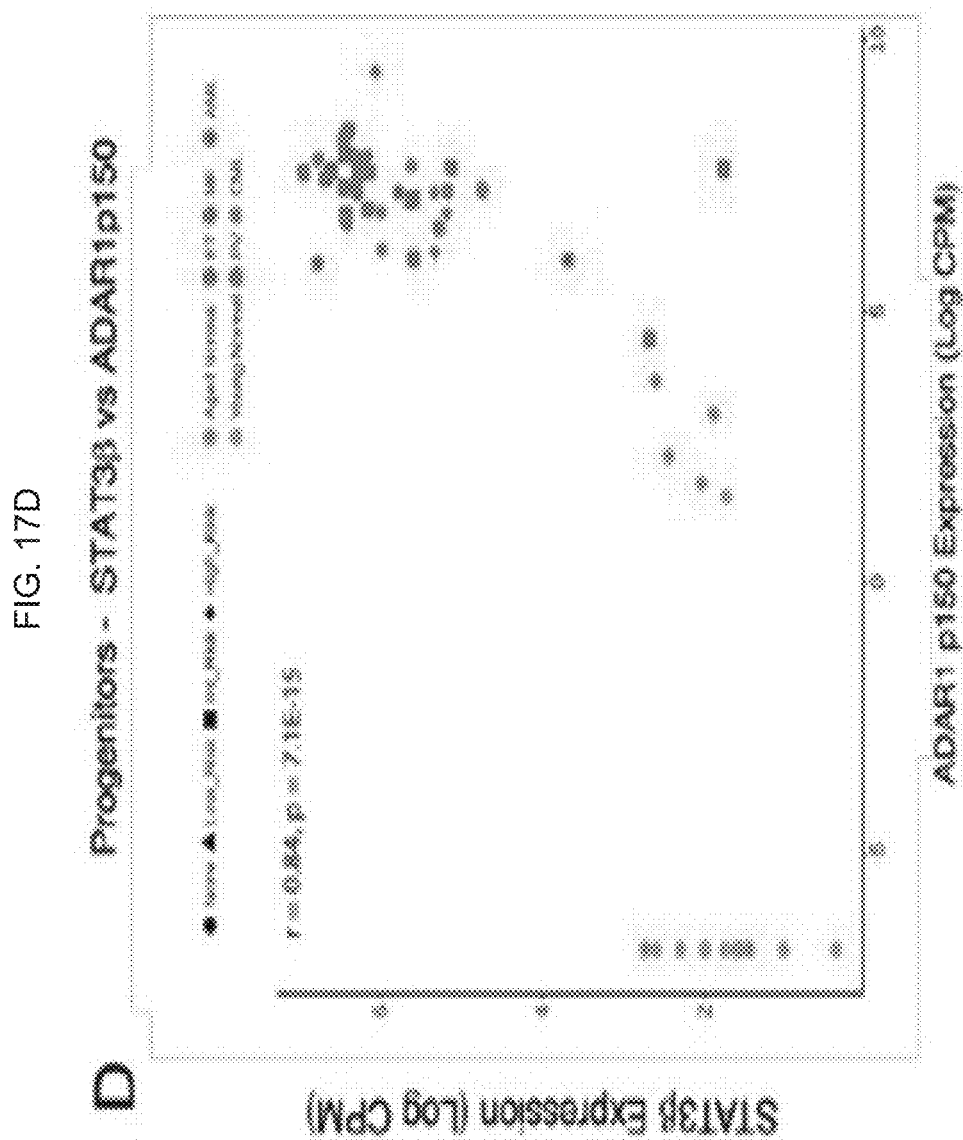

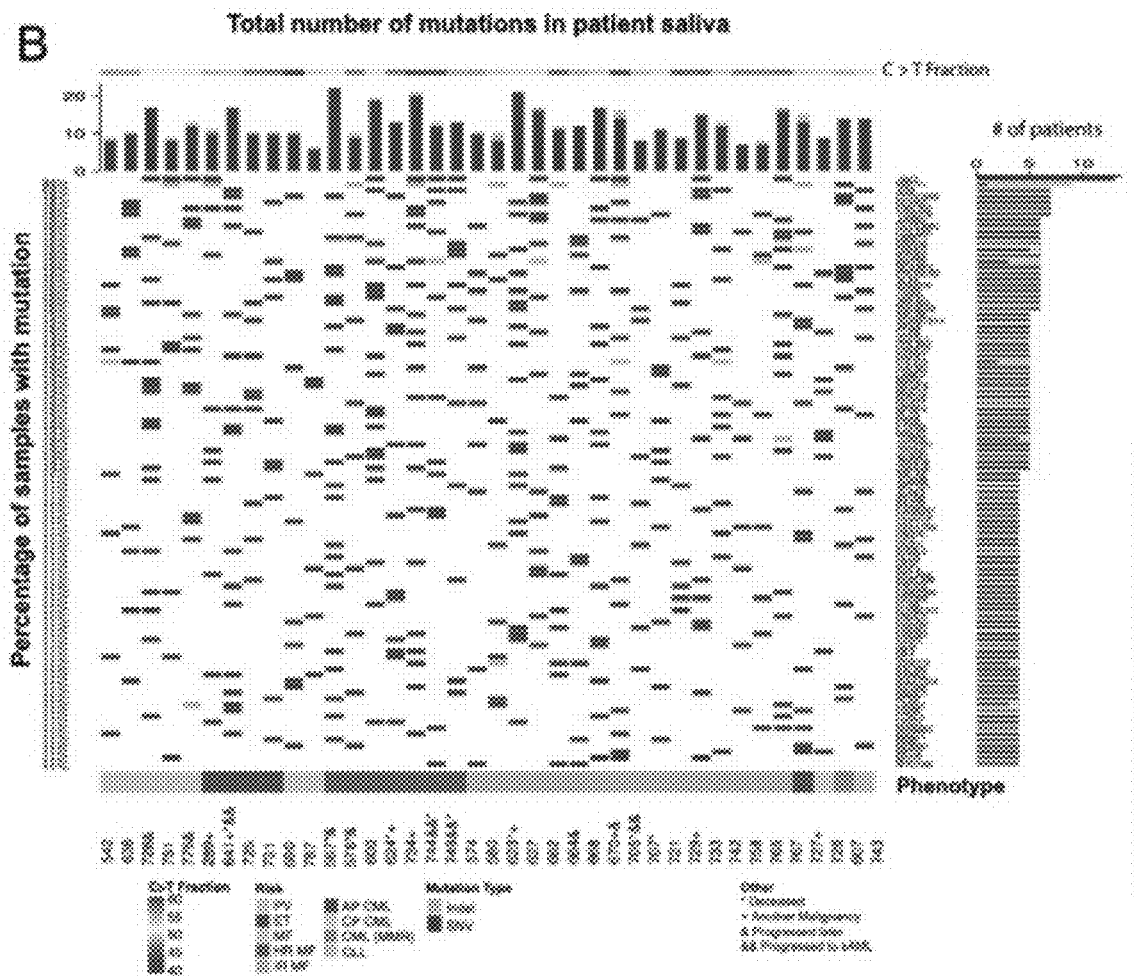

FIG. 18D
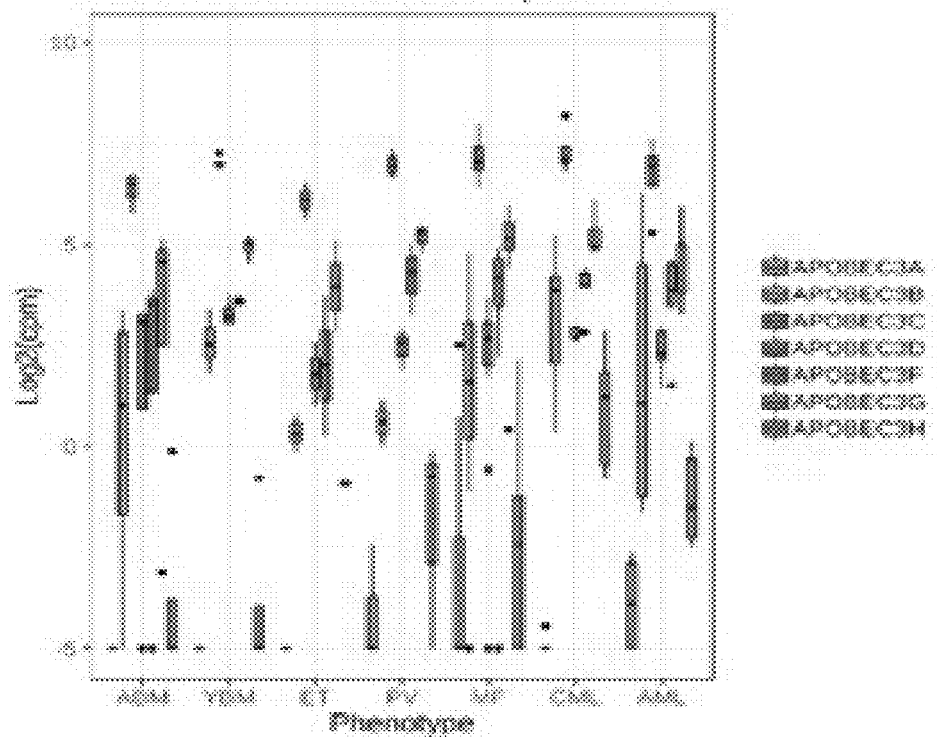
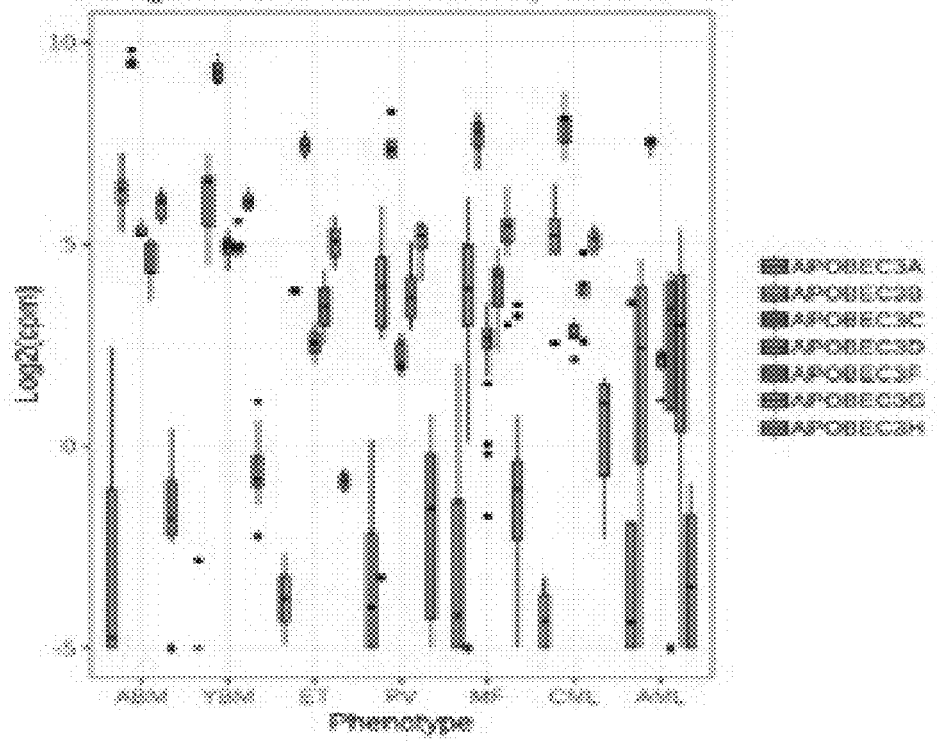

FIG. 20A
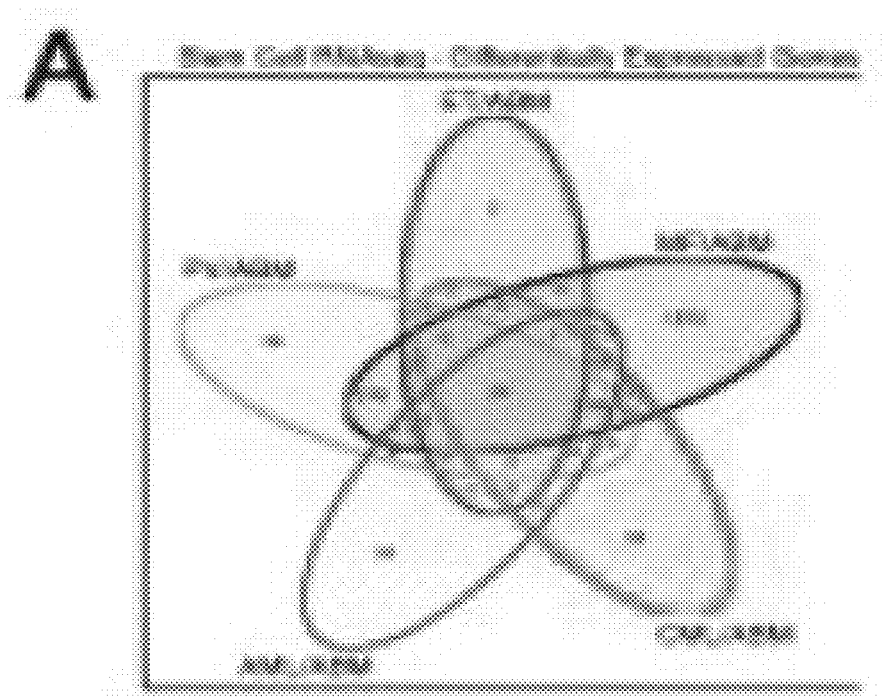
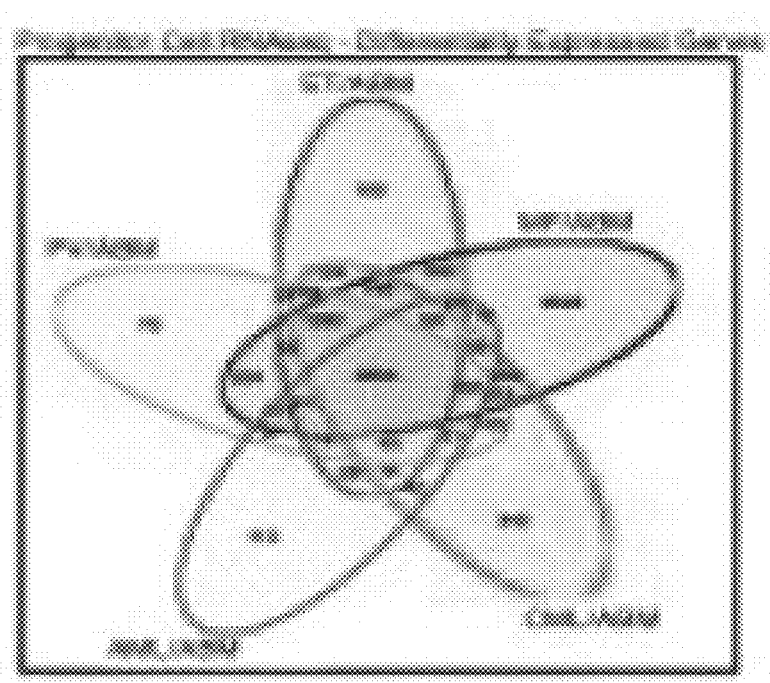

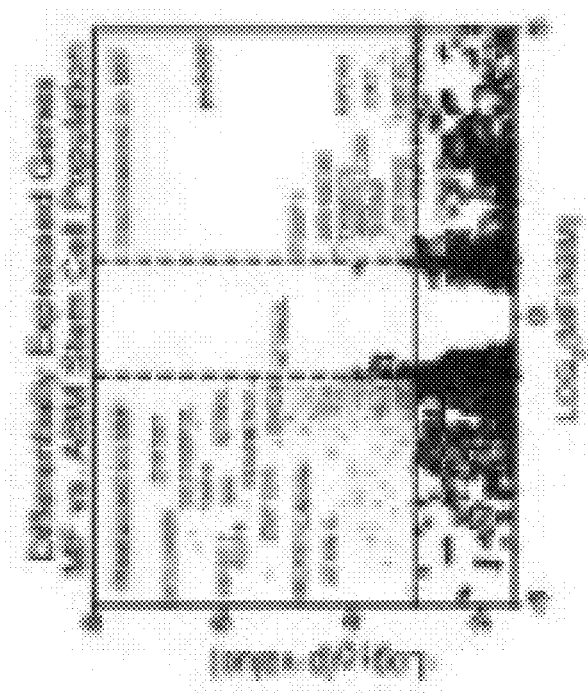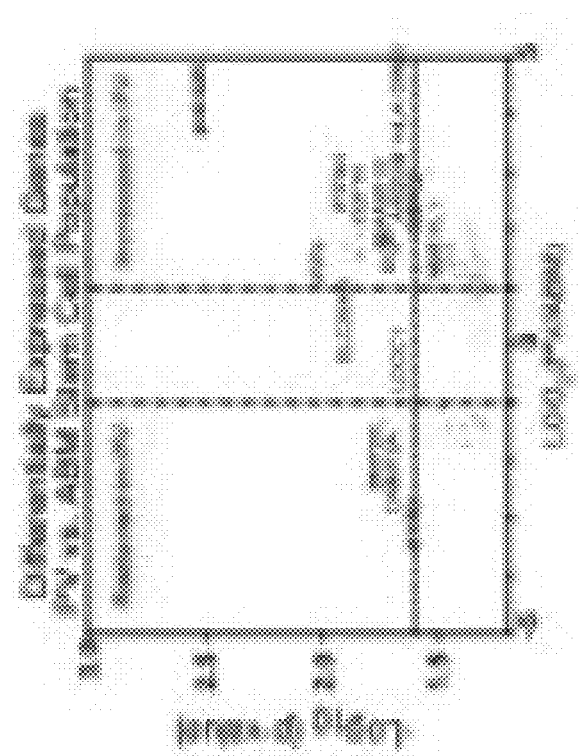
FIG. 20D

FIG. 21C
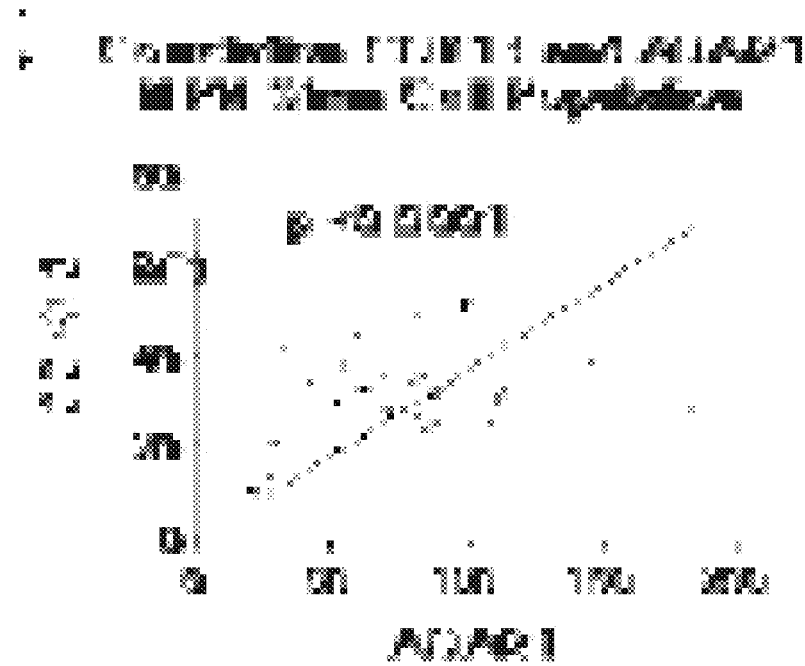
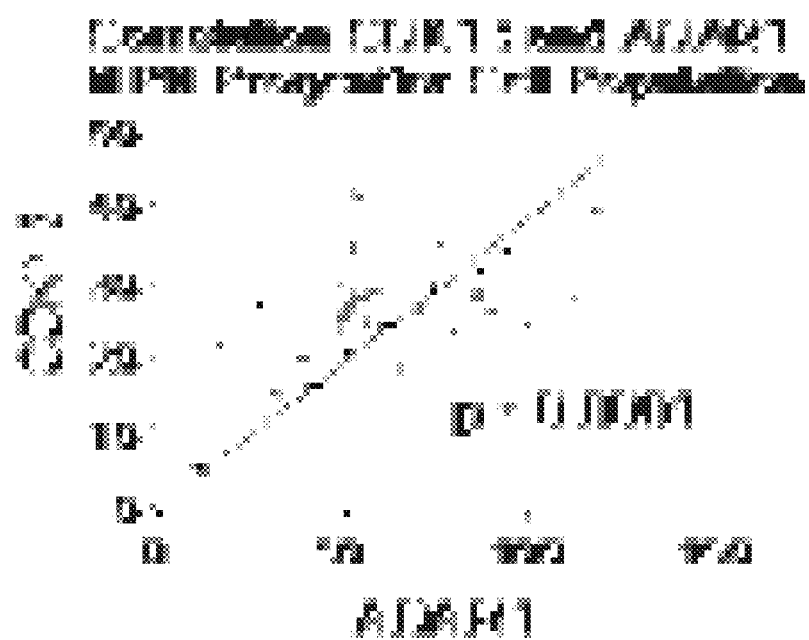

FIG. 21D
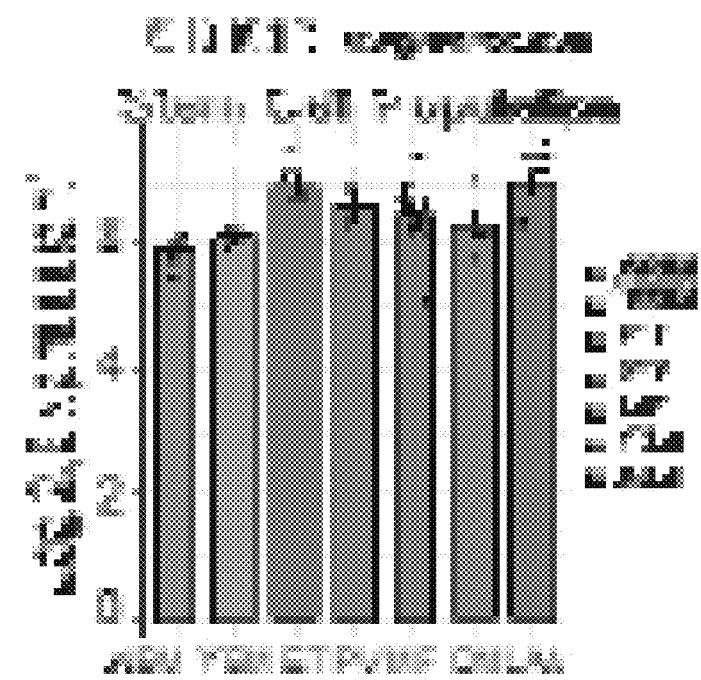
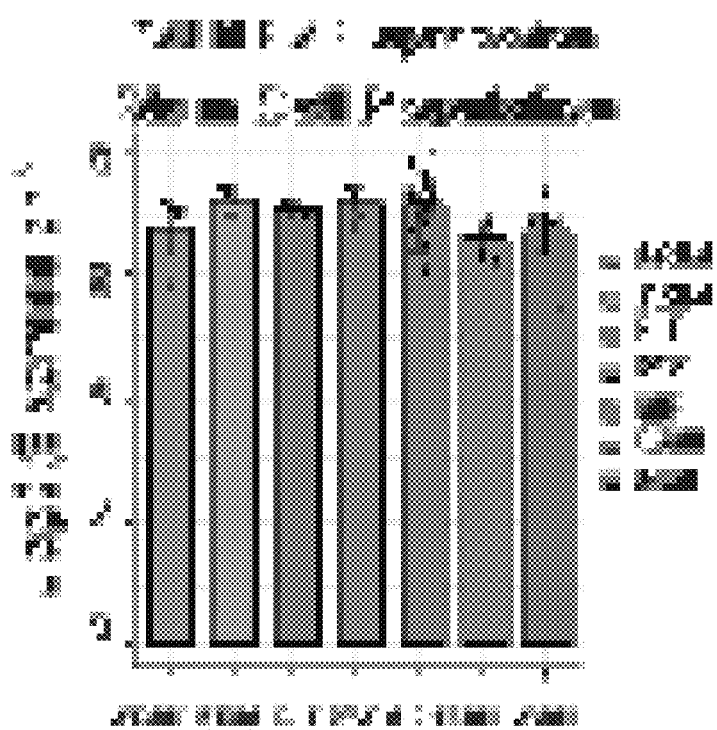

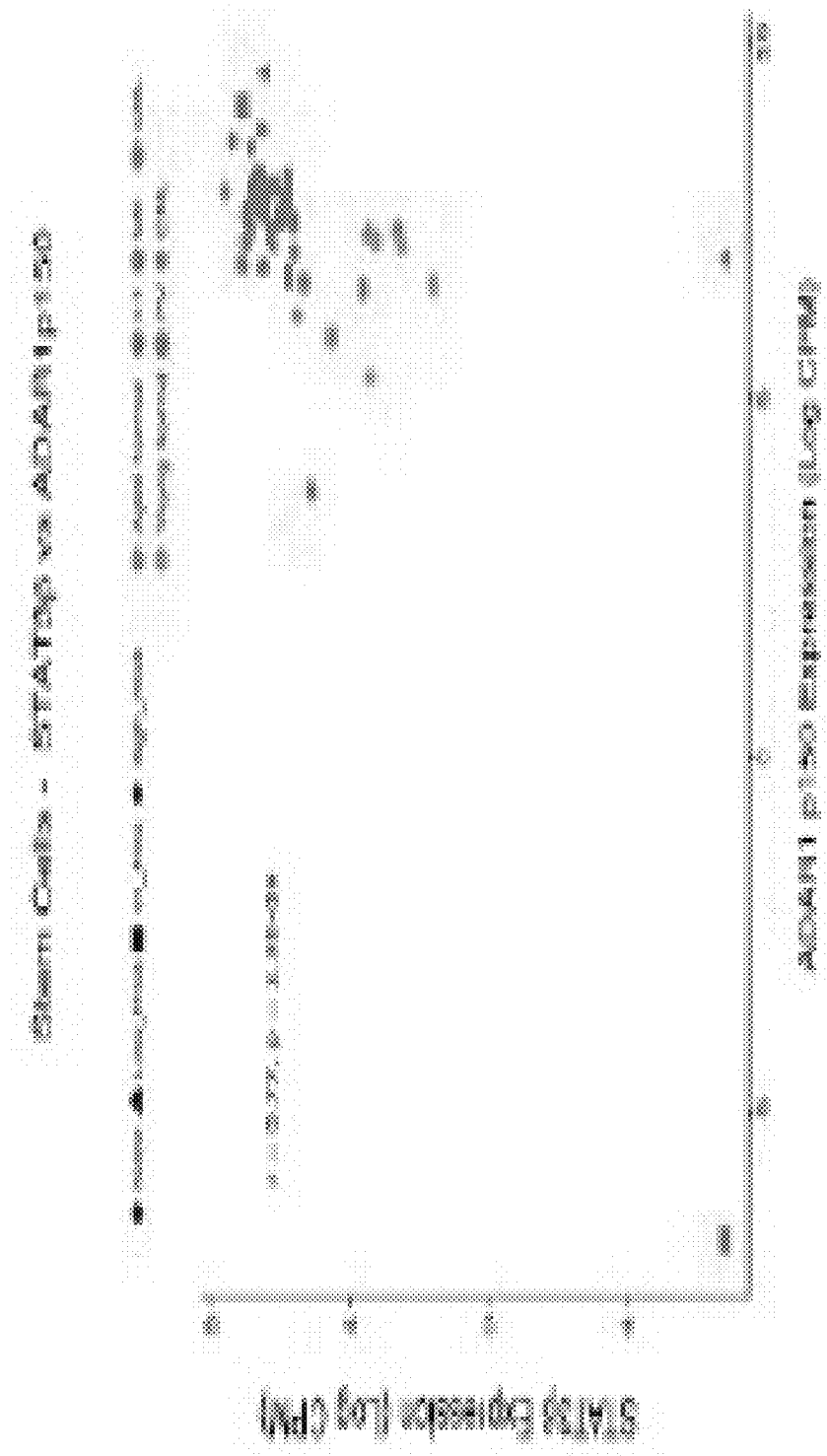

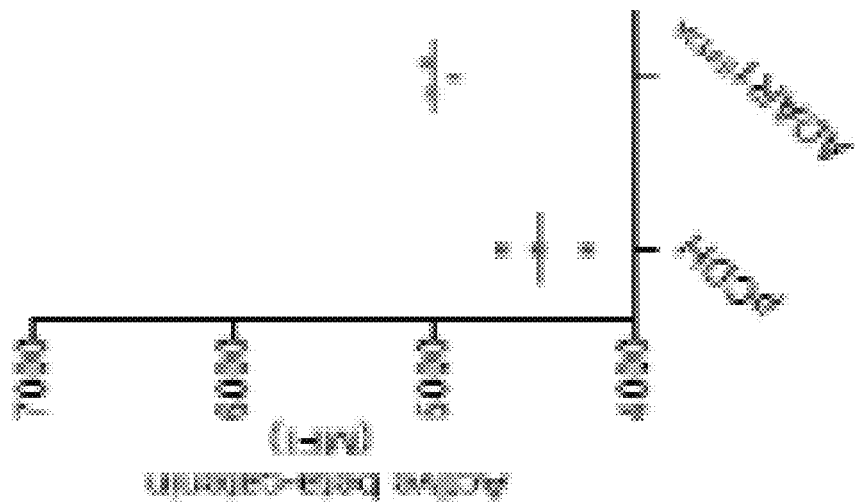
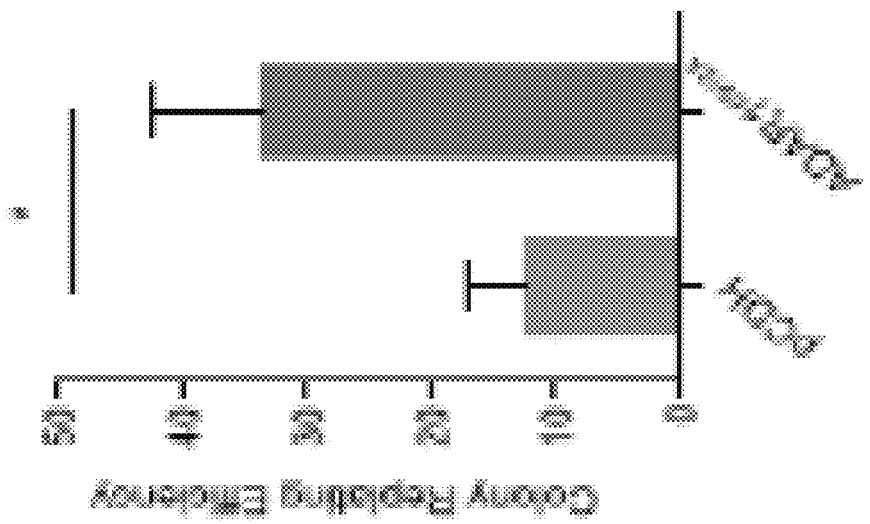
FIG. 22C
FIG. 22D

SEQUENCE LISTING

```
<160> NUMBER OF SEQ ID NOS: 16

<210> SEQ ID NO 1
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 1
aaaaagcagg ctccaccat                                                19

<210> SEQ ID NO 2
<211> LENGTH: 19
<212> TYPE: DNA
<213> ORGANISM: artificial sequence
```

```
<220> FEATURE:
<223> OTHER INFORMATION: synthetic oligonucleotide

<400> SEQUENCE: 2
aaaaagcagg ctccaccat                                                    19

<210> SEQ ID NO 3
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 3
tgctgctgaa ttcaagttgg                                                   20

<210> SEQ ID NO 4
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 4
tcgttctccc caatcaagac                                                   20

<210> SEQ ID NO 5
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 5
atgaaattca cccctttcc                                                    20

<210> SEQ ID NO 6
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 6
aggtgagggg actccaaagt                                                   20

<210> SEQ ID NO 7
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 7
atatgccttc ccccactacc                                                   20

<210> SEQ ID NO 8
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 8
cgtgagtgct cactccagaa                                                   20
```

<210> SEQ ID NO 9
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 9
ttcccagcct aggtttcaga                                               20

<210> SEQ ID NO 10
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 10
aacacggagc ttgagaggaa                                               20

<210> SEQ ID NO 11
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 11
gcccaatggc atagcaaga                                                19

<210> SEQ ID NO 12
<211> LENGTH: 22
<212> TYPE: DNA
<213> ORGANISM: artificial sequence
<220> FEATURE:
<223> OTHER INFORMATION: synthetic oligonucleotide

<400> SEQUENCE: 12
ggccagtcat gcttacagtc ac                                            22

<210> SEQ ID NO 13
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 13
agctttataa ccgcatgtgc atac                                          24

<210> SEQ ID NO 14
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 14
cagatttccc cttcctggtt t                                             21

<210> SEQ ID NO 15
<211> LENGTH: 24
<212> TYPE: DNA
<213> ORGANISM: artificial sequence
<220> FEATURE:
<223> OTHER INFORMATION: synthetic oligonucleotide

```
<400> SEQUENCE: 15
tcagggattt gaatcatgtt tgtg                                          24

<210> SEQ ID NO 16
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 16
cgatgtcaat aggactccag atg                                           23
```

ANTICANCER COMPOSITIONS AND METHODS FOR MAKING AND USING THEM

RELATED APPLICATIONS

This application claims the benefit of priority to U.S. Provisional Patent Application Ser. No. (USSN) U.S. Ser. No. 62/718,997, filed Aug. 16, 2018; and, U.S. Ser. No. 62/863,778, filed Jun. 19, 2019. The aforementioned applications are expressly incorporated herein by reference in their entirety and for all purposes.

STATEMENT AS TO FEDERALLY SPONSORED RESEARCH

This invention was made with government support under CA023100, CA189705, CA205944, and DK114468 awarded by the National Institutes of Health. The government has certain rights in the invention.

TECHNICAL FIELD

This invention generally relates to cancer therapeutics. In alternative embodiments, provided are compositions, including products of manufacture and kits, and methods, for treating or ameliorating a cancer by inhibiting expression or activity of Mouse Double Minute 2 homolog (MDM2), an APOBEC3G (A3G) protein, message (mRNA) or gene, and/or an ADAR1p150 protein, message (mRNA) or gene, e.g., by increasing the presence of in a cell or adding to a cell a molecule inhibitory to MDM2, APOBEC3G and/or ADAR1p150 expression, such as an miRNA that binds to MDM2, APOBEC3G and/or ADAR1p150 transcripts, or any molecule that can inhibit or destabilize the transcripts, resulting in decreased MDM2, APOBEC3G and/or ADAR1p150 expression, to treat a cancer such as leukemia, e.g., by inhibiting the propagation of a cancer cell, a leukemia cell, a leukemia stem cell (LSC) or a pre-leukemia cell stem cell (pre-LSC).

BACKGROUND

Mouse Double Minute 2 homolog (MDM2), also known as E3 ubiquitin-protein ligase Mdm2, is a protein that in humans is encoded by the MDM2 gene. MDM2 is an important negative regulator of the p53 tumor suppressor. MDM2 protein functions both as an E3 ubiquitin ligase that recognizes the N-terminal trans-activation domain (TAD) of the p53 tumor suppressor and as an inhibitor of p53 transcriptional activation.

SUMMARY

In alternative embodiments, provided are methods for:
treating or ameliorating a cancer, wherein optionally the cancer is a leukemia or a myeloproliferative disorder in an individual in need thereof,
inhibiting or slowing a leukemia progenitor cell propagation, or
inhibiting or slowing a blast crisis chronic myeloid leukemia progenitor propagation in an individual in need thereof, or
eliminating or reducing the numbers of pre-leukemia stem cells (pre-LSCs) in an individual in need thereof,
reducing or eliminating the formation of leukemia stem cells (LCSs) in an individual in need thereof, or
treating or ameliorating a myeloproliferative disorder in an individual in need thereof,
the method comprising inhibiting the expression or activity of a Mouse Double Minute 2 homolog (MDM2) protein, message (mRNA) or gene, an APOBEC3G (A3G) protein, message (mRNA) or gene, and/or an ADAR1p150 protein, message (mRNA) or gene, by:
(a) (i) providing or having provided an inhibitor of the expression or activity of:
a Mouse Double Minute 2 homolog (MDM2) protein, message (mRNA) or gene,
an APOBEC3G (A3G) protein, message (mRNA) or gene, and/or
an ADAR1p150 protein, message (mRNA) or gene; and
(ii) administering or having administered to an individual in need thereof, or administering the inhibitor to or expressing the inhibitor in a cancer cell, a leukemia cell, a leukemia stem cell (LSC) or a pre-leukemia cell stem cell (pre-LSC);
(b) administering or having administered to an individual in need thereof, or administering or expressing in a cancer cell, a leukemia cell, a leukemia stem cell (LSC) or a pre-leukemia cell stem cell (pre-LSC), an inhibitor of the expression or activity of:
a Mouse Double Minute 2 homolog (MDM2) protein, message (mRNA) or gene,
an APOBEC3G (A3G) protein, message (mRNA) or gene, and/or
an ADAR1p150 protein, message (mRNA) or gene;
(c) inducing expression or inducing increased expression in a cancer or leukemia cell an endogenous inhibitor of the expression or activity of:
a Mouse Double Minute 2 homolog (MDM2) protein, message (mRNA) or gene,
an APOBEC3G (A3G) protein, message (mRNA) or gene, and/or
an ADAR1p150 protein, message (mRNA) or gene;
(d) expressing in a cancer cell, a leukemia cell, a leukemia stem cell (LSC) or a pre-leukemia cell stem cell (pre-LSC), a heterologous inhibitor of the expression or activity of:
a Mouse Double Minute 2 homolog (MDM2) protein, message (mRNA) or gene,
an APOBEC3G (A3G) protein, message (mRNA) or gene, and/or
an ADAR1p150 protein, message (mRNA) or gene; or
(e) any combination of (a) to (d).

In alternative embodiments of methods as provided herein, the (optionally endogenous or heterologous) inhibitor of the expression or activity of the:
a Mouse Double Minute 2 homolog (MDM2) protein, message (mRNA) or gene,
an APOBEC3G (A3G) protein, message (mRNA) or gene, and/or
an ADAR1p150 protein, message (mRNA) or gene,
comprises or is:
(a) an miRNA,
and optionally the miRNA comprises an miR-200b/c, an miR-204/204b/211, and/or an miR-155; or
(b) an antisense nucleotide sequence capable of inhibiting the expression or activity of:
a Mouse Double Minute 2 homolog (MDM2) protein, message (mRNA) or gene,
an APOBEC3G (A3G) protein, message (mRNA) or gene, and/or
an ADAR1p150 protein, message (mRNA) or gene.

In alternative embodiments of methods as provided herein, the individual in need thereof is a patient who has elevated RNA editing in a cancer promoter 3'UTR, or decreased RNA editing in a cancer suppressor 3′UTR, thus making the patient more susceptible to cancer progression or relapse, wherein optionally the RNA editing is 3′UTR A-to-I RNA editing.

In alternative embodiments of methods as provided herein, the miRNA or antisense nucleotide sequence is heterologous to the cancer cell, the leukemia cell (LC), the leukemia stem cell (LSC) or the pre leukemia stem cell (pre-LSC), and optionally the heterologous miRNA or antisense nucleotide sequence is operably contained within a vector or recombinant virus, and the vector or recombinant virus is placed inside or within the cancer or leukemia cell to express intracellularly the heterologous miRNA or antisense nucleotide sequence, and optionally the expression of the heterologous miRNA or antisense nucleotide sequence by the vector or recombinant virus is under control of an inducible promoter.

In alternative embodiments, provided are uses of an inhibitor of the expression or activity of: a Mouse Double Minute 2 homolog (MDM2) protein, message (mRNA) or gene; an APOBEC3G (A3G) protein, message (mRNA) or gene; and/or, an ADAR1p150 protein, message (mRNA) or gene, as set forth in any of the preceding claims for:

treating or ameliorating a cancer, wherein optionally the cancer is a leukemia or a myeloproliferative disorder in an individual in need thereof, inhibiting or slowing a leukemia progenitor cell propagation, or inhibiting or slowing a blast crisis chronic myeloid leukemia progenitor propagation in an individual in need thereof, or eliminating or reducing the numbers of pre-leukemia stem cells (pre-LSCs) in an individual in need thereof, reducing or eliminating the formation of leukemia stem cells (LCSs) in an individual in need thereof, or treating or ameliorating a myeloproliferative disorder in an individual in need thereof.

In alternative embodiments, provided are inhibitors of the expression or activity of a Mouse Double Minute 2 homolog (MDM2) protein, message (mRNA) or gene, an APOBEC3G (A3G) protein, message (mRNA) or gene, and/or an ADAR1p150 protein, message (mRNA) or gene.

as set forth in any of the preceding claims for use in:

treating or ameliorating a cancer, wherein optionally the cancer is a leukemia or a myeloproliferative disorder in an individual in need thereof, inhibiting or slowing a leukemia progenitor cell propagation, or inhibiting or slowing a blast crisis chronic myeloid leukemia progenitor propagation in an individual in need thereof, or eliminating or reducing the numbers of pre-leukemia stem cells (pre-LSCs) in an individual in need thereof, reducing or eliminating the formation of leukemia stem cells (LCSs) in an individual in need thereof, or treating or ameliorating a myeloproliferative disorder in an individual in need thereof.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

The drawings set forth herein are illustrative of exemplary embodiments provided herein and are not meant to limit the scope of the invention as encompassed by the claims.

FIG. 1A illustrates a representative picture of ADAR1-WT or lentiviral backbone transduced cord blood CD34$^+$ cells;

FIG. 1D illustrates an image of an immunofluorescent staining of Ki67, which shows increased expression of Ki67 in ADAR1 WT-expressing CD34$^+$ cells;

FIG. 1K schematically illustrates a representative image of ADAR1-mediated differentially expression targets in cell cycle stages;

FIG. 1P graphically illustrates data showing that reduction of ADAR1 by shRNA leads to reduced self-renewal of normal cord blood CD34+ HSBC as measured by colony re-plating assay, as discussed in further detail in Example 1, below.

FIG. 2A illustrates a pie chart of differentially expressed miRNAs in cord blood CD34$^+$ HSPC overexpression ADAR1 WT or ADAR1$^{E912A}$ mutant compared with pCDH vector control derived from miRNome array of 1008 miR-NAs;

FIG. 2B graphically illustrates the top ten significantly affected pathways by differentially expressed miRNAs targeted by ADAR1 WT or ADAR1$^{E912A}$ mutant compared with lentiviral backbone;

FIG. 2C-D graphically illustrate volcano plot analyses derived from miRNome showing significantly differentially expressed miRNAs in cord blood CD34$^+$ cells transduced with lenti-pCDH vector control, lenti-ADAR1 WT, or lenti-ADAR1$^{E912A}$; where FIG. 2C illustrates ADAR1 WT versus (vs) pCDH HSPC; and FIG. 2D illustrates ADAR1-E918A versus (vs) pCDH HSPC, as discussed in further detail in Example 1, below.

FIG. 3A-P illustrate data showing the important role of miR-26a in self-renewal capacity of normal hematopoietic progenitors:

FIG. 3A schematically illustrates an exemplary lentiviral construct for human primary (pri-) miR-26a expression;

FIG. 3E graphically illustrates data showing that overexpression of miR-26a also reduced the expression of LIN28B in cord blood HSPCs;

FIG. 3F graphically illustrates data showing representative cell cycle flow analysis of CB HSBC transduced with either backbone or hsa-miR-26a overexpression lentivirus;

FIG. 3H graphically illustrates data showing that expression of CDKN1A mRNA levels are upregulated by overexpression of miR-26a in cord blood CD34$^+$ cells;

FIG. 3N graphically illustrates data confirmation of lentiviral constructs of "unedited" and "edited" pri-miR-26a, where the arrow points to the A-to-I (G) mutation site;

FIG. 3P graphically illustrates data from a cell cycle flow analysis that revealed significant changes of $G_0$ population in 293T cells transduced with ADAR1 WT in combination with "unedited" or "edited" miR-26a, as discussed in further detail in Example 1, below.

FIG. 4A graphically illustrates data showing a reduction of miR-26a expression in CML CP and CML BC CD34$^+$ cells as measured by RT-qPCR;

FIG. 4B graphically illustrates data showing suppression of miR-26a expression in CML CP CD34$^+$ cells transduced with ADAR1 WT measured by miRNA PCR array;

FIG. 4C graphically illustrates data showing validation of miR-26a expression in CP CML CD34$^+$ cells transduced with backbone or ADAR1 WT lentivirus by RT-qPCR;

FIG. 4D-E graphically illustrate data showing the number of colonies formed in primary colony-formation assay (FIG. 4D) and percentage of secondary colonies formed after re-plating primary colonies (FIG. 4E) by BC CML CD34$^+$ cells transduced with lenti-miR-26a;

FIG. 4F schematically illustrates an exemplary experimental design of in vivo xenograft mouse studies with RAG2$^{-/-}$γc$^{-/-}$ mice;

FIG. 4G graphically illustrates data showing overexpression of lenti-miR-26a in BC CD34$^+$ cells reduces the percentage of granulocyte macrophage progenitors (GMP) engraftment in RAG2$^{-/-}$γc$^{-/-}$ mice;

FIG. 4H graphically illustrates data from a cell cycle flow analysis of backbone or lenti-miR-26a transduced CD34$^+$ cells isolated from engrafted BC bone marrow;

FIG. 4I graphically illustrates data showing an RNA-seq analysis of the expression of CDKN1A and EZH2 in CP and BC CML CD34$^+$ cells;

FIG. 4J graphically illustrates data showing gene expression of EZH2, CDKN1A, and LIN28B in BC CD34$^+$ cells transduced with lentiviral vector overexpressing miR-26a or the backbone control;

FIG. 4K graphically illustrates data showing an RNA-seq analysis (RT-qPCR) of the expression of c-Myc in CP and BC CML CD34$^+$ cells, as discussed in further detail in Example 1, below.

FIG. 5A-K illustrate data showing differential A-to-I RNA editing in 3'UTR regions of normal HSPCs and BC LSC:

FIG. 5A-B illustrate volcano plots showing the A-to-I(G) editome of KEGG cell cycle transcripts (genes) in ADAR1 WT-transduced cord blood CD34$^+$ cells compared with lentiviral vector controls (FIG. 5A) and in CP progenitors compared with BC counterparts (FIG. 5B);

FIG. 5C graphically illustrates A-to-I RNA editing of MDM2 3'UTR in individual CP and BC samples;

FIG. 5D graphically illustrates data showing the relative miRNA expression determined by miRNA qPCR array of 84 miRNAs in CML CP CD34$^+$ cells transduced with backbone or ADAR1 WT;

FIG. 5E graphically illustrates relative miRNA expression (measured by RT-qPCR) in normal aged-matched (greater than 55 year (yr) old) CD34$^+$ cells and BC CML CD34$^+$ cells;

FIG. 5F-G graphically illustrate data showing the expression (measured by RNA-seq) of MDM2-p53 pathway transcripts, MDM2 (FIG. 5F) and tp53 (FIG. 5G) in progenitor population of normal peripheral blood (NPB), CML CP (n=7), and CML BC determined by RNA-seq;

FIG. 5H graphically illustrates data showing the regulation of MDM2 expression (measured by RT-qPCR) by ADAR1 WT, ADAR1$^{E912A}$ alone and in combination with miR-155;

FIG. 5I schematically illustrates data showing a "Wt" or "edited" MDM2 3'UTR reporter construct with A-to-G changes introduced at miRNA targeting sites (highlighted in red), and the miRNA targeting efficiency was measured as the relative luciferase activity (GLuc/SEAP ratio), where the wt reporter motifs are GAAGT, AAATAAT, TTACC, CAAGC, and the "edited" reporter motifs are GAGGT, AAGTGAT, TTGCC, and CAGGC;

FIG. 5J graphically illustrates data where MDM2 3'UTR reporters were transfected into 293T cells and then challenged with miR-155 overexpressing lentivirus, and the relative luciferase activity was measured and showed that the "edited" reporter can evade miR-155 targeting;

FIG. 5K graphically illustrates data that knockdown of ADAR1 by shRNA decreases MDM2 and LIN28B expression (measured by RT-qPCR) in BC CML CD34$^+$ cells, as discussed in further detail in Example 1, below.

FIG. 7A-F (or FIG. S1, Example 1) illustrates ADAR1 overexpression in normal HSPC (see FIG. 1):

FIG. 7A graphically illustrates expression of lenti-ADAR1 WT in normal cord blood (CB) CD34$^+$ cells (n=3) as measured by RT-qPCR;

FIG. 7B illustrates a representative bright-field (BF) microscopy image showing normal cord blood stem cells (upper image) and progenitors (lower image) transduced with lentiviral vector backbone (upper left and lower left images) or human ADAR1 WT lentivirus (upper right and lower right images);

FIG. 7C graphically illustrates data from a flow analysis of stem and progenitor cells in backbone or lenti-ADAR1 WT transduced cord blood CD34$^+$ cells (APC-CD34$^+$), also showing Pecv7-CD38$^+$ cells;

FIG. 7D schematically illustrates an experimental design for DiR tracing of cord blood cells, as shown in FIG. 7E-F;

FIG. 7E-F graphically illustrates data from a (FACS) flow analysis showing FSC-A expression and DiR tracing of cord blood cells (ADAR1 WT) (FIG. 7E) and backbone (FIG. 7E) from the experimental design of FIG. 7D;

FIG. 7G graphically illustrates data from a flow analysis showing the percentage of sub-population of progenitors including CMP, GMP, and MEP in backbone or lenti-ADAR1 WT transduced cord blood CD34$^+$ cells (as compared to backbone transduction);

FIG. 8A-C (or FIG. S2, Example 1) illustrate the differential expression of cell cycle transcripts induced by ADAR1 activation, related to FIG. 1:

FIG. 8A graphically illustrates the significantly differentially expressed transcripts of KEGG Cell Cycle Pathway in ADAR1 WT-transduced cord blood (n=3) versus lentiviral vector control (n=3) by RNA-seq analysis; the TPM gene expression value was transformed to Log$_2$(TPM+1);

FIG. 8B graphically illustrates data showing confirmation of CDKN1A and CDKN2A mRNA expression by RT-qPCR in cord blood CD34$^+$ cells transduced with backbone, ADAR1 WT, or ADAR1$^{E912A}$ mutant (n=4);

FIG. 8C graphically illustrates a representative cell cycle FACS plot of shRNA targeting ADAR1 in normal cord blood CD34$^+$ HSPC as measured by Ki-67 and 7AAD levels;

all graphs show mean with SEM and statistical analysis was calculated using the Student's t-test. *p<0.05, as discussed in further detail in Example 1, below.

Figure 9C:
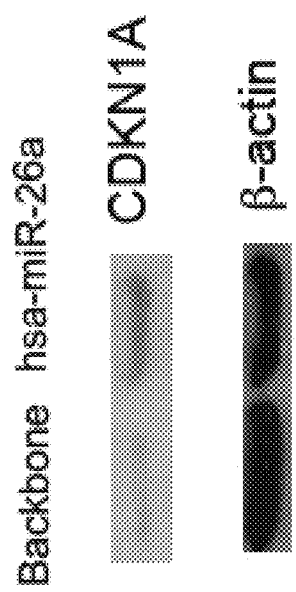
Figure 9B:

FIG. 9A-C (or FIG. S3, Example 1) illustrate MiR-26a regulated normal HSPC cell cycle transit and self-renewal, related to FIG. 3:

FIG. 9A illustrates images of representative pictures of cord blood HSPC colonies;

FIG. 9B graphically illustrates data showing the correlation analysis of pri-miR-26a expression and increased expression of CDKN1A as measured by RT-qPCR in 293T cells transduced with pri-miR-26a lentivirus (n=3);

FIG. 9C illustrates images of western blot analysis gels in 293T cells transduced with miR-26a lentivirus confirming CDKN1A protein expression;

graphs show mean with SEM and statistical analysis was calculated using the Student's t-test. *p<0.05, as discussed in further detail in Example 1, below.

Figure 10A:
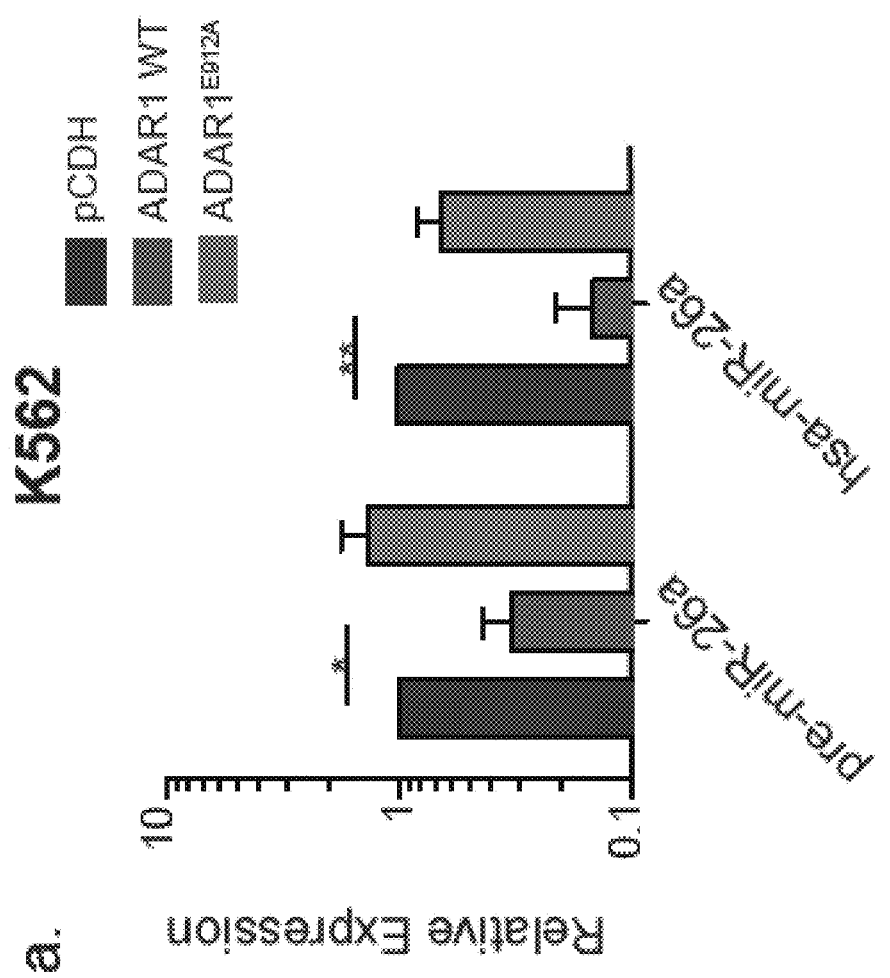
Figure 10B:
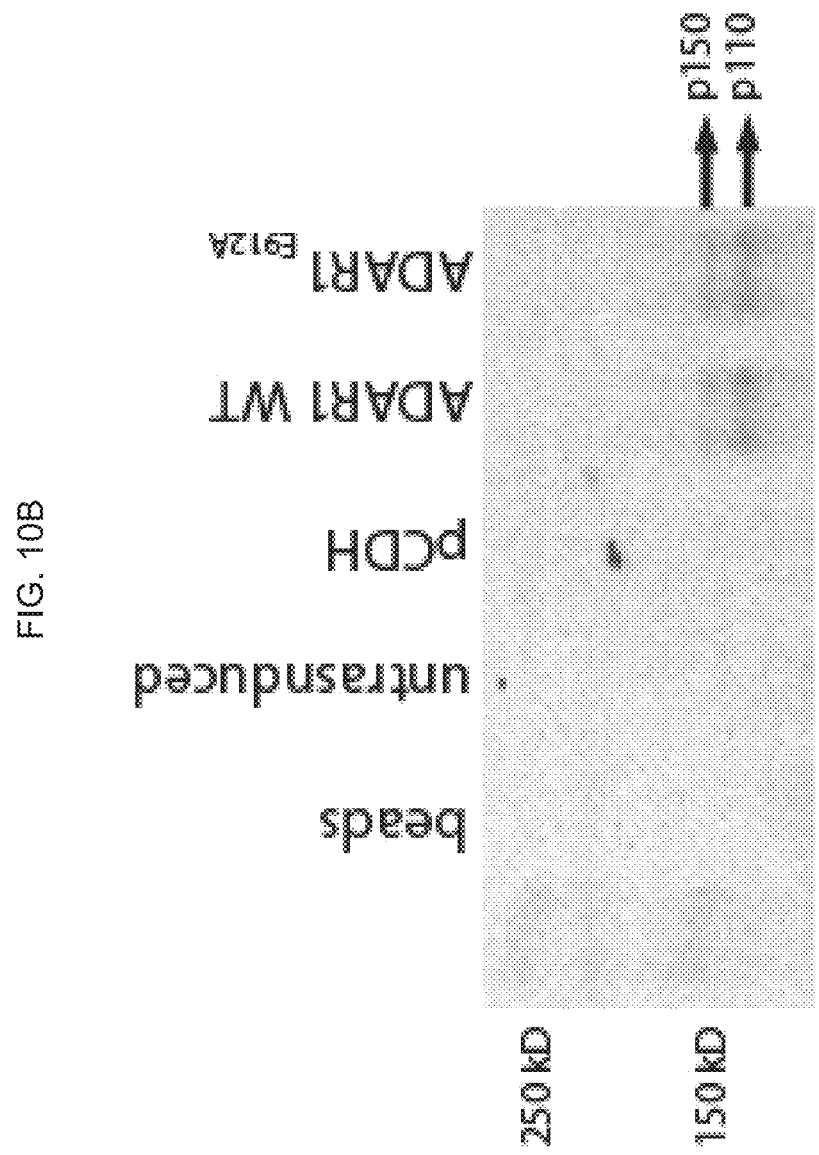
Figure 10C:
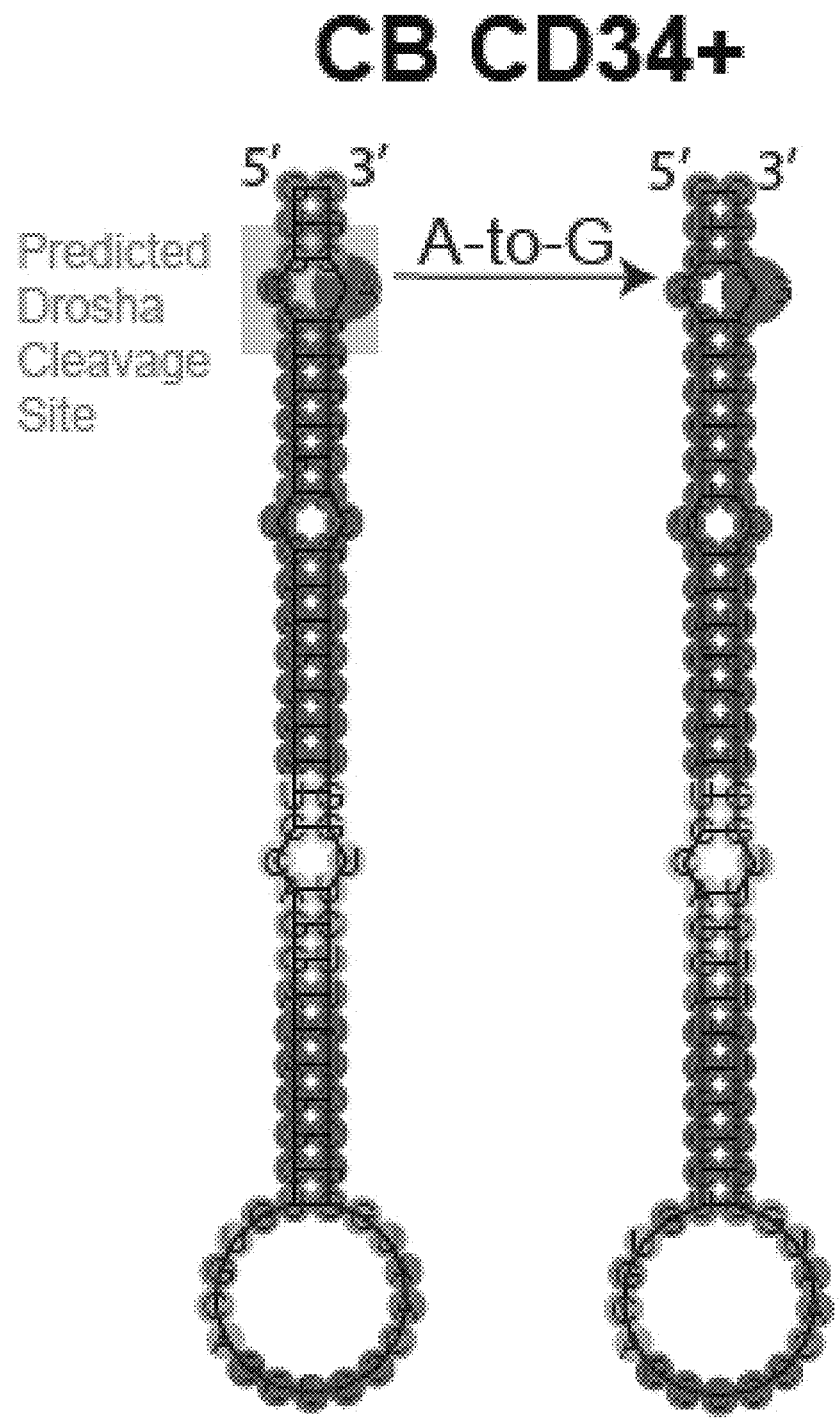

FIG. 10A-D (or FIG. S4, Example 1) illustrates data showing that ADAR1 directly binds to pri-miR-26a transcripts, related to FIG. 3:

FIG. 10A graphically illustrates data showing that expression of pre- and mature miR-26a was measured by RT-qPCR in K562 transduced with pCDH backbone, ADAR1 WT, or ADAR1$^{E912A}$ (n=3);

FIG. 10B illustrates an image of a crosslinking RNA immunoprecipitation (CLIP) in K562 stably expressing pCDH vector, lenti-ADAR1 WT, and lenti-ADAR1$^{E912A}$ with an ADAR1 antibody confirmed that both ADAR1 WT and ADAR1$^{E912A}$ mutant are associated with pri-miR-26a transcript, the experiment was performed in triplicate;

FIG. 10C illustrates an image of a ViennaRNA predicted secondary structure changes in pri-miR-26a induced by A-to-I editing occurring near DGCR8/DROSHA cleavage site (highlighted in orange), which blocks the maturation to pre-miR-26a;

FIG. 10D illustrates an image schematically depicting A-to-I RNA editing dependent inhibition of miR-26a expression by preventing the DROSHA cleavage of pri-miR-26a that results in reduction of pre-miR-26a and mature miR-26a; Graphs show mean with SEM and statistical analysis was calculated using the Student's t-test. *p<0.05, **p<0.005;

as discussed in further detail in Example 1, below.

Figure 11A:
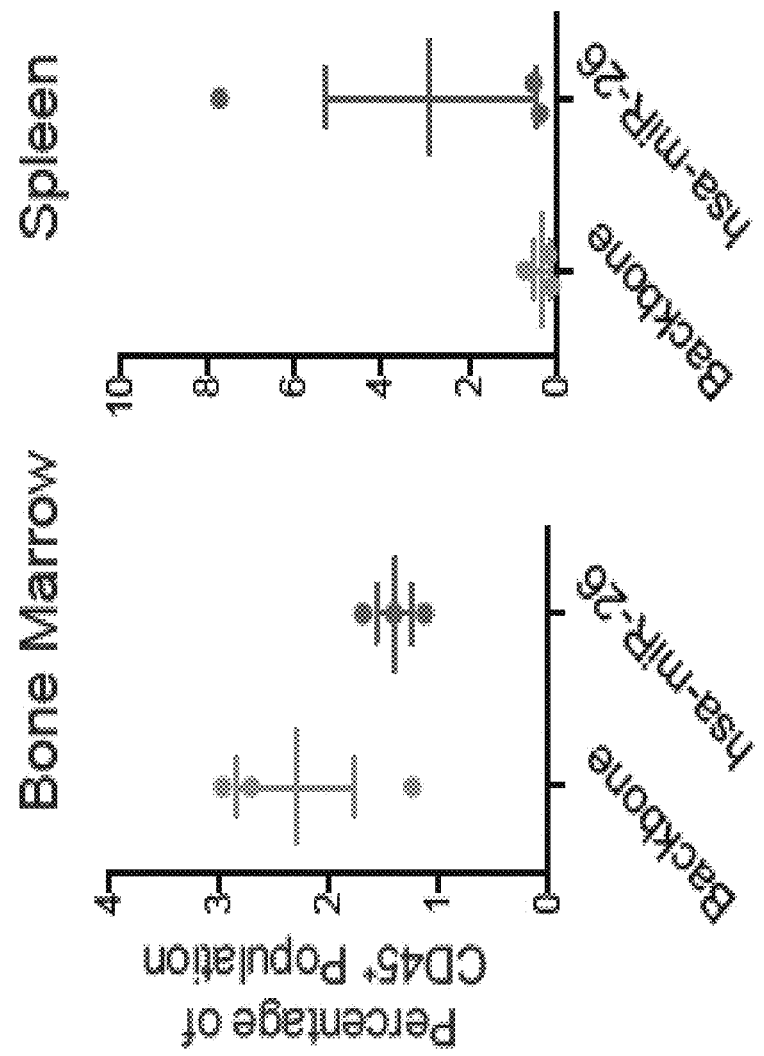
Figure 11B:
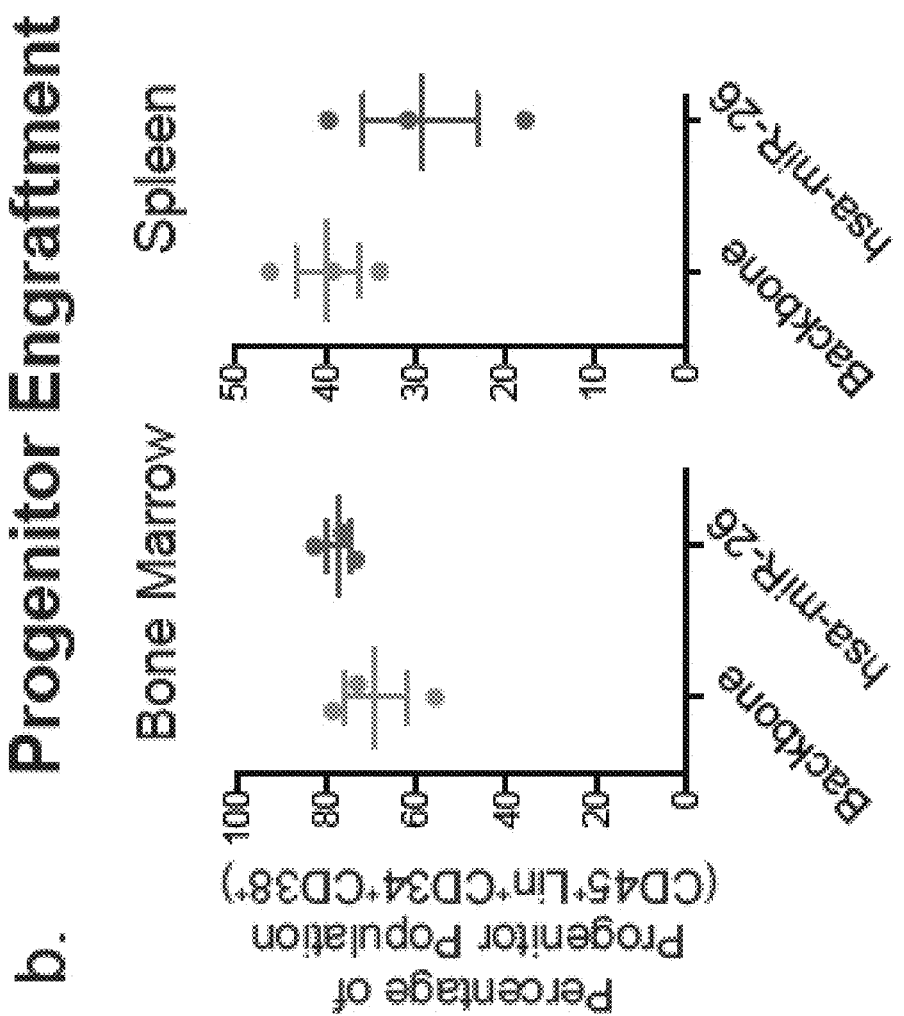
Figure 11D:
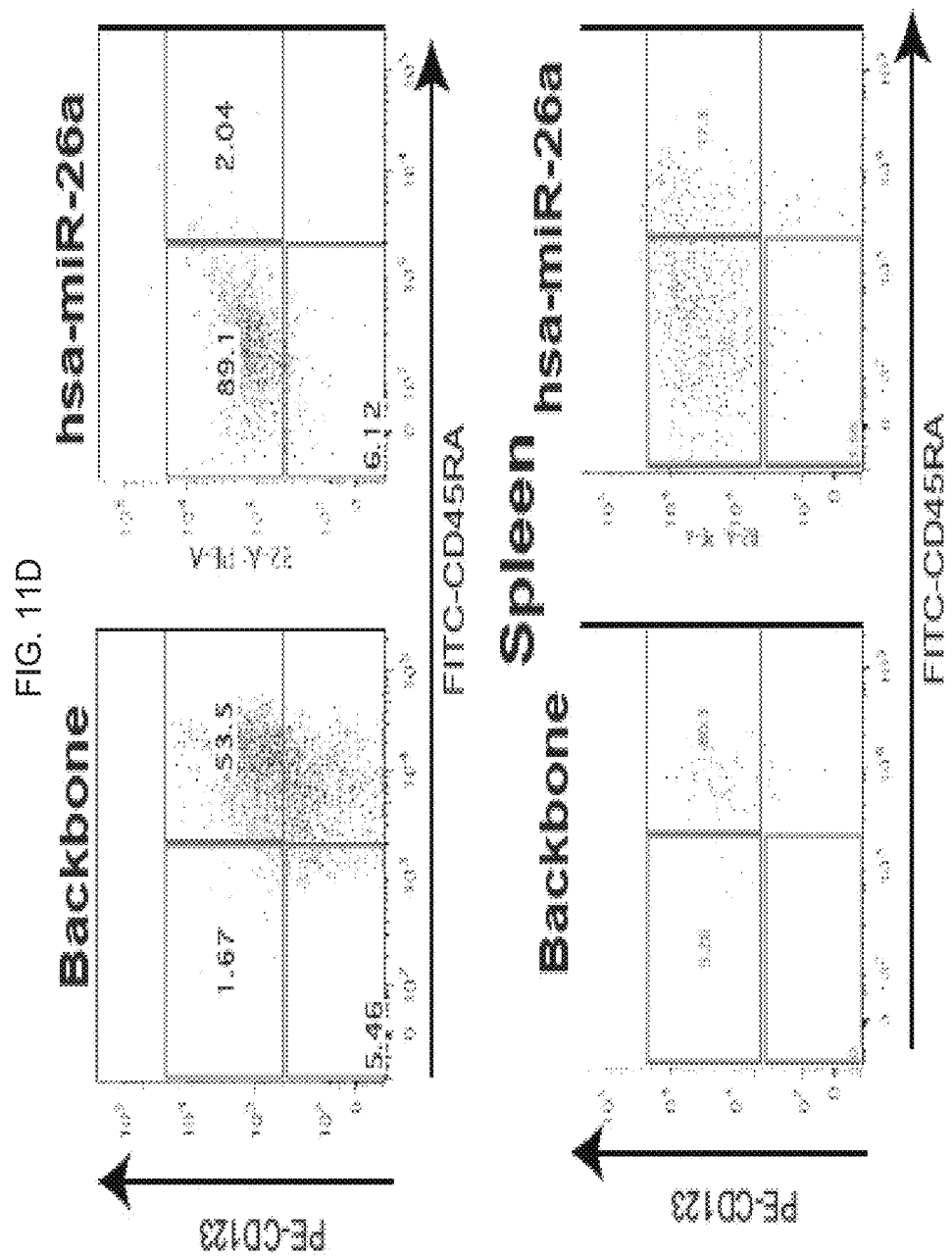
Figure 11F:
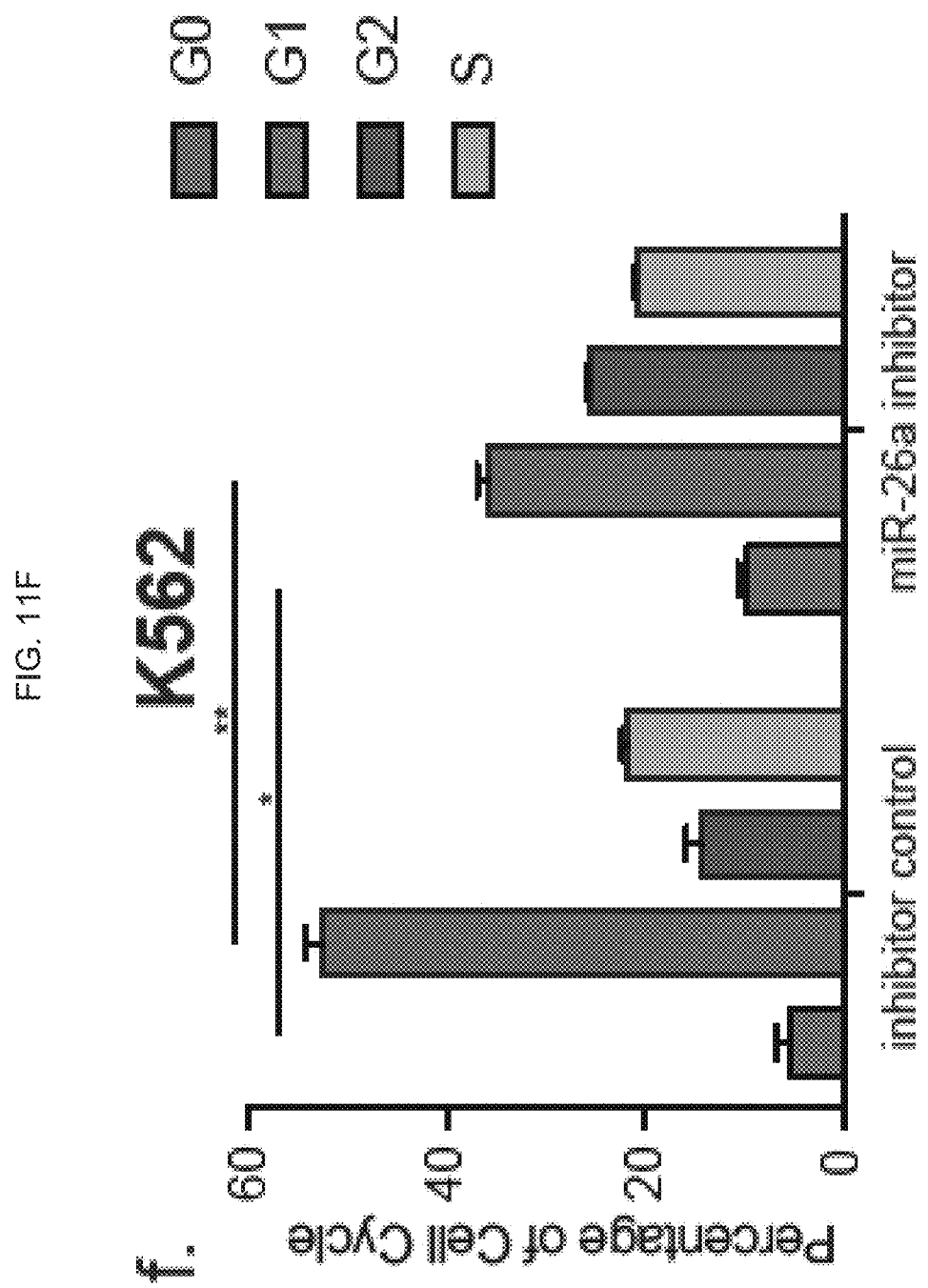

FIG. 11A-J (or Figure S5, Example 1) illustrate data showing the differential effect of miR-26a overexpression on normal HSPC and CML progenitors, related to FIG. 4:

FIG. 11A-B graphically illustrate data of the percentage of human CD45$^+$ (FIG. 11A) or progenitor (CD45$^+$Lin$^-$CD34$^+$CD38$^+$) (FIG. 11B) engraftment in bone marrow and spleen of BC CML xenografted mice (n=3 mice per group), *p<0.05, **p<0.005;

FIG. 11C graphically illustrates FACS data from representative CD45$^+$ and progenitor engraftment of BC CML cells transduced with backbone or miR-26a in bone marrow;

FIG. 11D graphically illustrates FACS data from representative GMP engraftment (% of parent cells) of BC CML cells transduced with backbone or miR-26a in bone marrow and spleen (n=3 mice per group);

FIG. 11E graphically illustrates FACS data from representative cell cycle flow of engrafted CD45$^+$ cells in BC CML cells transduced with backbone and miR-26a in bone marrow;

FIG. 11F graphically illustrates data showing the down-regulation of miR-26a by transfecting a miR-26a inhibitor into K562 BC CML cells induced cell quiescence. (n=3 experimental triplicate).

Figure 11H:
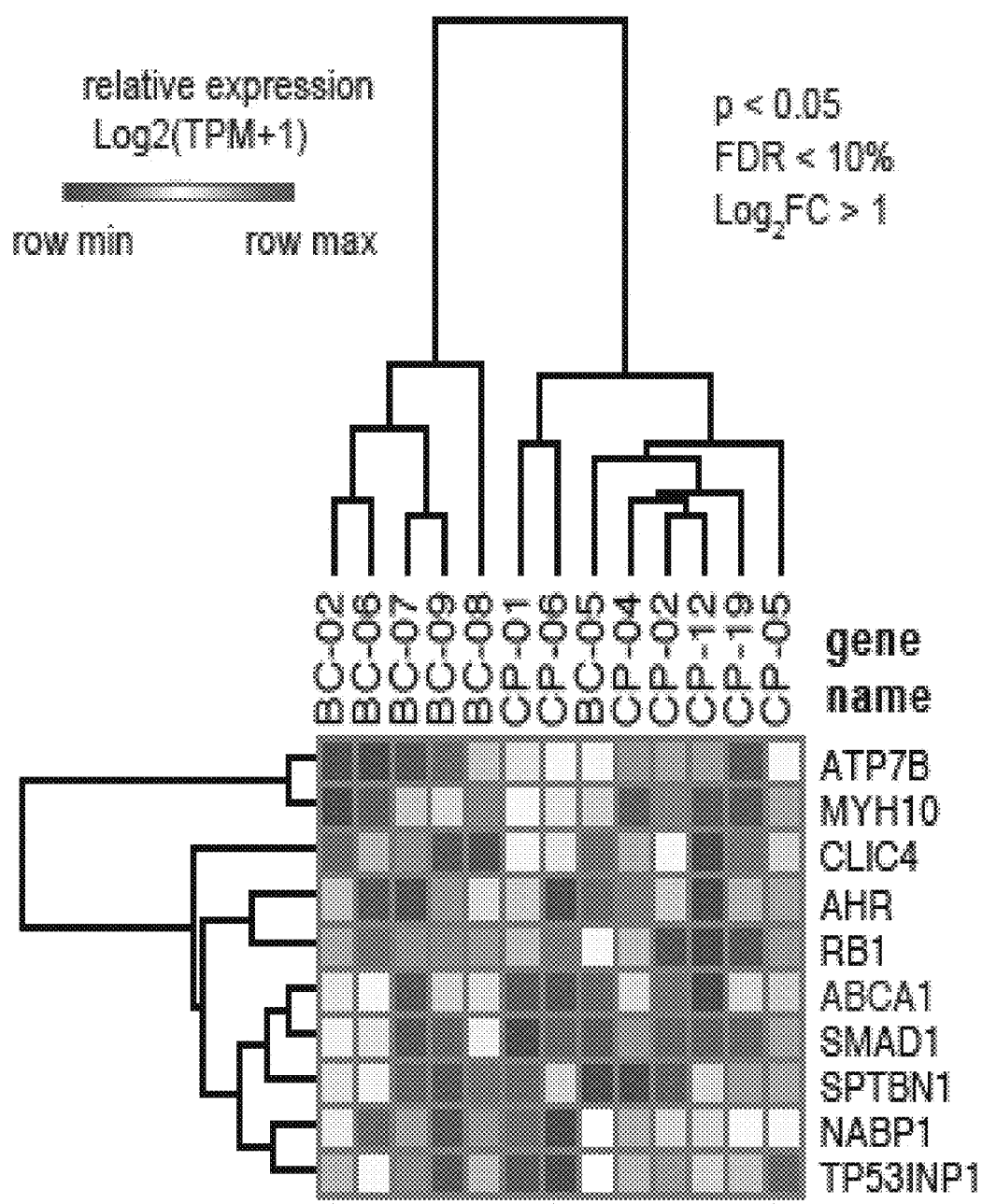

FIG. 11G illustrates an graphic image of RNA-seq quantification on ADAR1 WT transduced cord blood (n=3) and lentiviral vector control (n=3) for differentially expressed genes corresponding to Functional MTIs from miRTarBase for miR-26a targets (Loge Fold Change>1, p<0.05, FDR<0.10);

FIG. 11H illustrates an graphic image of data showing differentially expressed miR-26a targets in BC progenitors (n=6) compared to CP counterparts (n=7) by RNA-seq analysis;

All graphs show mean with SEM and statistical analysis was calculated using the Student's t-test;

FIG. 11I-J graphically illustrate data showing that MYC expression was not significantly changed upon ADAR1 WT overexpression by RNA-seq analysis (FIG. 1) or ADAR1 knockdown by shRNA RT-qPCR (FIG. J) in normal cord blood HSPCs (n=3). *p<0.05, **p<0.005, as discussed in further detail in Example 1, below.

Figure 12A:
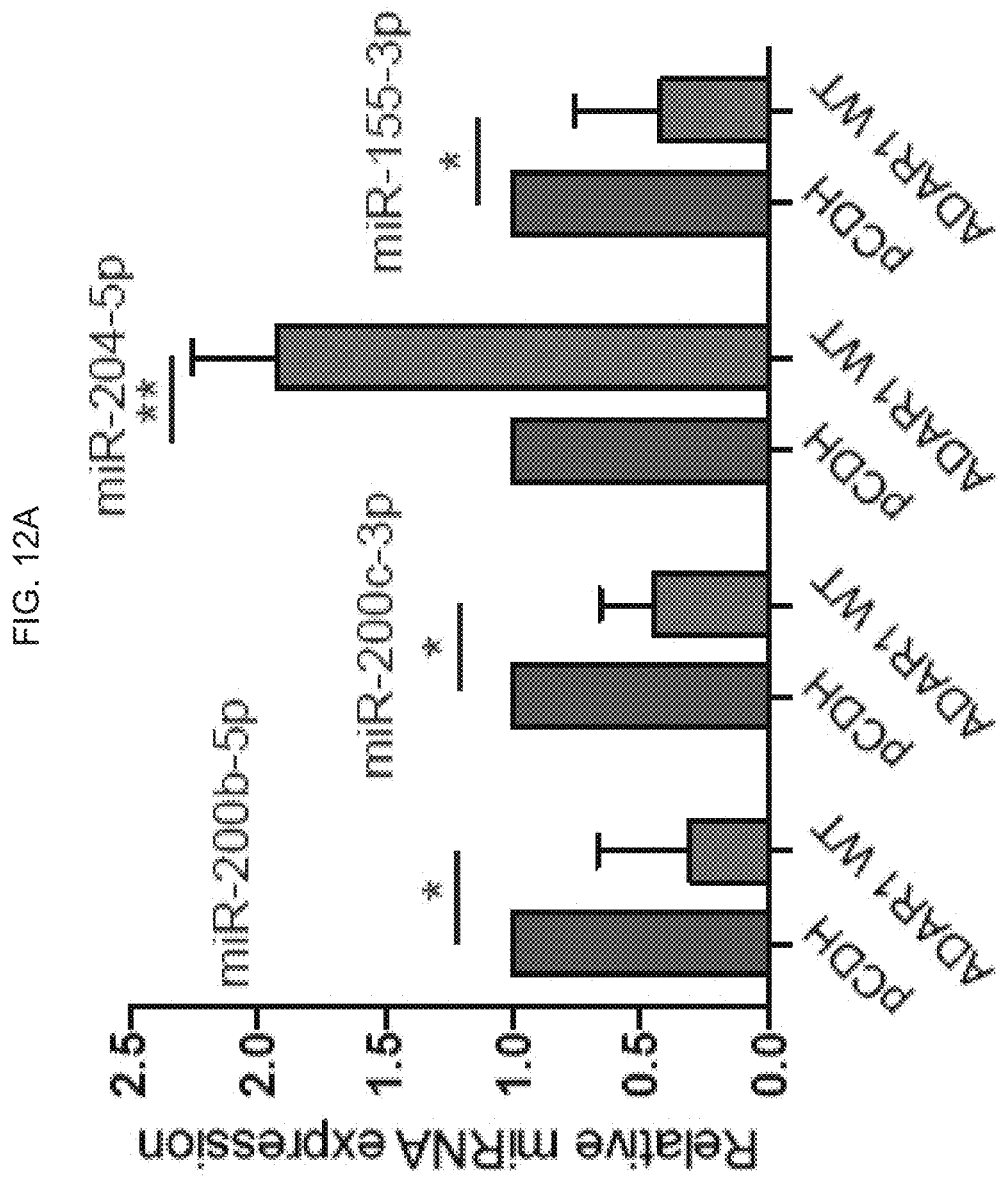
Figure 12B:
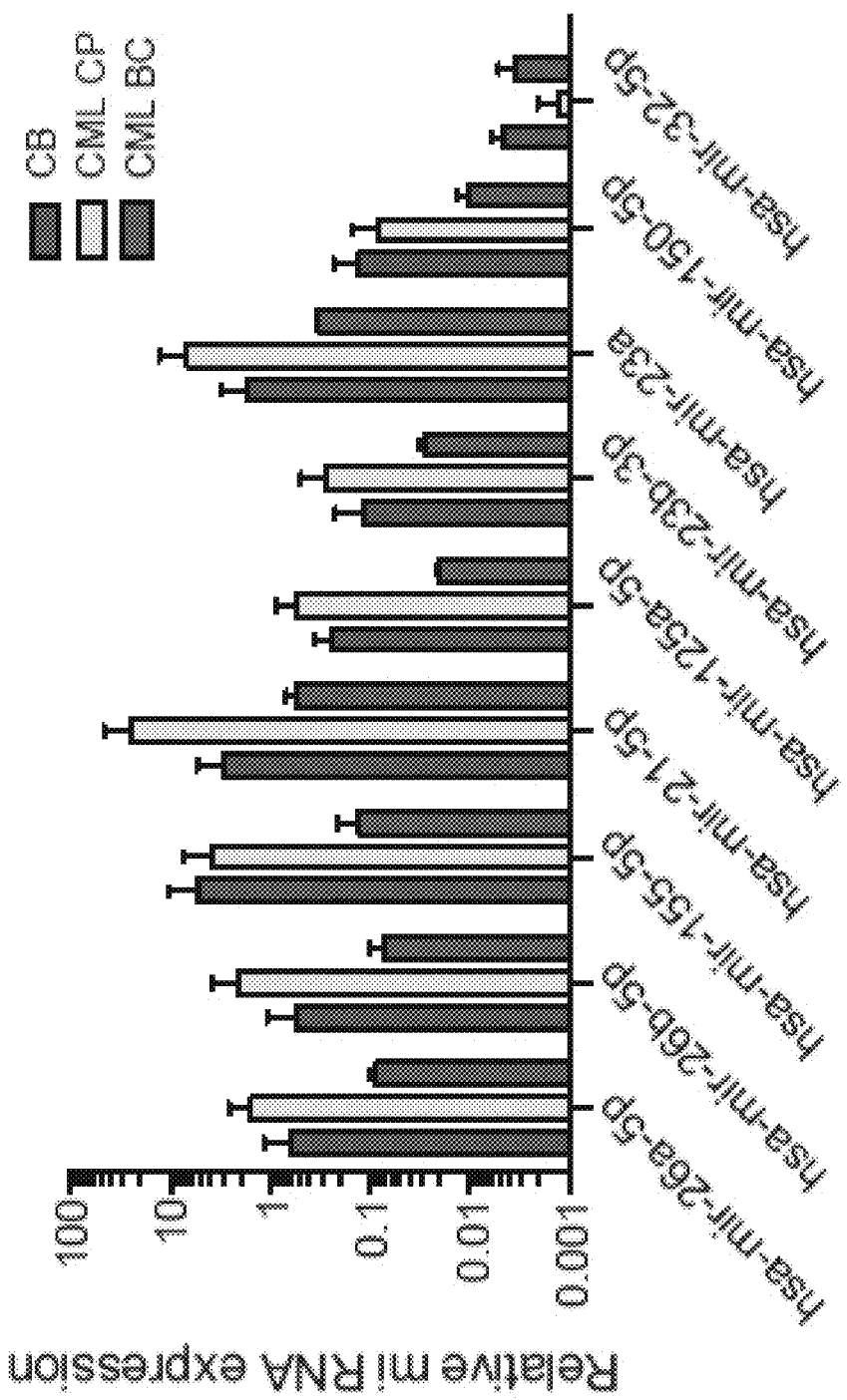
Figure 12C:
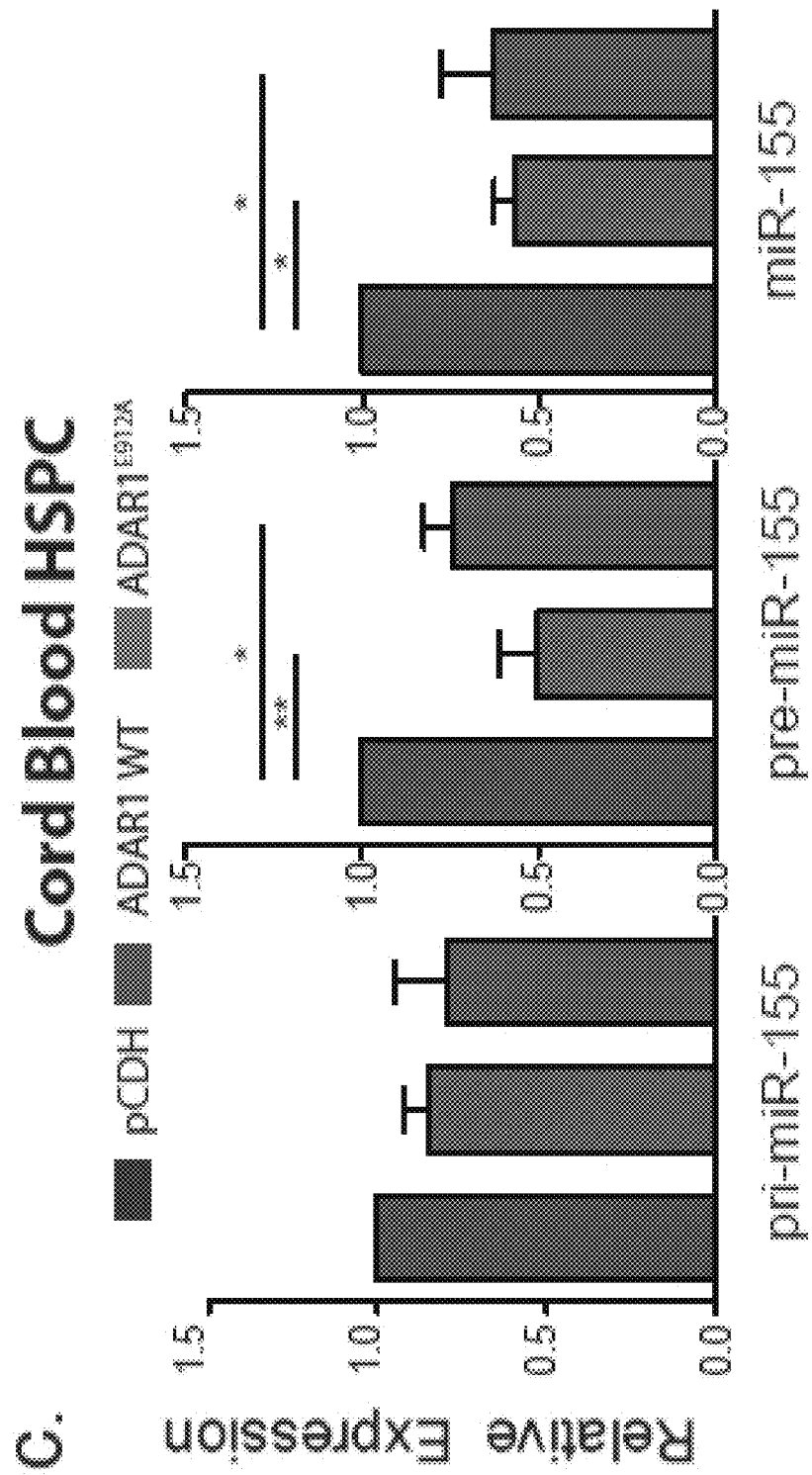
Figure 12D:
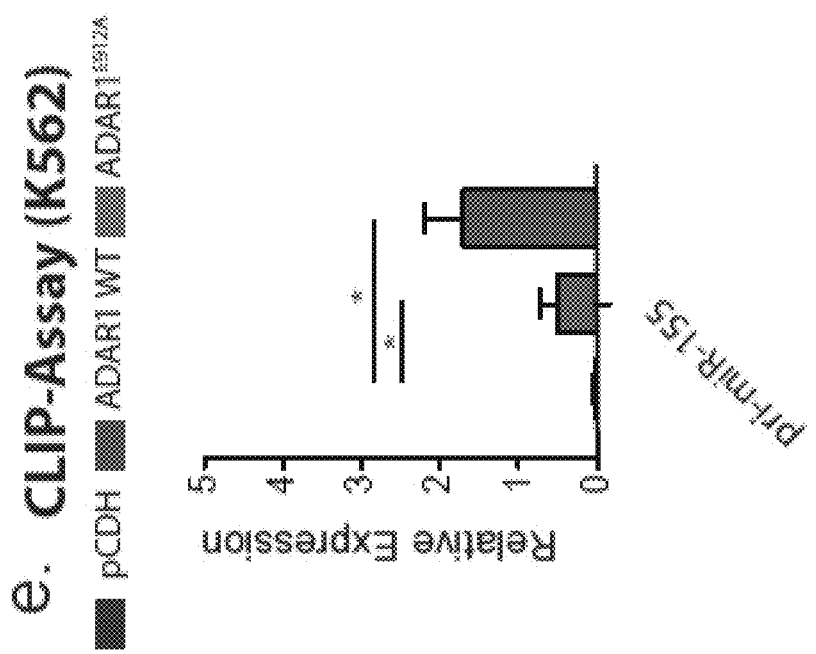
Figure 12E:
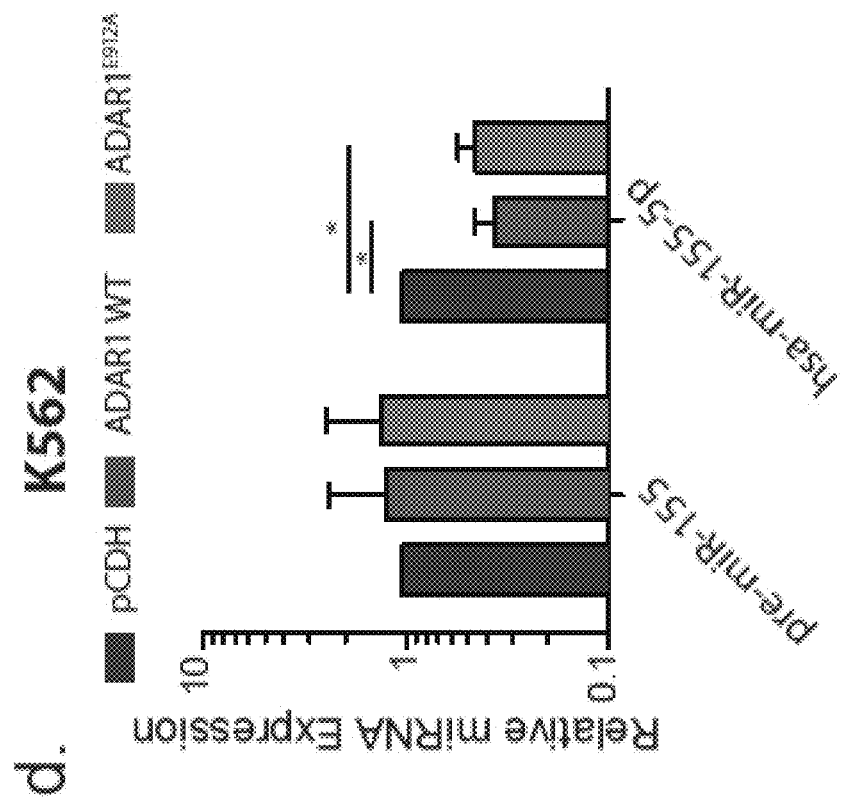
Figure 12F:
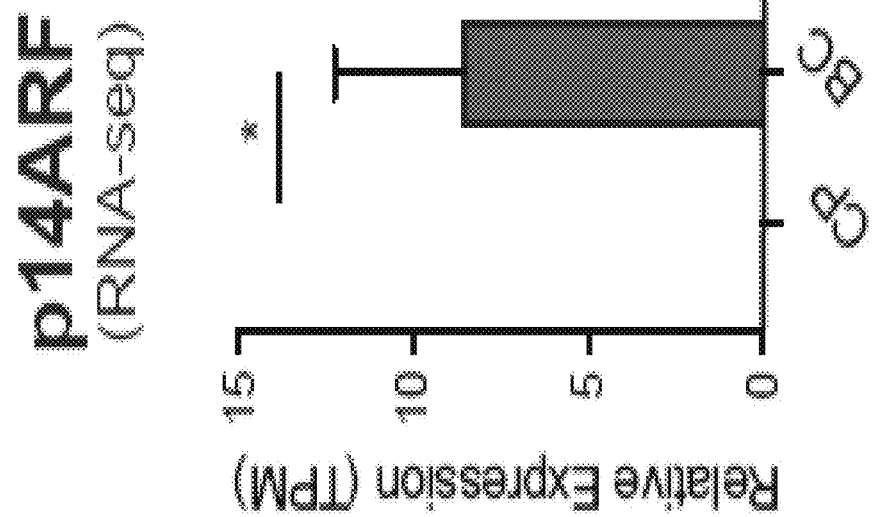
Figure 12G:
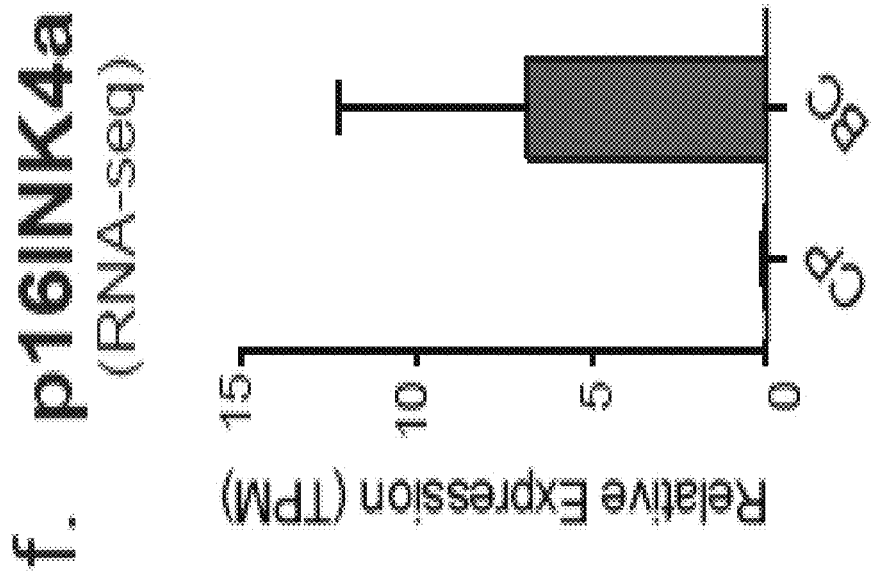

FIG. 12A-G (or Figure S6, Example 1) graphically illustrate data showing that ADAR1 regulates MDM2 3'UTR targeting and miRNA biogenesis in CML progenitors, related to FIG. 5:

FIG. 12A graphically illustrates miRNome array-derived expression of miRNAs that are predicted to bind to MDM2 3'UTR region in cord blood CD34$^+$ HSPC overexpression ADAR1 WT or ADAR1$^{E912A}$ mutant compared with pCDH vector control (n=3-4);

FIG. 12B illustrates relative miRNA expression determined by miRNA qPCR array of 84 miRNAs in cord blood, CML CP, and CML BC CD34$^+$ cells (n=3 per patient group);

FIG. 12C graphically illustrates expression of primary (pri-), precursor (pre-) and mature miR-155 transcripts was measured by RT-qPCR in cord blood CD34$^+$ HSPCs transduced with pCDH backbone, ADAR1 WT, or ADAR1$^{E912A}$ (n=3);

FIG. 12D graphically illustrates expression of pre- and mature miR-155 in K562 leukemia cells stably transduced with pCDH, ADAR1 WT, or ADAR1$^{E912A}$, experiments were performed in triplicate;

FIG. 12E graphically illustrates Crosslinking RNA Immunoprecipitation (CLIP) in K562 stably expressing pCDH vector, ADAR1 WT, and ADAR1$^{E912A}$ with an ADAR1 antibody confirmed that both ADAR1 WT and ADAR1$^{E912A}$ mutant both binds to pri-miR-155 transcripts, All graphs show mean with SEM and statistical analysis was calculated using the Student's t-test;

FIG. 12F-G graphically illustrate the expression of CDKN2A transcripts, p16INK4a (FIG. 12F) and p14ARF (FIG. 12G), in progenitor population of normal peripheral blood (NPB), CML CP (n=7), and CML BC (n=6) determined by RNA-seq. *p<0.05, **p<0.005, as discussed in further detail in Example 1, below.

Figure 13A:
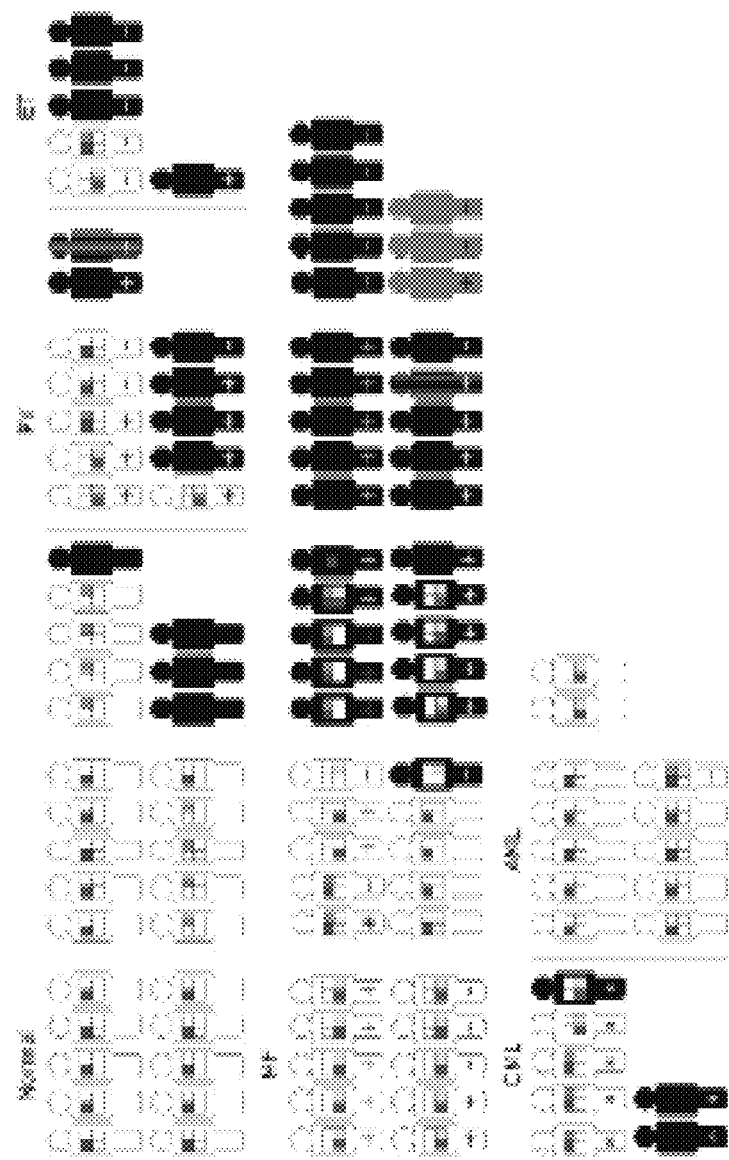
Figure 13B:
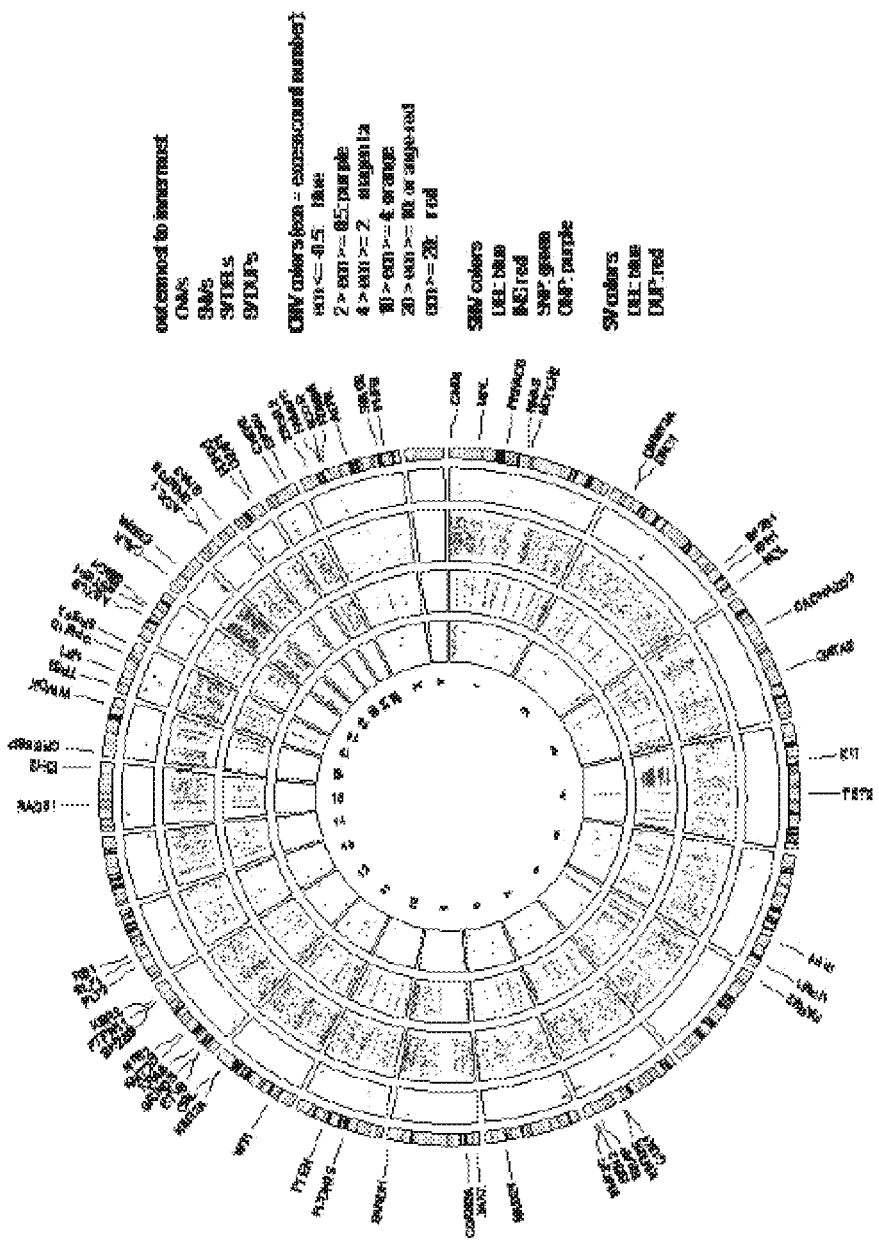
Figure 13C:
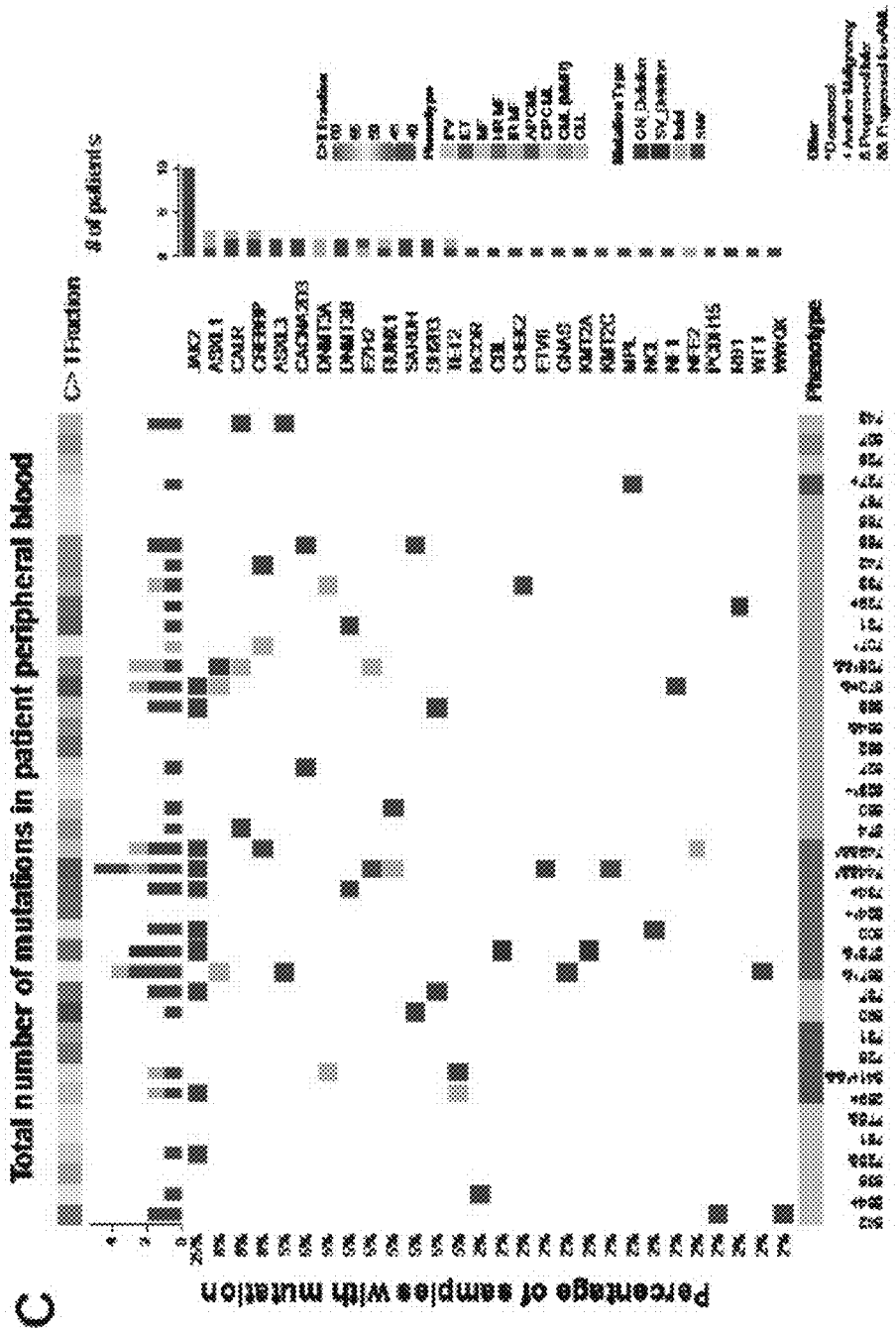
Figure 13D:
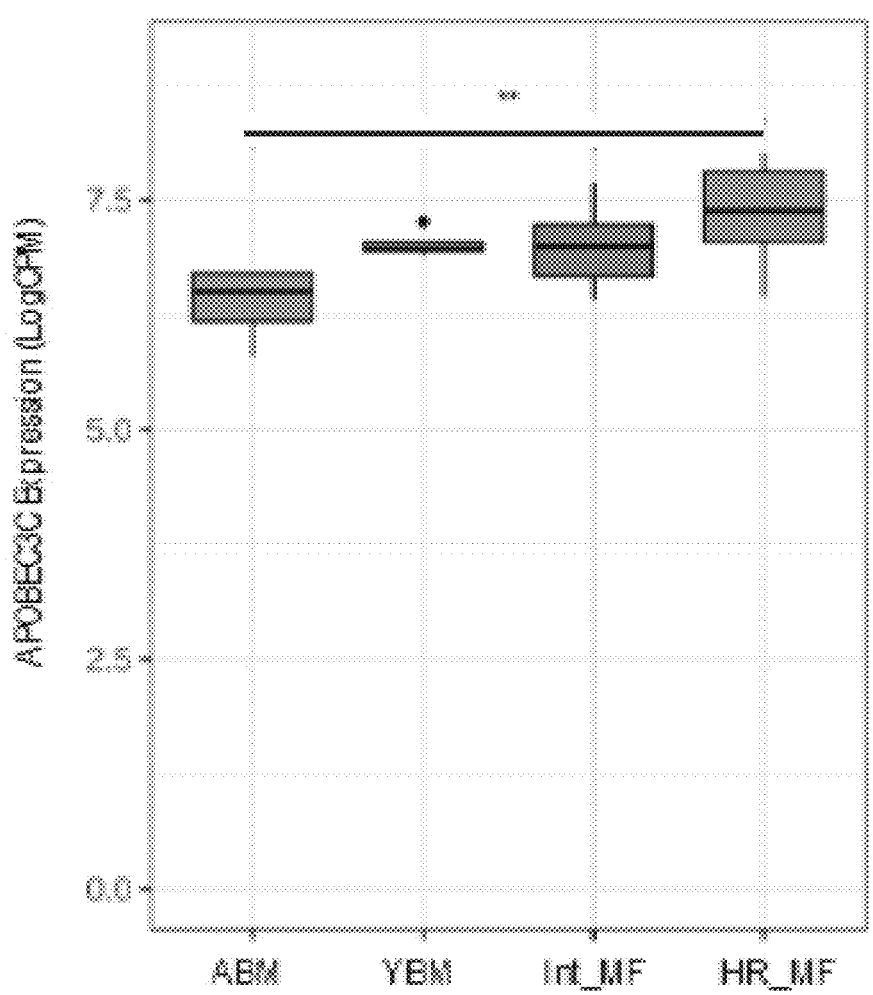
Figure 13E:
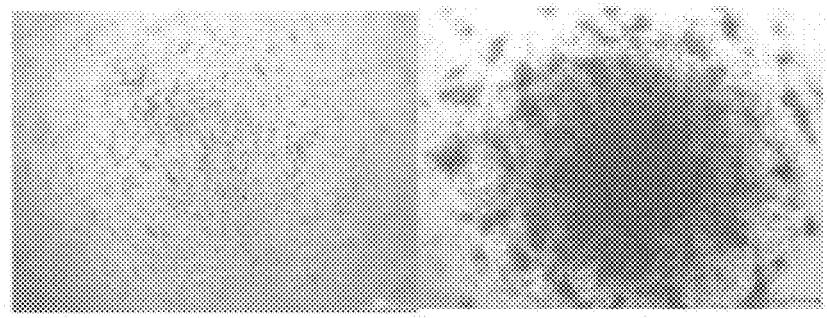
Figure 13F:
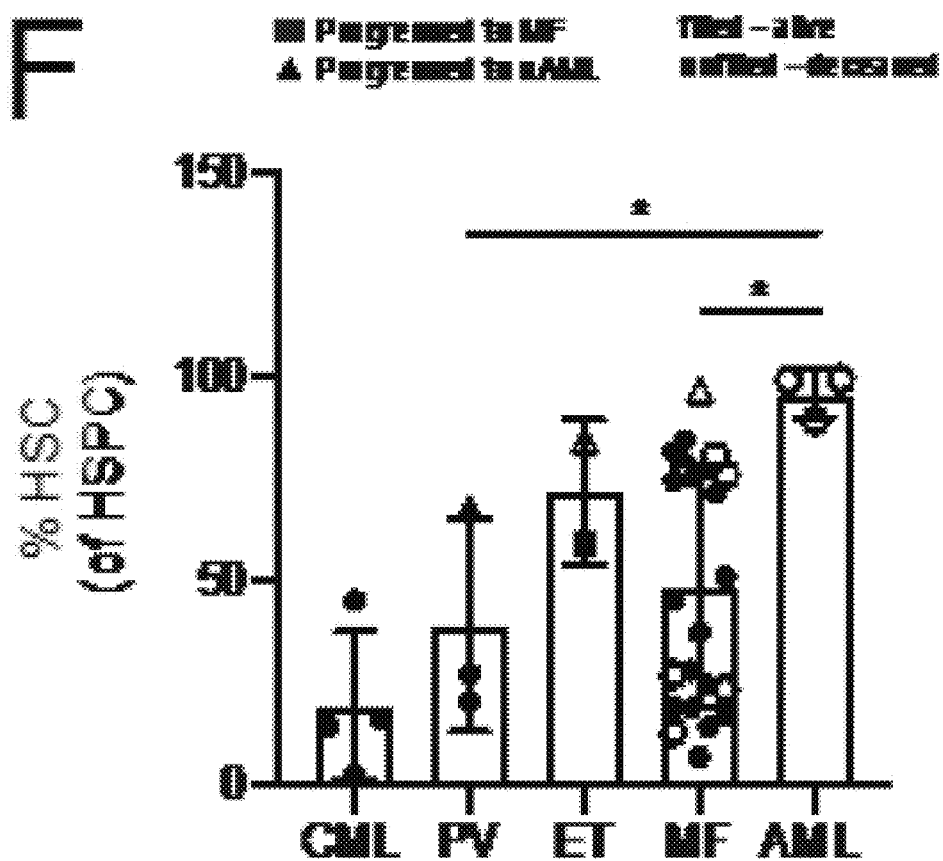

FIG. 13A-E (or FIG. 1, Example 2):

FIG. 13A schematically illustrates a sample distribution in this study;

FIG. 13B schematically illustrates a Circos plot depicting somatic mutations, copy number variation and structural variation in Labels indicate the 69 genes;

FIG. 13C graphically illustrates differential expression of APOBEC3C mRNA in MPN stem population by RNA-seq;

FIG. 13D graphically illustrates Differential Expression of APOBEC3C mRNA in MPN stem population by RNA-seq;

FIG. 13E graphically illustrates a Brightfield image of cord blood CD34+ cells transduced with APOBEC3C;

FIG. 13F graphically illustrates a comparison of HSC percentage in MPN samples by flow cytometry, as described in detail in Example 2, below.

Figure 14A:
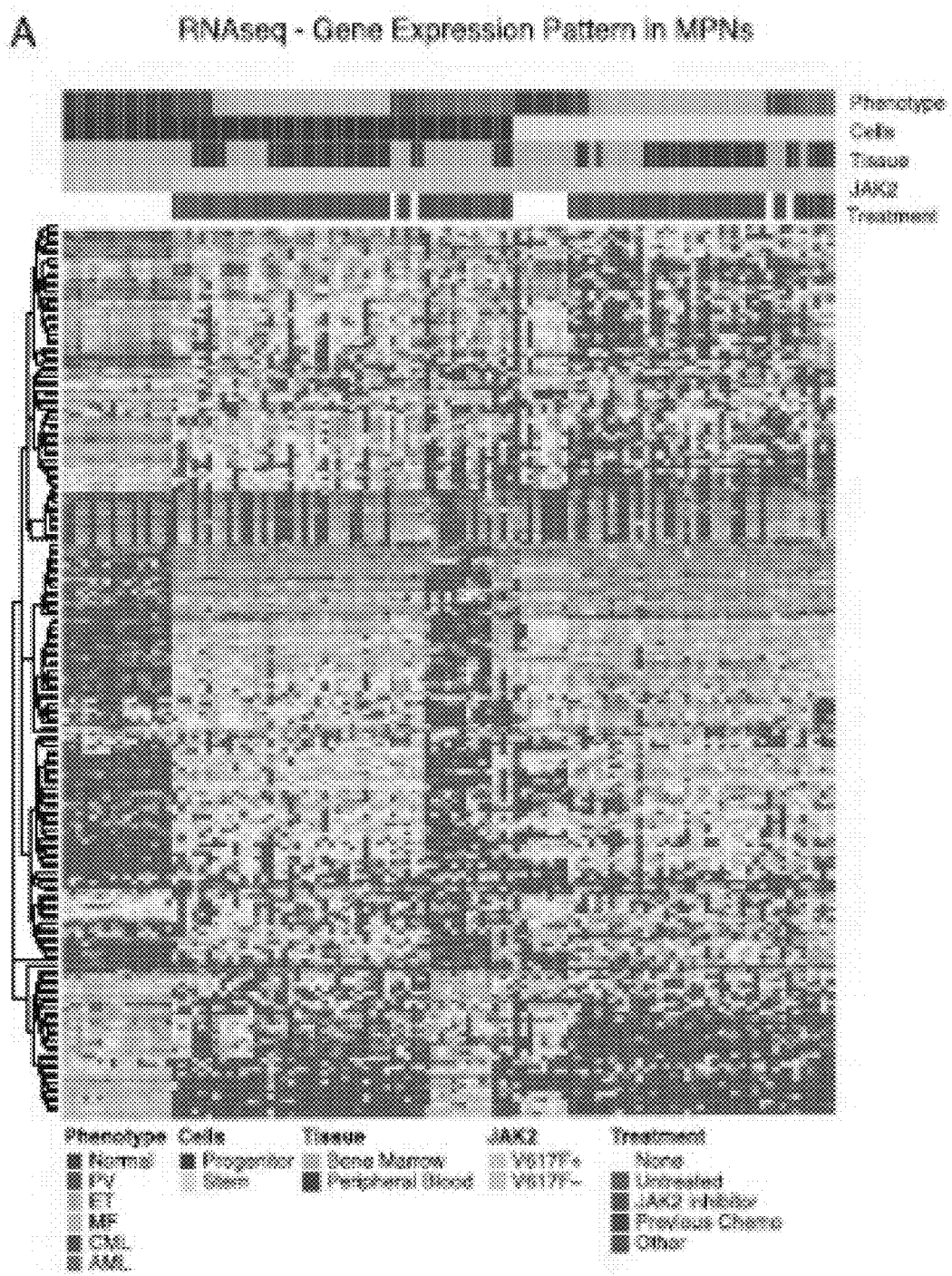
Figure 14B:
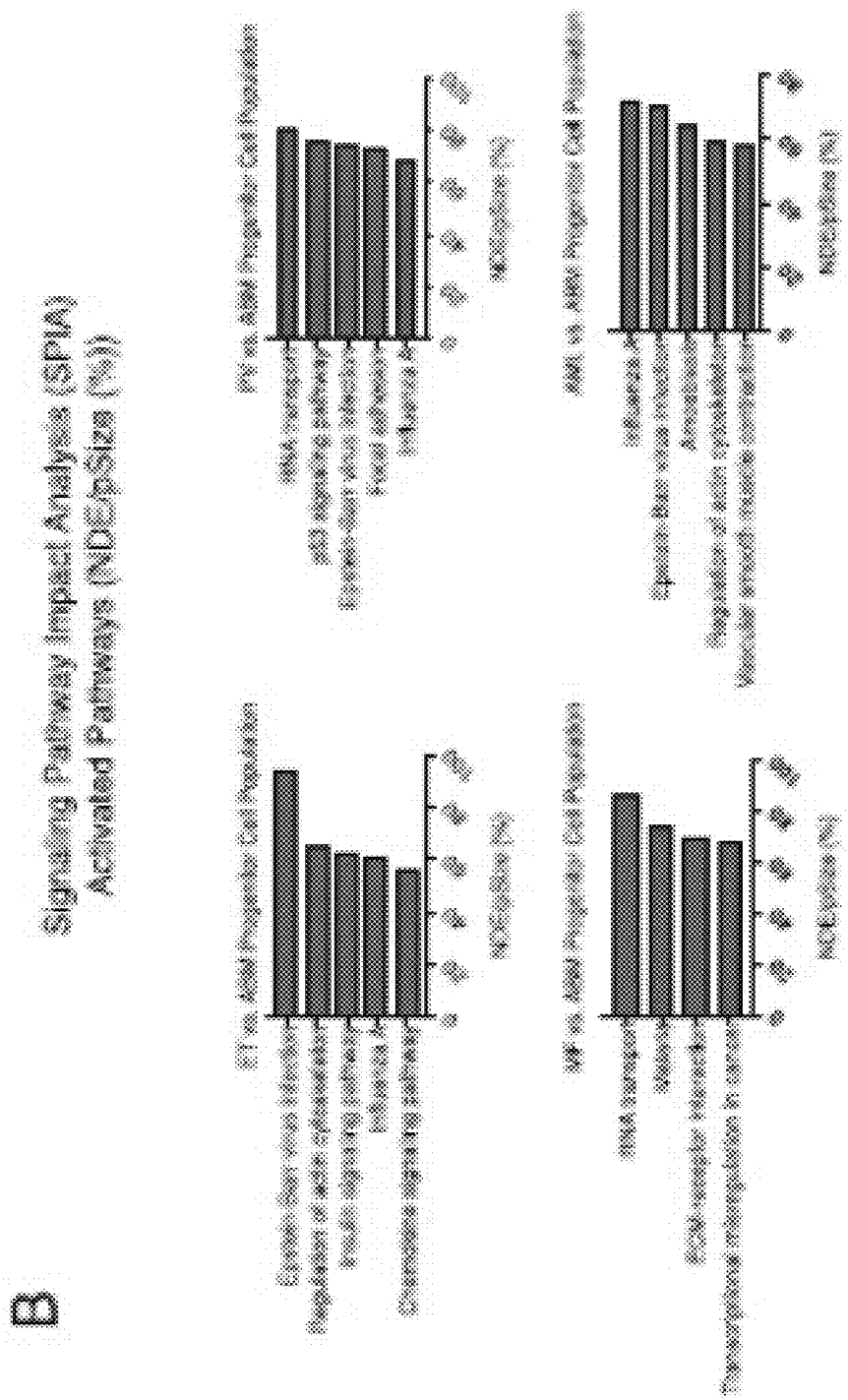
Figure 14C:
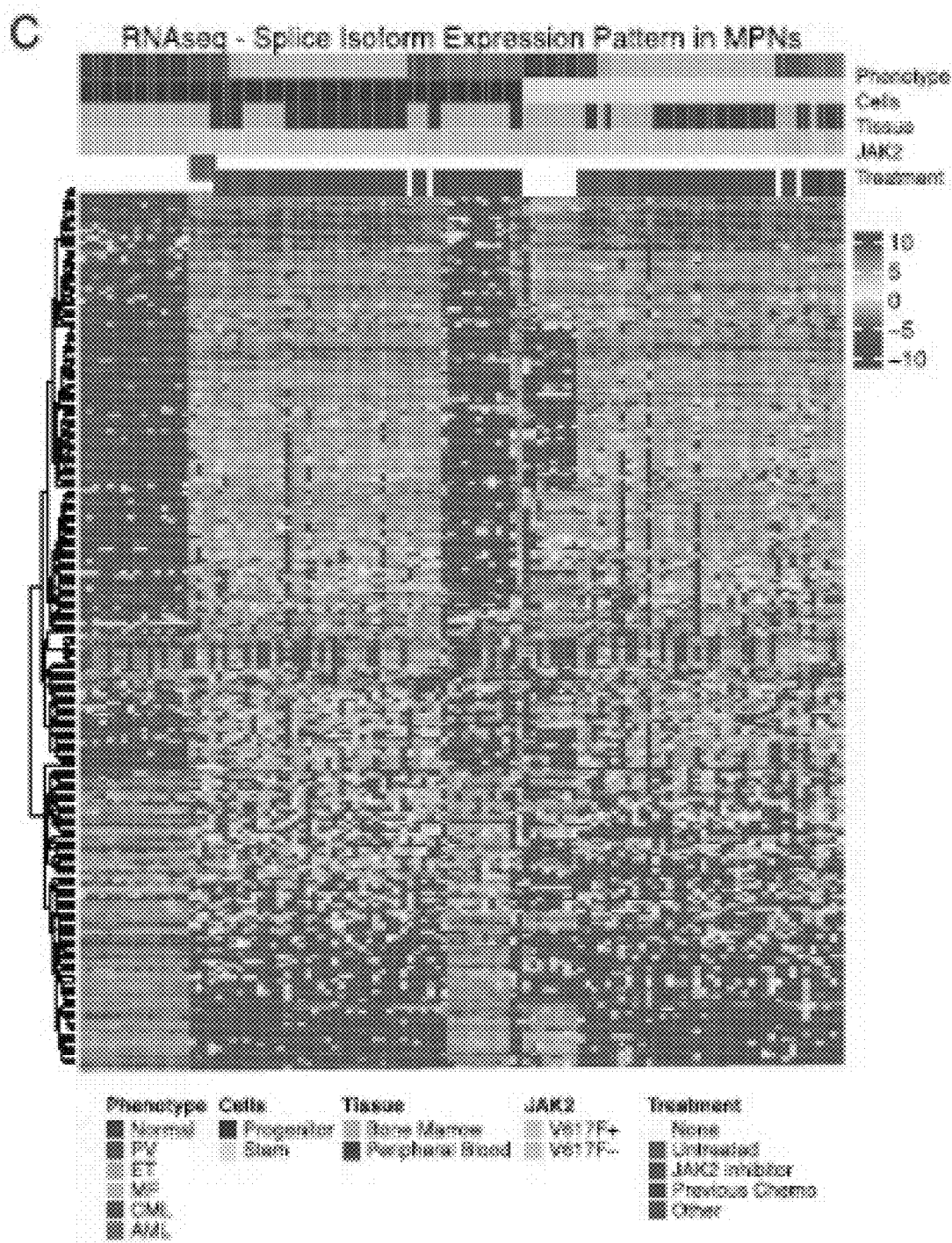
Figure 14D:
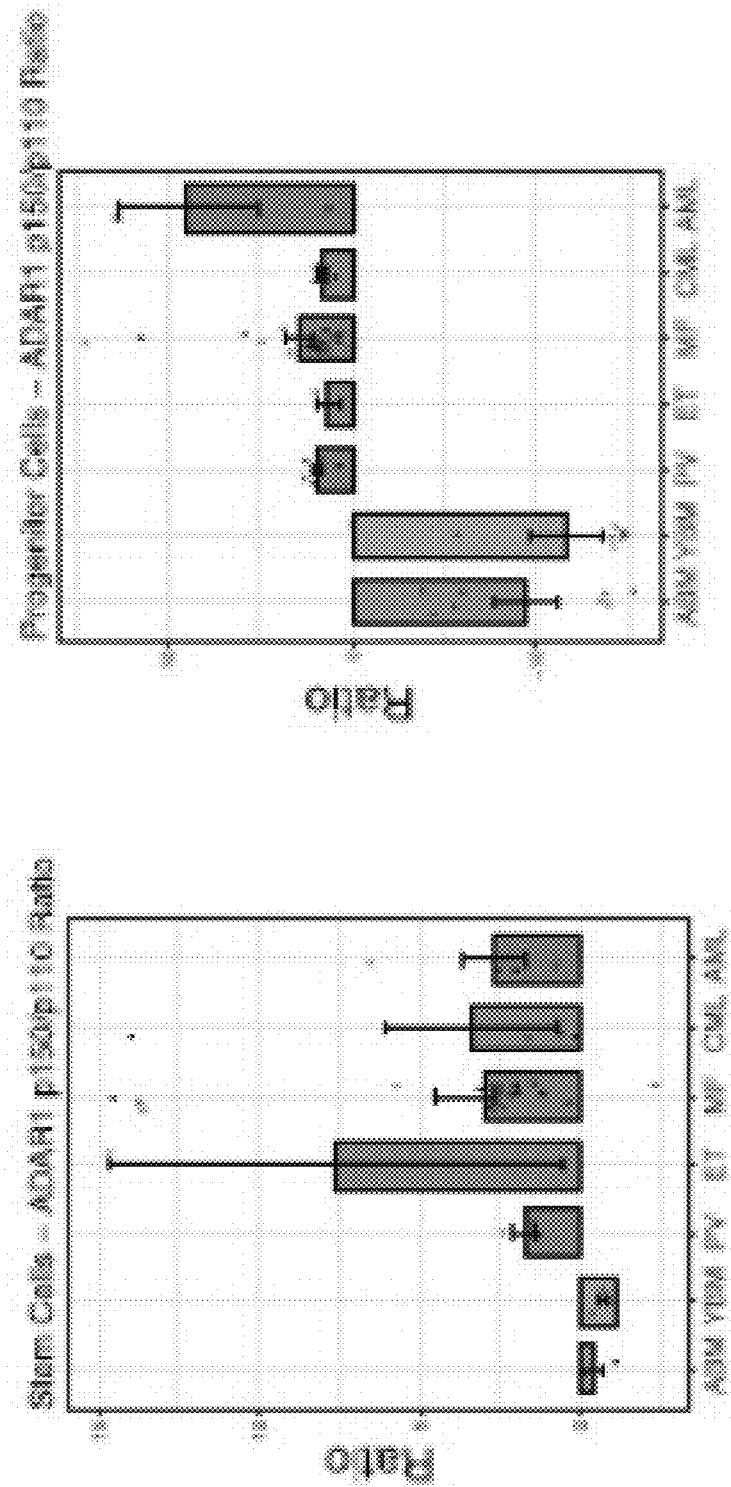
Figure 14E:
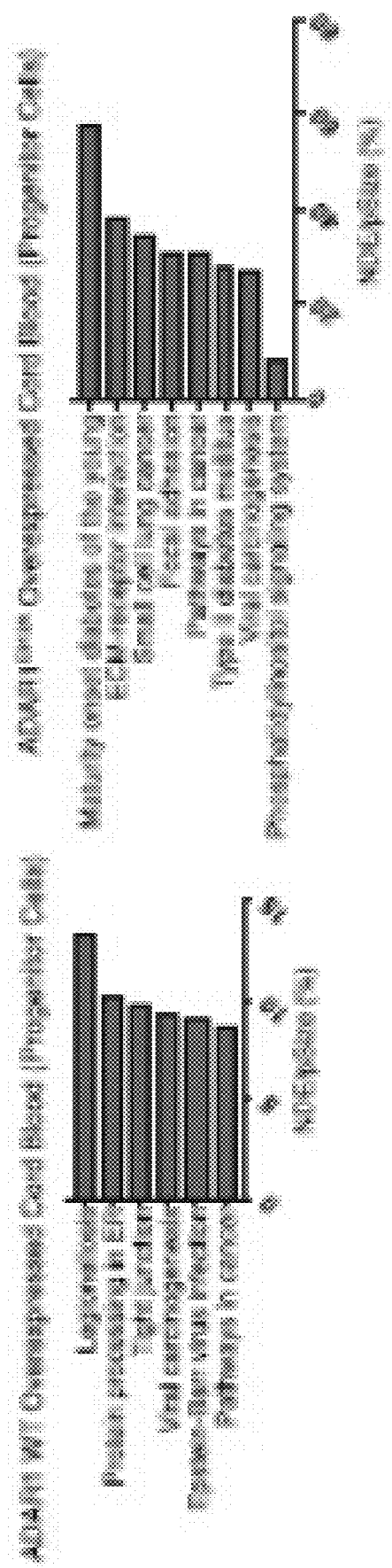

FIG. 14A-F (or FIG. 2, Example 2):

FIG. 14A illustrates a schematic of a heatmap based on normalized RNA-Seq expression for the top one percent of genes ranked by variance across all samples;

FIG. 14B graphically illustrates data from a Signaling Pathway Impact Analysis (SPIA) in ET, PV, MF and AML compared to ABM, respectively, .isted are the top 5 activated pathways based on the NDE (number of genes dysregulated in sample set)/pSize (number of genes in pathway) in percent;

FIG. 14C illustrates a schematic of a heatmap of normalized RNA-Seq expression of differentially expressed splicing isoforms for the top one percent of genes ranked by variance across all samples;

FIG. 14D graphically illustrates data showing the ratio of ADAR1 isoforms (p150/p110) is analyzed in each MPN disease type using normalized RNA-Seq expression data from both stem cells and progenitor cells;

FIG. 14E graphically illustrates data from a Signaling Pathway Impact Analysis (SPIA) in cord blood lentivirally overexpressed with ADAR1 WT (top) and deamination deficient mutant ADAR1$^{E912A}$ (bottom) compared to pCDH backbone control (n=3), listed are the top 6 activated pathways based on the NDE (number of genes in pathway)/pSize (number of genes dysregulated in sample set) in percent;

FIG. 14E graphically illustrates data showing the correlation of APOBEC3C with ADAR1 p150 isoform in stem cells and progenitors of aged bone marrow, young bone marrow, and MPN samples, as described in detail in Example 2, below.

Figure 15A:
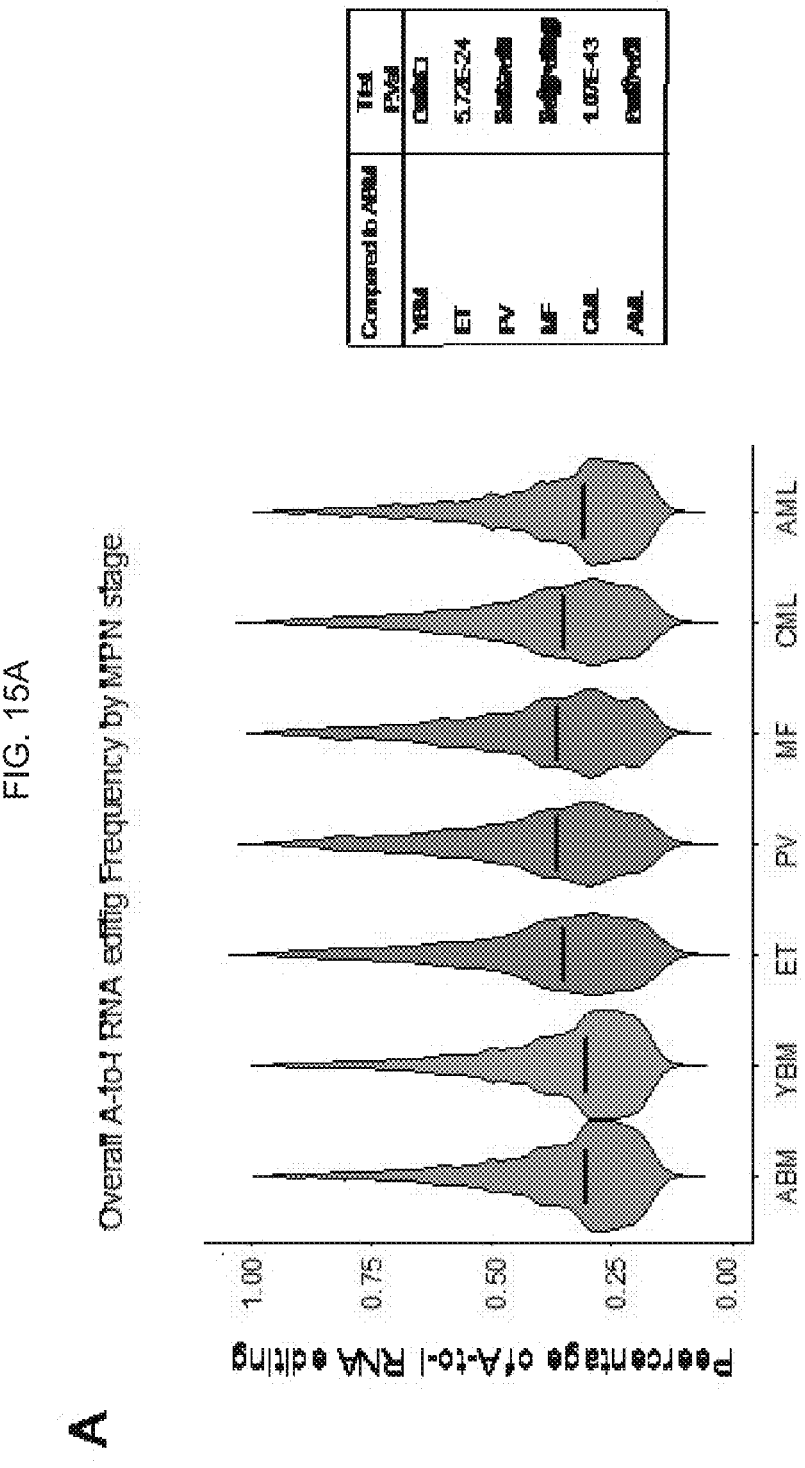
Figure 15B:
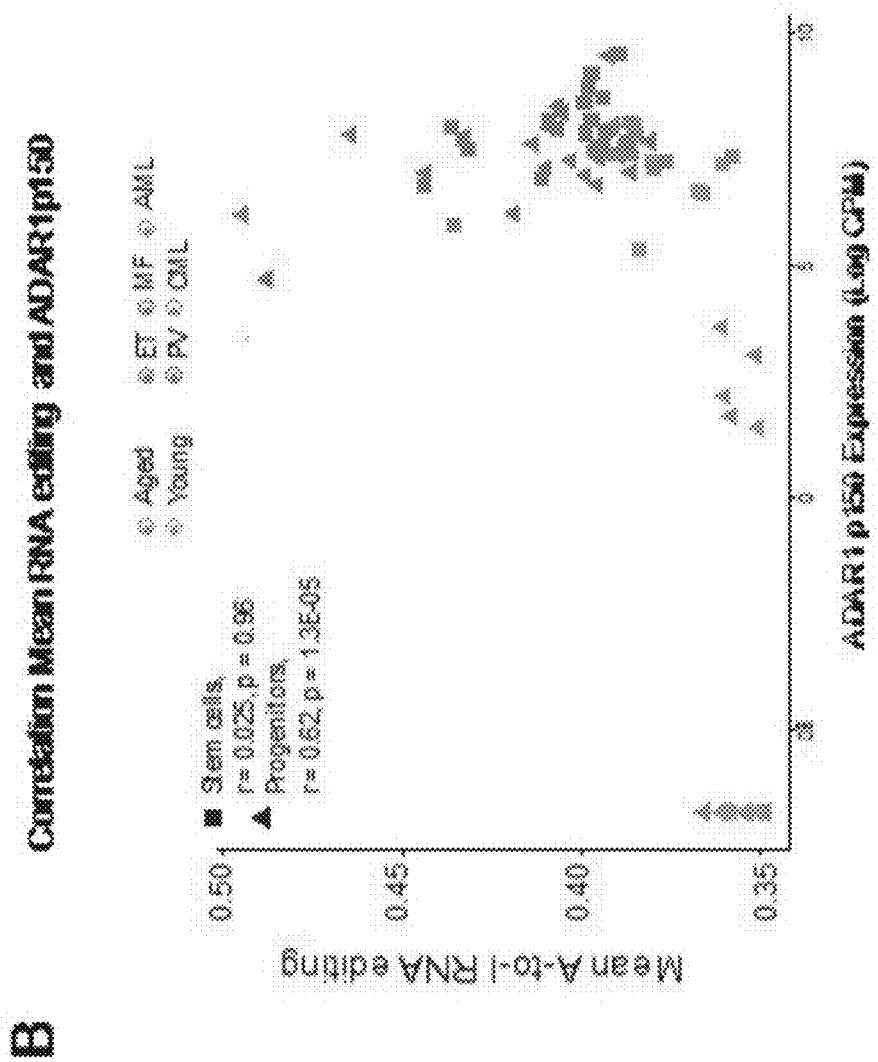
Figure 15C:
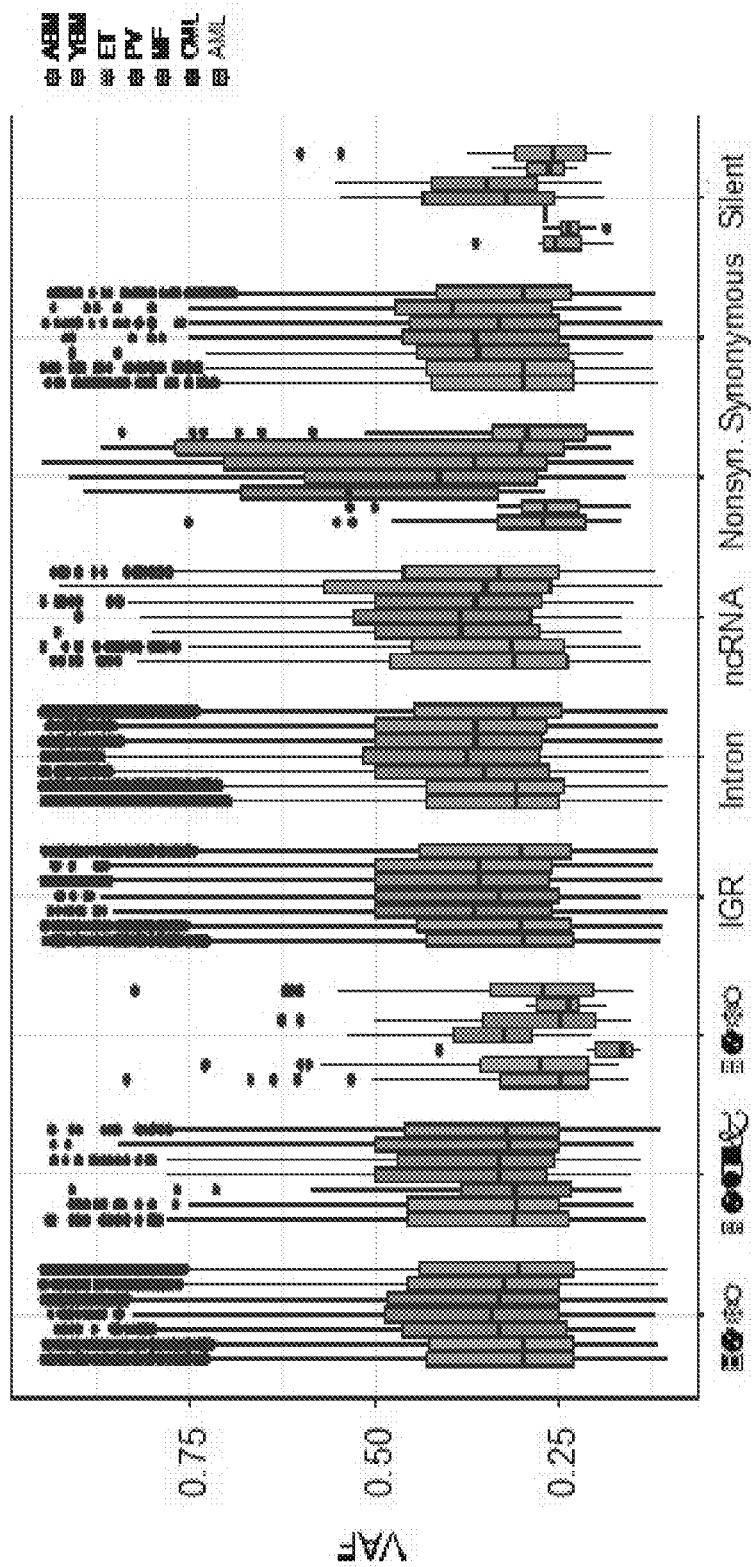
Figure 15E:
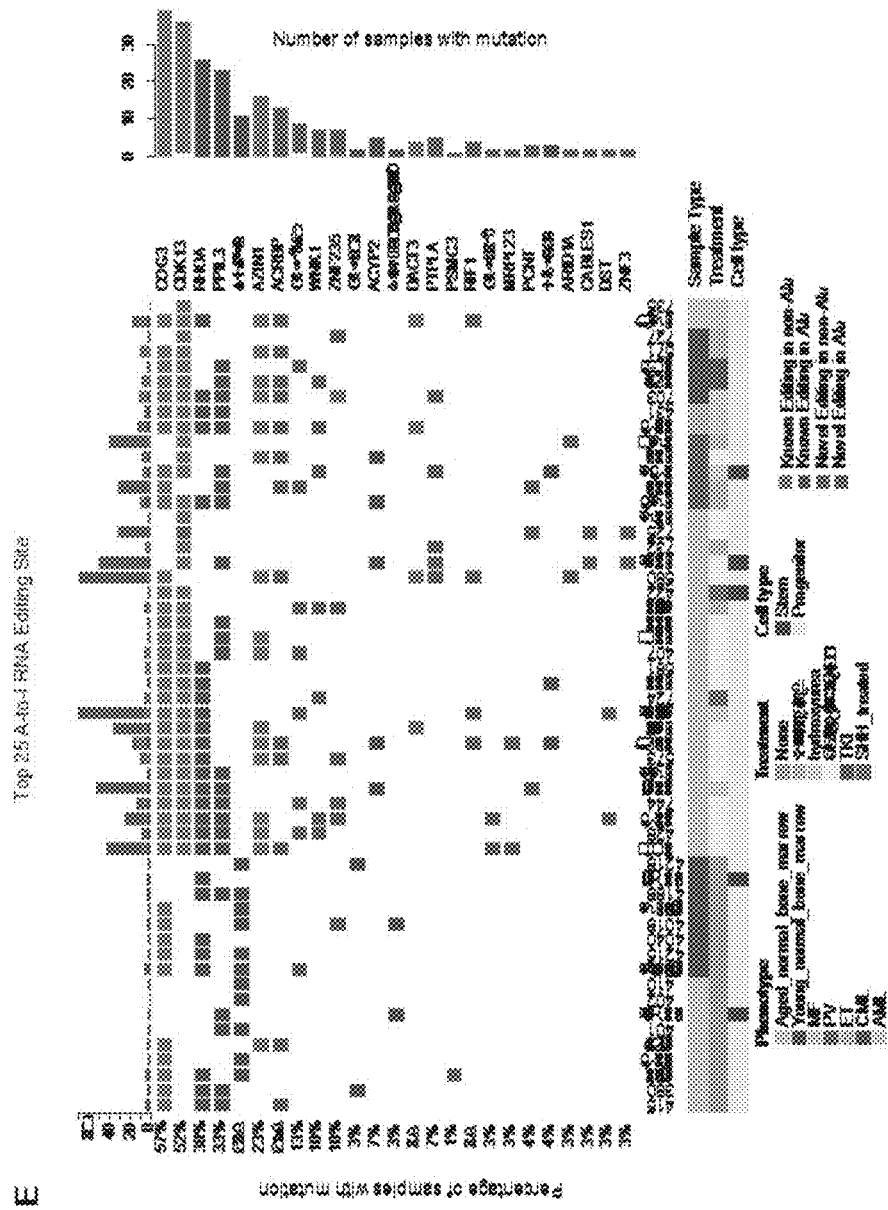

FIG. 15A-F (or FIG. 3, Example 2):

FIG. 15A schematically illustrates a Violin plot of overall RNA editing frequency (VAF) by MPN subtype and young (YBM) and aged bone marrow (ABM) controls;

FIG. 15B graphically illustrates data showing the correlation of mean A-to-I RNA editing level to ADAR1 p150 isoform expression level in both stem cells (square) and progenitors (triangle), each color represents a MPN disease stage;

FIG. 15C illustrates Box plots comparing RNA edit VAF of each MPN phenotype broken down by genomic region in progenitor population;

FIG. 15D illustrates a table showing a statistical comparison of RNA edit VAF (A to I RNA editing) of each MPN phenotype broken down by genomic region in progenitor population (a comparison of A to I RNA editing between each MPN stage and ABM in progenitors);

FIG. 15E illustrates a table showing the top 25 ranked genes by occurrence of nonsynonymous RNA edit mutations broken down by known non Alu and Alu region, and novel non-Alu and Alu regions stratified by MPN phenotype, treatment and cell type;

FIG. 15F graphically illustrates normalized and Log 2 transformed RNA-Seq expression data for CDK13 and SUMF2 in the progenitor population plotted by MPN phenotype, as described in detail in Example 2, below.

Figure 16A:
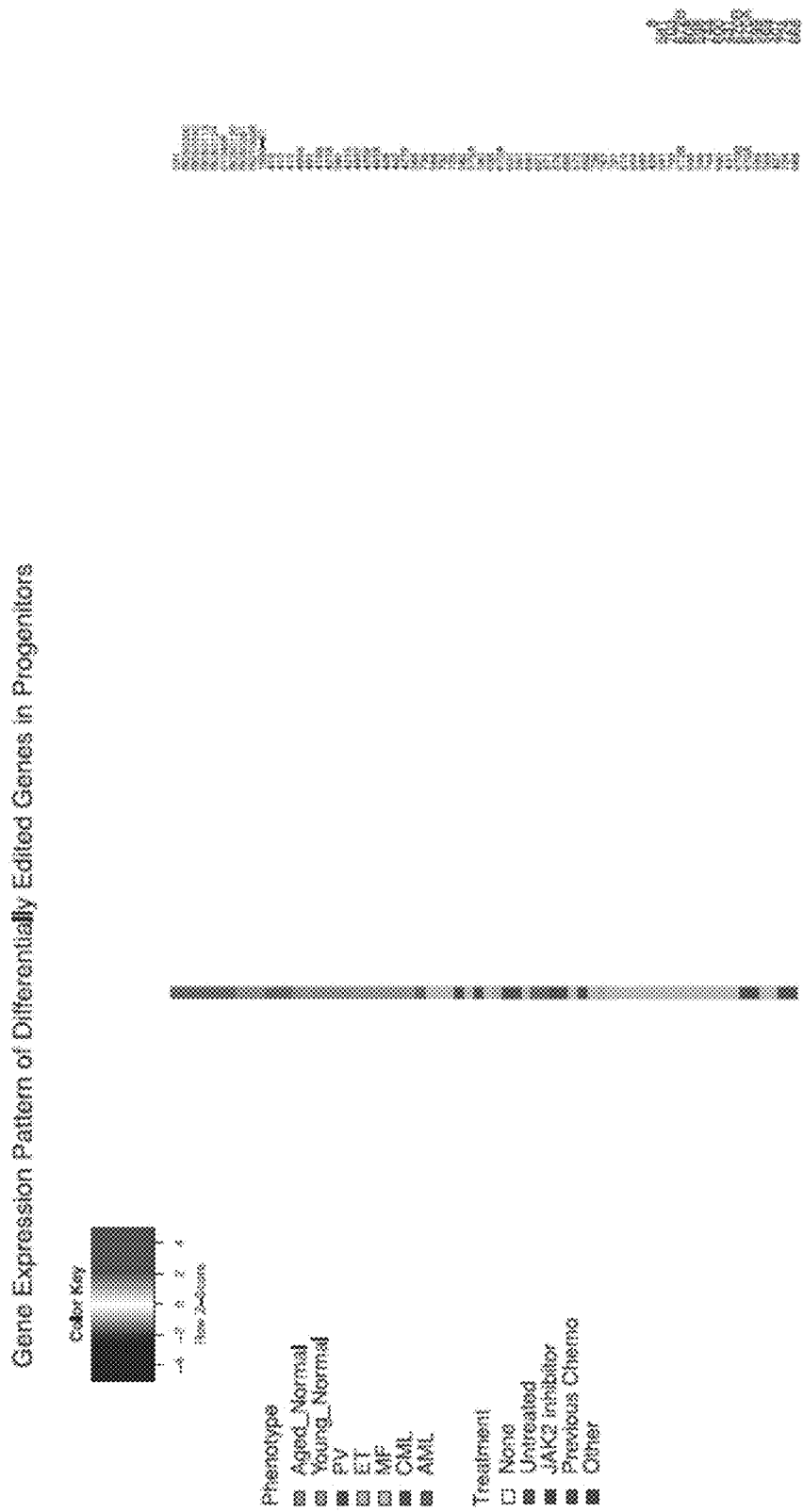
Figure 16B:
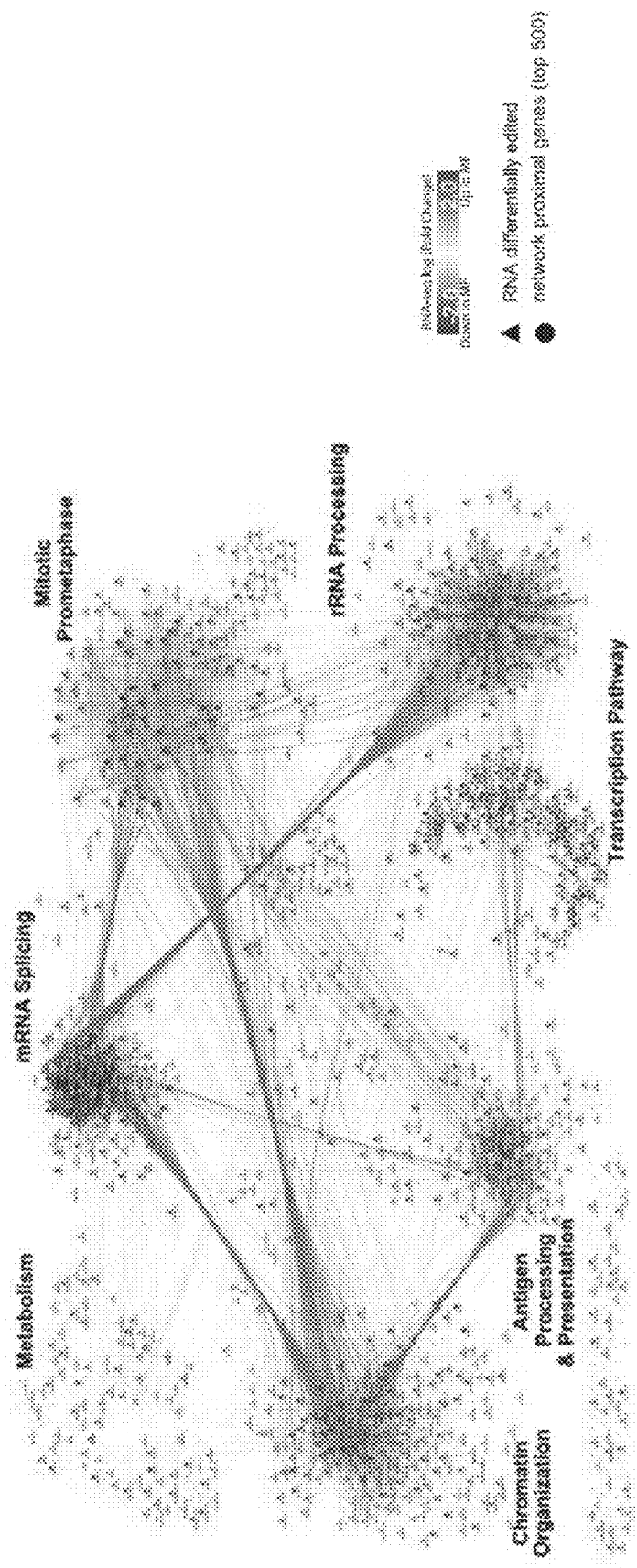

FIG. 16A-C (or FIG. 4, Example 2):

FIG. 16A illustrates a Heatmap based on gene expression z-scores of 1295 differentially edited genes in progenitors;

FIG. 16B illustrates a Network analysis of differentially edited genes between normal aged sample and MF;

FIG. 16C illustrates a Network analysis of differentially edited genes between normal aged samples and AML, as described in detail in Example 2, below.

Figures 17A, 17B:
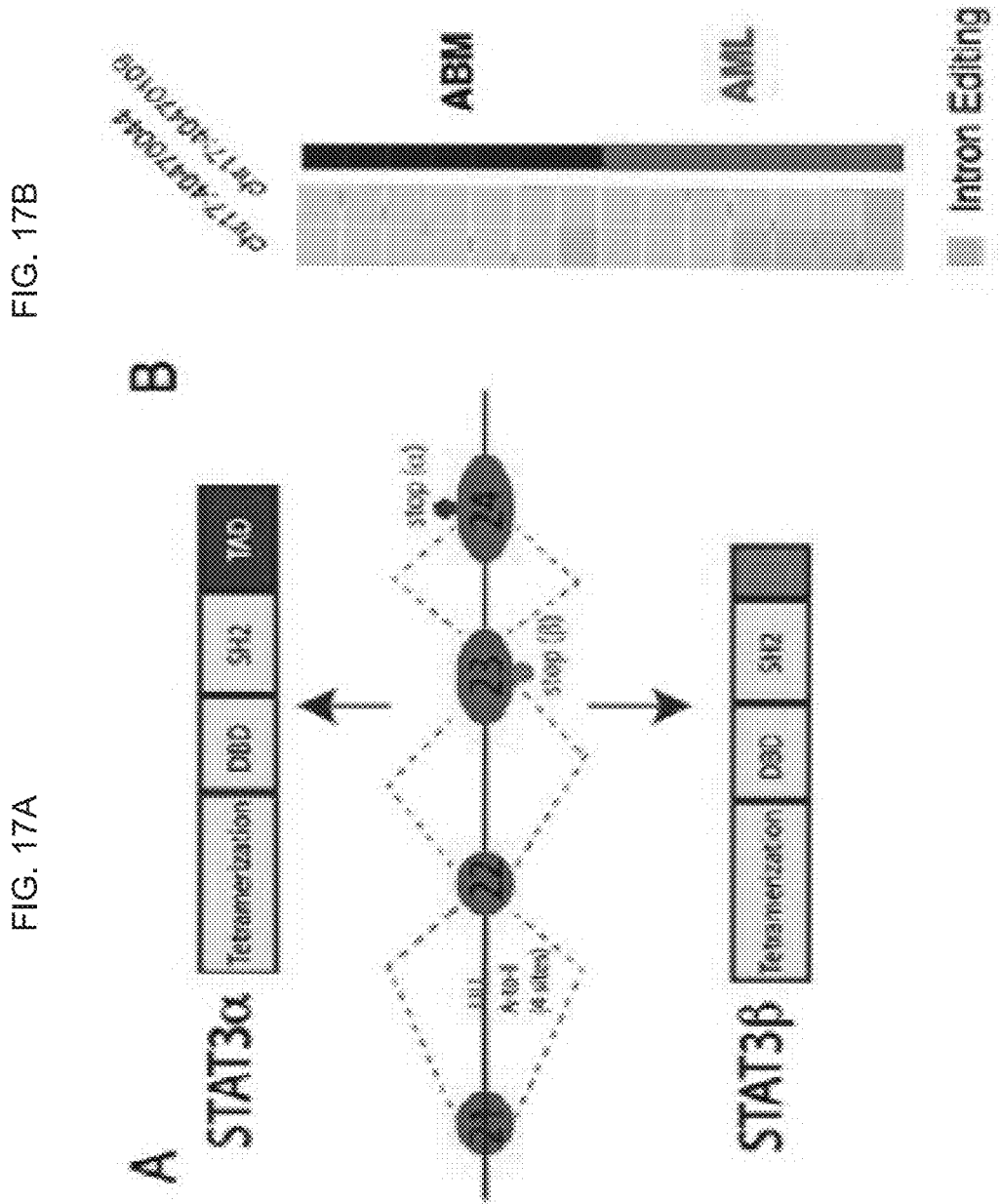
Figure 17C:
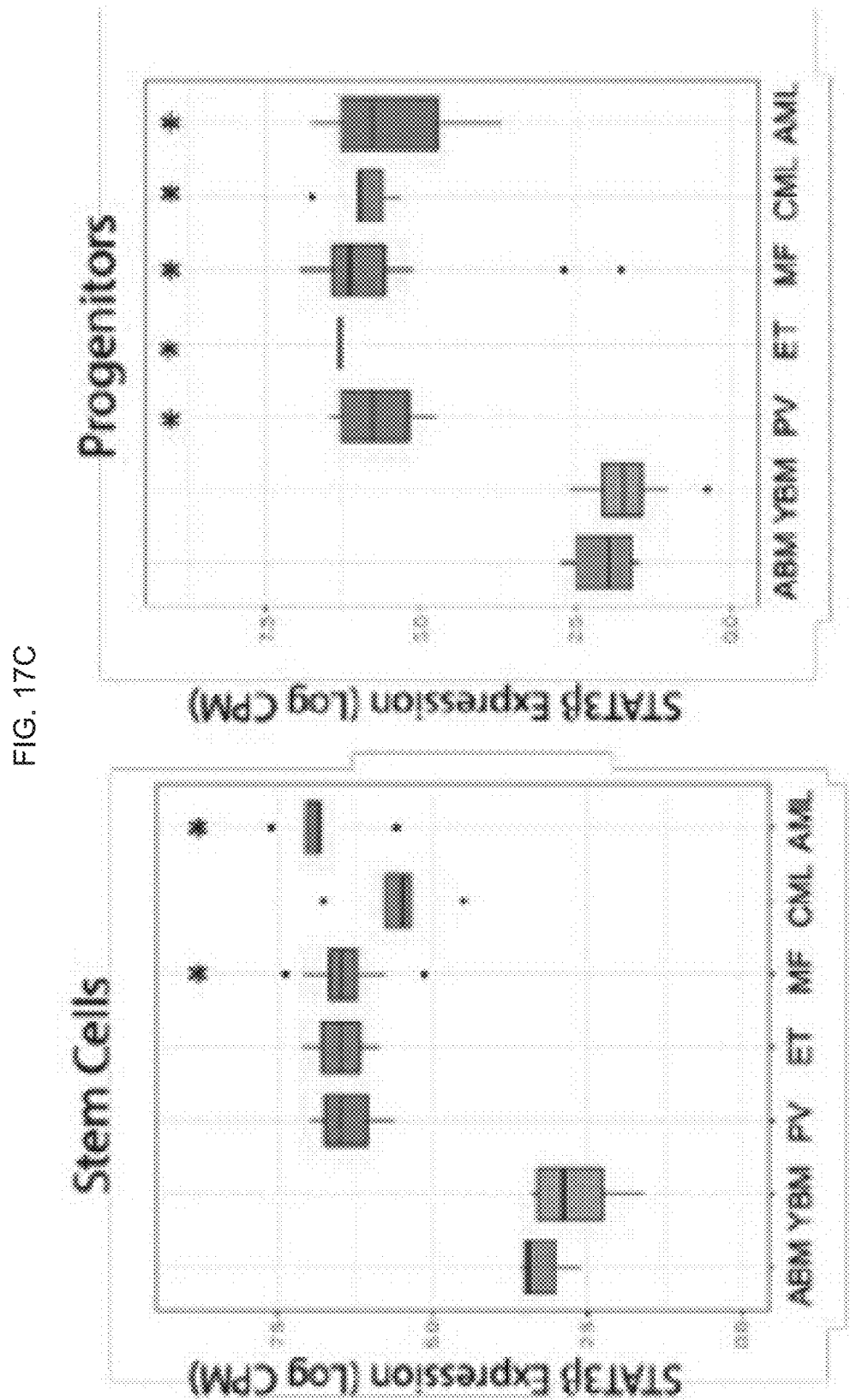
Figure 17E:
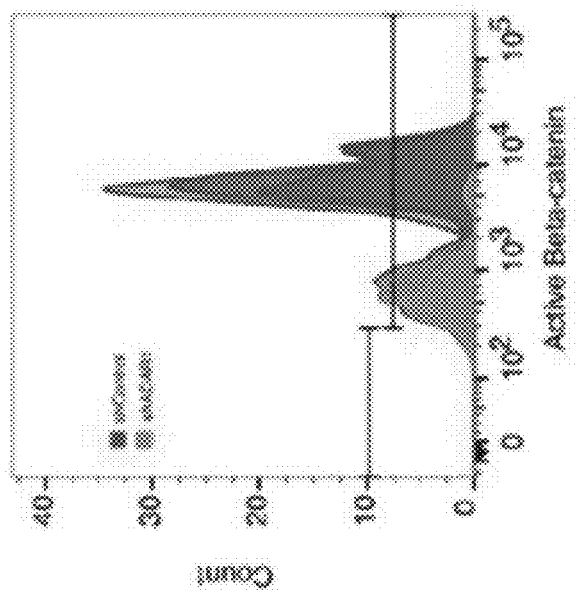
Figure 17F:
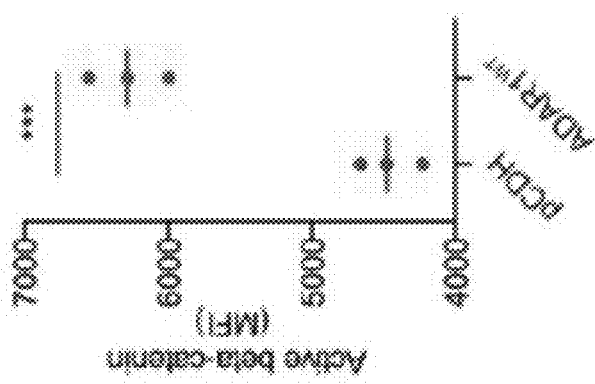
Figure 17G:
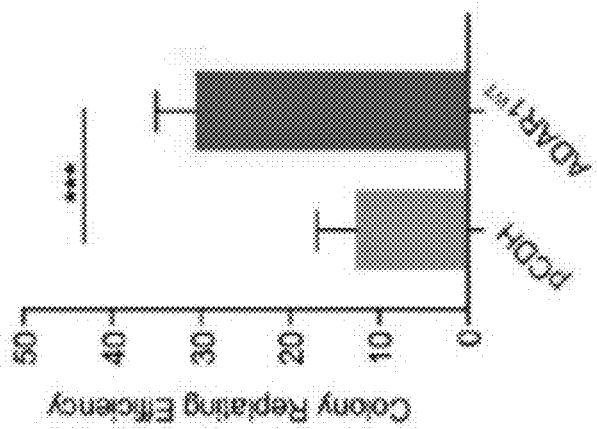

FIG. 17A-G (or FIG. 5, Example 2):

FIG. 17A schematically illustrates STAT3 isoforms generation by alternative splicing and stop codon;

FIG. 17B graphically illustrates known A-to-I RNA editing locations (35) in normal aged (ABM) and AML as determined by RNA-seq data;

FIG. 17C graphically illustrates the expression of STAT3β isoform in normal young (YBM), normal aged (ABM), and MPN stem cell and progenitor population using normalized RNA-Seq data;

FIG. 17D graphically illustrates a correlation of STAT3β isoform with ADAR1 p150 isoform in progenitors of aged bone marrow (ABM), young bone marrow (YBM), and MPN samples;

FIG. 17E graphically illustrates self-renewal capacity as measured by colony re-plating assay in MF CD34+ HSPC transduced pCDH backbone or ADAR1 WT;

FIG. 17F graphically illustrates data of beta-catenin activity as measured by flow cytometry in K562 BC CML cells stably transduced with pCDH lentiviral backbone or ADAR1 WT;

FIG. 17G graphically illustrates data of beta-catenin activity by flow cytometry in KG-1a cells with ADAR1 knockdown by shRNA. The shRNA is marked by GFP signal, as described in detail in Example 2, below.

Figure 18A:
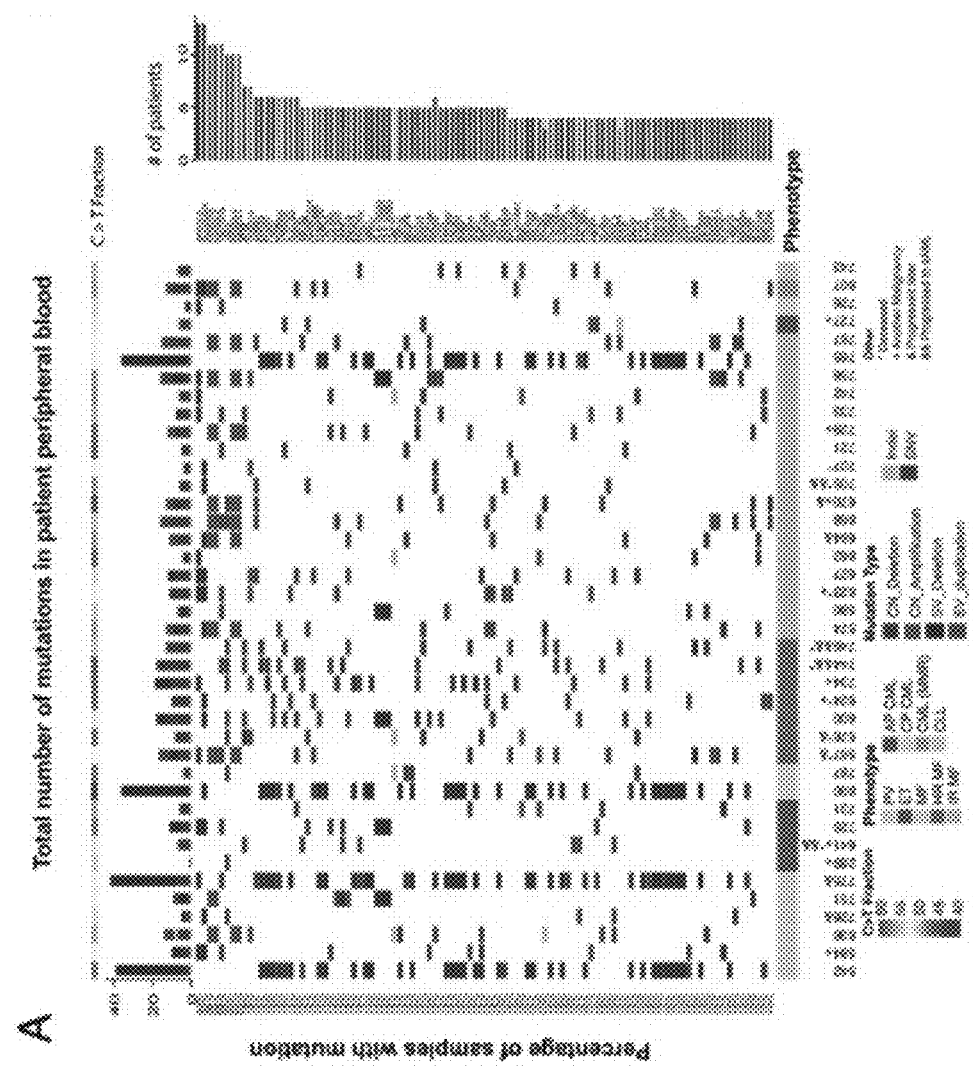
Figure 18C:
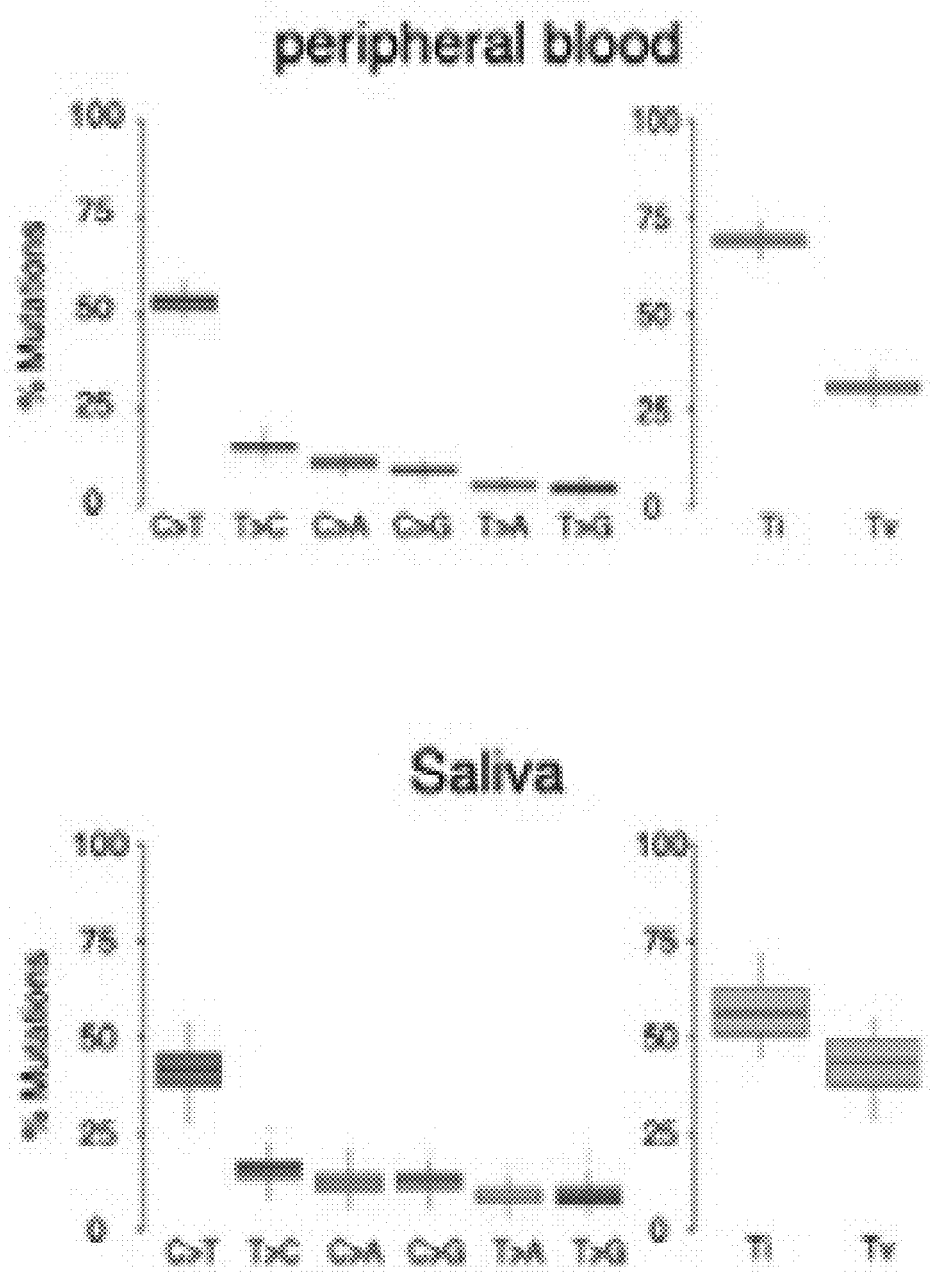

FIG. 18A-D (or, FIG. S1—Example 2), Top DNA mutations in MPN peripheral blood or saliva samples:

FIG. 18A graphically illustrates top mutations in MPN patients from peripheral blood including single nucleotide variants (SNVs), copy number variants (CNVs) and structural variants (SVs);

FIG. 18B graphically illustrates top mutations in MPN patients saliva including single nucleotide variants (SNVs), copy number variants (CNVs) and structural variants (SVs). MPN disease stage depicted in colored bar at the bottom of the figure;

FIG. 18C graphically illustrates a Boxplot of the number of somatic mutations in peripheral blood or saliva broken down by nucleotide change and transitions/transversions;

FIG. 18D graphically illustrates data showing expression of APOBEC3 family genes in stem cells and progenitors of normal aged (ABM), normal young (YBM), MPN and AML progenitors, as described in detail in Example 2, below.

Figure 19A:
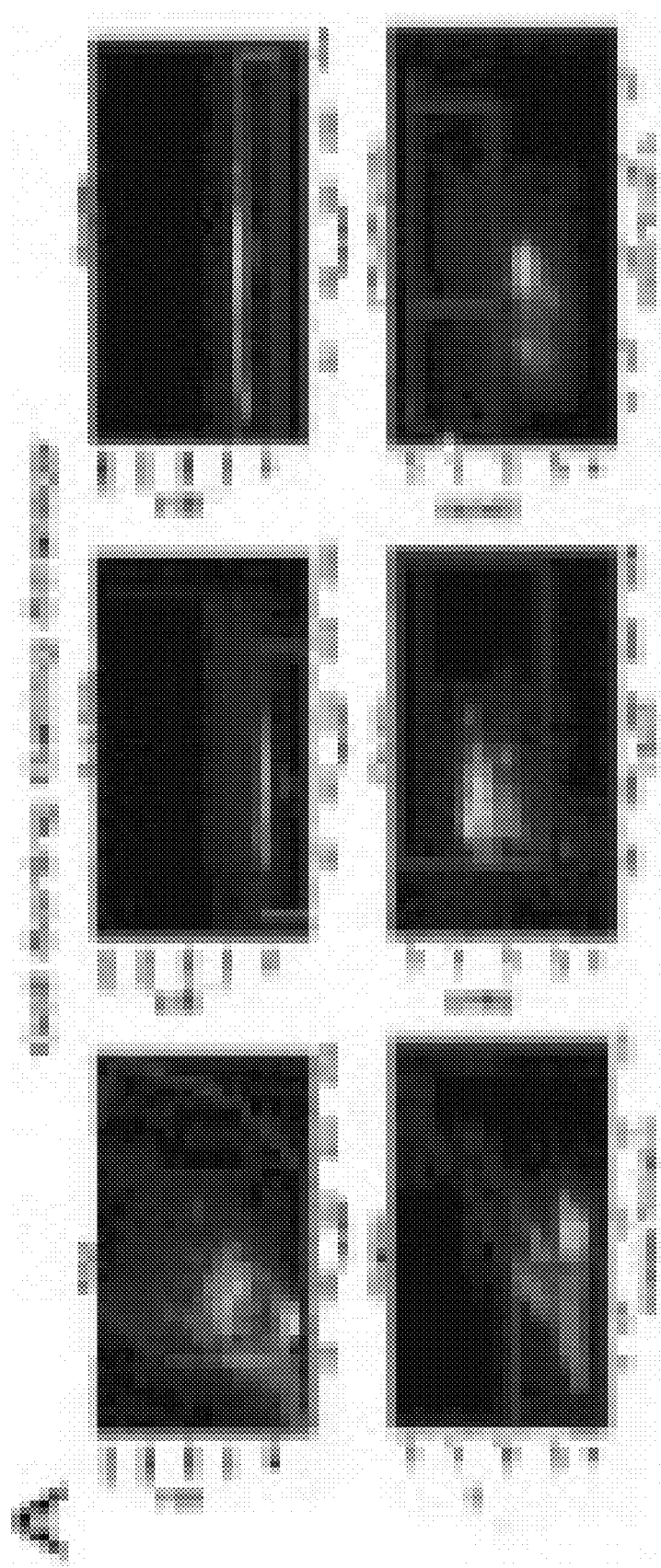
Figure 19B:
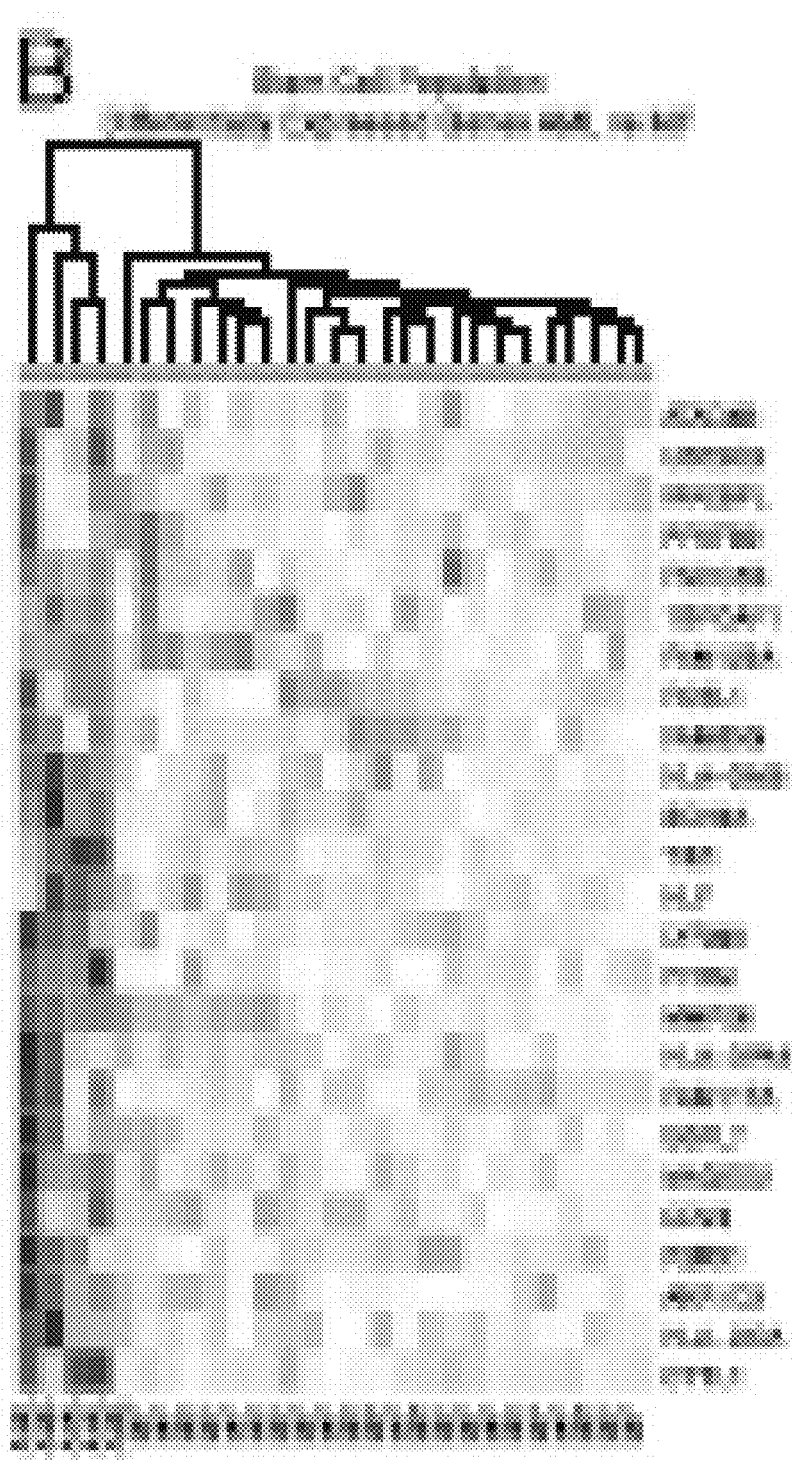
Figure 19C:
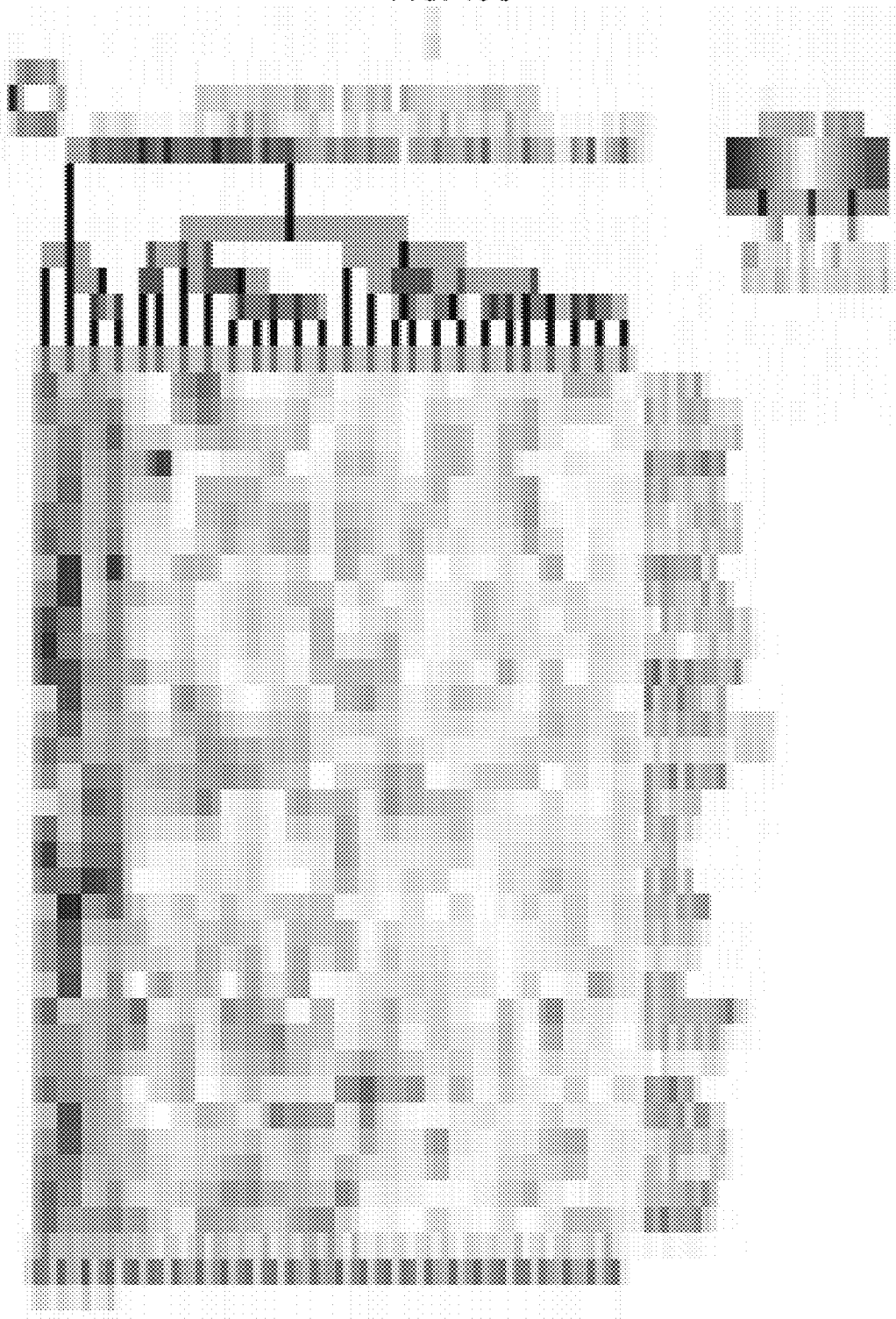

FIG. 19A-C (or FIG. S2, Example 2), Different gene expression in purified MPN stem cells and progenitors:

FIG. 19A illustrates images of gating strategy for FACS-purified stem cell (CD34$^+$CD38$^-$Lin$^-$) and progenitor (CD34$^+$CD38$^+$Lin$^-$) populations from 54 unique patients and 24 young and aged healthy controls;

FIG. 19B illustrates a Heatmap shown of the top 25 differentially expressed genes in AML stem cells compared with MF stem cells (987 total DE genes);

FIG. 19C illustrates a Heatmap shown of the top 25 differentially expressed genes in AML progenitors compared with MF progenitors (678 total DE genes), as described in detail in Example 2, below.

Figure 20B:
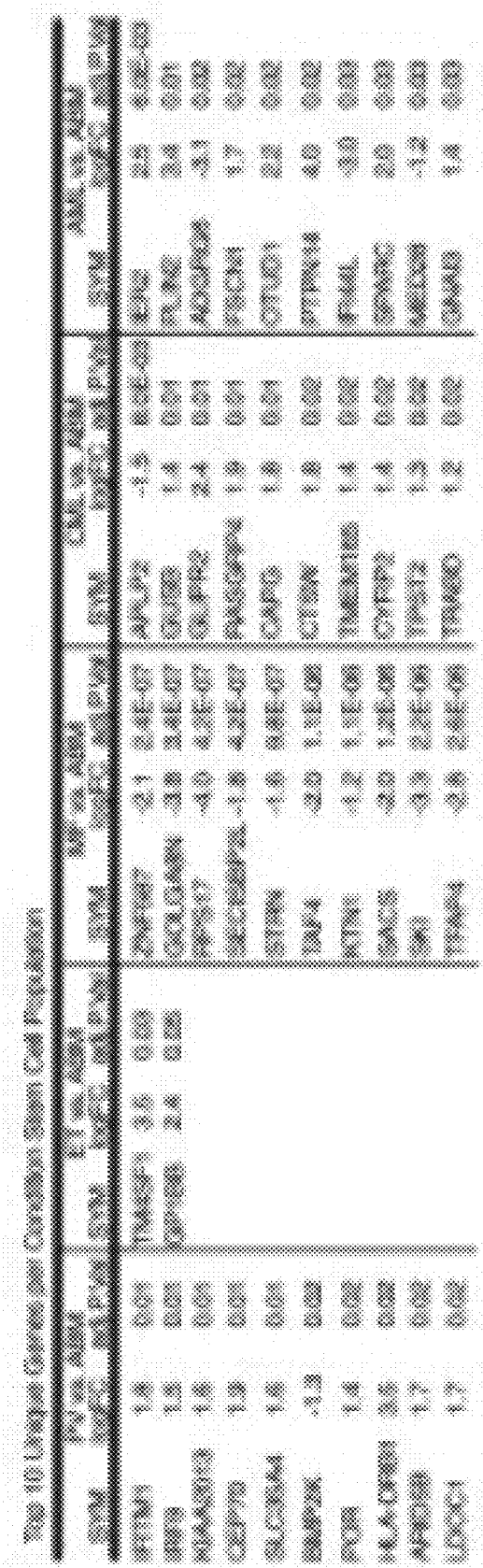
Figure 20C:
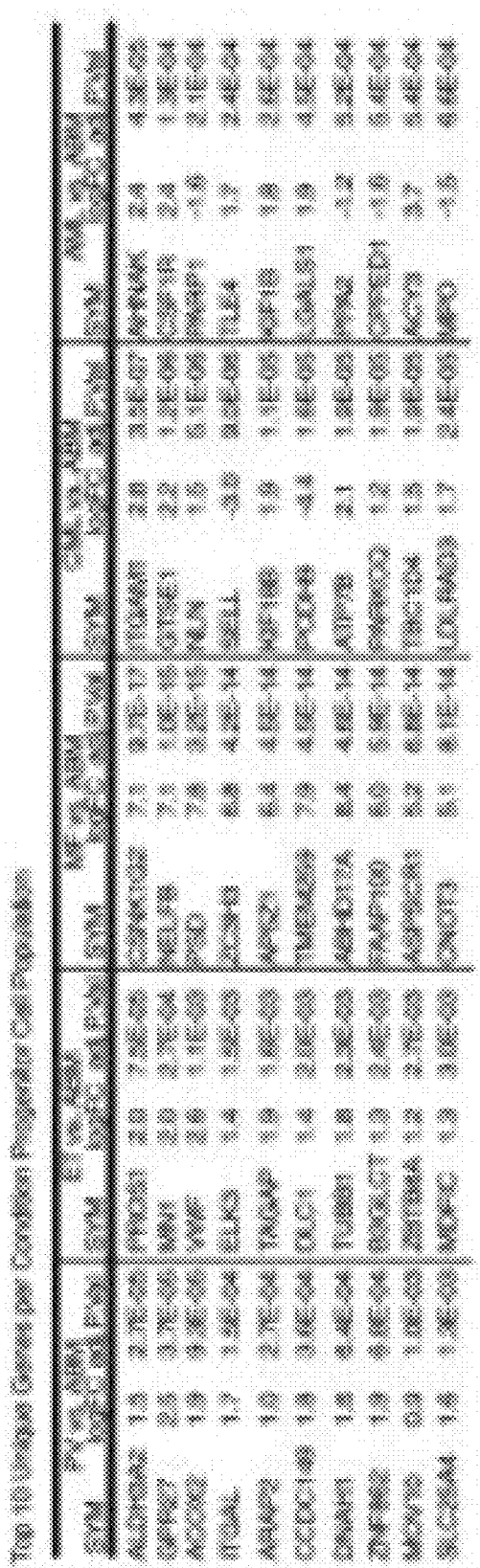
Figure 20D:
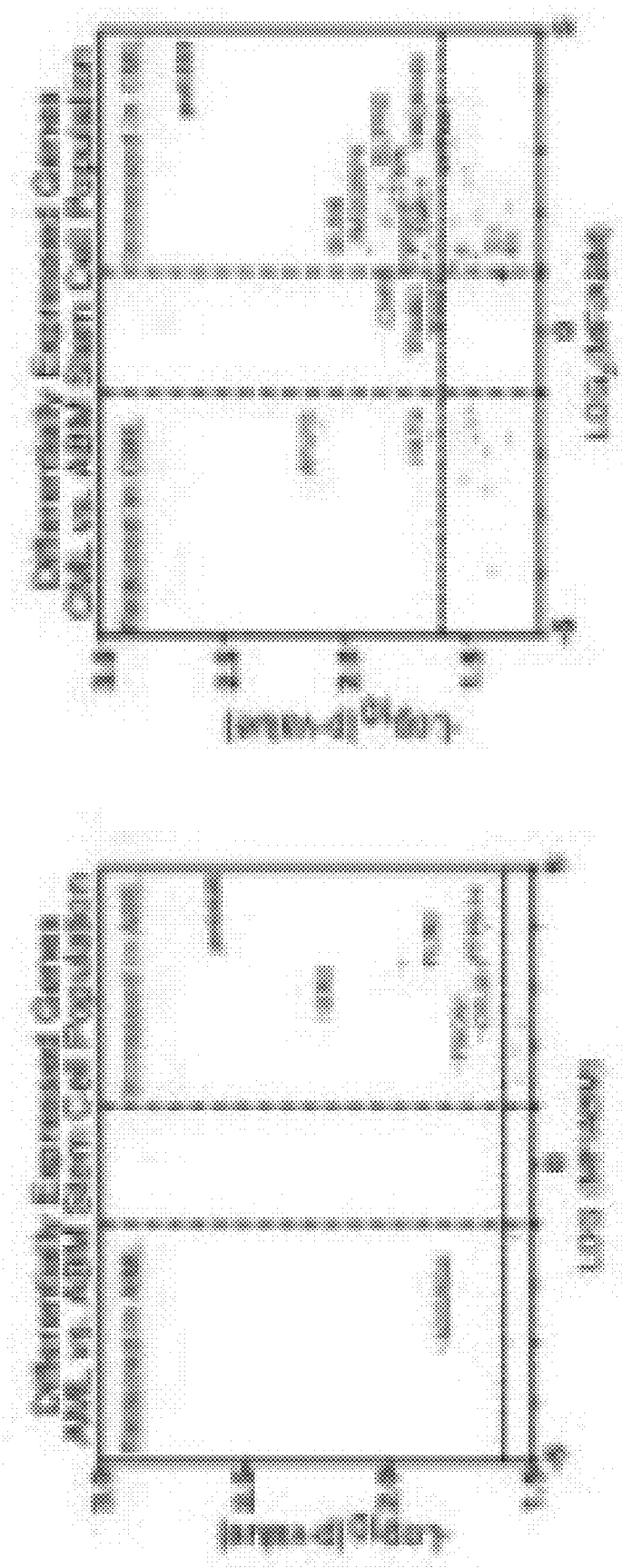

FIG. 20A-E (or FIG. S3, Example 2), Top unique genes in MPN stem cells or progenitors:

FIG. 20A schematically illustrates results for differential expression analysis of RNA-Seq data between patients with various phenotypes in stem and progenitor cells, the Venn diagram shows the overlap of significantly different genes (adjusted p-val<0.05) between the comparisons FIG. 20B illustrates a table of the top 10 statistically significant genes in the stem cell population are listed in table;

FIG. 20C illustrates a table of the top 10 statistically significant genes in the progenitor cell population are listed in table;

FIG. 20D illustrates Volcano plots of stem cell population of MPN compared to ABM for genes with an adjusted p-value with 0.025 or less (PV, AML and CML), an adjusted p-value of 0.001 (MF);'

Figure 20E:
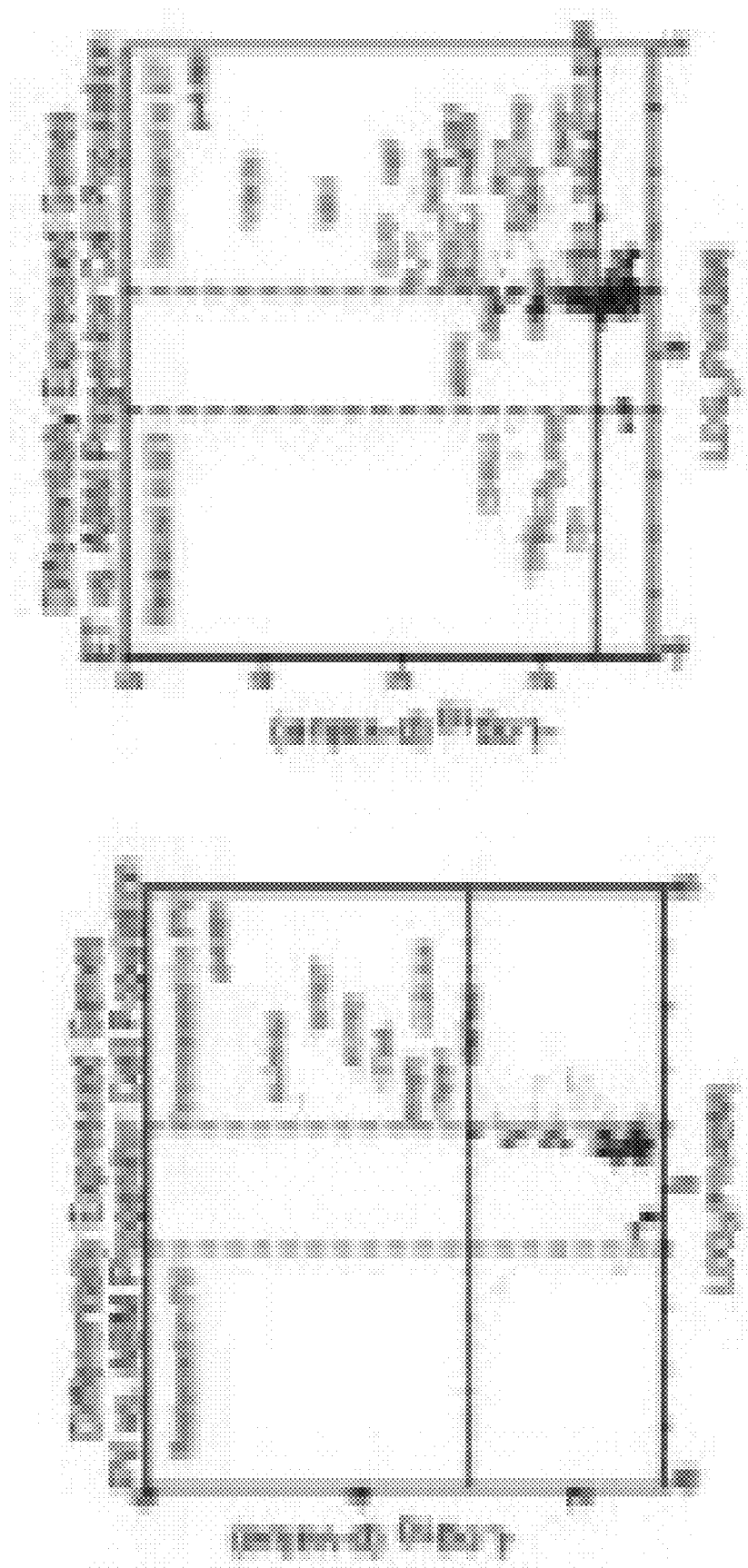
Figure 20E:
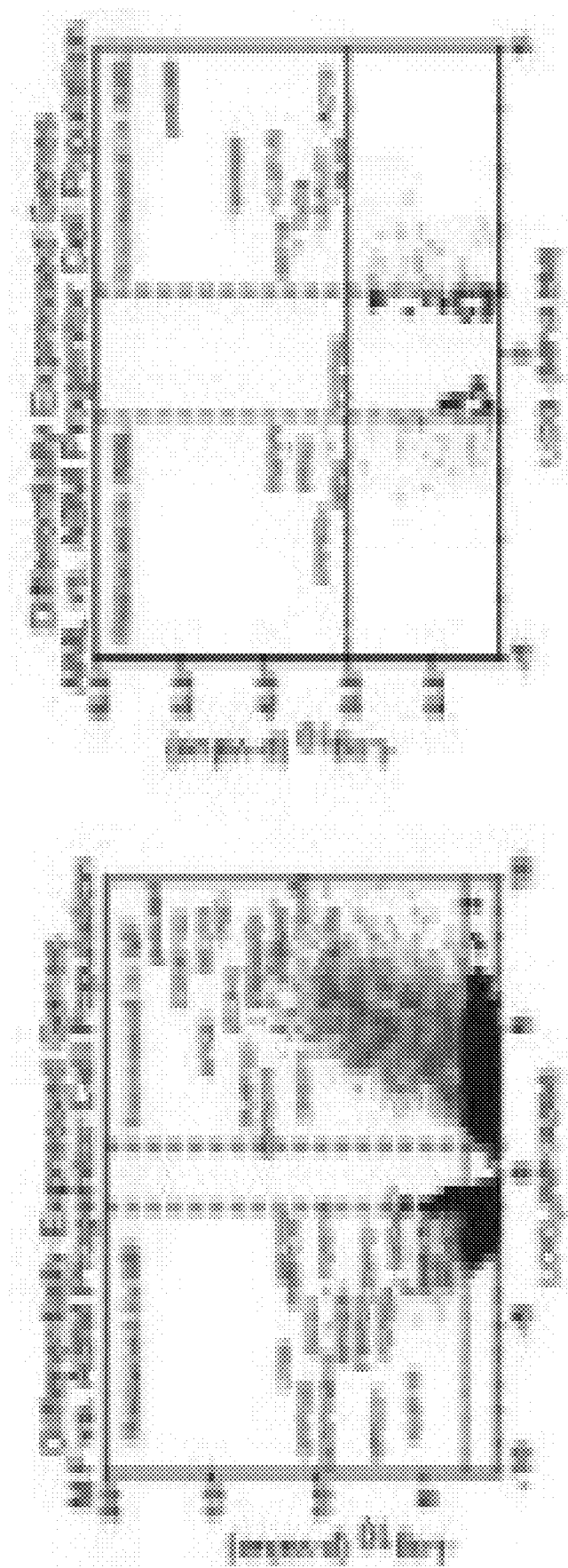
Figure 20E:
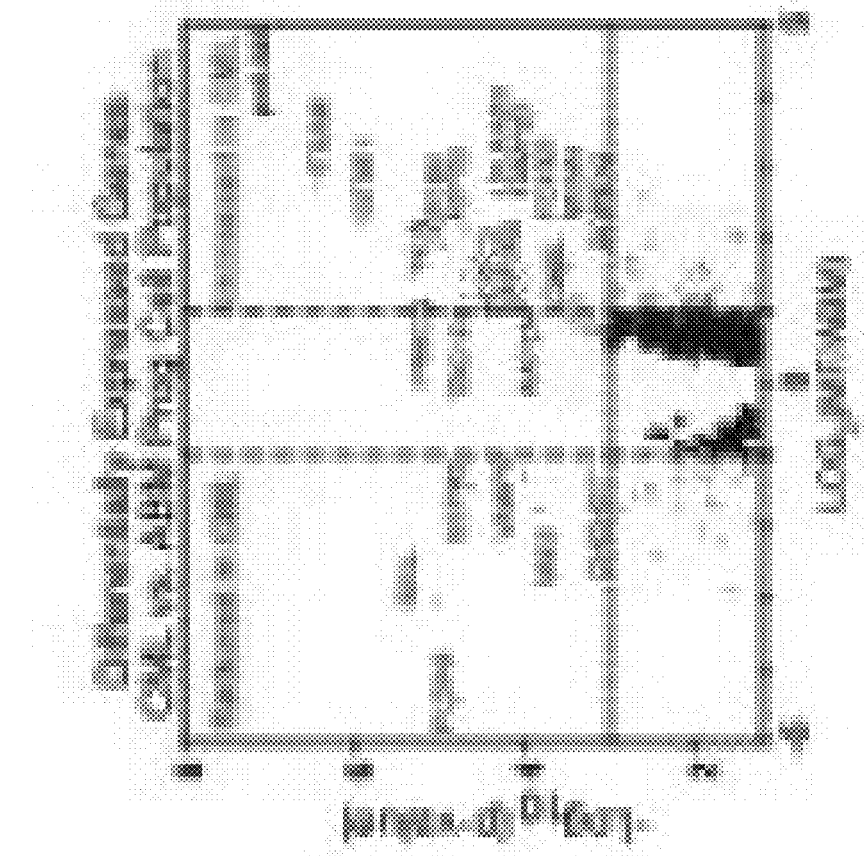

FIG. 20E illustrates Volcano plots for the progenitor cell population of MPN compared to ABM for genes with an adjusted p-value of 0.001 or less (PV, MF and AML), and an adjusted p-value of 0.025 (CML and ET), as described in detail in Example 2, below.

Figure 21A:
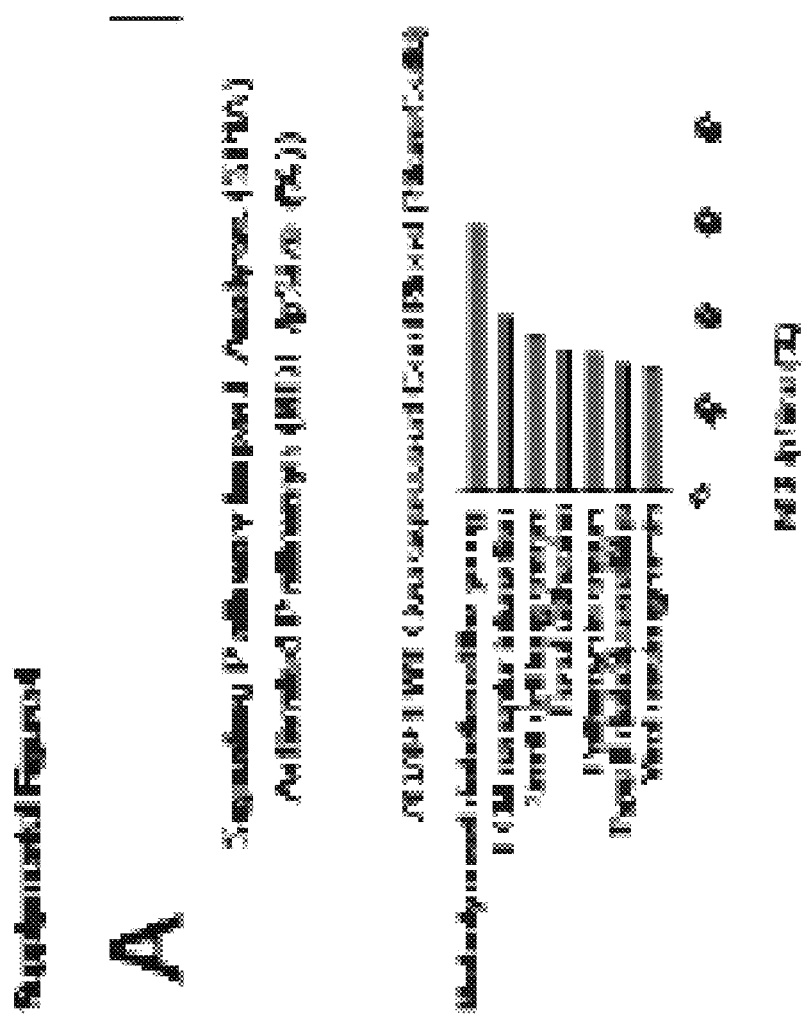
Figure 21B:
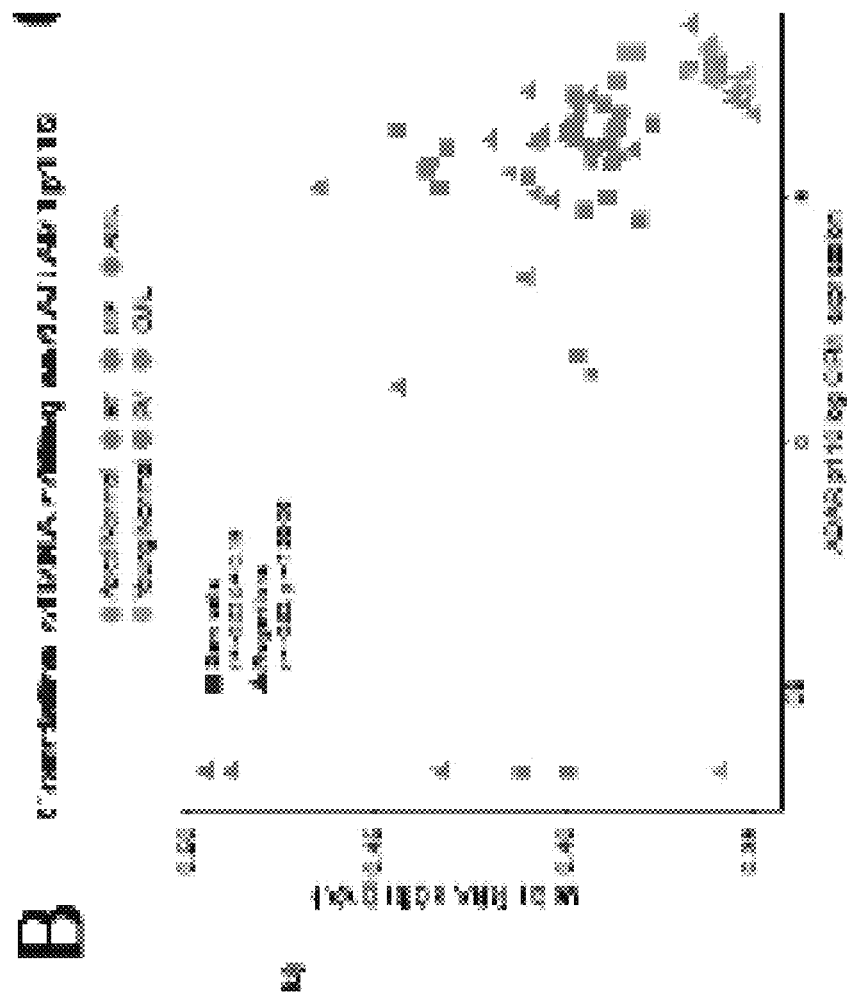
Figure 21E:
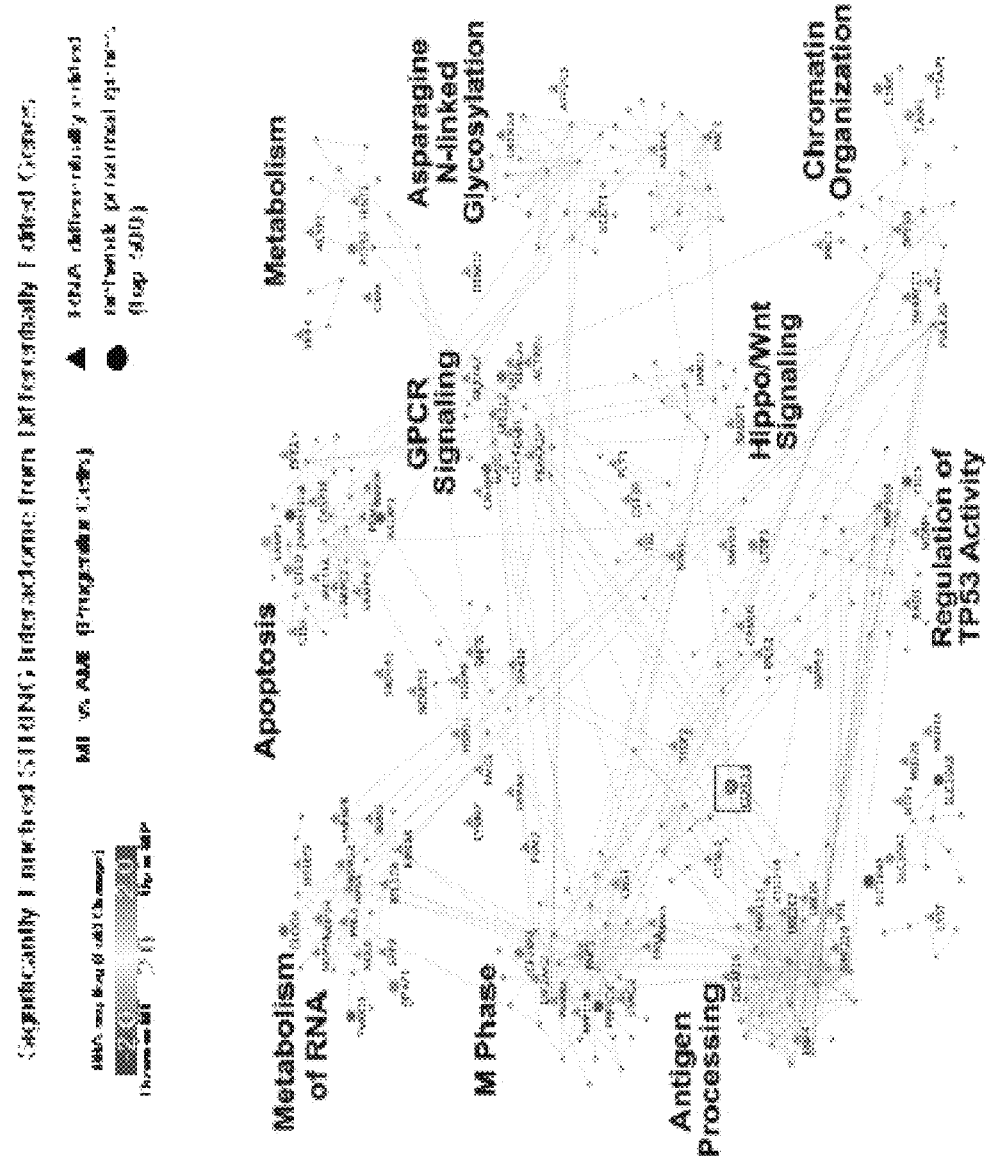

FIG. 21A-E (or FIG. S4, Example 2), A-to-I RNA editing between MPN stage and normal aged bone marrow:

FIG. 21A schematically illustrates a Signaling Pathway Impact Analysis (SPIA) in cord blood stem cells lentivirally overexpressed with ADAR1 compared to pCDH backbone control (n=3). listed are the top 6 activated pathways based on the NDE (number of genes in pathway)/pSize (number of genes dysregulated in sample set) in percent;

FIG. 21B graphically illustrates correlation of ADAR1 p110 isoform expression with mean A-to-I RNA editing in stem (square) or progenitor (triangle) population of each MPN subtype, each color represent a MPN subtype;

FIG. 21C graphically illustrates correlation of CDK13 expression and ADAR1 expression in stem and progenitor population of MPN;

FIG. 21D graphically illustrates Normalized and Log 2 transformed RNA-Seq expression data for CDK13 and SUMF2 in stem cells plotted by MPN phenotype;

FIG. 21E schematically illustrates a Network analysis of differentially edited genes between MF and AML, as described in detail in Example 2, below.

Figure 22A:
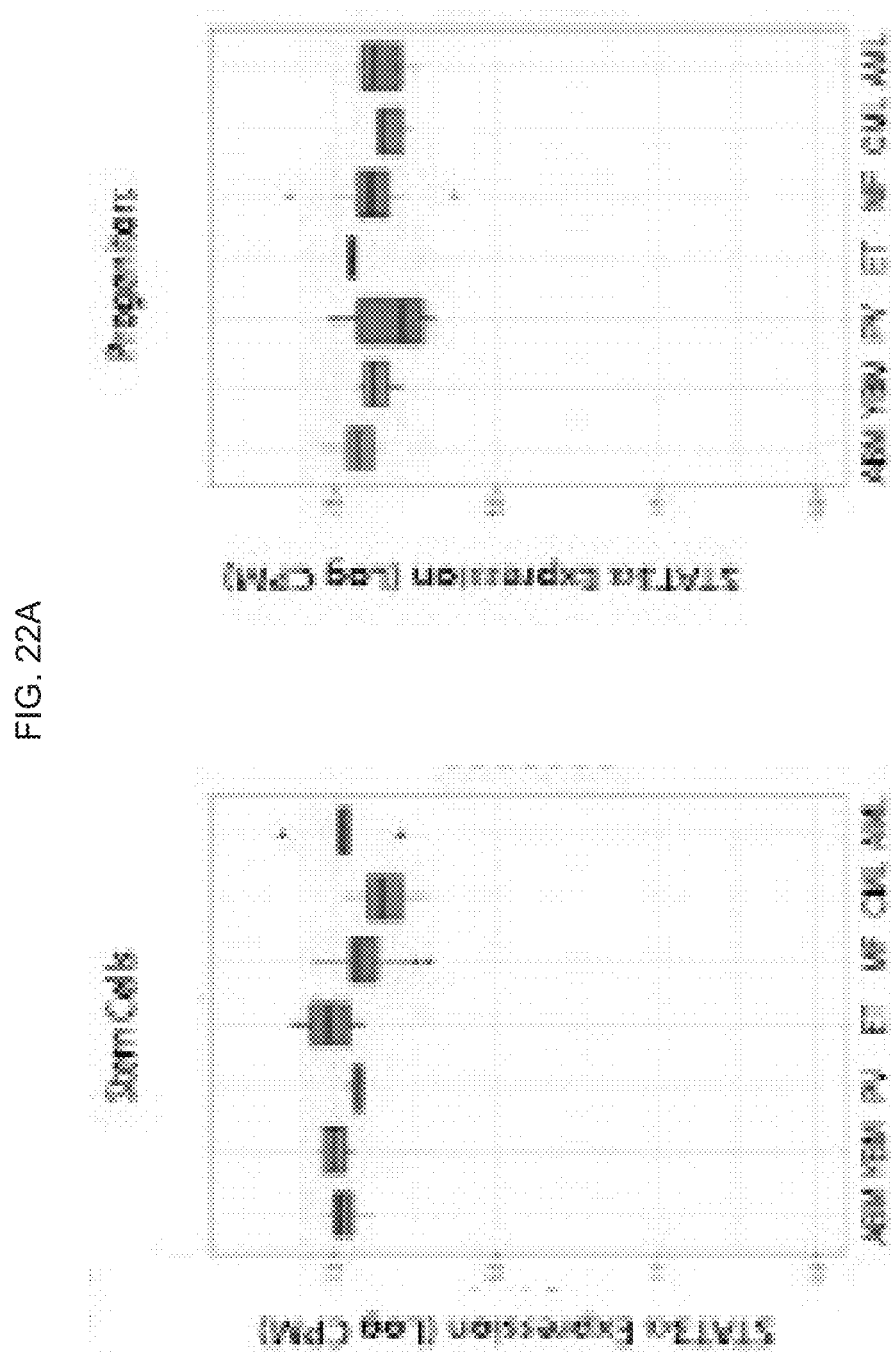

FIG. 22A-D (or FIG. S5, Example 2), A-to-I RNA editing between MPN stage and normal aged bone marrow:

FIG. 22A graphically illustrates expression STAT3α isoform in normal young (YBM), normal aged (ABM), and MPN stem cells and progenitors using normalized RNA-Seq data;

FIG. 22B graphically illustrates correlation of STAT3β isoform with ADAR1 p150 isoform in stem cells of aged bone marrow (ABM), young bone marrow (YBM), and MPN samples, the risk-group of MF patient is indicated;

FIG. 22C graphically illustrates self-renewal capacity as measured by colony replating assay in MF CD34+ HSPC transduced pCDH backbone or ADAR1 E912A deaminase mutant;

FIG. 22D graphically illustrates Beta-catenin activity was measured by flow cytometry in K562 BC CML cells stably transduced with pCDH lentiviral backbone or ADAR1 E912A mutant, as described in detail in Example 2, below.

Like reference symbols in the various drawings indicate like elements.

DETAILED DESCRIPTION

In alternative embodiments, provided are compositions, including products of manufacture and kits, and methods, for treating or ameliorating a cancer, such as a leukemia, by targeting a cancer cell such as a malignant leukemia progenitor.

Described herein is the discovery that in malignant leukemia progenitors, A-to-I editing of an miRNA binding site within the 3'UTR region (A-to-I editing prevents miRNA from binding) stabilizes MDM2 transcripts (MDM2 inhibits or represses expression of the p53 tumor suppressor protein), thereby enhancing blast crisis chronic myeloid leukemia progenitor propagation (i.e., non-edited miRNA binding sites within the 3'UTR region bind miRNA, resulting in de-stabilizing MDM2 transcripts, decreasing the amount of MDM2, increasing the amount of p53 tumor suppressor, decreasing e.g., leukemia cell, e.g., blast crisis chronic myeloid leukemia progenitor cell, propagation).

In an alternative embodiment, methods as provided herein further comprise inhibiting the expression of ADAR1, thereby inhibiting the stabilization of the MDM2 transcripts, which decrease the effective levels or activity of MDM2, thereby effectively increasing the amount or activity of p53 tumor suppressor protein (thereby decreasing e.g., leukemia cell, e.g., blast crisis chronic myeloid leukemia progenitor cell, propagation). In an alternative embodiment, inhibiting the expression of ADAR1 is by methods as described e.g., in U.S. Pat App pub no US/2017/0191057 A1.

We performed luciferase reporter assays that measured the efficiency of miRNA targeting of MDM2 3' UTR. The results indicated that once the RNA editable ADAR1 introduces A-to-G changes in an MDM2 3'UTR region, miRNA (i.e., miR-155) fails to target the transcript, resulting in up-regulation of MDM2 level in leukemia progenitors. Thus, for the first time we show functionally that 3'UTR A-to-I RNA editing in a 3'UTR region of a cancer promoter gene (MDM2) is associated with cancer progression by evading miRNA targeting.

In alternative embodiments, compositions and methods as provided herein are used to treat cancer, e.g., leukemia, patients who have elevated RNA editing in a cancer suppressor 3'UTR, or decreased RNA editing in a cancer promoter 3'UTR, thus making them more susceptible to cancer progression or relapse.

Pharmaceutical Compositions

In alternative embodiments, provided are pharmaceutical compositions and methods for: treating or ameliorating a cancer, wherein optionally the cancer is a leukemia or a myeloproliferative disorder in an individual in need thereof; inhibiting or slowing a leukemia progenitor cell propagation, inhibiting or slowing a blast crisis chronic myeloid leukemia progenitor propagation in an individual in need thereof; eliminating or reducing the numbers of pre-leukemia stem cells (pre-LSCs) in an individual in need thereof; reducing or eliminating the formation of leukemia stem cells (LCSs) in an individual in need thereof; and/or treating or ameliorating a myeloproliferative disorder in an individual in need thereof.

In alternative embodiments, compositions used to practice methods as provided herein are formulated with a pharmaceutically acceptable carrier. In alternative embodiments, the pharmaceutical compositions used to practice methods as provided herein can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

Therapeutic agents used to practice methods as provided herein can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions used to practice methods as provided herein include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Pharmaceutical formulations used to practice methods as provided herein can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, geltabs, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations used to practice methods as provided herein can also be used orally using, e.g., push-fit capsules made of gelatin, as well as soft, sealed capsules made of gelatin and a coating such as glycerol or sorbitol. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., a composition used to practice methods as provided herein) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil-based pharmaceuticals are particularly useful for administration hydrophobic active agents used to practice methods as provided herein. Oil-based suspensions can be formulated by suspending an active agent in a vegetable oil, such as *arachis* oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102. The pharmaceutical formulations as provided herein can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

Pharmaceutical compounds used to practice methods as provided herein can also be administered by in intranasal, intraocular and intravaginal routes including suppositories, insufflation, powders and aerosol formulations (for examples of steroid inhalants, see Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

Pharmaceutical compounds used to practice methods as provided herein can be delivered by transdermally, by a topical route, formulated as applicator sticks, solutions, suspensions, emulsions, gels, creams, ointments, pastes, jellies, paints, powders, and aerosols.

Pharmaceutical compounds used to practice methods as provided herein can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

Pharmaceutical compounds used to practice methods as provided herein can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations used to practice methods as provided herein can be lyophilized. Also provided are stable lyophilized formulations comprising a composition as provided herein, which can be made by lyophilizing a solution comprising a pharmaceutical as provided herein and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

The compositions and formulations used to practice methods as provided herein can be delivered by the use of liposomes (see also discussion, below). By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

The formulations used to practice methods as provided herein can be administered for prophylactic and/or therapeutic treatments. In therapeutic applications, compositions are administered to a subject already suffering from a condition, infection or disease in an amount sufficient to cure, alleviate or partially arrest the clinical manifestations of the condition, infection or disease and its complications (a "therapeutically effective amount"). For example, in alternative embodiments, pharmaceutical compositions as provided herein are administered in an amount sufficient to sensitize, increase sensitivity to or re-sensitize a tumor that is resistant to a cancer or anti-tumor drug. The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods as provided herein are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. For example, an exemplary pharmaceutical formulation for oral administration of compositions used to practice methods as provided herein can be in a daily amount of between about 0.1 to 0.5 to about 20, 50, 100 or 1000 or more ug per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The methods as provided herein can further comprise co-administration with other drugs or pharmaceuticals, e.g., compositions for treating cancer, septic shock, infection, fever, pain and related symptoms or conditions. For example, the methods and/or compositions and formulations as provided herein can be co-formulated with and/or co-administered with antibiotics (e.g., antibacterial or bacteriostatic peptides or proteins), particularly those effective against gram negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

Nanoparticles and Liposomes

Also provided are nanoparticles and liposomal membranes comprising compounds used to practice methods as provided herein, e.g., miRNA or antisense molecules, or small molecules, or antibodies. In alternative embodiments, also provided are nanoparticles and liposomal membranes targeting tumor (cancer) stem cells and dysfunctional stem cells. In one aspect, the compositions used to practice methods as provided herein are specifically targeted to cancer cells or cancer stem cells.

In alternative embodiments, also provided are nanoparticles and liposomal membranes comprising (in addition to comprising compounds used to practice methods as provided herein) molecules, e.g., peptides or antibodies, that selectively target abnormally growing, diseased, infected, dysfunctional and/or cancer (tumor) cell receptors. In alternative embodiments, also provided are nanoparticles and liposomal membranes using IL-11 receptor and/or the GRP78 receptor to targeted receptors on cells, e.g., on tumor cells, e.g., on prostate or ovarian cancer cells. See, e.g., U.S. patent application publication no. 20060239968.

Nanocells can be used to allow the sequential delivery of two different therapeutic agents with different modes of action or different pharmacokinetics, at least one of which comprises a composition used to practice methods as provided herein. A nanocell is formed by encapsulating a nanocore with a first agent inside a lipid vesicle containing a second agent; see, e.g., Sengupta, et al., U.S. Pat. Pub. No. 20050266067. The agent in the outer lipid compartment is released first and may exert its effect before the agent in the nanocore is released. The nanocell delivery system may be formulated in any pharmaceutical composition for delivery to patients suffering from a diseases or condition as described herein, e.g., cancer.

In one embodiment, a composition used to practice methods as provided herein is contained in the outer lipid vesicle of the nanocell, and another composition is loaded into the nanocore. This arrangement allows compositions used to practice methods as provided herein to be released first and delivered to the tumor.

Also provided are multilayered liposomes comprising compounds used to practice methods as provided herein, e.g., for transdermal absorption, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition used to practice methods as provided herein.

A multilayered liposome used to methods as provided herein may further include an antiseptic, an antioxidant, a stabilizer, a thickener, and the like to improve stability. Synthetic and natural antiseptics can be used, e.g., in an amount of 0.01% to 20%. Antioxidants can be used, e.g., BHT, erysorbate, tocopherol, astaxanthin, vegetable flavonoid, and derivatives thereof, or a plant-derived antioxidizing substance. A stabilizer can be used to stabilize liposome structure, e.g., polyols and sugars. Exemplary polyols include butylene glycol, polyethylene glycol, propylene glycol, dipropylene glycol and ethyl carbitol; examples of sugars are trehalose, sucrose, mannitol, sorbitol and chitosan, or a monosaccharides or an oligosaccharides, or a high molecular weight starch. A thickener can be used for improving the dispersion stability of constructed liposomes in water, e.g., a natural thickener or an acrylamide, or a synthetic polymeric thickener. Exemplary thickeners include natural polymers, such as acacia gum, xanthan gum, gellan gum, locust bean gum and starch, cellulose derivatives, such as hydroxy ethylcellulose, hydroxypropyl cellulose and carboxymethyl cellulose, synthetic polymers, such as polyacrylic acid, poly-acrylamide or polyvinylpyrollidone and polyvinylalcohol, and copolymers thereof or crosslinked materials.

Liposomes can be made using any method, e.g., as described in Park, et al., U.S. Pat. Pub. No. 20070042031, including method of producing a liposome by encapsulating a therapeutic product comprising providing an aqueous solution in a first reservoir; providing an organic lipid solution in a second reservoir, wherein one of the aqueous solution and the organic lipid solution includes a therapeutic product; mixing the aqueous solution with said organic lipid solution in a first mixing region to produce a liposome solution, wherein the organic lipid solution mixes with said aqueous solution so as to substantially instantaneously produce a liposome encapsulating the therapeutic product; and immediately thereafter mixing the liposome solution with a buffer solution to produce a diluted liposome solution.

Also provided are nanoparticles comprising compositions used to practice methods as provided herein, e.g., as a drug-containing nanoparticles (or a secondary nanoparticle), as described, e.g., in U.S. Pat. Pub. No. 20070077286. In one embodiment, also provided are nanoparticles comprising a fat-soluble drug used to practice methods as provided herein or a fat-solubilized water-soluble drug to act with a bivalent or trivalent metal salt.

Liposomes

The compositions and formulations used to practice methods as provided herein can be delivered by the use of liposomes. By using liposomes, particularly where the liposome surface carries ligands specific for target cells, or are otherwise preferentially directed to a specific organ or cell, e.g., cancer stem cells, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. For example, in one embodiment, compositions and formulations used to practice methods as provided herein are delivered by the use of liposomes having rigid lipids having head groups and hydrophobic tails, e.g., as using a polyethyleneglycol-linked lipid having a side chain matching at least a portion the lipid, as described e.g., in US Pat App Pub No. 20080089928. In another embodiment, compositions and formulations used to practice methods as provided herein are delivered by the use of amphoteric liposomes comprising a mixture of lipids, e.g., a mixture comprising a cationic amphiphile, an anionic amphiphile and/or neutral amphiphiles, as described e.g., in US Pat App Pub No. 20080088046, or 20080031937. In another embodiment, compositions and formulations used to practice methods as provided herein are delivered by the use of liposomes comprising a polyalkylene glycol moiety bonded through a thioether group and an antibody also bonded through a thioether group to the liposome, as described e.g., in US Pat App Pub No. 20080014255. In another embodiment, compositions and formulations used to practice methods as provided herein are delivered by the use of liposomes comprising glycerides, glycerophospholipides, glycerophosphinolipids, glycerophosphonolipids, sulfolipids, sphingolipids, phospholipids, isoprenolides, steroids, stearines, sterols and/or carbohydrate containing lipids, as described e.g., in US Pat App Pub No. 20070148220.

Antibodies as Pharmaceutical Compositions

In alternative embodiments, also provided are compositions and methods comprising antibodies or active fragments thereof for: treating or ameliorating a cancer, wherein optionally the cancer is a leukemia or a myeloproliferative disorder in an individual in need thereof; inhibiting or slowing a leukemia progenitor cell propagation, inhibiting or slowing a blast crisis chronic myeloid leukemia progenitor propagation in an individual in need thereof; eliminating or reducing the numbers of pre-leukemia stem cells (pre-LSCs) in an individual in need thereof; reducing or eliminating the formation of leukemia stem cells (LCSs) in an individual in need thereof; and/or treating or ameliorating a myeloproliferative disorder in an individual in need thereof.

In alternative embodiments, antibodies or active fragments thereof used to practice methods as provided herein can specifically bind to an inhibit: a Mouse Double Minute 2 homolog (MDM2) protein, message (mRNA) or gene; an APOBEC3G (A3G) protein, message (mRNA) or gene, and/or an ADAR1p150 protein, message (mRNA) or gene.

In alternative aspects, an antibody for practicing methods as provided herein can comprise a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. In alternative aspects, an antibody for practicing methods as provided herein includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

In alternative embodiments, methods as provided herein uses "humanized" antibodies, including forms of non-human (e.g., murine) antibodies that are chimeric antibodies comprising minimal sequence (e.g., the antigen binding fragment) derived from non-human immunoglobulin. In alternative embodiments, humanized antibodies are human immunoglobulins in which residues from a hypervariable region (HVR) of a recipient (e.g., a human antibody sequence) are replaced by residues from a hypervariable region (HVR) of a non-human species (donor antibody) such as mouse, rat, rabbit or nonhuman primate having the desired specificity, affinity, and capacity. In alternative embodiments, framework region (FR) residues of the human immunoglobulin are replaced by corresponding non-human residues to improve antigen binding affinity.

In alternative embodiments, humanized antibodies may comprise residues that are not found in the recipient antibody or the donor antibody. These modifications may be made to improve antibody affinity or functional activity. In alternative embodiments, the humanized antibody can comprise substantially all of at least one, and typically two, variable domains, in which all or substantially all of the hypervariable regions correspond to those of a non-human immunoglobulin and all or substantially all of Ab framework regions are those of a human immunoglobulin sequence.

In alternative embodiments, a humanized antibody used to practice methods as provided herein can comprise at least a portion of an immunoglobulin constant region (Fc), typically that of or derived from a human immunoglobulin.

However, in alternative embodiments, completely human antibodies also can be used to practice methods as provided herein, including human antibodies comprising amino acid sequence which corresponds to that of an antibody produced by a human. This definition of a human antibody specifically excludes a humanized antibody comprising non-human antigen binding residues.

In alternative embodiments, antibodies used to practice methods as provided herein comprise "affinity matured" antibodies, e.g., antibodies comprising with one or more alterations in one or more hypervariable regions which result in an improvement in the affinity of the antibody for antigen; e.g., a Mouse Double Minute 2 homolog (MDM2) protein, message (mRNA) or gene; an APOBEC3G (A3G) protein, message (mRNA) or gene, and/or an ADAR1p150 protein, message (mRNA) or gene, compared to a parent antibody which does not possess those alteration(s). In alternative embodiments, antibodies used to practice methods as provided herein are matured antibodies having nanomolar or even picomolar affinities for the target antigen, e.g., a Mouse Double Minute 2 homolog (MDM2) protein, message (mRNA) or gene; an APOBEC3G (A3G) protein, message (mRNA) or gene, and/or an ADAR1p150 protein, message (mRNA) or gene. Affinity matured antibodies can be produced by procedures known in the art.

Antisense, siRNAs and microRNAs as Pharmaceutical Compositions

In alternative embodiments, also provided are compositions and methods for inhibiting or depleting a Mouse Double Minute 2 homolog (MDM2) protein, message (mRNA) or gene; an APOBEC3G (A3G) protein, message (mRNA) or gene, and/or an ADAR1p150 protein, message (mRNA) or gene. In alternative embodiments, this is achieved by administration of inhibitory nucleic acids, e.g., siRNA, antisense nucleic acids, and/or inhibitory microRNAs.

In alternative embodiments, compositions used to practice methods as provided herein are formulated with a pharmaceutically acceptable carrier. In alternative embodiments, the pharmaceutical compositions used to practice methods as provided herein can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

While methods as provided herein is not limited by any particular mechanism of action: microRNAs (miRNAs) are short (20-24 nt) non-coding RNAs that are involved in post-transcriptional regulation of gene expression in multicellular organisms by affecting both the stability and translation of mRNAs. miRNAs are transcribed by RNA polymerase II as part of capped and polyadenylated primary transcripts (pri-miRNAs) that can be either protein-coding or non-coding. The primary transcript is cleaved by the Drosha ribonuclease III enzyme to produce an approximately 70-nt stem-loop precursor miRNA (pre-miRNA), which is further cleaved by the cytoplasmic Dicer ribonuclease to generate the mature miRNA and antisense miRNA star (miRNA*) products. The mature miRNA is incorporated into a RNA-induced silencing complex (RISC), which recognizes target mRNAs through imperfect base pairing with the miRNA and most commonly results in translational inhibition or destabilization of the target mRNA.

In alternative embodiments pharmaceutical compositions used to practice methods as provided herein are administered in the form of a dosage unit, e.g., a tablet, capsule, bolus, spray. In alternative embodiments, pharmaceutical compositions comprise a compound, e.g., an antisense nucleic acid, e.g., an siRNA or a microRNA, in a dose: e.g., 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, or 800 mg or more.

In alternative embodiments, an siRNA or a microRNA used to practice methods as provided herein is administered as a pharmaceutical agent, e.g., a sterile formulation, e.g., a lyophilized siRNA or microRNA that is reconstituted with a suitable diluent, e.g., sterile water for injection or sterile saline for injection. In alternative embodiments the reconstituted product is administered as a subcutaneous injection or as an intravenous infusion after dilution into saline. In alternative embodiments the lyophilized drug product comprises siRNA or microRNA prepared in water for injection, or in saline for injection, adjusted to pH 7.0-9.0 with acid or base during preparation, and then lyophilized. In alternative embodiments a lyophilized siRNA or microRNA as provided herein is between about 25 to 800 or more mg, or about 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of a siRNA or microRNA as provided herein. The lyophilized siRNA or microRNA as provided herein can be packaged in a 2 mL Type I, clear glass vial (e.g., ammonium sulfate-treated), e.g., stoppered with a bromobutyl rubber closure and sealed with an aluminum overseal.

In alternative embodiments, also provided are compositions and methods comprising in vivo delivery of antisense nucleic acids, e.g., siRNA or microRNAs. In practicing methods as provided herein, the antisense nucleic acids, siRNAs, or microRNAs can be modified, e.g., in alternative embodiments, at least one nucleotide of antisense nucleic acid, e.g., siRNA or microRNA, construct is modified, e.g., to improve its resistance to nucleases, serum stability, target specificity, blood system circulation, tissue distribution, tissue penetration, cellular uptake, potency, and/or cell-permeability of the polynucleotide. In alternative embodiments, the antisense nucleic acid, siRNA or microRNA construct is unmodified. In other embodiments, at least one nucleotide in the antisense nucleic acid, siRNA or microRNA construct is modified.

In alternative embodiments, guide strand modifications are made to increase nuclease stability, and/or lower interferon induction, without significantly decreasing antisense nucleic acid, siRNA or microRNA activity (or no decrease in antisense nucleic acid, siRNA or microRNA activity at all). In certain embodiments, the modified antisense nucleic acid, siRNA or microRNA constructs have improved stability in serum and/or cerebral spinal fluid compared to an unmodified structure having the same sequence.

In alternative embodiments, a modification includes a 2'-H or 2'-modified ribose sugar at the second nucleotide from the 5'-end of the guide sequence. In alternative embodiments, the guide strand (e.g., at least one of the two single-stranded polynucleotides) comprises a 2'-O-alkyl or 2'-halo group, such as a 2'-O-methyl modified nucleotide, at the second nucleotide on the 5'-end of the guide strand, or, no other modified nucleotides. In alternative embodiments, polynucleotide constructs having such modification may have enhanced target specificity or reduced off-target silencing compared to a similar construct without the 2'-O-methyl modification at the position.

In alternative embodiments, a second nucleotide is a second nucleotide from the 5'-end of the single-stranded polynucleotide. In alternative embodiments, a "2'-modified ribose sugar" comprises ribose sugars that do not have a 2'-OH group. In alternative embodiments, a "2'-modified ribose sugar" does not include 2'-deoxyribose (found in unmodified canonical DNA nucleotides), although one or more DNA nucleotides may be included in the subject constructs (e.g., a single deoxyribonucleotide, or more than one deoxyribonucleotide in a stretch or scattered in several parts of the subject constructs). For example, the 2'-modified ribose sugar may be 2'-O-alkyl nucleotides, 2'-deoxy-2'-fluoro nucleotides, 2'-deoxy nucleotides, or combination thereof.

In alternative embodiments, an antisense nucleic acid, siRNA or microRNA construct used to practice methods as provided herein comprises one or more 5'-end modifications, e.g., as described above, and can exhibit a significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified 5'-end modification, thus greatly improving the overall specificity of the antisense nucleic acid, siRNA or microRNA construct as provided herein.

In alternative embodiments, an antisense nucleic acid, siRNA or microRNA construct to practice methods as provided herein comprises a guide strand modification that further increase stability to nucleases, and/or lowers interferon induction, without significantly decreasing activity (or no decrease in microRNA activity at all). In alternative embodiments, the 5'-stem sequence comprises a 2'-modified ribose sugar, such as 2'-O-methyl modified nucleotide, at the second nucleotide on the 5'-end of the polynucleotide, or, no other modified nucleotides. In alternative embodiments the hairpin structure having such modification has enhanced target specificity or reduced off-target silencing compared to a similar construct without the 2'-O-methyl modification at same position.

In alternative embodiments, the 2'-modified nucleotides are some or all of the pyrimidine nucleotides (e.g., C/U). Examples of 2'-O-alkyl nucleotides include a 2'-O-methyl nucleotide, or a 2'-O-allyl nucleotide. In alternative embodiments, the modification comprises a 2'-O-methyl modification at alternative nucleotides, starting from either the first or the second nucleotide from the 5'-end. In alternative embodiments, the modification comprises a 2'-O-methyl modification of one or more randomly selected pyrimidine nucleotides (C or U). In alternative embodiments, the modification comprises a 2'-O-methyl modification of one or more nucleotides within the loop.

In alternative embodiments, the modified nucleotides are modified on the sugar moiety, the base, and/or the phosphodiester linkage. In alternative embodiments the modification comprise a phosphate analog, or a phosphorothioate linkage; and the phosphorothioate linkage can be limited to one or more nucleotides within the loop, a 5'-overhang, and/or a 3'-overhang.

In alternative embodiments, the phosphorothioate linkage may be limited to one or more nucleotides within the loop, and 1, 2, 3, 4, 5, or 6 more nucleotide(s) of the guide sequence within the double-stranded stem region just 5' to the loop. In alternative embodiments, the total number of nucleotides having the phosphorothioate linkage may be about 12-14. In alternative embodiments, all nucleotides having the phosphorothioate linkage are not contiguous. In alternative embodiments, the modification comprises a 2'-O-methyl modification, or, no more than 4 consecutive nucleotides are modified. In alternative embodiments, all nucleotides in the 3'-end stem region are modified. In alternative embodiments, all nucleotides 3' to the loop are modified.

In alternative embodiments, the 5'- or 3'-stem sequence comprises one or more universal base-pairing nucleotides. In alternative embodiments universal base-pairing nucleotides include extendable nucleotides that can be incorporated into a polynucleotide strand (either by chemical synthesis or by a polymerase), and pair with more than one pairing type of specific canonical nucleotide. In alternative embodiments, the universal nucleotides pair with any specific nucleotide. In alternative embodiments, the universal nucleotides pair with four pairings types of specific nucleotides or analogs thereof. In alternative embodiments, the universal nucleotides pair with three pairings types of specific nucleotides or analogs thereof. In alternative embodiments, the universal nucleotides pair with two pairings types of specific nucleotides or analogs thereof.

In alternative embodiments, an antisense nucleic acid, siRNA or microRNA used to practice methods as provided herein comprises a modified nucleoside, e.g., a sugar-modified nucleoside. In alternative embodiments, the sugar-modified nucleosides can further comprise a natural or modified heterocyclic base moiety and/or a natural or modified internucleoside linkage; or can comprise modifications independent from the sugar modification. In alternative embodiments, a sugar modified nucleoside is a 2'-modified nucleoside, wherein the sugar ring is modified at the 2' carbon from natural ribose or 2'-deoxy-ribose.

In alternative embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In alternative embodiments, the bicyclic sugar moiety is an L sugar in the beta configuration.

In alternative embodiments, the bicyclic sugar moiety comprises a bridge group between the 2' and the 4'-carbon atoms. In alternative embodiments, the bridge group comprises from 1 to 8 linked biradical groups. In alternative embodiments, the bicyclic sugar moiety comprises from 1 to 4 linked biradical groups. In alternative embodiments, the bicyclic sugar moiety comprises 2 or 3 linked biradical groups.

In alternative embodiments, the bicyclic sugar moiety comprises 2 linked biradical groups. In alternative embodiments, a linked biradical group is selected from —O—, —S—, —N(R1)-, —C(R1)(R$_2$)—, —C(R1)=C(R1)-, —C(R1)=N—, —C(=NR1)-, —Si(R1)(R$_2$)—, —S(=O)$_2$—, —S(=O)—, —C(=O)— and —C(=S)—; where each R1 and R$_2$ is, independently, H, hydroxyl, C1 to C$_{12}$ alkyl, substituted C1-C12 alkyl, C$_2$-C12 alkenyl, substituted C$_2$-C$_{12}$ alkenyl, C$_2$-C$_{12}$ alkynyl, substituted C$_2$-C12 alkynyl, C$_2$-C20 aryl, substituted C$_2$-C20 aryl, a heterocycle radical, a substituted heterocycle radical, heteroaryl, substituted heteroaryl, C$_2$-C$_7$ alicyclic radical, substituted C$_2$-C$_7$ alicyclic radical, halogen, substituted oxy (—O—), amino, substituted amino, azido, carboxyl, substituted carboxyl, acyl, substituted acyl, CN, thiol, substituted thiol, sulfonyl (S(=O)$_2$—H), substituted sulfonyl, sulfoxyl (S(=O)—H) or substituted sulfoxyl; and each substituent group is, independently, halogen, C1-C$_{12}$ alkyl, substituted C1-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, amino, substituted amino, acyl, substituted acyl, C1-C$_{12}$ aminoalkyl, C1-C$_{12}$ aminoalkoxy, substituted C1-C$_{12}$ aminoalkyl, substituted C1-C$_{12}$ aminoalkoxy or a protecting group.

In alternative embodiments, the bicyclic sugar moiety is bridged between the 2' and 4' carbon atoms with a biradical group selected from —O—(CH$_2$)x—, —O—CH$_{21}$—, —O—CH$_2$CH$_2$—, —O—CH(alkyl)-, —NH—(CH2)P—, —N(alkyl)-(CH$_2$)x-, —O—CH(alkyl)-, —(CH(alkyl))-(CH2)x-, —NH—O—(CH$_2$)x-, —N(alkyl)-O—(CH$_2$)x-, or —O—N(alkyl)-(CH$_2$)x-, wherein x is 1, 2, 3, 4 or 5 and each alkyl group can be further substituted. In certain embodiments, x is 1, 2 or 3.

In alternative embodiments, a 2'-modified nucleoside comprises a 2'-substituent group selected from halo, allyl, amino, azido, SH, CN, OCN, CF$_3$, OCF$_3$, O—, S—, or N(Rm)-alkyl; O—, S—, or N(Rm)-alkenyl; O—, S— or N(Rm)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(Rm)(Rn) or O—CH2-C(=O)—N(Rm)(Rn), where each Rm and Rn is, independently, H, an amino protecting group or substituted or unsubstituted C1-C10 alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In alternative embodiments, a 2'-modified nucleoside comprises a 2'-substituent group selected from F, O—CH$_3$, and OCH$_2$CH2OCH$_3$.

In alternative embodiments, a sugar-modified nucleoside is a 4'-thio modified nucleoside. In alternative embodiments, a sugar-modified nucleoside is a 4'-thio-2'-modified nucleoside. In alternative embodiments a 4'-thio modified nucleoside has a .beta.-D-ribonucleoside where the 4'-O replaced with 4'-S. A 4'-thio-2'-modified nucleoside is a 4'-thio modified nucleoside having the 2'-OH replaced with a 2'-substituent group. In alternative embodiments 2'-substituent groups include 2'-OCH$_3$, 2'-O—(CH2)$_2$-OCH$_3$, and 2'-F.

In alternative embodiments, a modified oligonucleotide of the present invention comprises one or more internucleoside modifications. In alternative embodiments, each internucleoside linkage of a modified oligonucleotide is a modified internucleoside linkage. In alternative embodiments, a modified internucleoside linkage comprises a phosphorus atom.

In alternative embodiments, a modified antisense nucleic acid, siRNA or microRNA comprises at least one phosphorothioate internucleoside linkage. In certain embodiments, each internucleoside linkage of a modified oligonucleotide is a phosphorothioate internucleoside linkage.

In alternative embodiments, a modified internucleoside linkage does not comprise a phosphorus atom. In alternative embodiments, an internucleoside linkage is formed by a short chain alkyl internucleoside linkage. In alternative embodiments, an internucleoside linkage is formed by a cycloalkyl internucleoside linkages. In alternative embodiments, an internucleoside linkage is formed by a mixed heteroatom and alkyl internucleoside linkage. In alternative embodiments, an internucleoside linkage is formed by a mixed heteroatom and cycloalkyl internucleoside linkages. In alternative embodiments, an internucleoside linkage is formed by one or more short chain heteroatomic internucleoside linkages. In alternative embodiments, an internucleoside linkage is formed by one or more heterocyclic internucleoside linkages. In alternative embodiments, an internucleoside linkage has an amide backbone, or an internucleoside linkage has mixed N, O, S and CH2 component parts.

In alternative embodiments, a modified oligonucleotide comprises one or more modified nucleobases. In certain embodiments, a modified oligonucleotide comprises one or more 5-methylcytosines, or each cytosine of a modified oligonucleotide comprises a 5-methylcytosine.

In alternative embodiments, a modified nucleobase comprises a 5-hydroxymethyl cytosine, 7-deazaguanine or 7-deazaadenine, or a modified nucleobase comprises a 7-deaza-adenine, 7-deazaguanosine, 2-aminopyridine or a 2-pyridone, or a modified nucleobase comprises a 5-substituted pyrimidines, 6-azapyrimidines and N-2, N-6 and O-6 substituted purines, or a 2 aminopropyladenine, 5-propynyluracil or a 5-propynylcytosine.

In alternative embodiments, a modified nucleobase comprises a polycyclic heterocycle, or a tricyclic heterocycle; or, a modified nucleobase comprises a phenoxazine derivative, or a phenoxazine further modified to form a nucleobase or G-clamp.

Therapeutically Effective Amount and Doses

In alternative embodiment, compounds, compositions, pharmaceutical compositions and formulations used to practice methods as provided herein can be administered for prophylactic and/or therapeutic treatments, e.g., for treating or ameliorating a cancer, wherein optionally the cancer is a leukemia or a myeloproliferative disorder in an individual in need thereof; inhibiting or slowing a leukemia progenitor cell propagation, inhibiting or slowing a blast crisis chronic myeloid leukemia progenitor propagation in an individual in need thereof; eliminating or reducing the numbers of pre-leukemia stem cells (pre-LSCs) in an individual in need thereof; reducing or eliminating the formation of leukemia stem cells (LCSs) in an individual in need thereof; and/or treating or ameliorating a myeloproliferative disorder in an individual in need thereof.

For example, also provided are compositions and methods for increasing the growth-inhibiting effectiveness of an anti-cancer drug, e.g., a Growth Factor inhibitor on a cell, e.g., a cancer cell, or, a method for re-sensitizing a cell to a Growth Factor Inhibitor.

In alternative embodiments, also provided are compositions and methods for treating, preventing or ameliorating: a disease or condition associated with dysfunctional stem cells or cancer stem cells (a "therapeutically effective amount"). In the methods as provided herein, a pharmaceutical composition is administered in an amount sufficient to treat (e.g., ameliorate) or prevent a disease or condition associated with dysfunctional stem cells or cancer stem cells.

The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

Products of Manufacture and Kits

Provided are products of manufacture and kits for practicing methods as provided herein, including instructions for practicing methods as provided herein. In alternative embodiments, also provided are kits, blister packages, lidded blisters or blister cards or packets, clamshells, trays or shrink wraps comprising a compound or a pharmaceutical composition used to practice a method as provided herein; for example, including instructions for: treating or ameliorating a cancer, wherein optionally the cancer is a leukemia or a myeloproliferative disorder in an individual in need thereof; inhibiting or slowing a leukemia progenitor cell propagation, inhibiting or slowing a blast crisis chronic myeloid leukemia progenitor propagation in an individual in need thereof; eliminating or reducing the numbers of pre-leukemia stem cells (pre-LSCs) in an individual in need thereof; reducing or eliminating the formation of leukemia stem cells (LCSs) in an individual in need thereof; and/or treating or ameliorating a myeloproliferative disorder in an individual in need thereof.

Any of the above aspects and embodiments can be combined with any other aspect or embodiment as disclosed here in the Summary and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects as provided herein. Although methods as provided herein have been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the examples described herein; however, it is to be understood that the invention is not limited to such examples.

EXAMPLES

Unless stated otherwise in the Examples, all recombinant DNA techniques are carried out according to standard protocols, for example, as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Example 1: Hyper-Editing of Cell Cycle Regulatory and Tumor Suppressor RNA Promotes Malignant Progenitor Propagation This example demonstrates that methods and compositions as provided herein are effective and can be used to inhibit the expression of MDM2 (a tumor promoting protein), e.g., by inhibiting or decreasing 3'UTR region A-to-I editing, which increases miRNA binding to destabilize MDM2 transcripts to increase e.g., p53 tumor suppressor protein, and thereby can be used to suppress propagation of a cancer cell, e.g., such as a leukemia cell, e.g., a malignant leukemia progenitor.

Here we show that ADAR1 drives malignant progenitor cell cycle deregulation through hyper-editing of cell cycle regulatory and tumor suppressor coding and non-coding transcripts. When activated in normal human hematopoietic progenitors, A-to-I editing impairs miR-26a maturation, which represses CDKN1A expression via EZH2 thereby accelerating cell cycle transit. However, in blast crisis chronic myeloid leukemia progenitors, decreased EZH2 and increased CDKN1A oppose the cell cycle accelerating effect. In malignant progenitors, A-to-I editing of miRNA binding site within 3'UTR region stabilizes MDM2 transcripts thereby enhancing BC progenitor propagation. These data reveal a dual mechanism governing pre-leukemic progenitor transformation that is predicated on hyper-editing of cell cycle regulatory miRNAs and the 3'UTR binding site of tumor suppressor miRNAs.

Results

Figure 7A:
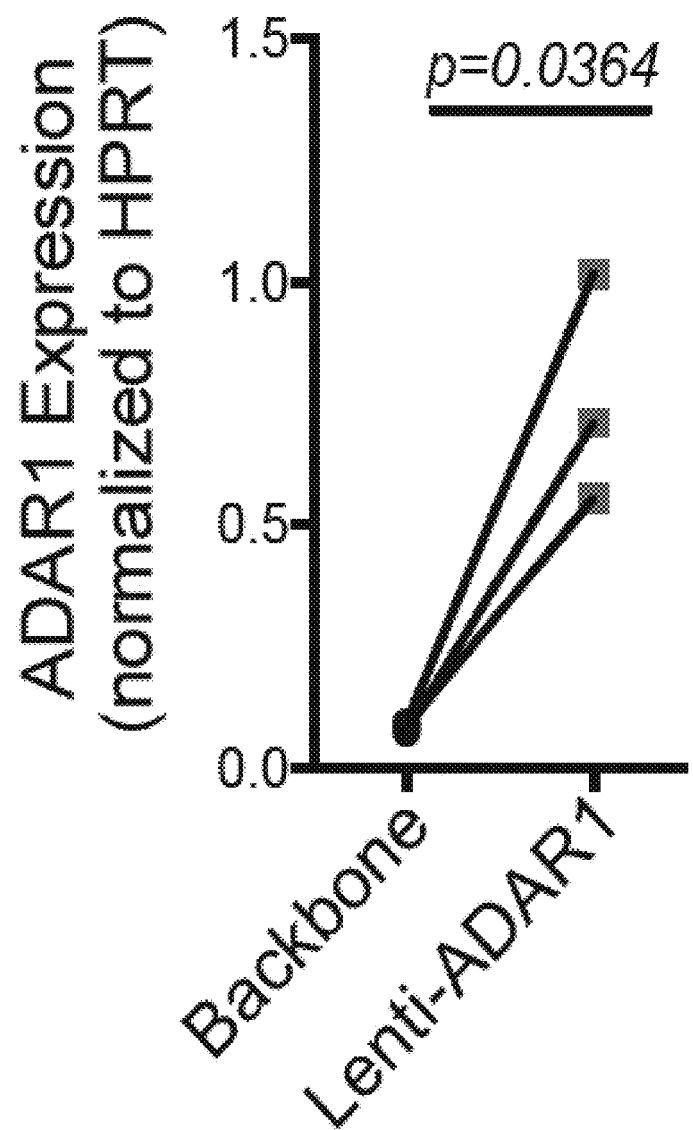
Figure 7C:
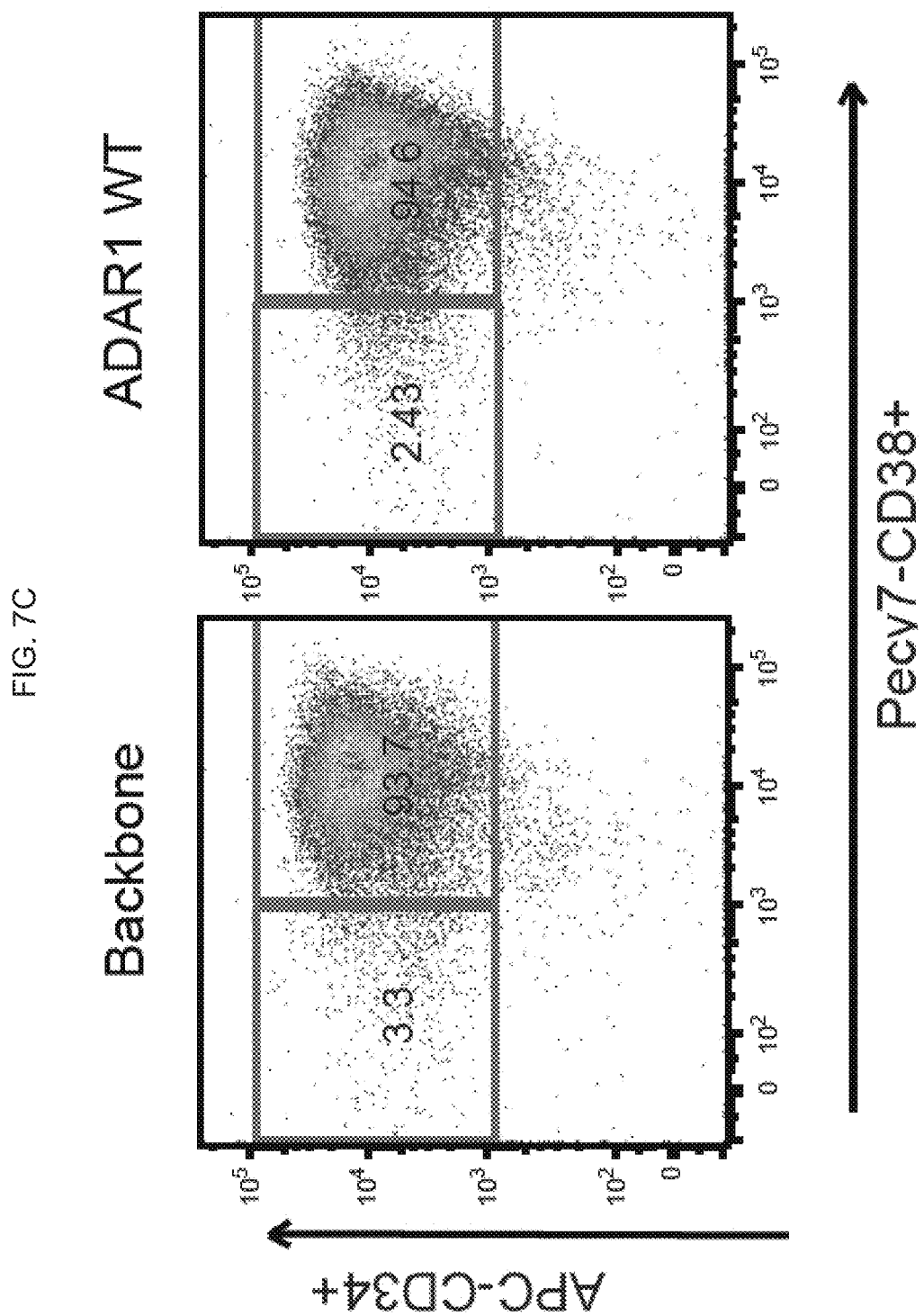
Figure 7D:
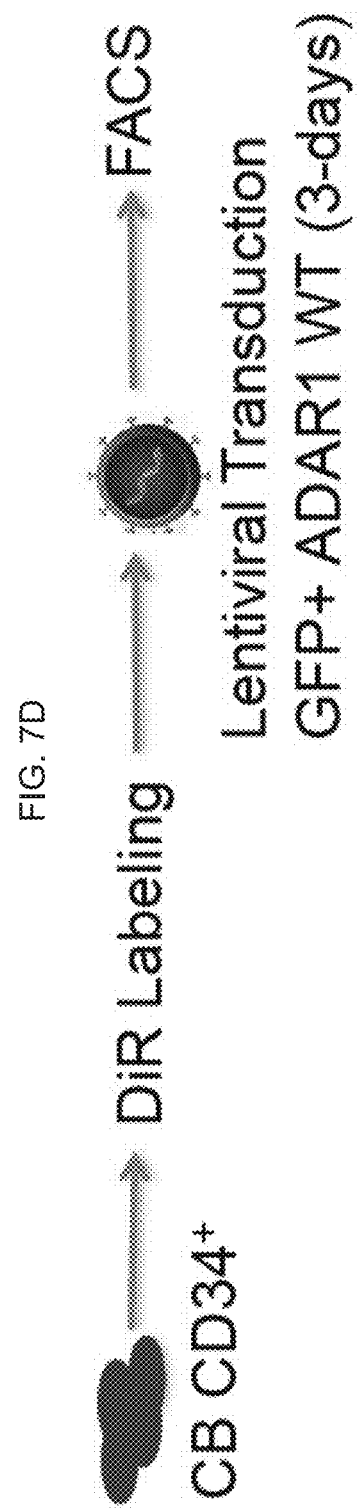
Figure 7E:
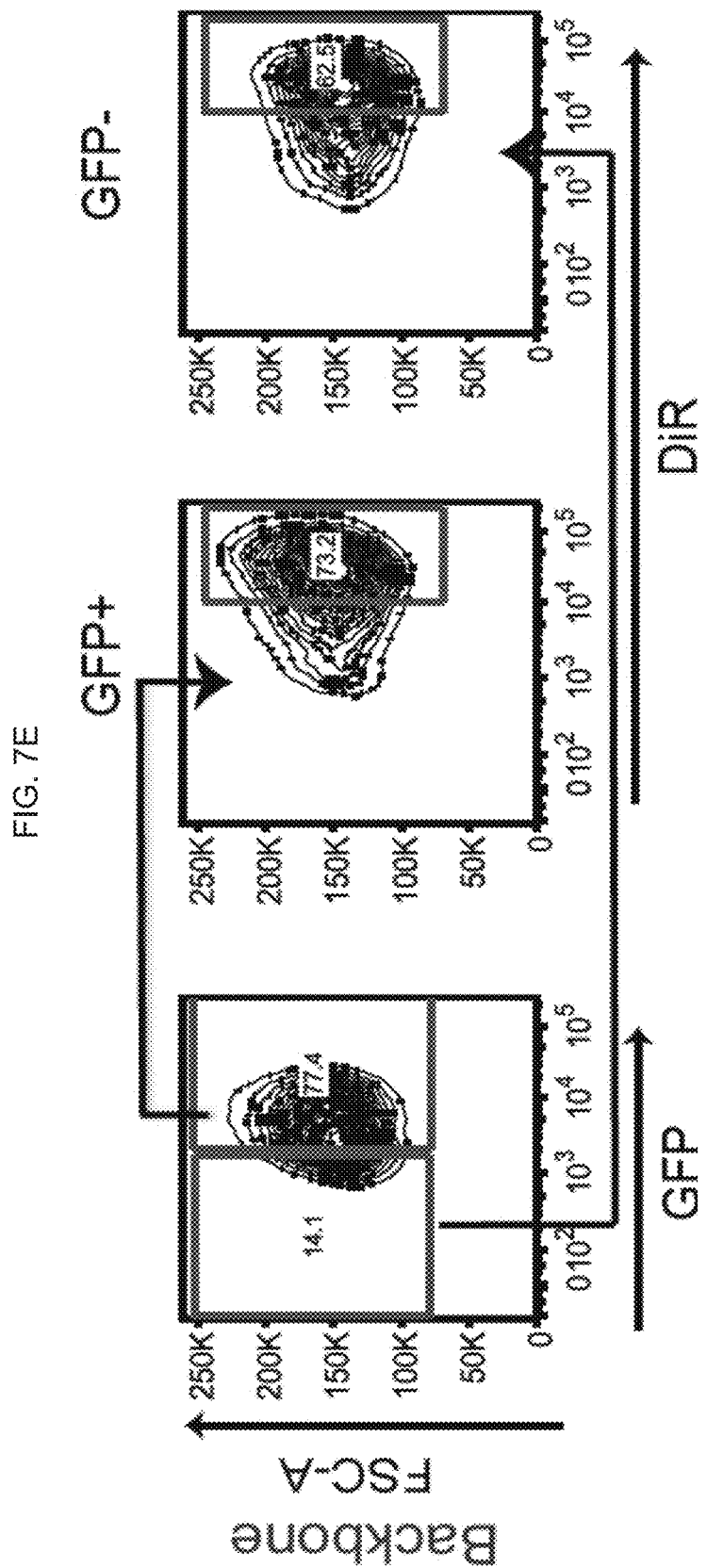
Figure 7F:
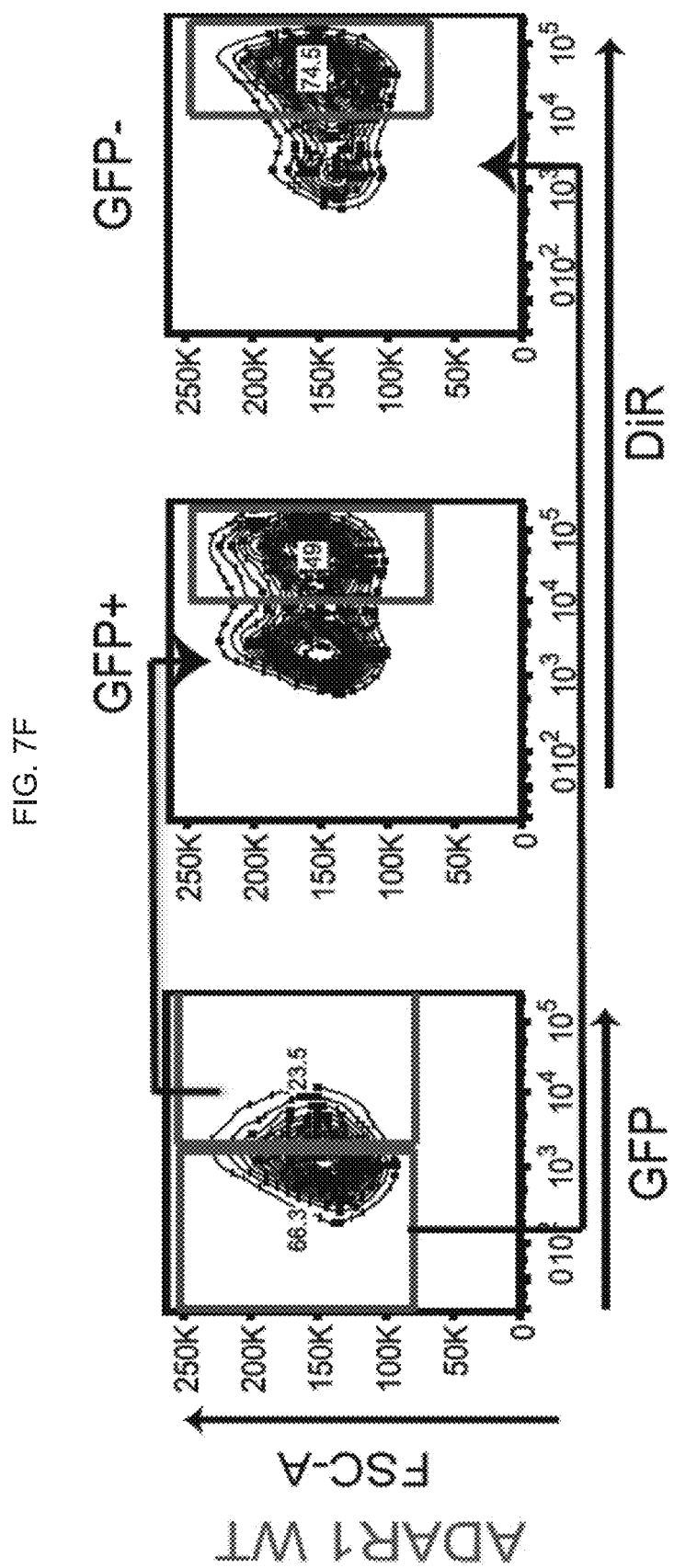
Figure 7H:
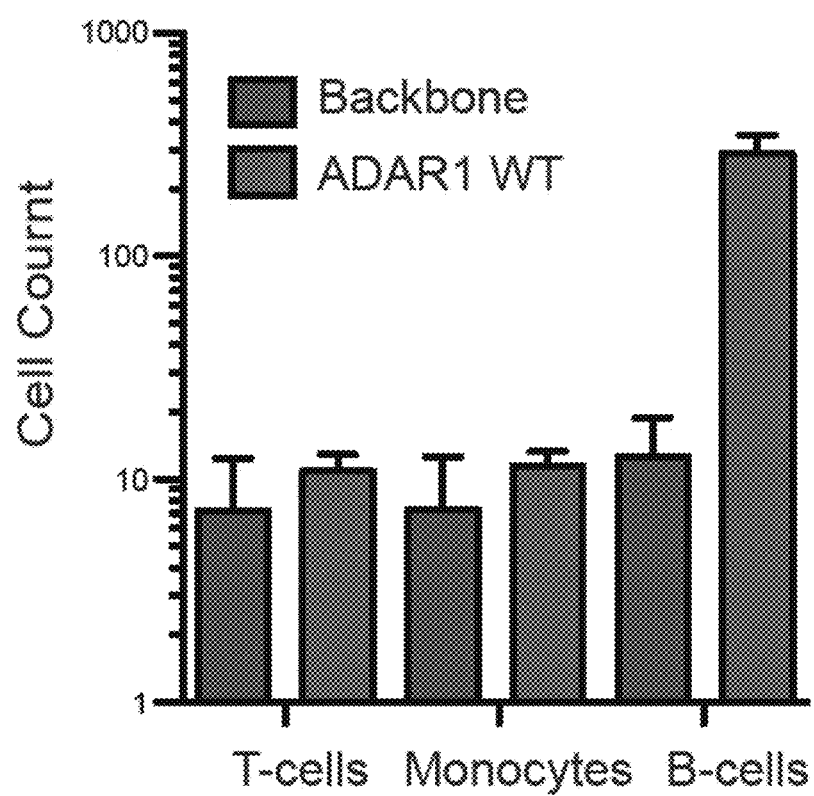
FIG. 7H graphically illustrates data from a flow analysis showing cell counts of differentiated cord blood CD34$^+$ cells post lenti-ADAR1 WT transduction (as compared to backbone transduction), as discussed in further detail in Example 1, below.
Figure 8B:
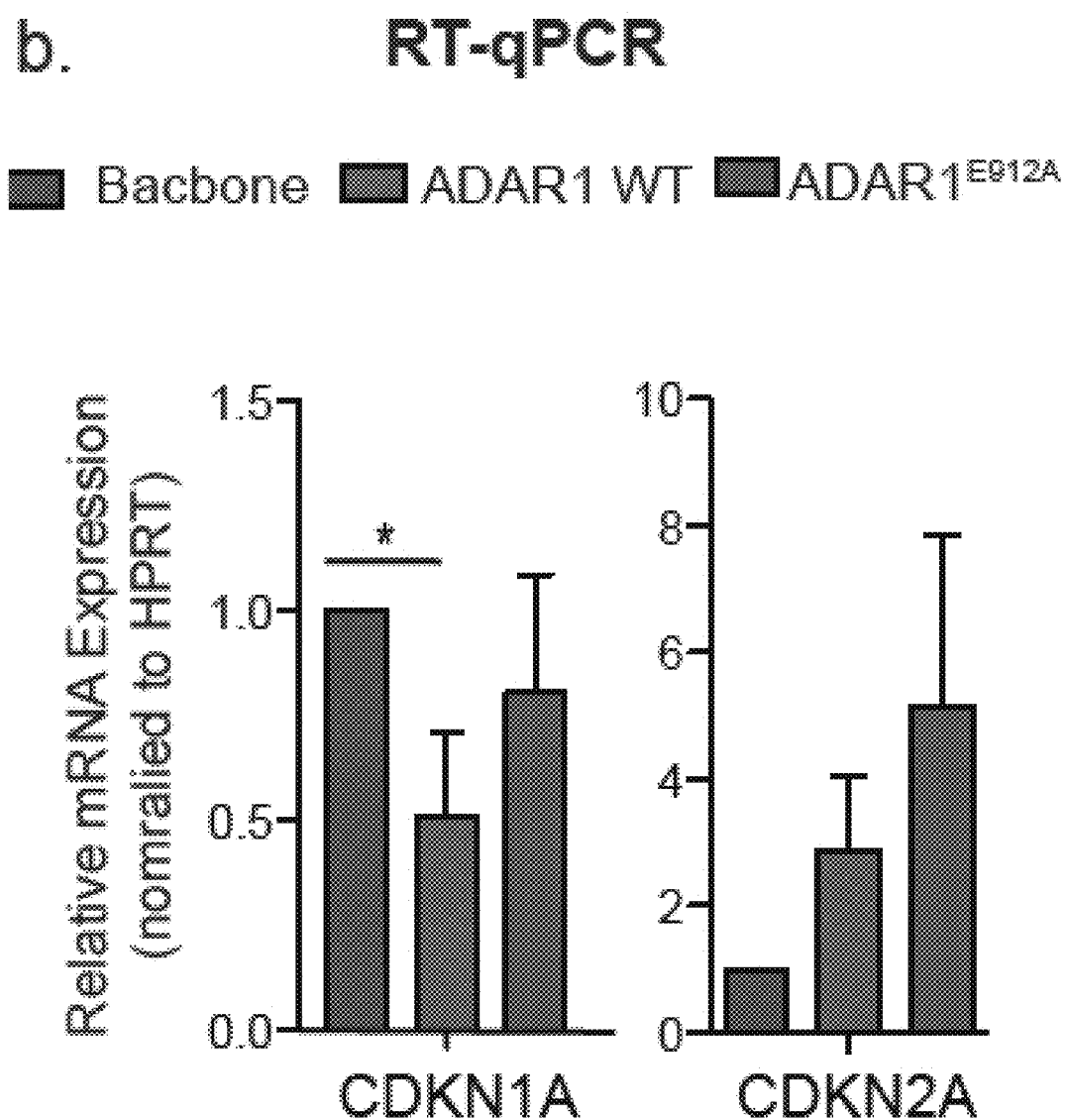
Figure 8C:
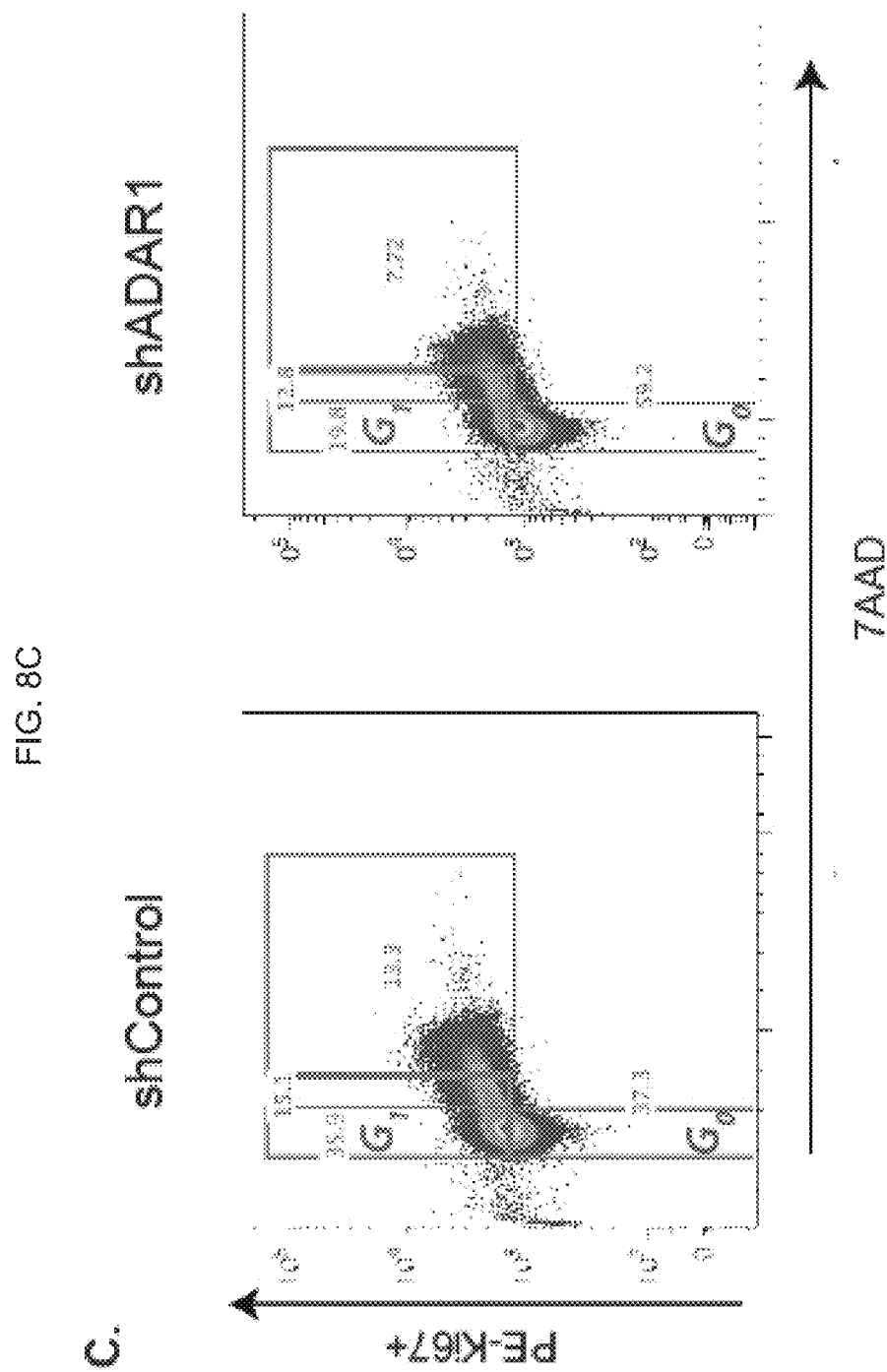

ADAR1 Activation Induces Hematopoietic Stem and Progenitor (HSPC) Cell Cycle Transit To gain insight into the function of ADAR1 in normal HSPC, normal cord blood CD34$^+$ cells were lentivirally transduced with ADAR1 wild-type (WT) or an editing defective mutant, ADAR1$^{E921A}$ labeled with GFP (FIG. 1). Overexpression of ADAR1 WT induced proliferation of both stem (CD34$^+$38$^-$Lin$^-$) and progenitor (CD34$^+$38$^+$Lin$^-$) populations and increased Ki67 expression, as shown by immunostaining (FIGS. 1A-1E and FIG. 7A-FIG. 7C). Moreover, DiR-labeled GFP$^+$ ADAR1-WT expressing HSPCs quickly lost DiR signal, indicative of accelerated cell cycle transit (FIGS. 1F-G and FIG. 7D-F). Interestingly, ADAR1 increased B cell (CD19$^+$) expansion, which concurs with the recent finding that ADAR1 is required for B-cell lineage development (Marcu-Malina et al., 2016) (FIG. 7G-H). Moreover, RNA-seq and q-RT-PCR array analyses revealed that overexpression of ADAR1 WT significantly altered KEGG cell cycle regulatory transcript expression (FIGS. 1I-K and FIG. 8A). Differential expression of certain cell cycle transcripts was observed with ADAR1 WT but not ADAR1$^{E921A}$ suggesting these cell cycle transcript changes were A-to-I RNA editing dependent (Zipeto et al., 2016) (FIG. 1H and FIG. 8B). Interestingly, expression of a cyclin-dependent kinase inhibitor, CDKN1A, which induces quiescence in response to DNA damage, was reduced following lentivirally enforced ADAR1 WT expression and is the central hub for cell cycle regulation by ADAR1 WT (FIGS. 1I-M). To ascertain the effect of ADAR1 in HSPC cell cycle regulation, we also performed ADAR1 knockdown in cord blood HSPCs with shRNA lentiviral construct targeting ADAR1 (Jiang et al., 2013; Zipeto et al., 2016) (FIGS. 1N-P and FIG. 2D). As expected, knockdown of ADAR1 displayed a reversal of ADAR1 overexpression phenotypes, including increased quiescent G$_0$ population, as well as increased CDKN1A expression (FIGS. 1N-P and FIG. 8D). In contrast to ADAR1 overexpression (Zipeto et al., 2016), ADAR1 knockdown reduced HSPC self-renewal (FIG. 1P).

ADAR1 Pri-miRNA Editing Regulates Progenitor Cell Cycle Transit

Figure 2A:
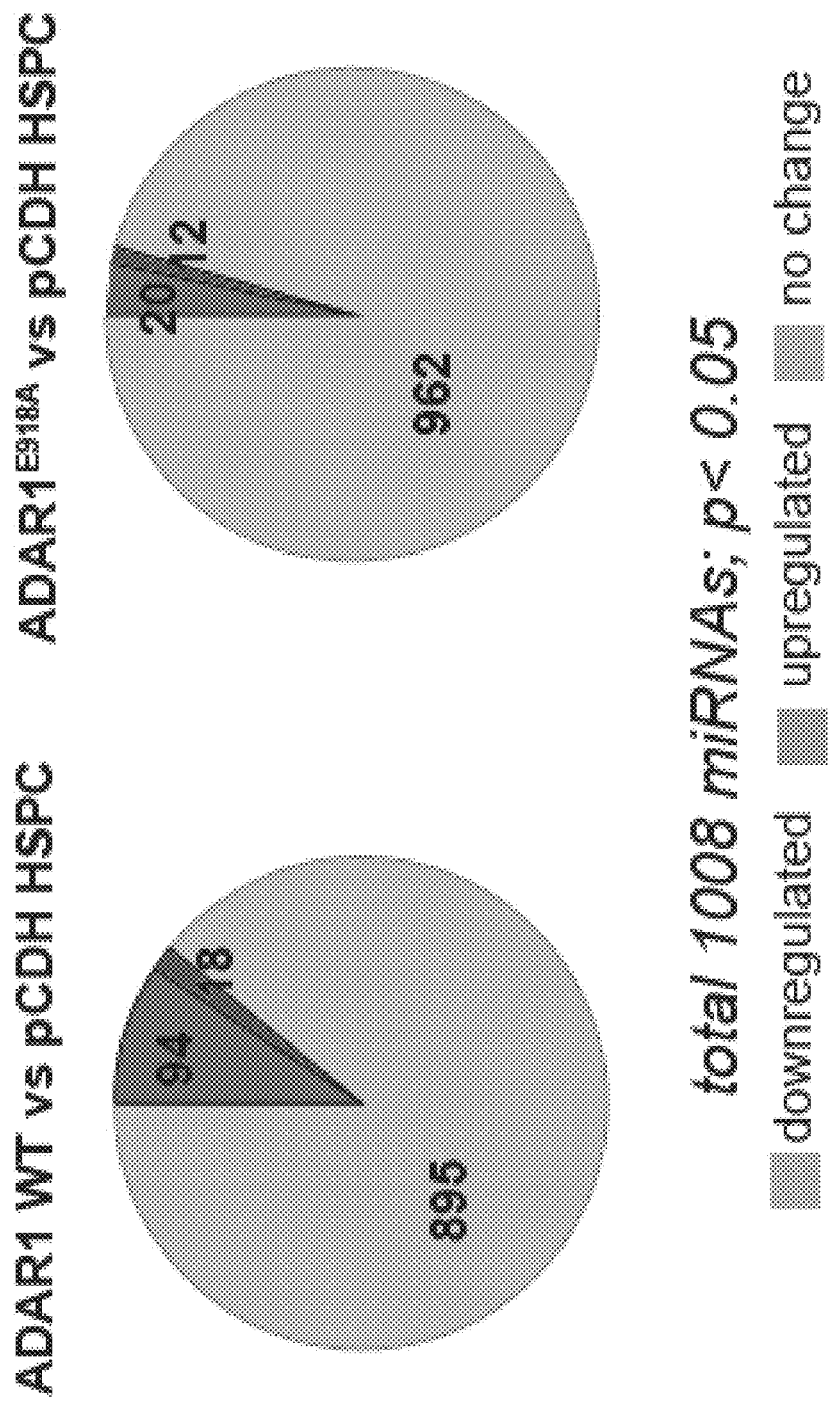
FIG. 2A-D illustrate the regulation of miRNome by ADAR1 in normal HSPCs.
Figure 2B:
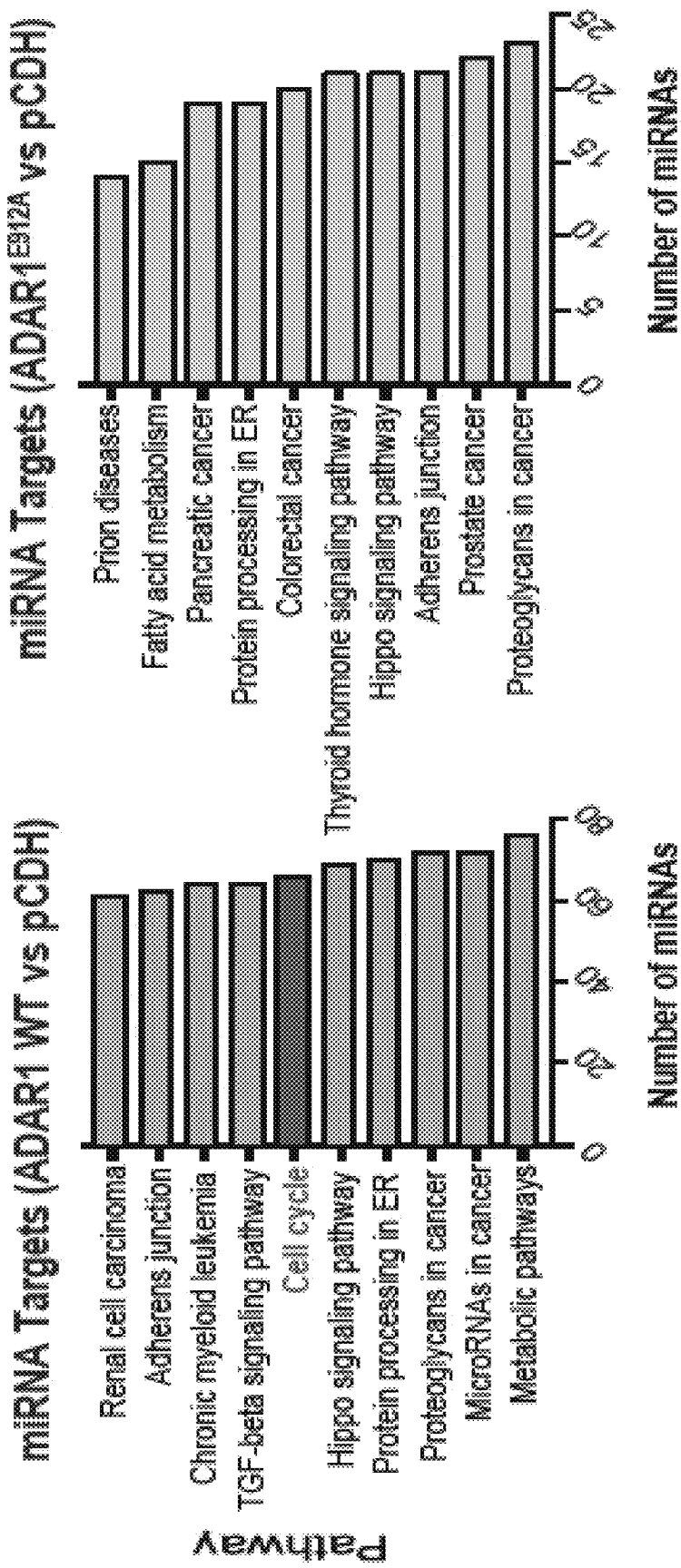
Figure 2C:
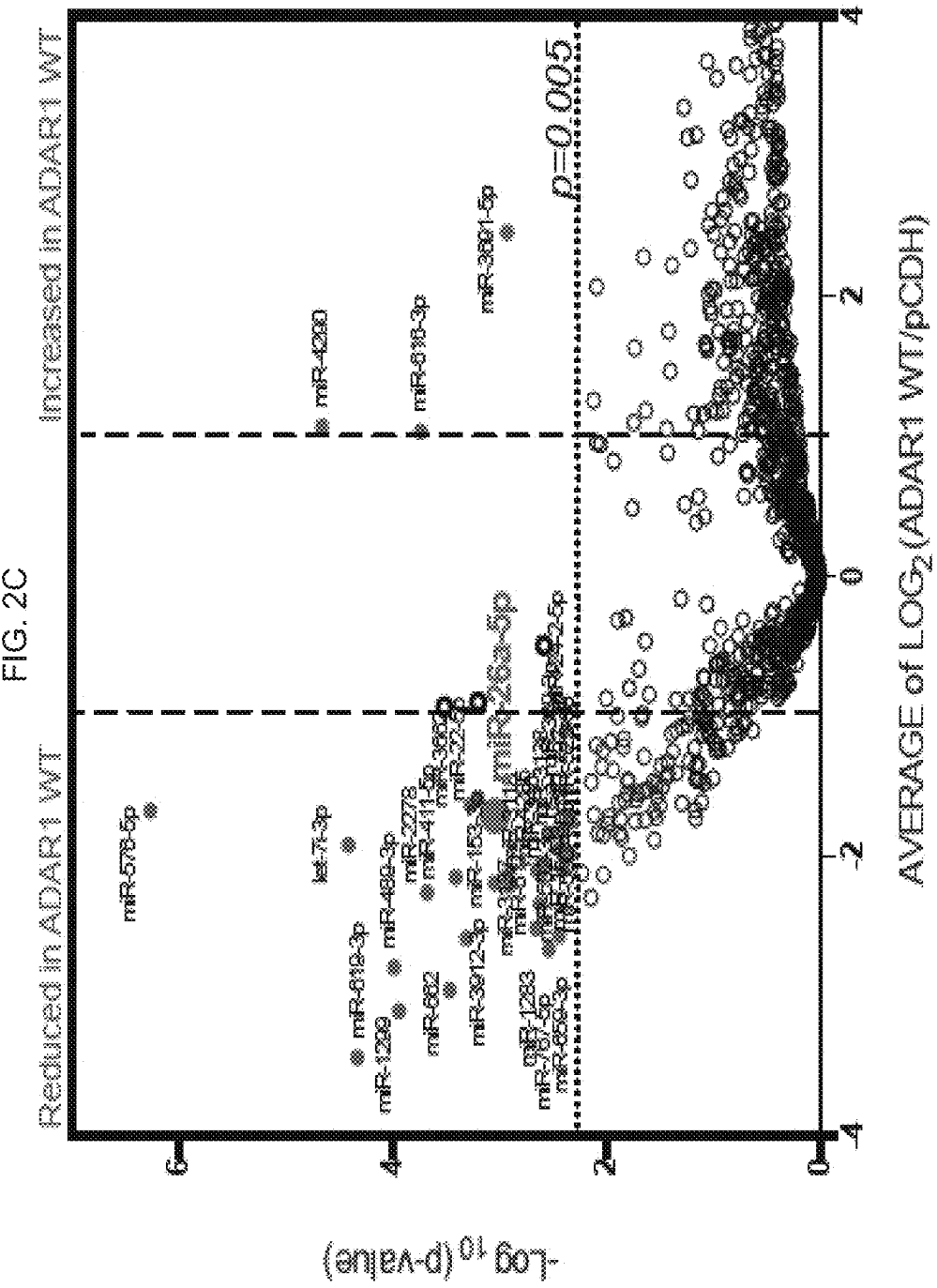
Figure 2D:
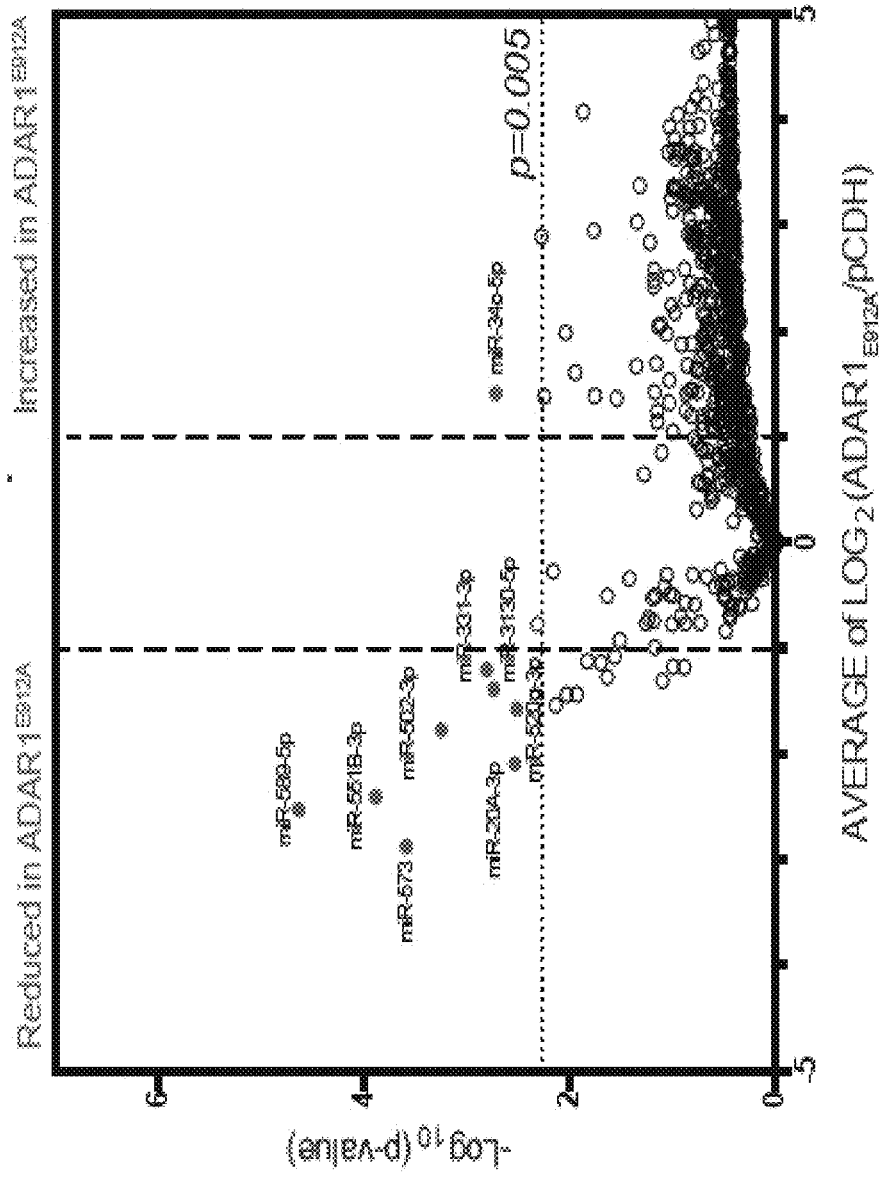

Next, we examined the molecular mechanisms governing cell cycle regulation by ADAR1 in HSPC. Since CDKN1A is the central hub (FIGS. 1L-M and FIG. 8B-C), we analyzed the A-to-I RNA editing in CDKN1A transcript using the ADAR1 WT transduced normal HSPC RNA-seq dataset, but we did not find any direct A-to-I editing events. Thus, we hypothesized that ADAR1 may control CDKN1A expression by regulating the function of specific miRNAs (Jiang et al., 2017). Although the role of ADAR1 in miRNAs biogenesis has been studied in human cell lines and leukemia stem cells (LSC) (Mallela and Nishikura, 2012; Nishikura, 2010, 2016; Zipeto et al., 2016), a complete profile of the edited miRNome and implications in normal hematopoietic stem and progenitor cell function has not been elucidated. To investigate the role of ADAR1 in global miRNA regulation, we performed miRNome miScript PCR array analysis of 1008 miRNAs in cord blood CD34$^+$ HSPCs overexpressing ADAR1 WT or ADAR1$^{E912A}$ (FIGS. 2A-D). Overall, 112 miRNAs were significantly differentially expressed following ADAR1 WT expression (FIGS. 2A and 2C-D). Using Diana miRNA target base (Chou et al., 2016), "cell cycle" was identified as the top cellular pathway significantly targeted by miRNAs regulated by ADAR1 WT but not ADAR1$^{E912A}$. These data suggest that ADAR1 may regulate cell cycle transit through modulation of miRNA biogenesis (FIG. 2B). Other than let-7 miRNAs, which were previously identified as ADAR1 editing targets (Zipeto et al., 2016), ADAR1 WT inhibited the expression of miR-2278, a tumor suppressor that targets STAT5 and restores tyrosine kinase inhibitor sensitivity in CML (Kaymaz et al., 2015), and miR-411, which induces cell proliferation in several human tumor types (Xia et al., 2015; Zhang et al., 2016b; Zhao et al., 2016b) (FIG. 2C). Notably, ADAR1-mediated A-to-I editing activity inhibited expression of miR-26a-5p, a tumor suppressor miRNA that is transcriptionally repressed by c-Myc (Salvatori et al., 2011; Sander et al., 2008) and frequently downregulated in hematological malignancies (Chen et al., 2016; Fatica and Fazi, 2013). Because overexpression of miR-26a is known to impair cell cycle progression, attenuate cell proliferation (Sander et al., 2008) and disrupt the let-7/LIN28B axis by directly targeting Lin28B (Fu et al., 2014), we hypothesized that inhibition of miR-26a expression by ADAR1 could accelerate cell cycle transit and increase self-renewal of HSPCs.

Figure 3A:
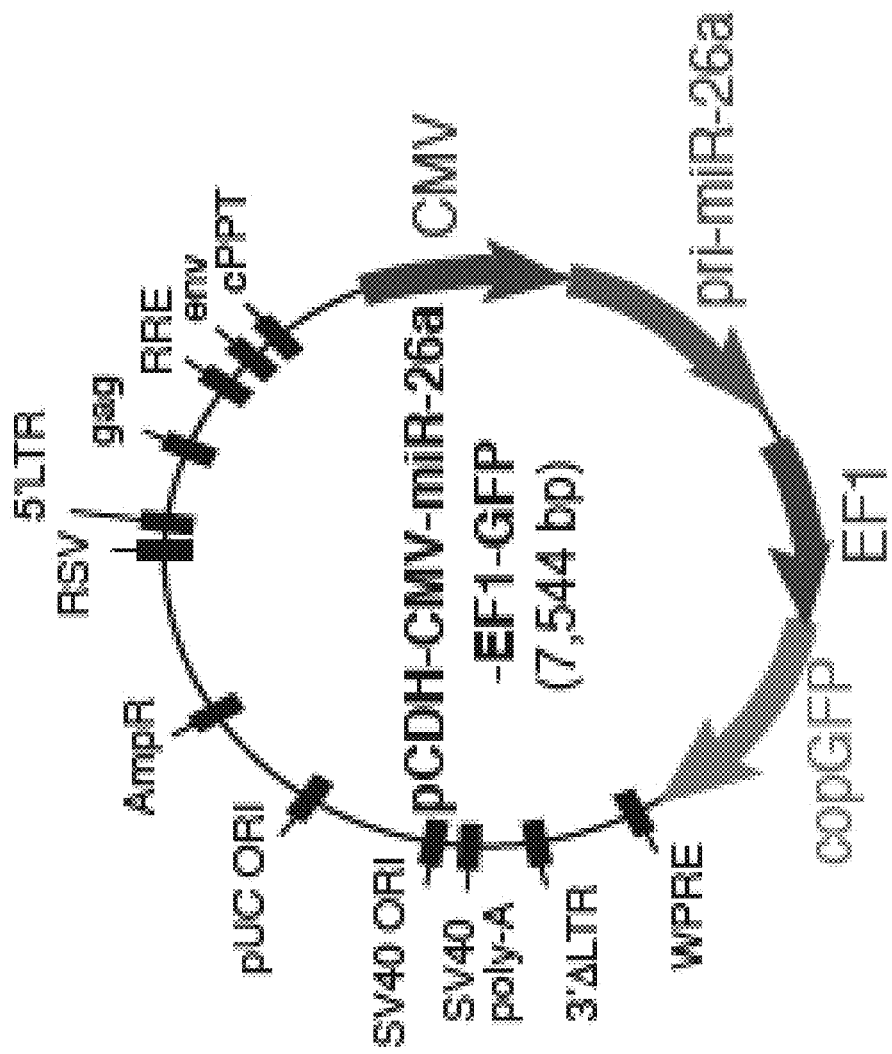
Figure 3B:
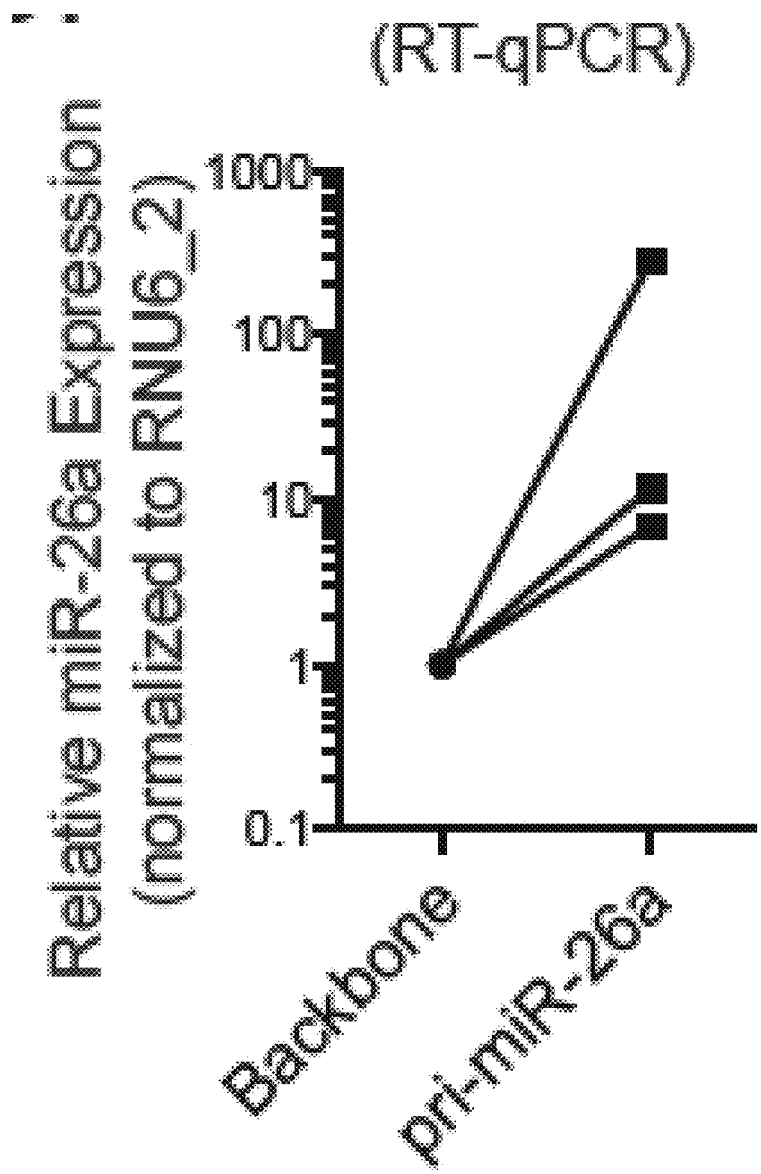
FIG. 3B graphically illustrates data showing that the expression of mature miR-26a was confirmed in cord blood CD34$^+$ cells.
Figure 3C:
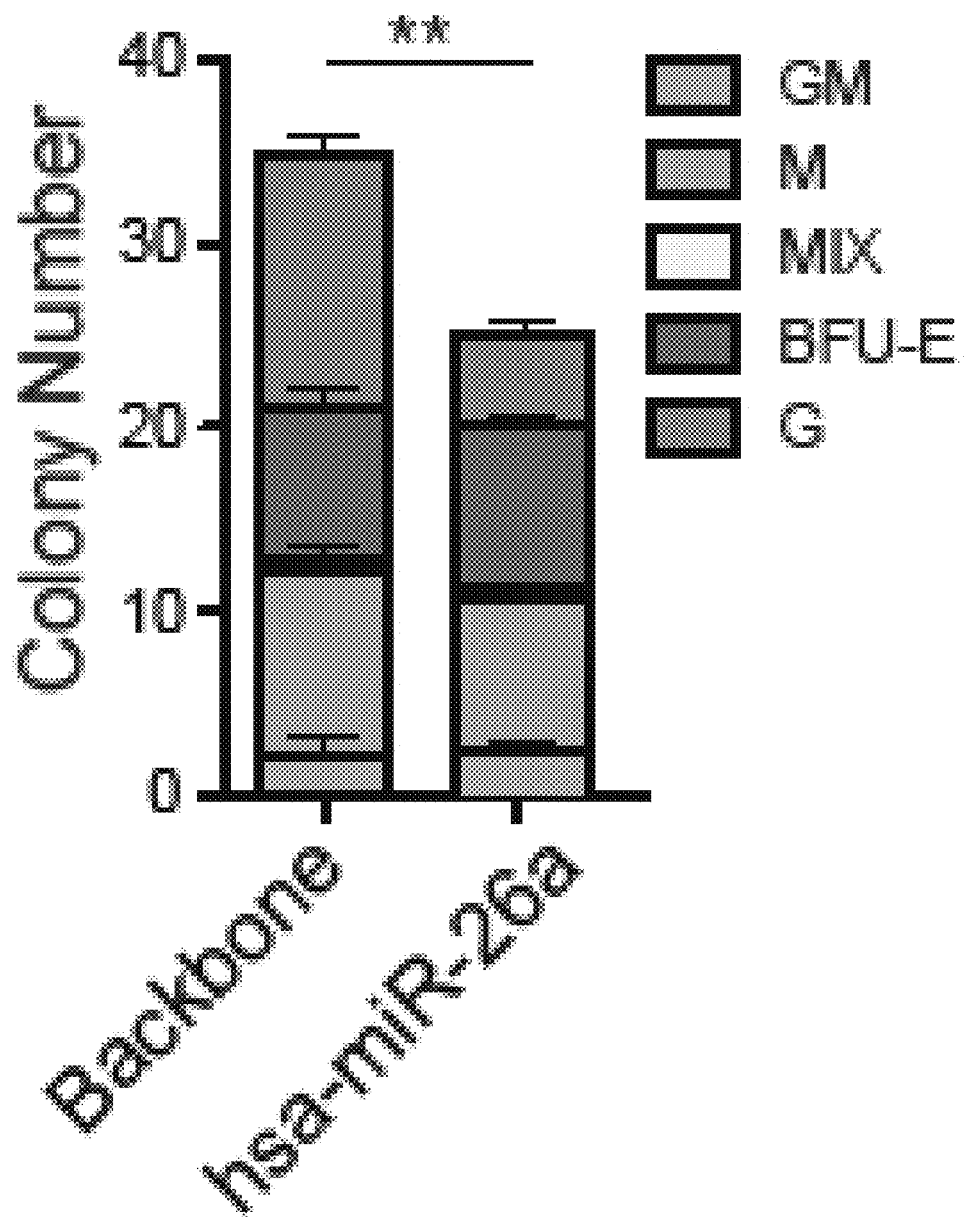
FIG. 3C-D graphically illustrates data showing that overexpression of miR-26a reduces the total number of primary colonies (FIG. 3C) and the self-renewal capacity measured by re-plated primary colonies (FIG. 3D) of cord blood CD34$^+$ cells.
Figure 3D:
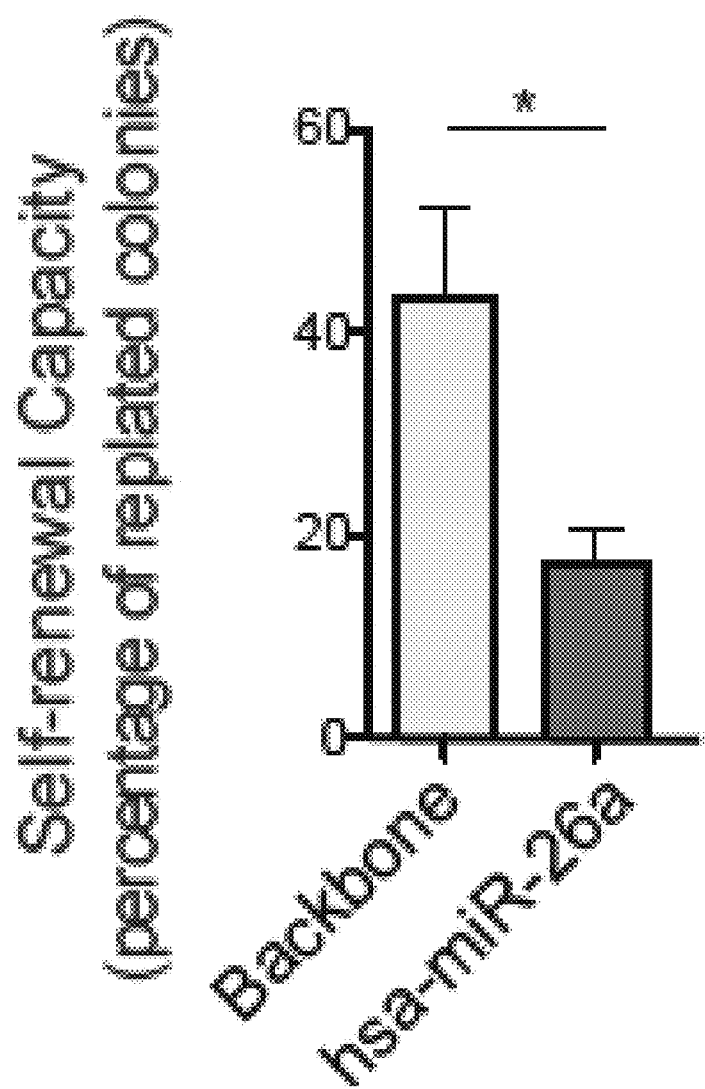
Figure 3G:
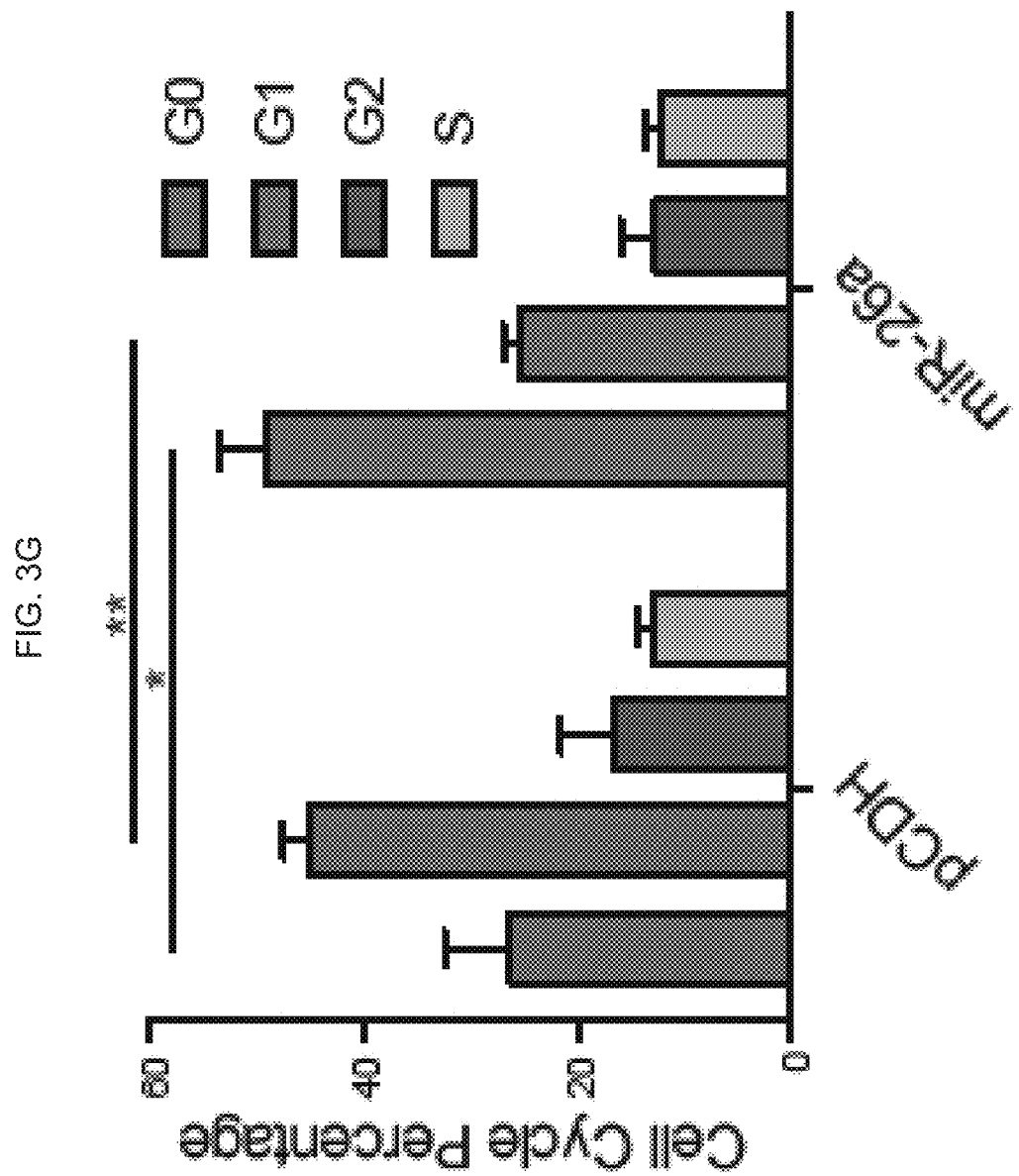
FIG. 3G graphically illustrates data showing that overexpression of hsa-miR-26a led to increase $G_0$ and decreased $G_1$ population in normal cord blood HSBC.
Figure 3I:
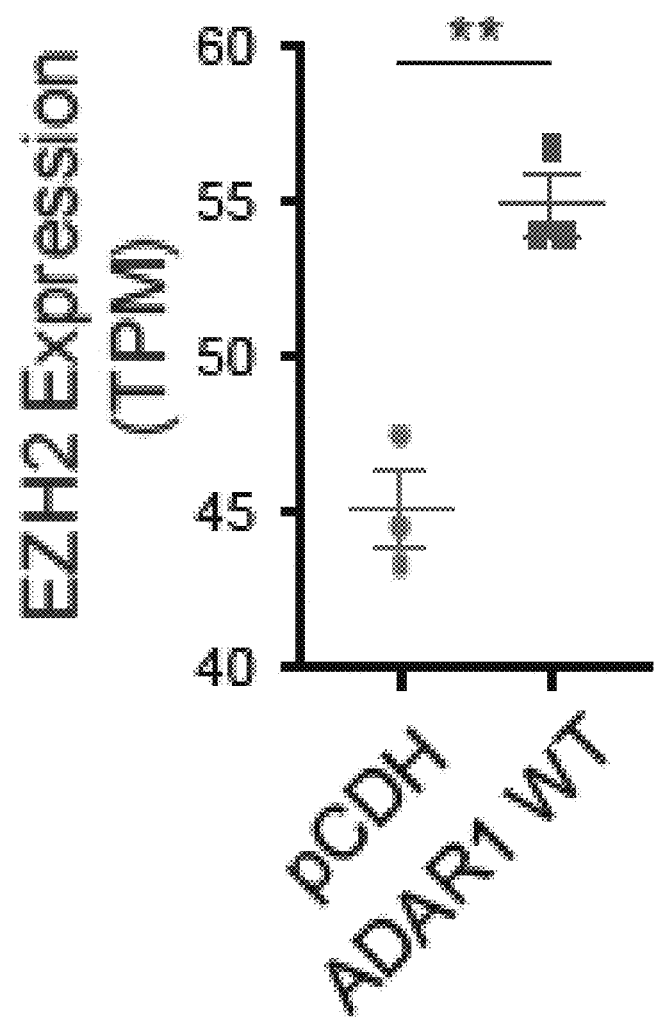
FIG. 3I graphically illustrates data showing that EZH2, a miR-26a target and inhibitor of CDKN1A, was upregulated with ADAR1 activation in cord blood CD34$^+$ cells.
Figure 3K:
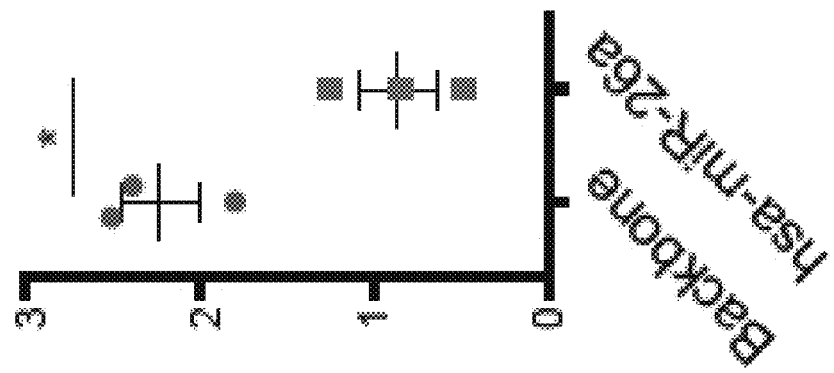
FIG. 3J-K graphically illustrate data showing that significant decrease in EZH2 expression is observed by either ADAR1 knockdown by shRNA (FIG. 3J) or overexpression of miR-26a (FIG. 3K) in cord blood CD34$^+$ cells.
Figure 3J:
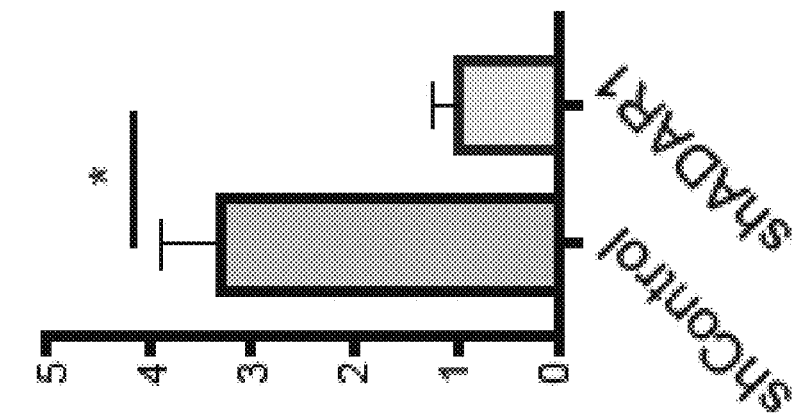
Figure 3L:
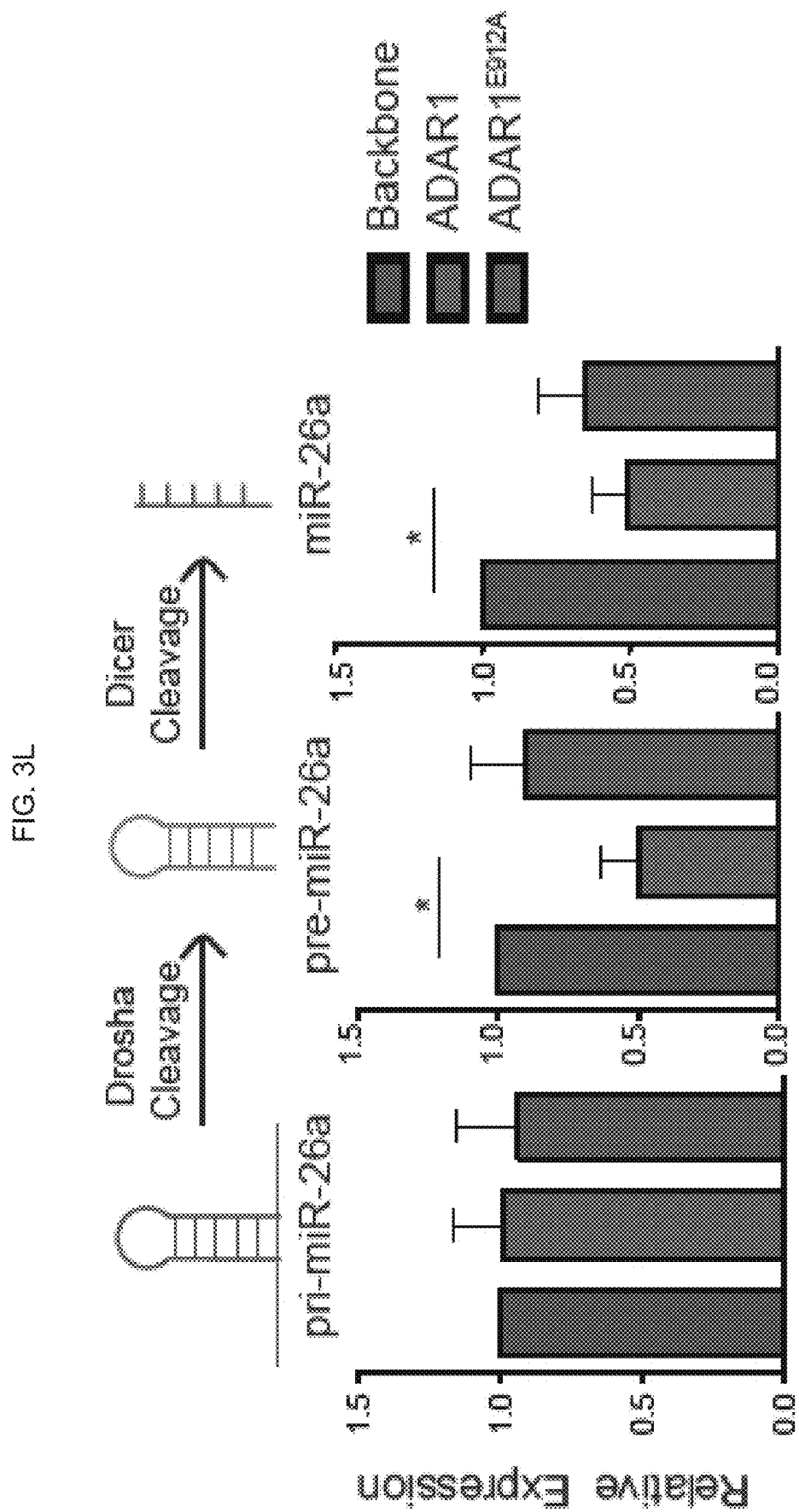
FIG. 3L graphically illustrates data showing expression of primary (pri-), precursor (pre-) and mature miR-26a transcripts as measured by RT-qPCR in cord blood CD34$^+$ HSPCs transduced with pCDH backbone, ADAR1 WT, or ADAR1$^{E912A}$ and the schematics about the graphs show pri-miR-26a, the pre-miR-26a after drosha cleavage, and mir-26a after dicer cleavage.

To test this hypothesis, we first examined the impact of miR-26a expression on normal HSPC survival and self-renewal using in vitro cord blood colony forming and replating assay system (FIGS. 3A-D). Lentivirally enforced miR-26a expression reduced total colony number, replating capacity, and LIN28B expression, indicative of inhibited self-renewal ability (Zipeto et al., 2016) (FIGS. 3C-E and S3A). Moreover, miR-26a overexpression was associated with blocked G$_0$ to G$_1$ transition and increased CDKN1A mRNA expression in normal cord blood HSPC (FIGS. 3F-H). This was further validated by a positive correlation between pri-miR-26a transcript level and CDKN1A expression, and increased CDKN1A protein level with in 293T cell line transduced with miR-26a overexpressing vector (FIG. S3B-C). Interestingly, ADAR1 WT significantly enhanced the expression of enhancer of zeste homolog 2 (EZH2), a known target of miR-26a (Lu et al., 2011; Salvatori et al., 2011; Sander et al., 2008) (FIG. 3I). As a polycomb protein that mediates global gene expression by histone 3 lysine 27 trimethylation (H3K27me3), EZH2 suppresses CDKN1A expression by altering H3K27me3 at the CDKN1A promoter region and transcriptional start site (TSS) (Fan et al., 2011; Pawlyn et al., 2017). Both knockdown of ADAR1 with a lentiviral shRNA system and lentiviral overexpression of miR-26a inhibited EZH2 expression in cord blood CD34+ HSPCs (FIGS. 3J-K). Taken together, these data suggest that ADAR1 editase regulates cell cycle transit and self-renewal, at least in part, through inhibition of miR-26a biogenesis.

ADAR1 Impairs Pri-miR-26a Biogenesis by Preventing Drosha Cleavage

Figure 3M:
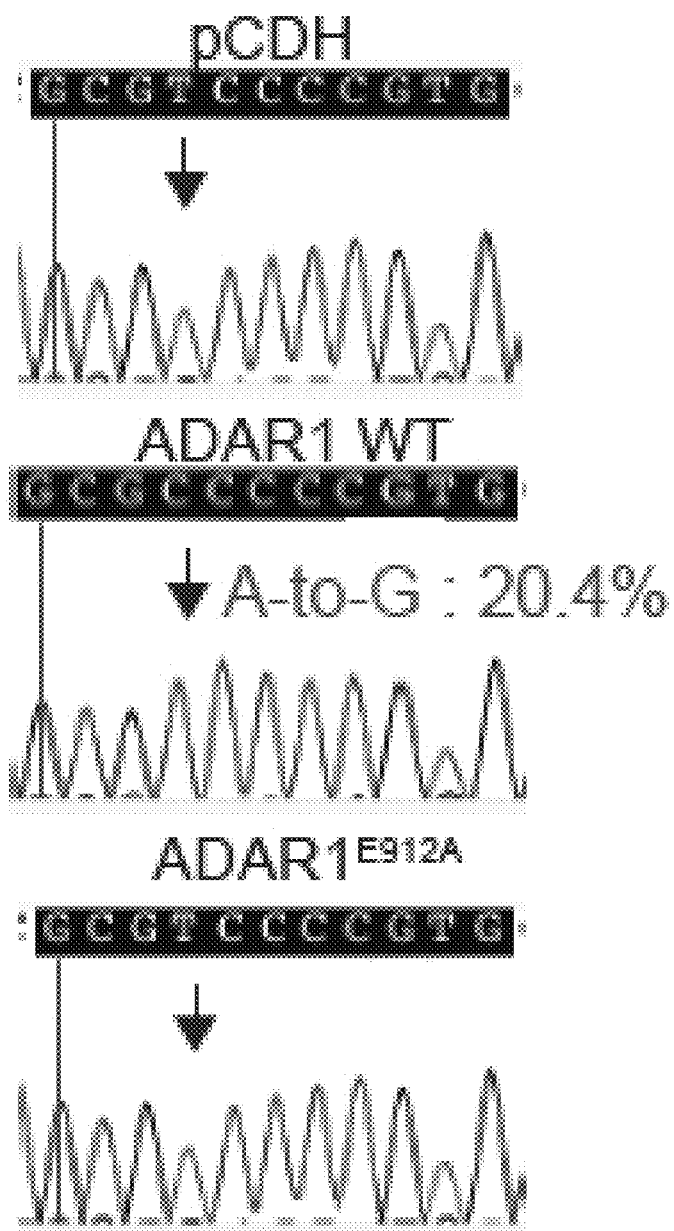
FIG. 3M graphically illustrates TOPO sequencing of blood CD34$^+$ cells overexpressing pCDH, ADAR1 WT, or ADAR1$^{E912A}$, and the arrow points to the A-to-G mutation site, reverse sequenced as T-to-C change.
Figure 3O:
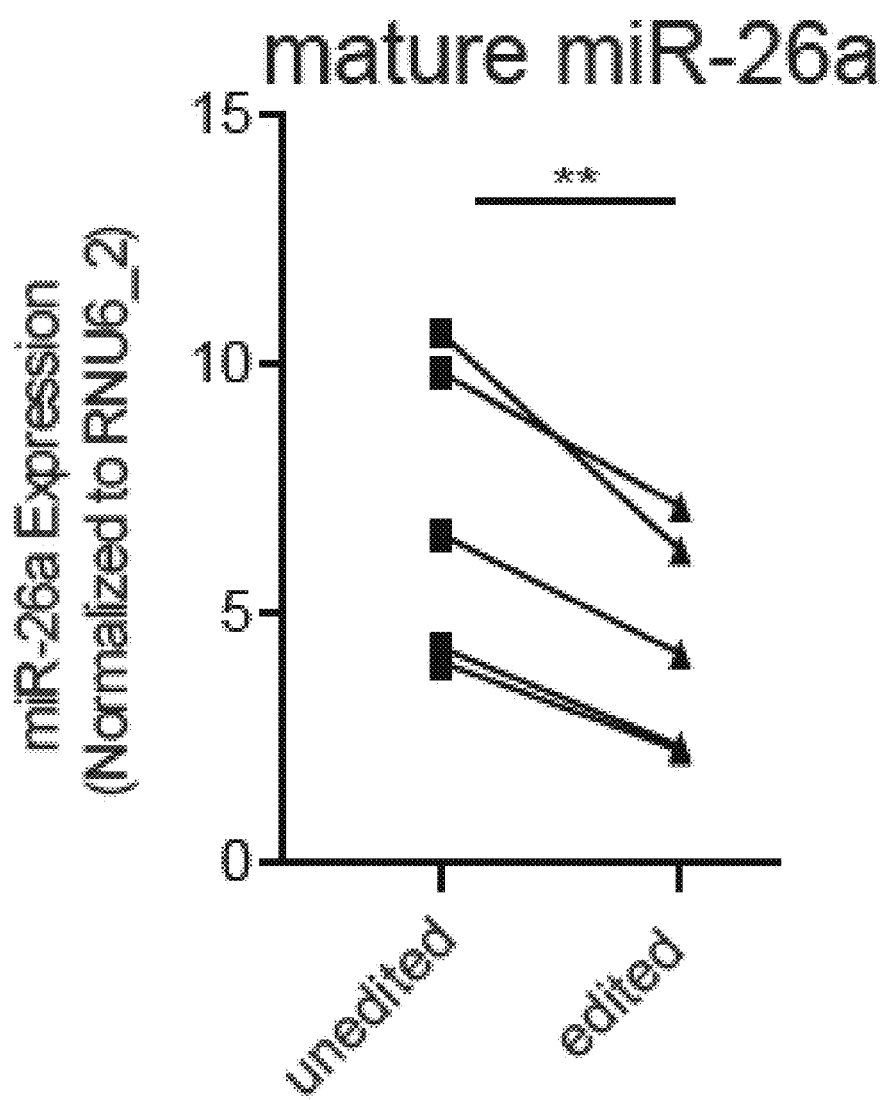
FIG. 3O graphically illustrates data where 293T cells were transfected with "unedited" or "edited" pri-miR-26a lentivirus, and the mature miR-26a expression was determined by RT-qPCR.
Figure 4C:
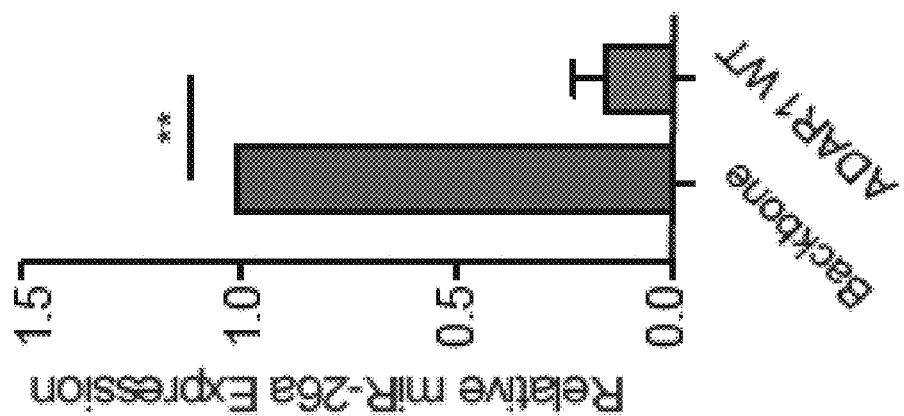
FIG. 4A-K illustrate data showing that reduced miR-26a enhances self-renewal capacity of CML Progenitors.
Figure 4B:
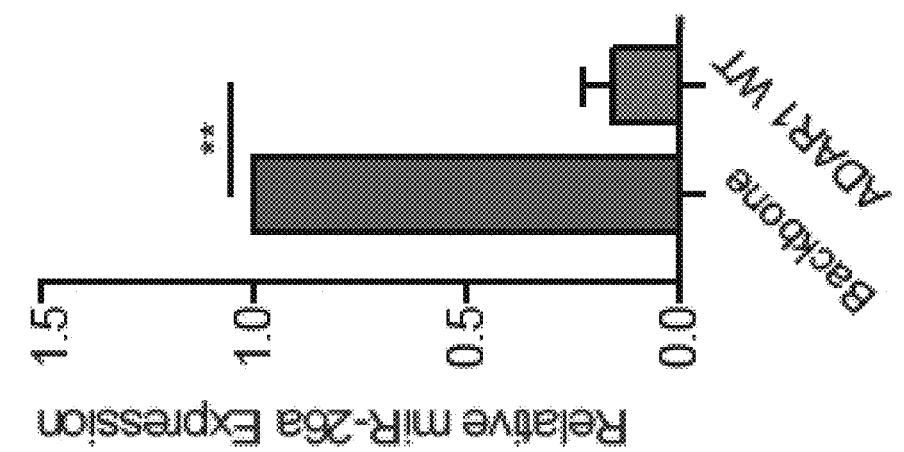

As previously shown for miR-142 and let-7 family miR-NAs, A-to-I editing of DROSHA or DICER cleavage sites can impair miRNA maturation (Yang et al., 2006; Zipeto et al., 2016). The editing dependent reduction of precursor (pre-) and mature miR-26a compared to unaltered primary (pri-) miRNA expression suggested that A-to-I editing may occur in the DROSHA cleavage site of primary pri-miR-26a (FIG. 3I). Indeed, TOPO cloning of pri-miR-26a transcripts identified 20.4% A-to-I(G) RNA editing at DROSHA cleavage site in ADAR1 WT expressing cells, where ADAR1$^{E912A}$ did not reveal any A-to-I(G) changes (FIG. 3M). Cross-linking RNA Immunoprecipitation (CLIP) in the K562 leukemic cell line stably expressing ADAR1 WT or ADAR1$^{E912A}$ revealed both ADAR1 WT and ADAR1$^{E912A}$ directly interact with pri-miR-26a transcripts (FIG. 10A and FIG. 4B). Next, we performed site-directed mutagenesis at the DROSHA cleavage site in pri-miR-26a (FIG. 3N and FIG. 10C). Compared to WT pri-miR-26a, editing of pri-mir-26a at the DROSHA cleavage site resulted in a significant reduction in mature miR-26a production (FIG. 3O). In a manner similar to lentivirally enforced ADAR1 WT, overexpression of edited miR-26a reduced the $G_0$ population. A combination of ADAR1 WT with unedited miR-26a or edited miR-26a exhibited the same phenotype (FIG. 3P). These data suggest that A-to-I RNA hyper-editing of miR-26a was accelerated cell cycle progression in cord blood HSPCs (FIG. 10D).

Enforced miR-26a Expression Prevents CML Progenitor Self-Renewal

Figure 4A:
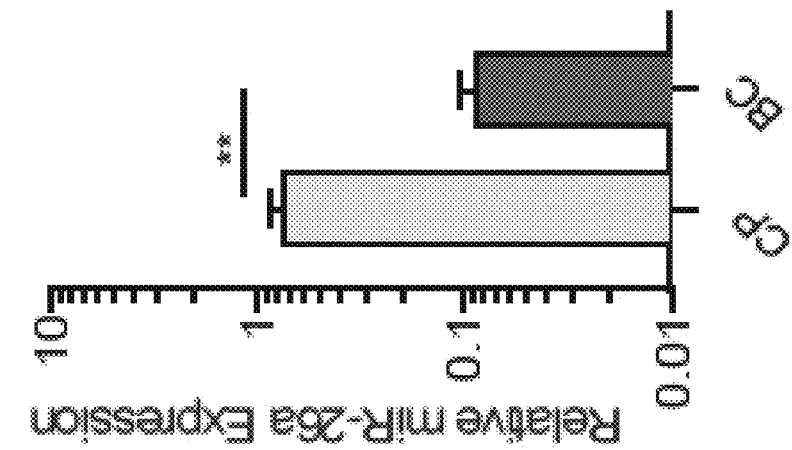
Figure 4E:
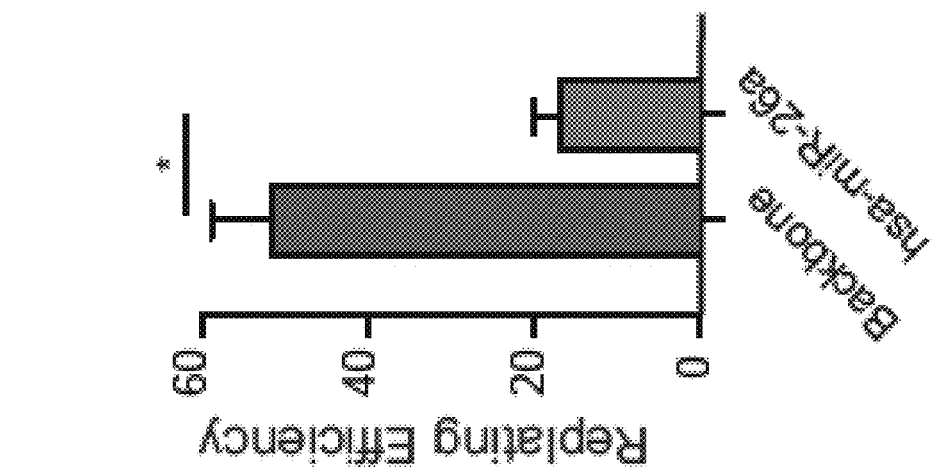
Figure 4D:
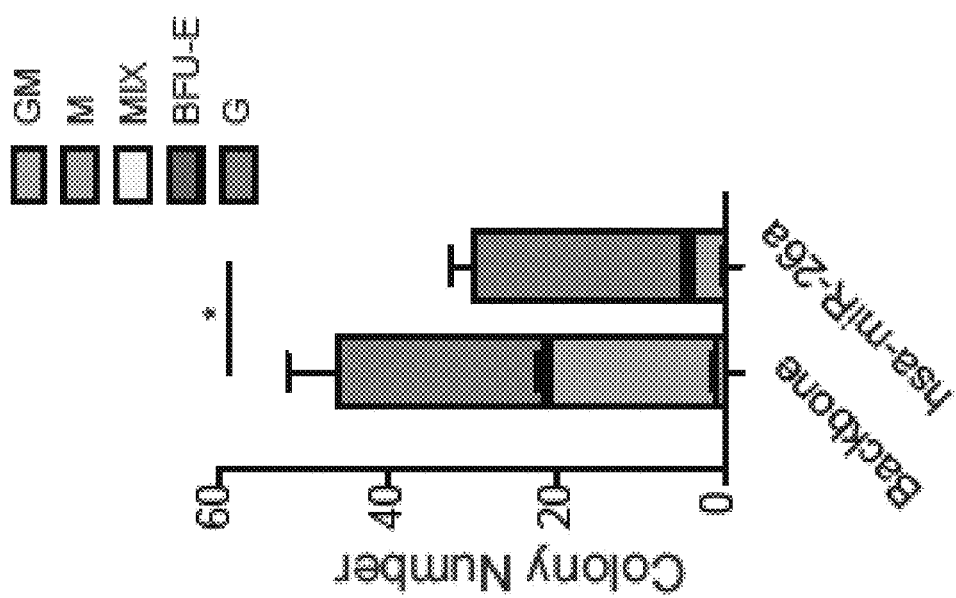
Figure 4F:
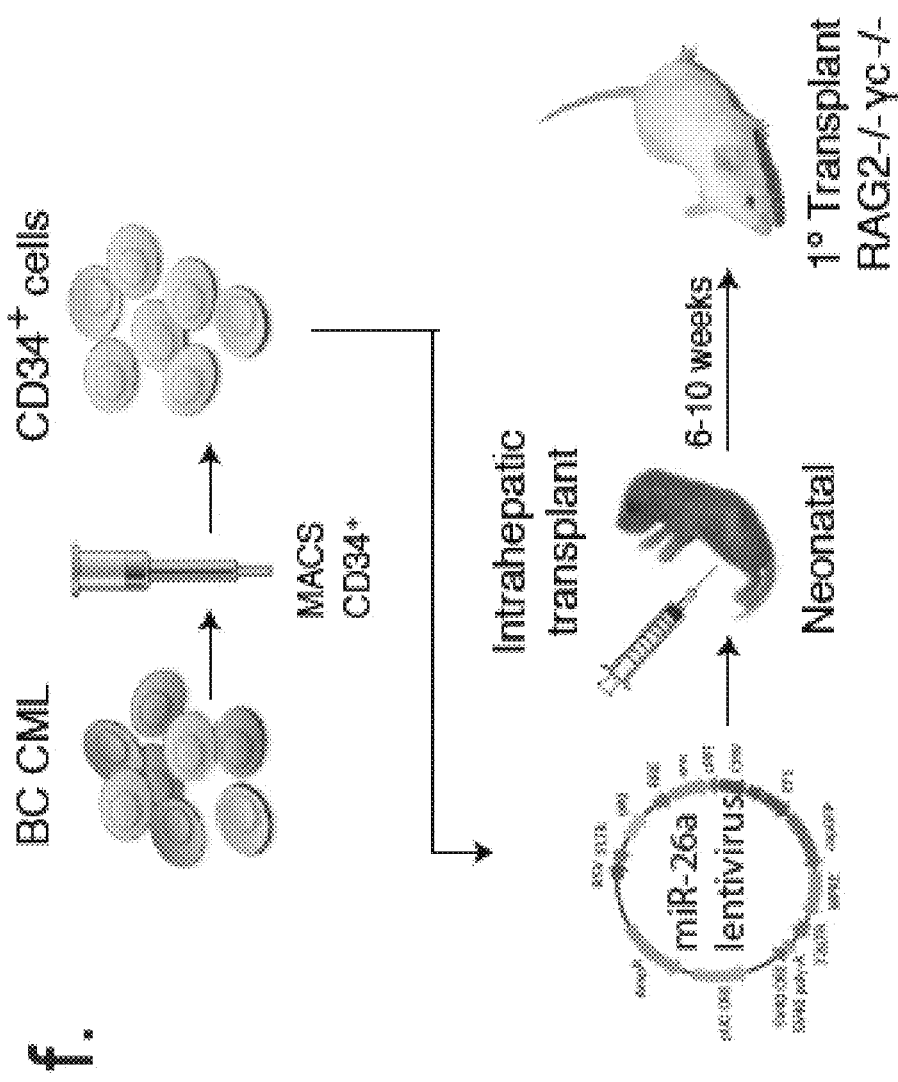
Figure 4G:
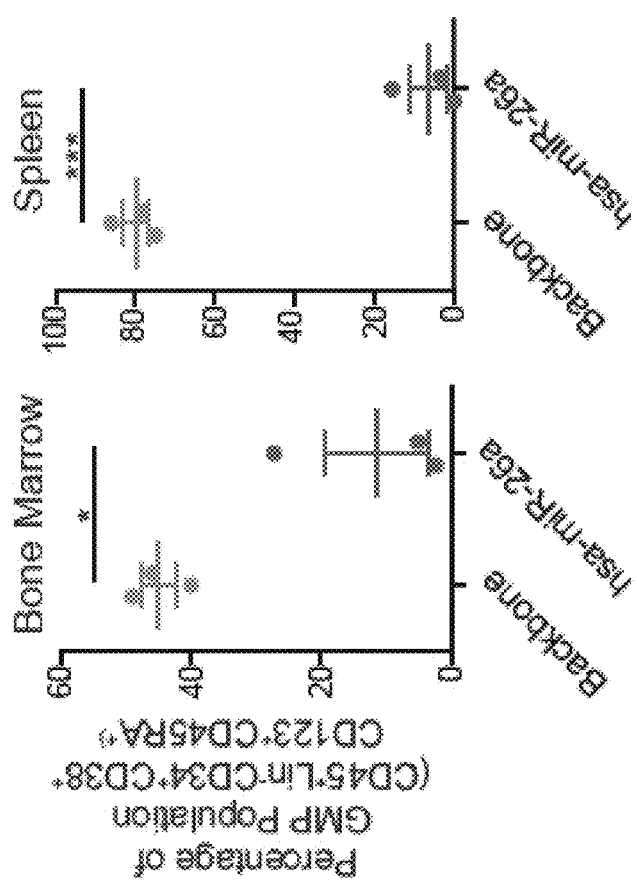

Advances in functional miRNA studies in hematological malignancies have provided a novel array of biomarkers and therapeutic targets for leukemia patients (Lechman et al., 2016; Wojtowicz et al., 2016). The transition from pre-malignant progenitor to therapy resistant CSC is often accompanied by aberrant ADAR1 activation (Chen et al., 2013; Han et al., 2015; Jiang et al., 2013). Thus, we hypothesized that ADAR1-mediated impairment of miRNA biogenesis, including miR-26a, contributed to progression from CP to BC CML. A pilot study revealed significantly reduced expression of miR-26a during CP to BC transformation (FIG. 4A). This was validated in CP CD34+ cells transduced with ADAR1 WT (FIGS. 4B and 4C). To assess the effect of miR-26a on BC LSC maintenance, lentiviral miR-26a was introduced into BC CD34+ cells followed by colony forming assays (FIGS. 4D-E) and transplantation into RAG2$^{-/-}$γc$^{-/-}$ immunocompromised mice (FIG. 4F). MiR-26a expression reduced total colony number and replating capacity of BC CD34+ cells, a reversal of ADAR1-mediated increased self-renewal as previously demonstrated (Zipeto et al., 2016) (FIGS. 4D-E). Although no significant change was observed in total human CD45+ cells and progenitor population (Figures FIG. 11A-C), FACS analysis revealed that miR-26a expression significantly reduced engraftment of granulocyte-macrophage progenitors (GMP, CD45+Lin−CD34+CD38+CD123+CD45RA+) that harbored LSC self-renewal capacity (Abrahamsson et al., 2009; Jamieson et al., 2004) (FIG. 4G and FIG. 11D). These data confirmed the important role of miR-26a as a tumor suppressor.

Figure 4H:
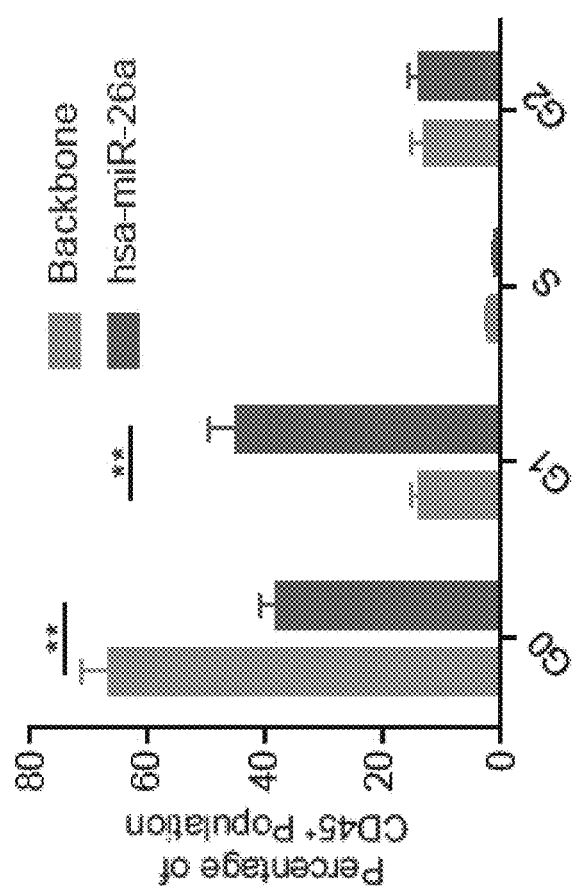

In human BC leukemia cells, miR-26a overexpression enhanced the $G_0$ to G1 phase transition in the bone marrow niche and reduced LSC dormancy (FIG. 4H and FIG. 11E). This was further validated using a single-stranded modified RNA specifically targeting miR-26a in K562 CML cells (FIG. 9F). Moreover, knockdown of miR-26a resulted in a reduction in the $G_0$ to G1 phase transition. Divergent effects of miRNA have been reported in normal HSPC and LSC (Lechman et al., 2016). To understand the differential effects of ADAR1-editing of pri-miR-26a on normal versus malignant hematopoiesis, we examined the differentially expressed miR-26a targets by RNA-seq analysis of normal HSPC overexpressing ADAR1 WT compared with CP and BC progenitors (Figures FIG. 11G and FIG. 11H). In keeping with reduced mature miR-26a levels, RNA-seq analysis showed increased expression of miR-26a target transcripts in cord blood CD34+ cells transduced with ADAR1 WT compared to lentiviral backbone (Figure FIG. 11G). Remarkably, the miR-26a target mRNA profile revealed a different set of targets in BC CML compared to cord blood HSPC (Figures FIG. 11G and FIG. 11H). Several upregulated miR-26a target transcripts were unique to BC CML progenitors (FIG. 11H), including SMAD1 and TP53INP1, which are important transcription factors that activate CDKN1A. These data suggest that miR-26a may target different pathways in normal versus malignant progenitors and thus has divergent roles in cell cycle regulation.

Figure 4I:
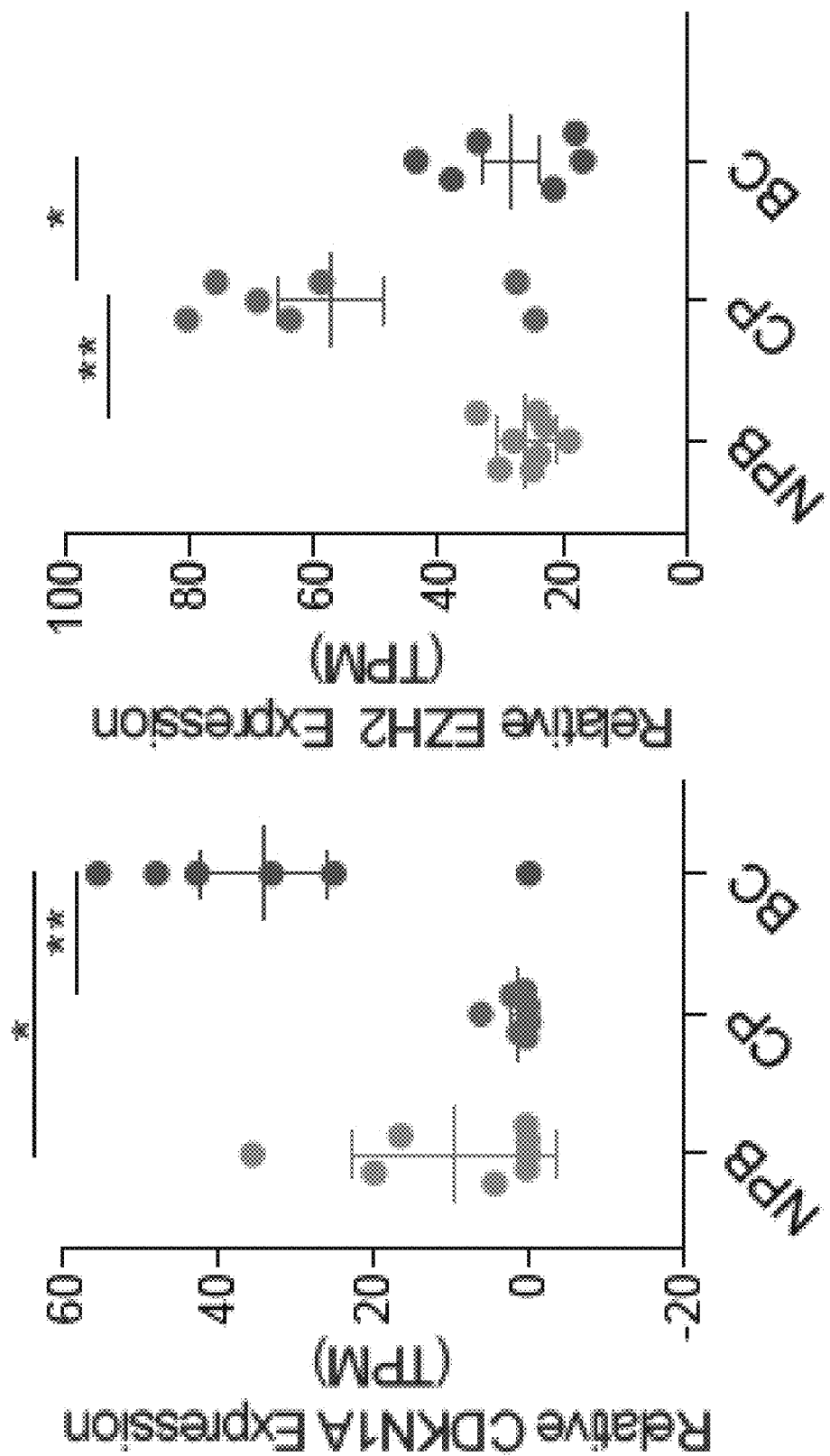
Figure 4J:
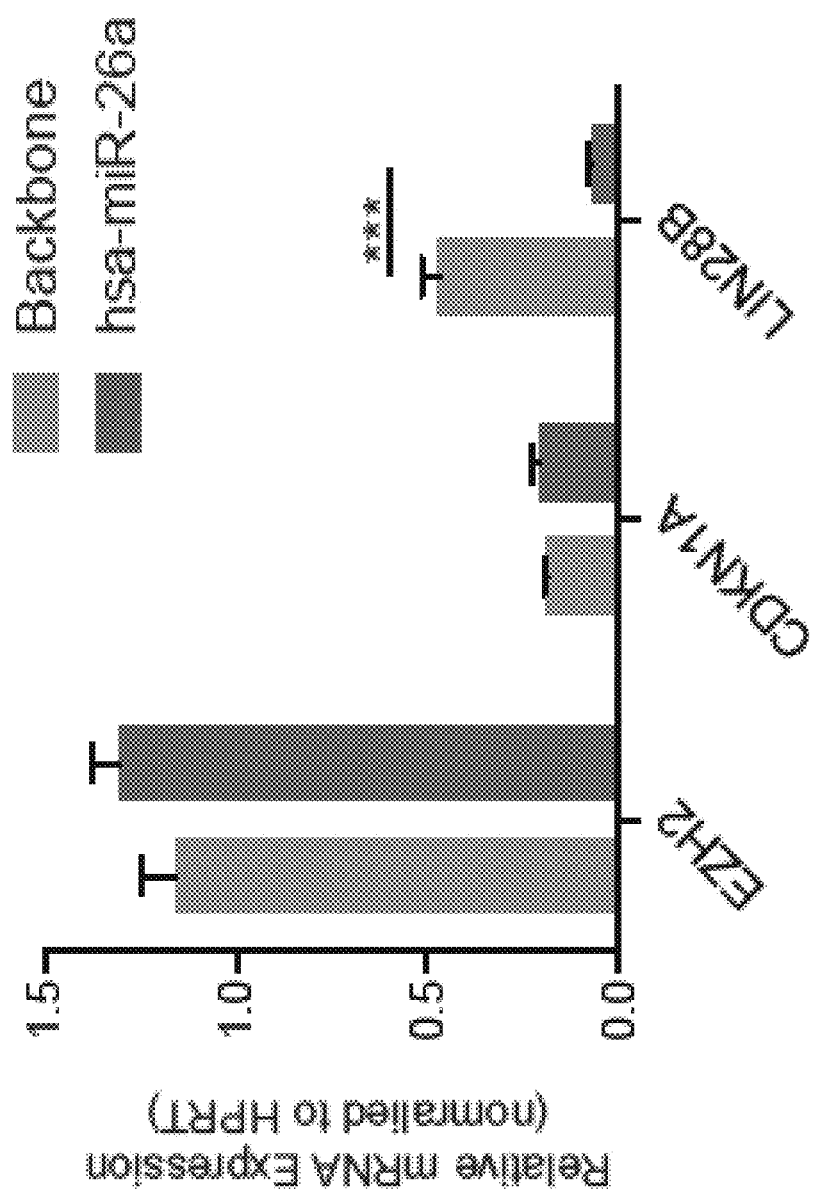

Despite the activation of ADAR1 (Jiang et al., 2013; Zipeto et al., 2016) and miR-26a downregulation during BC transformation of CML, CDKN1A was upregulated by approximately 30-fold in BC progenitors (FIG. 4I). While EZH2 expression was upregulated in CP compared to normal aged progenitors (Xie et al., 2016), it returned to low expression levels in BC progenitors (FIG. 4I). To confirm this, we overexpressed miR-26a in CML CD34+ cells. Of note, miR-26a was able to drive LIN28B downregulation and therefore reduced self-renewal capacity but did not alter EZH2 and CDKN1A expression (FIG. 4J). Taken together, these data suggest that accumulation of additional oncogenic events in CML BC progenitors may contribute to EZH2 downregulation.

Figure 4K:
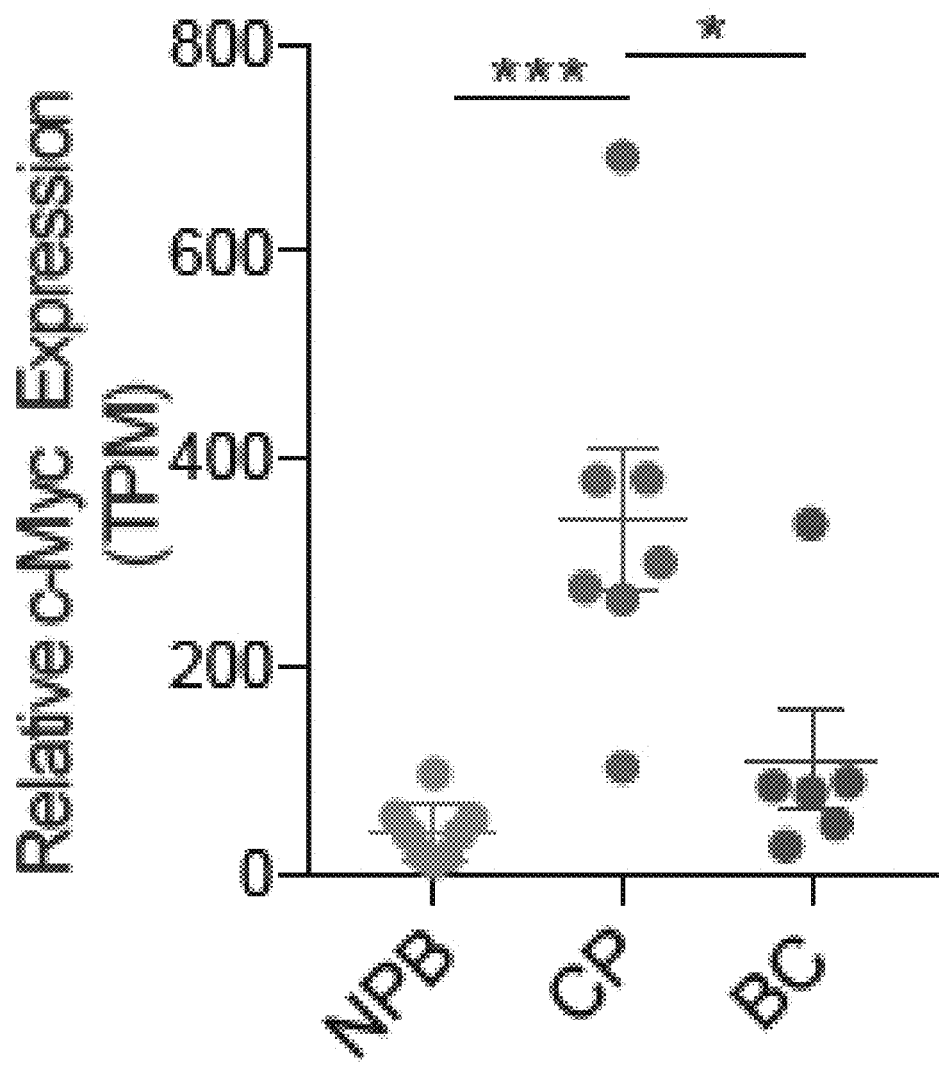

The MYC oncogene, which is frequently deregulated during tumor progression, has been reported to stimulate EZH2 expression through miR-26a inhibition (Sander et al., 2008) or by direct binding to regulatory elements to activate Ezh2 transcription (Neri et al., 2012). We therefore analyzed the expression of c-Myc in CML progenitor RNA-seq dataset to determine if MYC is responsible for EZH2 downregulation in BC progenitors. Indeed, the expression of c-Myc followed the same trend as EZH2; it was highly upregulated in CP progenitors compared to normal aged controls and returned to a lower level during CP progenitor transformation into dormant BC progenitor LSC (FIG. 4K). However, c-Myc expression was not altered by either ADAR1 overexpression or knockdown, suggesting c-Myc expression change in CML progression was unrelated to ADAR1 activation (FIG. 11I-J. Thus, RNA editing independent Myc protein deregulation in BC progenitors likely results in inhibition of EZH2 transcription and contributes to CDKN1A upregulation despite reduced expression of miR-26a in BC progenitors.

Figure 5A:
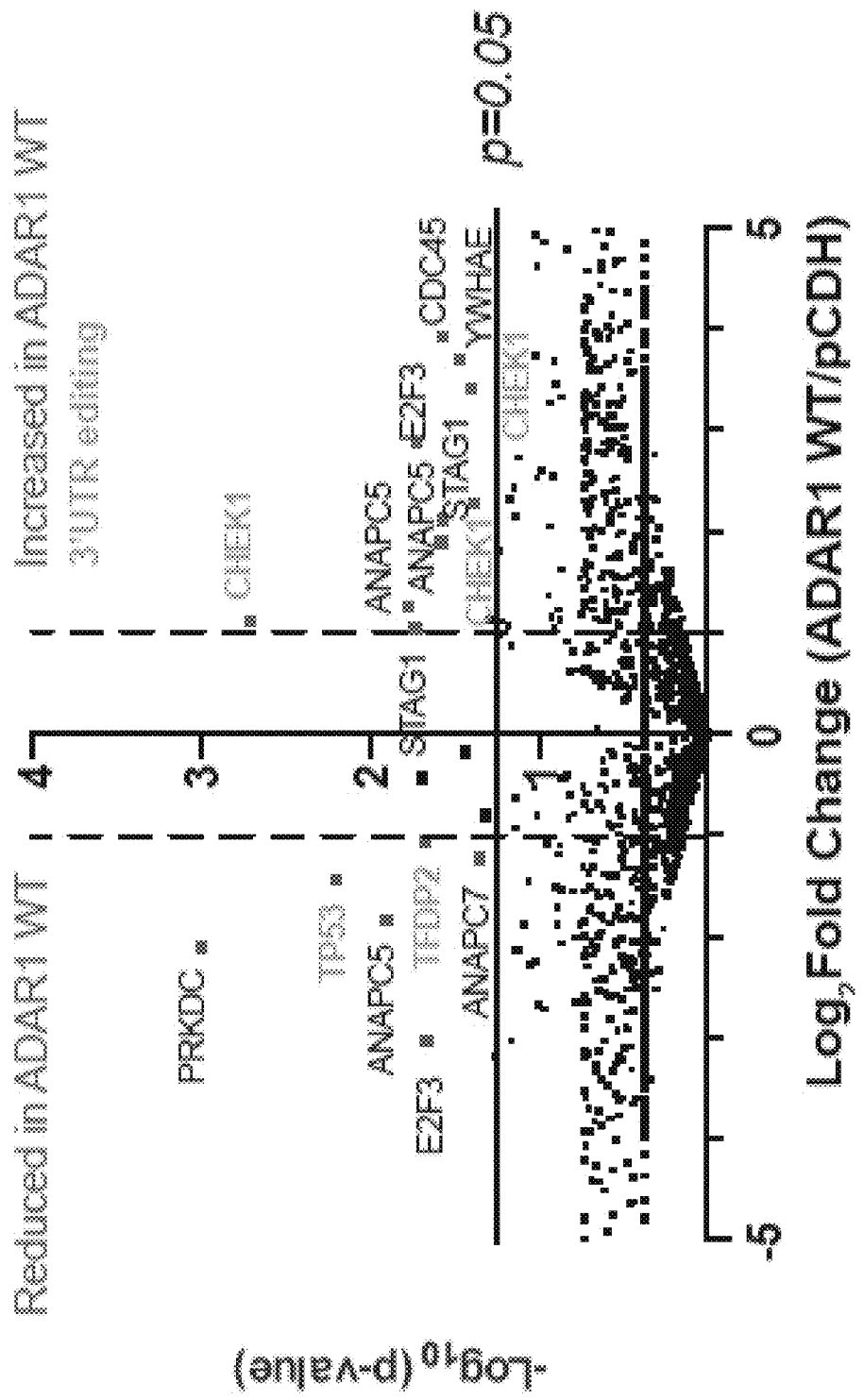
Figure 5B:
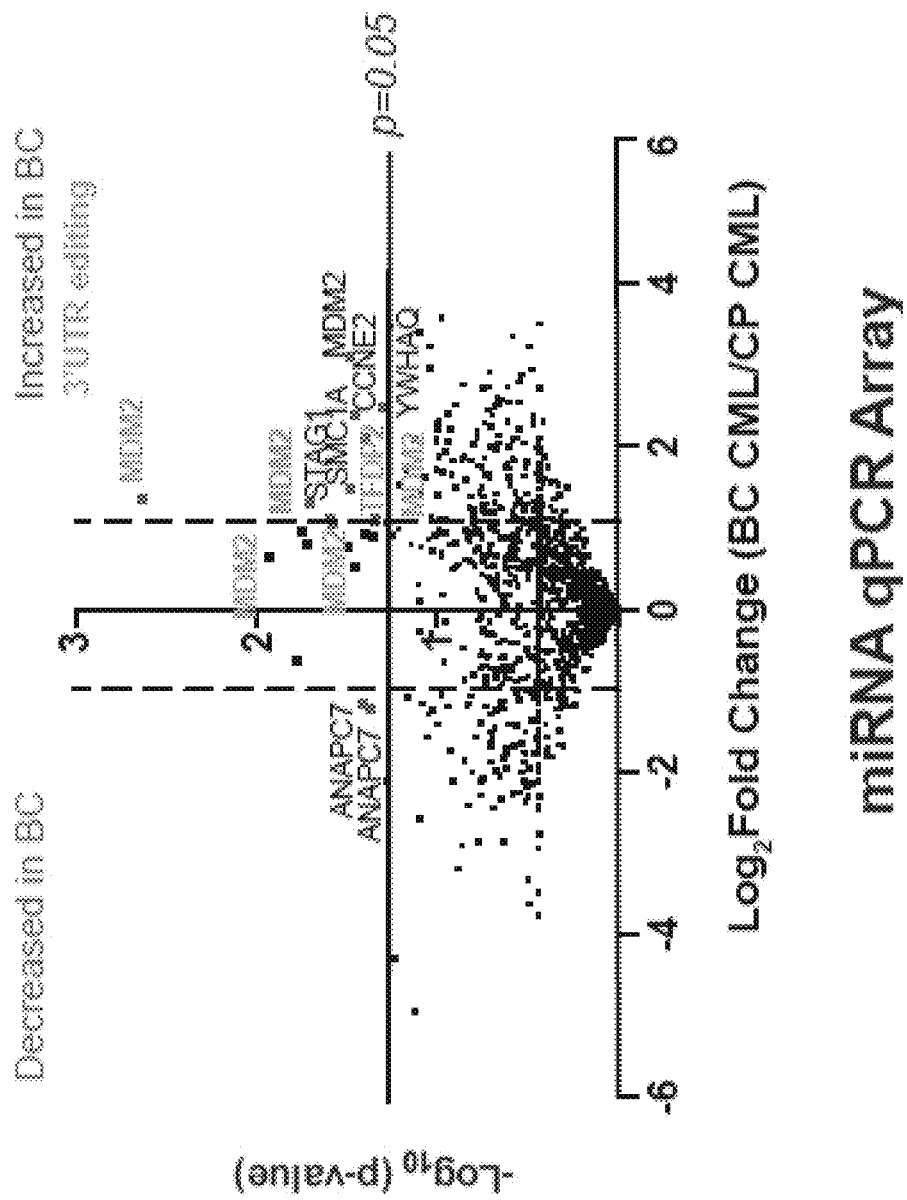

ADAR1 Editing of MDM2 3' UTR Prevents miRNA Binding and Inhibits p53 Transcription Other than directly modifying miRNA sequences, A-to-I RNA editing has also been shown to alter the miRNA targeting sequences within 3' UTR regions. Also, ADAR1 can directly compete with the RNA transport regulator, STAU1, for 3' UTR occupancy resulting in incomplete transcript suppression or translation (Jiang et al., 2017; Yang et al., 2017; Zhang et al., 2016a). However, the link between ADAR1 and disruption of 3' UTR targeting by miRNA has never been established in LSCs. We therefore investigated the location of A-to-I RNA editing within cell cycle transcripts (FIG. 5). Compared to pCDH lentiviral backbone, differential A-to-I editing in 3' UTR was observed in CHEK1, TP53, and TFDP2 transcripts in cord blood CD34+ cells overexpressing ADAR1 WT (FIG. 5A). A comparison between BC and CP progenitors revealed an increase of 3' UTR editing during BC transformation commensurate with increased ADAR1 expression. Strikingly, most 3'UTR editing events occurred within MDM2 transcripts (FIGS. 5B-C). As an E3 ubiquitin ligase that binds to the N-terminal transactivation domain of the p53 tumor suppressor, MDM2 inhibits transcriptional activation of the p53 tumor suppressor. Thus, upregulation of MDM2 and the corresponding downregulation of p53 were associated with accelerated phase (AP) and BC CML (Trotta et al., 2003). Using the miRcode, whole transcriptome human miRNA target prediction tool (Jeggari et al., 2012), we discovered that several miRNA targeting sites overlapped with the RNA-editing regions. In CML, we observed a cluster of targeting sites for miR-200b/c, one site for miR-204/204b/211, and one site for miR-155 (FIG. 5C). These sites were located within an approximately 600 nt region, suggesting "hyper" RNA editing in MDM2 3'UTR occurred specifically in BC progenitors thereby underscoring the cell type and context specific effects of ADAR1 editing. In comparison, there was only one A-to-I RNA editing site (#68843263) in MDM2 transcripts in cord blood CD34+ cells overexpressing ADAR1 WT compared to backbone control although it did not occur at a known miRNA targeting site.

Figure 5K:
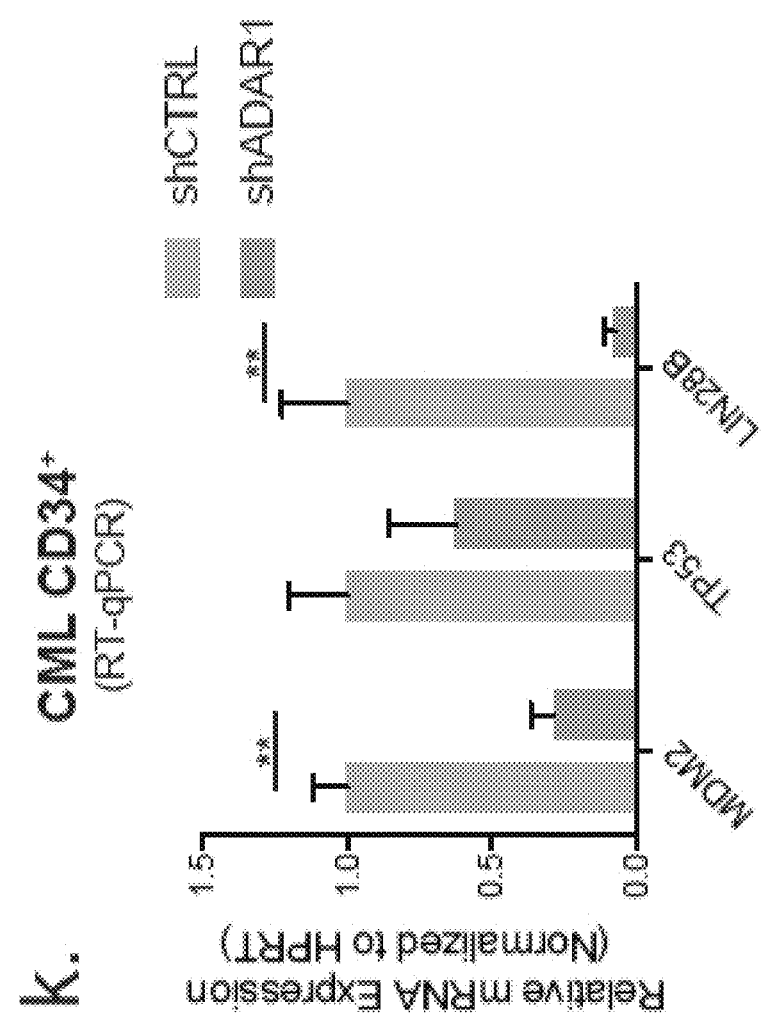
Figure 5J:
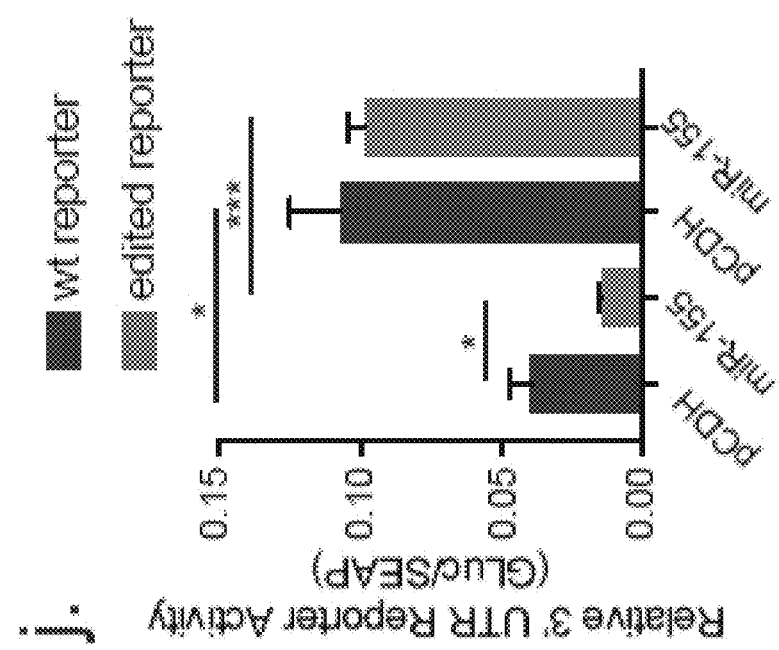
Figures 6A, 6B:
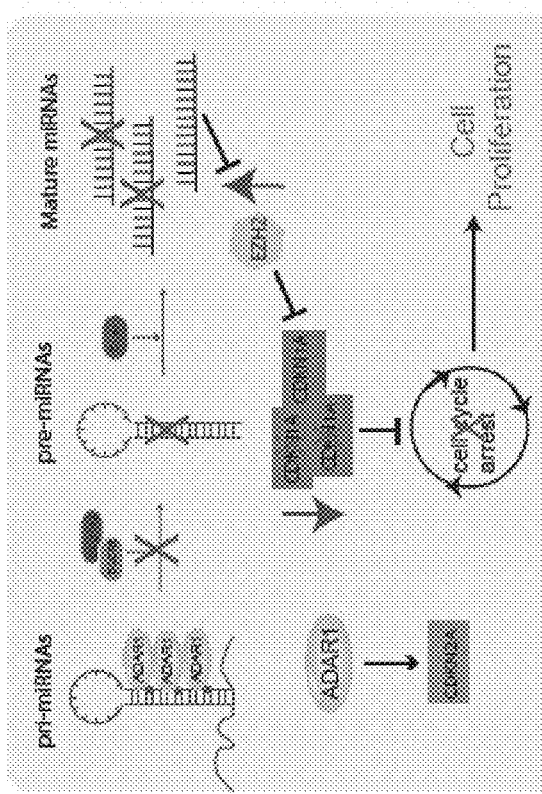
FIG. 6A-B illustrate a summary of A-to-I RNA editing function in normal HSPCs and BC LSC, including a summary of ADAR1 regulated pathways in normal hematopoiesis (normal progenitors with lenti-ADAR1) (FIG. 6A) and CML LSC homeostasis (BC CML progenitors) (FIG. 6B).

Interestingly, miR-155, a miRNA that normally targets SPI1 (PU.1), was consistently suppressed in cord blood HSPC and CP progenitors transduced with ADAR1 WT and during CML BC transformation thereby explaining the previously observed increase in PU.1 in ADAR1 overexpressing progenitors (FIGS. 5D-E and FIG. 12A-B)(Jiang et al., 2013). Several other important miRNAs, including miR-125 and miR-150, also showed a reduced expression upon ADAR1 WT activation in CP CD34+ cells (FIG. 5D). Interestingly, the inhibition of miR-155 biogenesis does not dependent on ADAR1's A-to-I RNA editing since ADAR1$^{E912A}$ deaminase deficient mutant had the same effect on miR-155 expression compared to ADAR1 WT (FIG. 12C-E). Therefore, it is likely ADAR1 affects MDM2 expression by dual mechanisms of both 3'UTR editing therefore evades miRNA targeting and inhibition of miR-NAs that directly target MDM2 such as miR-155. In keeping with this hypothesis that increased 3'UTR RNA editing and suppression of miRNA biogenesis allows transcripts to evade miRNA targeting, we observed a significant increase in MDM2 expression and a decrease in transcript levels of TP53, which is a target of MDM2, in BC compared to CP progenitors (FIGS. 5F-G). Expression of downstream target genes in the MDM2/p53 pathway, such as p16INK4a and p14ARF, were also increased during BC transformation (FIGS. 12F-G). To determine if increased MDM2 transcript abundance was due to ADAR1 activation in BC CML, we expressed ADAR1 WT or ADAR1$^{E912A}$ mutant in combination with miR-155 and quantified MDM2 transcripts by qRT-PCR. Indeed, A-to-I editing activity of ADAR1 was required for upregulation of MDM2, and this increase was abolished by lentiviral transduction with miR-155 (FIG. 5H). To directly show that the A-to-I RNA editing of MDM2 3'UTR prevented miR-155 targeting, we utilized a luciferase reporter with either wild-type ("unedited") or mutant ("edited") miRNA targeting sites (FIG. 5I). The relative luciferase activity increased in the "edited" reporter compared to wild-type reporter, likely due to the endogenous miRNA fails to target the "edited" reporter. Moreover, we challenged both wild-type and "edited" reporter with miR-155 expressing lentivirus. Only the "edited" reporter was insensitive to miR-155 (FIG. 5J). These data suggest that 3'UTR RNA editing enables MDM2 to evade targeting by miR-155. Lastly, shRNA knockdown of ADAR1 in BC CML CD34+ cells reduced MDM2 expression as well as increased transcript levels of TP53 (FIG. 5K). Together, these data reveal dual mechanism of ADAR1-dependent LSC generation involving 1) impaired biogenesis of cell cycle regulatory miRNAs, and 2) 3'UTR editing resulting in disruption of miRNA binding (FIGS. 6A-B).

DISCUSSION

Seminal murine studies underscore the importance of ADAR1 in murine hematopoiesis. Functional deletion of ADAR1 in embryonic stem cells induces embryonic lethality as a result of loss of erythropoiesis while conditional deletion in hematopoietic stem cells impairs multi-lineage reconstitution potential (Hartner et al., 2009; Wang et al., 2000). As a result of advances in RNA sequencing technology, RNA editing has emerged as a dynamic regulator of mammalian transcriptomic diversity (Ramaswami and Li, 2014, 2016; Tan et al., 2017). Striking differences in A-to-I editing between humans and mice are related, at least in part, to the propensity of ADAR1 to edit within double-stranded RNA (dsRNA) loops, which are frequently formed by inverted Alu repetitive elements that represent 11% of the human genome (Tan et al., 2017) but do not exist in mice. In addition to protecting stem cells from retroviral integration, a vital physiological role of ADAR1 is to edit endogenous dsRNA to prevent sensing of endogenous dsRNA as non-self by MDA5 (Liddicoat et al., 2015). Recently, A-to-I RNA editing by ADAR1 was shown to play a key role in translational control and proteomic diversity (Chung et al., 2018; Peng et al., 2018). In addition, A-to-I editing events are dynamically regulated in a tissue specific manner. However, the functional role of ADAR1 in human benign and malignant hematopoietic stem and progenitor cell maintenance has not been clearly elucidated. Malignant deregulation of ADAR1-mediated RNA editing has been linked to progression and therapeutic resistance of at least twenty types of human cancer (Han et al., 2015; Jiang et al., 2013; Qi et al., 2014; Qin et al., 2014; Shah et al., 2009; Zipeto et al., 2016). Because the majority of A-to-I RNA editing events occur within dsRNA loops created by Alu repeat sequences (Deininger, 2011; Jiang et al., 2017; Tan et al., 2017), the functional role of ADAR1 in cancer progression is best studied mechanistically in humanized systems.

In this study, we observed that ADAR1 activation is sufficient to induce normal HSPC cell expansion by inducing differential expression of cell cycle transcripts. Tightly controlled expression of cell cycle regulatory genes is achieved by A-to-I RNA editing of pri-miRNAs and 3'UTR of transcripts in cell cycle pathways. Using cytoscape analysis of RNA-seq dataset, it is revealed that CDKN1A is the central hub ADAR1 regulated cell cycle transit in normal HSPC. CDKN1A maintains HSC in a quiescent state after induction of DNA repair pathways and ADAR1-regulated depletion of CDKN1A has resulted in accelerated cell cycle. Moreover, the decreased expression of miR-26a and its role in self-renewal and cell cycle regulation supports our hypothesis that ADAR1-regulated miRNA biogenesis is essential for maintenance of HSC proliferation. Remarkably, miR-26a inhibits LIN28B expression in both normal HSPC and BC CML cells, suggesting that ADAR1-mediated miR-26a reduction is a parallel pathway of LIN28B/let-7 axis regulation, working in parallel to direct editing of let-7 by ADAR1 (Zipeto et al., 2016). In pre-malignant progenitors with mutations that promote survival, such as BCR-ABL, deregulated ADAR1 contributes to the malignant reprogramming of progenitors into dormant LSCs. In this setting, ADAR1 mediated A-to-I editing prevents binding of miRNA to the 3'UTR of MDM2, which results in increased MDM2 expression and repression of the p53 tumor suppressor. Thus, ADAR1 inhibition may represent a potent method for eradicating LSC.

A recent study of dynamic RNA editing in mammals showed that ADAR1 is the primary editor of repetitive sites and ADAR2 is the editor of non-repetitive coding region (Tan et al., 2017). Indeed, ADAR1 editing sites in cell cycle transcripts in both normal HSPC and CML progenitors occurs in non-coding regions such as Alu-rich intronic sequences and 3' UTRs. However, ADAR1 clearly possesses disease-specific preferential targeting of certain editing sites, such as MDM2 3' UTR in BC progenitors. It is possible this preferential A-to-I targeting is caused by disease- or cell type-specific expression of ADAR1 activity regulators as recently reported (Tan et al., 2017). The dichotomous role of A-to-I RNA editing in HSPC and LSC suggest future studies of malignant CSC reprogramming should incorporate disease-, cell type-, and tissue-specific mechanisms.

Moreover, these results highlight a previously unrecognized link between ADAR1 activation and EZH2 expression. EZH2 is the core subunit of the polycomb repressive complex 2 (PRC2) with histone methyltransferase activity that introduces H3K27me3 at target gene promoters thereby suppressing gene expression. Ezh2 expression is tightly associated with cell proliferation (Margueron et al., 2008) and is upregulated in ADAR1-overexpressing HSPC through inhibition of miR-26a that directly targets EZH2. However, EZH2 upregulation by ADAR1 is disrupted in LSC due to activation of oncogenes, such as c-Myc. This raises the possibility that post-transcriptional A-to-I RNA editing may epigenetically influence normal HSPC maintenance and that disruption of this regulation by cancer-specific oncogenic pathways may lead to malignant progenitor generation. Since deregulated RNA editing activity is associated with many types of cancer, further work is needed to elucidate ADAR1's role in epigenetic disruption in other cancer types, as well as identification of the corresponding coding and non-coding RNA editing target transcripts. Understanding the cell type and context specific effects of A-to-I editing has become even more pressing since a recent groundbreaking set of studies showed that a catalytically inactive Cas13 can be used to direct ADAR-mediated RNA editing to specific transcripts. While RNA Editing for Programmable A to I Replacement (REPAIR) holds promise for treating intractable genetic diseases, particularly in post-mitotic cells (Cox et al., 2017).

In conclusion, we have uncovered a dichotomous role for ADAR1 in normal and malignant progenitor cell cycle regulation and maintenance that is predicated on suppression of miRNA biogenesis and 3'UTR editing of miRNA binding sites. The dual mechanism provides an efficient way to regulate gene expression through A-to-I RNA editing of noncoding sequences. Dormant BC CML LSCs in the bone marrow protective niche often escape therapies that target dividing cells thereby contributing to therapeutic resistance and disease relapse (Goff et al., 2013). Therefore, ADAR1 inhibition may represent an effective modality for eliminating dormant LSCs that evade tyrosine kinase inhibitor in CML but also in other advanced malignancies that co-opt ADAR1.

Figure Legends

FIG. 1. ADAR1 Regulates Cell Cycle in Normal Hematopoiesis:

(a) Representative picture of ADAR1-WT or lentiviral backbone transduced cord blood $CD34^+$ cells. See also FIG. 7 for other stem and progenitor populations.

(b-c) Accelerated cell expansion as observed by increased total cell number (b), stem cells ($CD34^+CD38^-Lin^-$), and progenitors ($CD34^+CD38^+Lin^-$) (c) (n=3).

(d-e) Immunofluorescent staining of Ki67 suggests increased expression of Ki67 in ADAR1 WT-expressing $CD34^+$ cells (n=3).

(f-g) ADAR1 WT overexpression in cord blood $CD34^+$ cells induced accelerated loss of DiR signal compared with backbone control (n=3). See Figure FIG. 7 for experimental design and FACS plot.

(h) Significant differential expressed cell cycle transcripts were determined by RT-qPCR array of 84 transcripts on cord blood HSPC (n=5) transduced with ADAR1 WT, $ADAR1^{E912A}$ inactive mutant, or lentiviral vector control.

(i) Cytoscape analysis of differentially expressed transcripts of KEGG Cell Cycle Pathway in ADAR1 WT-transduced cord blood (n=3) versus lentiviral vector control (n=3) by whole transcriptome RNA sequencing.

(j) RNA-seq quantification on ADAR1 WT-transduced cord blood (n=3) and lentiviral vector control (n=3) for genes corresponding to the KEGG Cell Cycle Pathway visualized in a heatmap ($p<0.05$, FDR<10%). See FIG. 8 for all differentially expressed cell cycle genes.

(k) Representative image of ADAR1-mediated differentially expression targets in cell cycle stages.

(l-m). Immunofluorescent showed decreased CDKN1A protein expression in ADAR1 WT-expressing $CD34^+$ cells (n=3).

(n) shRNA targeting ADAR1 reduced cell cycle acceleration and increased $G_0$ population of normal cord blood $CD34^+$ HSPC as measured by flow cytometry of Ki-67 and 7AAD (n=4). See FIG. 8 for representative FACS plot.

(o). Gene expression by RT-qPCR showed increased CDKN1A expression in cord blood HSBC (n=3). (p) Reduction of ADAR1 by shRNA leads to reduced self-renewal of normal cord blood HSBC as measured by colony replating assay (n=3).

All graph show mean with SEM and statistical analysis was calculated using the Student's t-test. *$p<0.05$, $p<0.005$, *$p<0.0005$.

FIG. 2. Regulation of miRNome by ADAR1 in Normal HSPCs:

(a) Pie chart of differentially expressed miRNAs in cord blood CD34+ HSPC overexpression ADAR1 WT or ADAR1$^{E912A}$ mutant compared with pCDH vector control (n=3-4) derived from miRNome array of 1008 miRNAs.

(b) Top ten significantly affected pathways by differentially expressed miRNAs targeted by ADAR1 WT or ADAR1$^{E912A}$ mutant compared with lentiviral backbone.

(c-d) Volcano plot analysis derived from miRNome showing significantly differentially expressed miRNAs (p<0.005, Student's t-test, Log 2Fold change>2) in cord blood CD34+ cells transduced with lenti-pCDH vector control, lenti-ADAR1 WT, or lenti-ADAR1$^{E912A}$ (n=3-4).

FIG. 3. Important Role of miR-26a in Self-Renewal Capacity of Normal Hematopoietic Progenitors:

(a) Lentiviral construct for human primary (pri-) miR-26a expression.

(b) The expression of mature miR-26a was confirmed in cord blood CD34+ cells (n=3).

(c-d) Overexpression of miR-26a reduces the total number of primary colonies (c) and the self-renewal capacity measured by replated primary colonies (d) of cord blood CD34+ cells (n=3). See FIG. 9 for representative colony images.

(e) Overexpression of miR-26a also reduced the expression of LIN28B in cord blood HSPCs (n=3).

(f). Representative cell cycle flow analysis of CB HSBC (n=3) transduced with either backbone or hsa-miR-26a overexpression lentivirus.

(g). Overexpression of hsa-miR-26a led to increase $G_0$ and decreased $G_1$ population in normal cord blood HSBC (n=3).

(h) Expression of CDKN1A mRNA level are upregulated by overexpression of miR-26a in cord blood CD34+ cells (n=3). See FIG. 9 for cell cycle transit modulation by miR-26a overexpression.

(i) EZH2, a miR-26a target and inhibitor of CDKN1A, was upregulated with ADAR1 activation in cord blood CD34+ cells (n=3).

(j-k). Significant decreased of EZH2 expression is observed by either ADAR1 knockdown by shRNA (j) or overexpression of miR-26a (k) in cord blood CD34+ cells (n=3).

(l). Expression of primary (pri-), precursor (pre-) and mature miR-26a transcripts was measured by RT-qPCR in cord blood CD34+ HSPCs transduced with pCDH backbone, ADAR1 WT, or ADAR1$^{E912A}$ (n=3). See FIG. 11 for expression of pri- and pre-miR26a in K562 cell line and direct binding of ADAR1 to pri-miR-26a in K562.

(m). TOPO sequencing of blood CD34+ cells overexpression pCDH, ADAR1 WT, or ADAR1$^{E912A}$ (n=3) suggests A-to-I RNA editing efficiency is 20.4% (% G) at the DROSHA cleavage site. The arrow pointed to the A-to-G mutation site, reverse sequenced as T-to-C change.

(n). Confirmation of lentiviral constructs of "unedited" and "edited" pri-miR-26a. The arrow points to the A-to-I (G) mutation site.

(o). 293T cells were transfected with "unedited" or "edited" pri-miR-26a lentivirus, and the mature miR-26a expression was determined by RT-qPCR (n=5 experiments).

(p). Cell cycle flow analysis revealed significant changes of $G_0$ population in 293T cells transduced with ADAR1 WT in combination with "unedited" or "edited" miR-26a (n=3 experimental triplicate).

All graph show mean with SEM and statistical analysis was calculated using the Student's t-test. *p<0.05, p<0.005, *p<0.0005.

FIG. 4. Reduced miR-26a Enhances Self-Renewal Capacity of CML Progenitors:

(a) Reduction of miR-26a expression in CML CP (n=3) and CML BC (n=3) CD34+ cells measured by RT-qPCR (n=3).

(b). Suppression of miR-26a expression in CML CP CD34+ cells transduced with ADAR1 WT measured by miRNA PCR array (n=3).

(c). Validation of miR-26a expression in CP CML CD34+ cells transduced with backbone or ADAR1 WT lentivirus by RT-qPCR (n=3).

(d-e). Number of colonies formed in primary colony-formation assay (d) and percentage of secondary colonies formed after replating primary colonies (e) by BC CML CD34+ cells transduced with lenti-miR-26a (n=3).

(f). Experimental design of in vivo xenograft mouse studies.

(g). Overexpression of lenti-miR-26a in BC CD34+ cells reduces the percentage of granulocyte macrophage progenitors (GMP) engraftment in RAG2$^{-/-}$γc$^{-/-}$ mice (n=3 mice per group). See FIG. 11 for engraftment of other populations.

(h) Cell cycle flow analysis of backbone or lenti-miR-26a transduced CD34+ cells isolated from engrafted BC bone marrow (n=3 mice per group). See FIG. 11 for differential targeting of miR-26a in normal HSPC and CML progenitors.

(i). RNA-seq analysis of the expression of CDKN1A and EZH2 in CP (n=7) and BC CML (n=6).

(j). Gene expression of EZH2, CDKN1A, and LIN28B in BC CD34+ cells transduced with lentiviral vector overexpressing miR-26a or the backbone control (n=3).

(k). RNA-seq analysis of the expression of c-Myc in CP (n=7) and BC CML (n=6).

All graph show mean with SEM and statistical analysis was calculated using the Student's t-test. *p<0.05, p<0.005, *p<0.0005.

FIG. 5. Differential A-to-I RNA Editing in 3'UTR Regions of Normal HSPCs and BC LSC:

(a-b) Volcano plot showing the A-to-I(G) editome of cell cycle genes in ADAR1 WT-transduced cord blood CD34+ cells compared with lentiviral vector controls (n=3) (a) and in CP progenitors (n=7) compared with BC counterparts (n=6) (b).

(c). A-to-I RNA editing of MDM2 3'UTR in individual CP (n=7) and BC (n=6) samples. The predicted miRNA binding sites within MDM2 3'UTR using miRcode transcriptome-wide miRNA target prediction tool are shown (Jeggari et al., 2012).

(d). Relative miRNA expression determined by miRNA qPCR array of 84 miRNAs in CML CP CD34+ cells transduced with backbone or ADAR1 WT (n=3). See FIG. 12 for differential expression of other miRNAs and regulation of miR-155 by ADAR1.

(e) Relative miRNA expression in normal aged-matched (greater than 55 yr old) CD34+ cells (n=4) and BC CML CD34+ cells (n=3).

(f-g) The expression of MDM2-p53 pathway transcripts, MDM2 (f) and tp53 (g) in progenitor population of normal peripheral blood (NPB), CML CP (n=7), and CML BC (n=6) determined by RNA-seq.

(h). Regulation of MDM2 expression by ADAR1 WT, ADAR1$^{E912A}$ alone and in combination with miR-155 (n=3).

(i) "Wt" or "edited" MDM2 3'UTR reporter construct with A-to-G changes introduced at miRNA targeting sites (highlighted in red). The miRNA targeting efficiency was measured as the relative luciferase activity (GLuc/SEAP ratio).

(j). The MDM2 3′UTR reporters were transfected into 293T cells and then challenged with miR-155 overexpressing lentivirus (n=3 experimental triplicate). The relative luciferase activity showed that the "edited" reporter can evade miR-155 targeting.

(k). Knockdown of ADAR1 by shRNA decreases MDM2 and LIN28B expression in BC CML CD34$^+$ cells (n=3).

All graph show mean with SEM and statistical analysis was calculated using the Student's t-test. *p<0.05, p<0.005, *p<0.0005.

FIG. 6. Summary of A-to-I RNA Editing Function in Normal HSPCs and BC LSC:

Summary of ADAR1 regulated pathways in normal hematopoiesis (a) and CML LSC homeostasis (b).

FIG. 7: ADAR1 Overexpression in Normal HSPC, Related to FIG. 1:

(a). Expression of lenti-ADAR1 WT in normal cord blood CD34$^+$ cells (n=3) as measured by RT-qPCR.

(b) Representative bright-field (BF) microscopy showing normal cord blood stem cells and progenitors transduced with lentiviral vector backbone or human ADAR1 WT lentivirus.

(c) Flow analysis of stem and progenitor cells in backbone or lenti-ADAR1 WT transduced cord blood CD34$^+$ cells (n=3).

(d) Experimental design, and examples of FACS gates of DiR tracing of cord blood cells.

(g) Percentage of sub-population of progenitors including CMP, GMP, and MEP in backbone or lenti-ADAR1 WT transduced cord blood CD34$^+$ cells (n=3).

(h). Cell counts of differentiated cord blood CD34$^+$ cells post lenti-ADAR1 WT transduction. All graphs show mean with SEM.

FIG. 8. Differential Expression of Cell Cycle Transcripts Induced by ADAR1 Activation, Related to FIG. 1:

(a). Significantly differentially expressed transcripts of KEGG Cell Cycle Pathway in ADAR1 WT-transduced cord blood (n=3) versus lentiviral vector control (n=3) by RNA-seq analysis. The TPM gene expression value was transformed to $Log_2$ (TPM+1).

(b). Confirmation of CDKN1A and CDKN2A mRNA expression by RT-qPCR in cord blood CD34$^+$ cells transduced with backbone, ADAR1 WT, or ADAR1$^{E912A}$ mutant (n=4).

(c). Representative cell cycle FACS plot of shRNA targeting ADAR1 in normal cord blood CD34$^+$ HSPC as measured by Ki-67 and 7AAD levels. All graphs show mean with SEM and statistical analysis was calculated using the Student's t-test. *p<0.05.

FIG. 9. MiR-26a Regulated Normal HSPC Cell Cycle Transit and Self-Renewal, Related to FIG. 3:

(a). Representative pictures of cord blood HSPC colonies.

(b). Correlation analysis of pri-miR-26a expression and increased expression of CDKN1A as measured by RT-qPCR in 293T cells transduced with pri-miR-26a lentivirus (n=3).

(c). Confirmation of CDKN1A protein expression by western blot analysis in 293T cells transduced with miR-26a lentivirus.

Graphs show mean with SEM and statistical analysis was calculated using the Student's t-test. *p<0.05.

FIG. 10. ADAR1 Directly Binds to Pri-miR-26a Transcripts, Related to FIG. 3:

(a). Expression of pre- and mature miR-26a was measured by RT-qPCR in K562 transduced with pCDH backbone, ADAR1 WT, or ADAR1$^{E912A}$ (n=3).

(b). Crosslinking RNA Immunoprecipitation (CLIP) in K562 stably expressing pCDH vector, lenti-ADAR1 WT, and lenti-ADAR1$^{E912A}$ with an ADAR1 antibody confirmed that both ADAR1 WT and ADAR1$^{E912A}$ mutant are associated with pri-miR-26a transcript. The experiment was performed in triplicate.

(c). ViennaRNA predicted secondary structure changes in pri-miR-26a induced by A-to-I editing occurring near DGCR8/DROSHA cleavage site (highlighted in orange), which blocks the maturation to pre-miR-26a.

(d). Summary Figure of A-to-I RNA editing dependent inhibition of miR-26a expression by preventing the DROSHA cleavage of pri-miR-26a that results in reduction of pre-miR-26a and mature miR-26a.

Graphs show mean with SEM and statistical analysis was calculated using the Student's t-test. *p<0.05, **p<0.005.

FIG. 11. Differential effect of miR-26a overexpression on normal HSPC and CML progenitors, related to FIG. 4.

(a-b). Percentage of human CD45$^+$ (h) or progenitor (CD45$^+$Lin$^-$CD34$^+$CD38$^+$) (i) engraftment in bone marrow and spleen of BC CML xenografted mice (n=3 mice per group). *p<0.05, **p<0.005.

(c). Representative CD45$^+$ and progenitor engraftment of BC CML cells transduced with backbone or miR-26a in bone marrow.

(d). Representative GMP engraftment (% of parent cells) of BC CML cells transduced with backbone or miR-26a in bone marrow and spleen (n=3 mice per group).

(e). Representative cell cycle flow of engrafted CD45$^+$ cells in BC CML cells transduced with backbone and miR-26a in bone marrow.

(f). Downregulation of miR-26a by transfecting a miR-26a inhibitor into K562 BC CML cells induced cell quiescence. (n=3 experimental triplicate).

(g). RNA-seq quantification on ADAR1 WT transduced cord blood (n=3) and lentiviral vector control (n=3) for differentially expressed genes corresponding to Functional MTIs from miRTarBase for miR-26a targets (Loge Fold Change>1, p<0.05, FDR<0.10).

(h). Differentially expressed miR-26a targets in BC progenitors (n=6) compared to CP counterparts (n=7) by RNA-seq analysis. All graph show mean with SEM and statistical analysis was calculated using the Student's t-test.

(i-j). MYC expression was not significantly changed upon ADAR1 WT overexpression by RNA-seq analysis (i) or ADAR1 knockdown by shRNA RT-qPCR (j) in normal cord blood HSPCs (n=3). *p<0.05, **p<0.005.

FIG. 12. ADAR1 regulates MDM2 3′UTR targeting and miRNA biogenesis in CML progenitors, related to FIG. 5:

(a). miRNome array-derived expression of miRNAs that are predicted to bind to MDM2 3′UTR region in cord blood CD34$^+$ HSPC overexpression ADAR1 WT or ADAR1$^{E912A}$ mutant compared with pCDH vector control (n=3-4).

(b). Relative miRNA expression determined by miRNA qPCR array of 84 miRNAs in cord blood, CML CP, and CML BC CD34$^+$ cells (n=3 per patient group).

(c). Expression of primary (pri-), precursor (pre-) and mature miR-155 transcripts was measured by RT-qPCR in cord blood CD34$^+$ HSPCs transduced with pCDH backbone, ADAR1 WT, or ADAR1$^{E912A}$ (n=3).

(d). Expression of pre- and mature miR-155 in K562 leukemia cells stably transduced with pCDH, ADAR1 WT, or ADAR1$^{E912A}$. Experiment were performed in triplicate.

(e). Crosslinking RNA Immunoprecipitation (CLIP) in K562 stably expressing pCDH vector, ADAR1 WT, and ADAR1$^{E912A}$ with an ADAR1 antibody confirmed that both ADAR1 WT and ADAR1$^{E912A}$ mutant both binds to pri-miR-155 transcripts. All graph show mean with SEM and statistical analysis was calculated using the Student's t-test.

(f-g). The expression of CDKN2A transcripts, p16INK4a (h) and p14ARF (i), in progenitor population of normal peripheral blood (NPB), CML CP (n=7), and CML BC (n=6) determined by RNA-seq. *p<0.05, **p<0.005.

Materials and Methods

Mice:

All mouse studies were completed in accordance with University Laboratory Animal Resources and Institutional Animal Care and Use Committee of the University of California regulations. Immunocompromised RAG2$^{-/-}$γc$^{-/-}$ mice were bred and maintained in the Sanford Consortium vivarium according to IACUC approved protocols. Neonatal mice of both sexes were used in the study.

amplification reactions. Three different pre-amplification reactions were set up for each sample, each one using a different set of primer mix to cover the entire miRNOme™ (Qiagen, MBHS-3216Z). Following pre-amplification, pre-amplified miRNA was pulled in one tube and used for miRNOme™ qPCR assay. The miRNA expression was normalized to RNU6_2 housekeeping gene and the fold change to pCDH lentiviral vector control was calculated. Significantly differentiated miRNAs were analyzed for mRNA targets using DIANA mirPath™ software (Vlachos et al., 2015) (http://diana.imis.athena-innovation.gr/Diana-Tools/index.php). The predicted miRNA binding sites were determined using miRcode transcriptome-wide miRNA target prediction tool (Jeggari et al., 2012) (http://mircode.org/index.php).

DiR Staining and Measurement by FACS

Cord blood CD34$^+$ cells ($1\times10^5$) were isolated and stained with 4 mg/mL DiR (Invitrogen) in PBS according to the manufacturer's specifications as described previously (Goff et al., 2013). DiR stained cells were then washed and transduced with GFP$^+$ lentiviral vectors. After 3-days, cells were collected and analyzed by FACS for GFP$^+$ and DiR$^+$ cells.

FACS Cell Cycle Analysis

FACS cell cycle analysis was performed with 7-AAD and Ki-67 as previously described (Goff et al., 2013). Single cell suspensions of bone marrow cells of engrafted mice with either lentiviral backbone or miR-26a conditions were immunostained with Alexa405-conjugated anti-human CD45 (Invitrogen), Alexa647-anti-human CD38 (Ab Serotec) and biotin-anti-human CD34 (Invitrogen) plus Alexa488-strepavidin (Invitrogen) in 2% fetal bovine serum/PBS—followed by live cell staining using the LIVE/DEAD® Fixable Near-IR Dead Cell Stain Kit (Invitrogen). Surface stained cells were then fixed in 70% ethanol overnight and were immunostained with PE-conjugated anti-Ki-67 (BD) in 0.15% saponin/2% fetal bovine serum/PBS, washed and incubated with 7-AAD (Invitrogen, 10 µg/mL in 0.1M sodium citrate/5 mM EDTA pH8.0/0.15M NaCl/0.5% BSA/0.02% saponin). For 293T cells, cells were transduced with lentiviral backbone or miR-26a for 3-days and then stained with the LIVE/DEAD® Fixable Near-IR Dead Cell Stain Kit (Invitrogen). Cells were then fixed in 70% ethanol for 4 hrs at 4° C. and immunostained with PE-conjugated anti-Ki-67 (BD) and 7-AAD as described. Stained samples were analyzed using a FACSAria™ and FlowJo™

Western Blots 293T cell lysate (10 µg) was mobilized onto nitrocellulose member after electrophoresis on a 4-20% gradient acrylamide gel. The member was blocked in 5% BSA/20 mM Tris-HCl for 1 hr. The blot was incubated with primary CDKN1A antibody (Abcam, ab18209) in 5% BSA/20 mM Tris-HCl/0.1% Tween-20 overnight at 4° C., followed by secondary HPR-linked Rabbit IgG antibody (Cell Signaling, #70745) for 2-4 hrs at room temperature. The member was incubated in SuperSignal West Femto Substrate™ (ThermoFisher, #34096) for chemiluminescent reading on ChemiDoc System™ (Bio-Rad).

IF Staining

Cord blood CD34$^+$ cells ($2\times10^5$ cells, 200 µL) was cytospined onto slides at 500 rpm for 5 min, fixed for 10 min in 4% PFA at room temperature, rinsed with PBS, and incubated with 5% normal donkey serum/0.2% Triton X-100 followed by incubation with primary antibodies overnight at 4° C. Primary antibodies used were anti-human PE-conjugated Ki-67 (BD) and anti-CDKN1A (CP74) Biotin (Abcam, ab79467™) Stained slides were then incubated with secondary Alexa Fluor® 488™ Goat Anti-Mouse IgG (H+L) Antibody (Life Technologies, A11029) and mounted using Prolong® Gold antifade with DAPI. Epifluorescent images were acquired using confocal microscopy (Olympus Fluoview FV10i™) and Adobe Photoshop CS5™ Hematopoietic colony formation assay.

After lentiviral transduction, normal cord blood or CML patient CD34$^+$ cells were plated into Methocult Medium™ (50-100 cells per well, 12-well plate). After two weeks, colonies were scored and individual colonies were re-plated into fresh MethoCult™ media as previously described (Jiang et al., 2013). Secondary colonies were scored after an additional two weeks in culture.

Human Progenitor Xenotransplantation

BC CML CD34$^+$ cells were transduced with lentiviral backbone or miR-26a with a MOI of 200 for 3-days. Neonatal mice were transplanted intrahepatically with $1\times10^5$–$2\times10^5$ transduced BC CML CD34$^+$ cells according to our published methods (Abrahamsson et al., 2009; Goff et al., 2013; Jiang et al., 2013; Zipeto et al., 2016). Transplanted mice were FACS screened for human engraftment in peripheral blood at 6-10 weeks. Once human engraftment was confirmed (>1% human CD45$^+$ cells in peripheral blood), mice were euthanized and single cell suspensions of hematopoietic tissues were analyzed by FACS for human CD45$^+$ engraftment and cell cycle analysis (Goff et al., 2013).

RNA-Sequencing Read Preprocessing

Primary normal and CML samples were obtained and RNA-Seq analysis were performed according to published methods (Abrahamsson et al., 2009; Goff et al., 2013; Jiang et al., 2013; Zipeto et al., 2016). For 50 bp paired end reads from previously aligned data, the reads were converted from BAM to FASTQ using SAMTOOLS BAM2FQ (Li et al., 2009). For 100 bp paired end reads, the reads were entered into pre-processing as is. Reads were cleaned using CUTADAPT™ to remove Illumina universal adapters (Martin, 2011).

Read Alignment and Gene Counts

Reads were aligned using STAR's two-pass alignment method, using the GRCh38.84 reference genome and corresponding Ensembl GTF™ (Aken et al., 2016; Guo et al., 2017). STAR was used to output a sorted genome-coordinate based BAM file, as well as a transcriptome-coordinate based BAM file (Dobin et al., 2013) (https://github.com/alexdobin/STAR). STAR also was used to output the number of reads aligned to each gene similar to hi-seq count. STAR settings were based on those used for the ENCODE STAR-RSEM™ pipeline. The infer_experiment.py script from the RSeQC package was used to confirm the strandedness option corresponding to the correct read counts (Li and Dewey, 2011; Wang et al., 2012) (http://rseqc.sourceforge.net/), and also to confirm the forward strand probability for input to RSEM. The total reads per million (TPM) (Mortazavi et al., 2008) over the total collapsed exonic regions represent the 'gene' expression level.

RNA Editing Analysis

Coordinates from the DARNED and RADAR databases were combined and converted to GRCh38 using Crossmap (Kiran and Baranov, 2010; Ramaswami and Li, 2014; Zhao et al., 2014). The resulting coordinates were used as input to the REDItoolKnown.py script from the REDItools™ package to determine the number of A, C, G, and T base calls at each coordinate (Picardi and Pesole, 2013) (http://srv00.recas.ba.infn.it/reditools/). Only coordinates with coverage greater than or equal to 5 in all samples for a given comparison were reported. The percentage of bases called as G at bases with reference A was reported. Coordinates with a percentage G of 0 in all samples for a given sample were not reported. Using percentage G at a coordinate as an input metric, the mean percentage G in each group, the loge fold change of percentage G of one group versus another, the p values, and minus $\log_{10}$ p values by both the Wilcox and student t-tests were recorded for each coordinate similar to published methods (Jiang et al., 2013). Coordinates were annotated with the name of the closest gene using bedtools closest and bedtools intersect (Quinlan and Hall, 2010) (http://bedtools.readthedocs.io/en/latest/). The coordinates annotated with the names of genes in the KEGG cell cycle gene set were recorded.

Transcript and Gene Quantification and Differential Expression

The transcriptome-coordinate based BAM from the read alignment step was input to RSEM, using settings based on the ENCODE STAR-RSEM pipeline (Li and Dewey, 2011). RSEM was provided the GRCh38.84 reference genome and corresponding Ensembl GTF™ for its transcriptome reference. RSEM was used to provide TPM and expected counts for genes and transcripts. For genes, the gene count data generated by STAR in the alignment step was used as input to EdgeR™ (Dobin et al., 2013; Robinson et al., 2010) (http://bioconductor.org/packages/release/bioc/html/edgeR.html). For transcripts, the expected counts data from RSEM was used as input to edgeR. Only features with a minimum CPM of 0.5 (in at least half the samples in the comparison) as measured by EdgeR were submitted to EdgeR's differential expression, to yield loge fold change, p value, and FDR for each feature for the comparison. The threshold for significant genes and transcripts was set at a P value less than 0.05 and an FDR less than 0.10. An additional threshold based on the absolute value of the log 2-fold change was also used to filter features for inclusion in a heatmap. Heatmaps visualize the log 2 (TPM+1) transformed TPM quantity from RSEM for each feature, and were generated using GENE-E with default settings for a row and column clustered heatmap and dendrogram.

TABLE S1

CML patient sample information

| Patient ID | Diagnosis | Treatment | Gender/Age | Date | WBC count (K/mm3) | % Blast (PB) |
|---|---|---|---|---|---|---|
| CP-01 | CML CP | None | M/60 | 13 Nov. 2008 | 189 | <5 |
| CP-02 | CML CP | None | F/63 | 23 May 2008 | 326 | 5 |
| CP-04 | CML CP | None | M/44 | 14 Oct. 2008 | 306 | 5.6 |
| CP-05 | CML CP | None | M/26 | 21 Sep. 2009 | 231 | <1 |
| CP-06 | CML CP | None | F/62 | 25 Sep. 2009 | 87.7 | <5 |
| CP-12 | CML CP | None | N/A | 26 Aug. 2009 | 390 | <5 |
| CP-19 | CP | None | M/40 | 20 Oct. 2010 | 221 | 13 |
| BC-02 | CML BC | None | M/34 | 26 Aug. 2004 | 241 | 92 |
| BC-05 | CML BC | None | M/43 | 8 Dec. 2003 | 82.4 | 32 |
| BC-06 | CML BC | Hydroxyurea | M/30 | 26 Oct. 1993 | 170 | 94 |
| BC-07 | CML BC | Hydroxyurea | M/48 | 29 Oct. 1993 | 209 | 86 |
| BC-08 | CML BC | Hydroxyurea | M/53 | 27 Jul. 2000 | 98 | 82.6 |
| BC-09 | CML BC | None | M/65 | 17 Oct. 1991 | 72 | 42 |
| BC-11 | CML BC | Hydroxyurea | M/31 | 15 Mar. 2006 | 40.1 | 79 |
| BC-19 | CML BC | Imatinib followed by dasatinib | M/46 | 23 Nov. 2007 | 127 | 30 |

TABLE S2

List of RT-qPCR primers.

| Transcript | FW primer (5'-3') | Rev primer (5'-3') |
|---|---|---|
| Lenti-ADAR1 | AAA AAG CAG GCT CCA T (SEQ ID NO: 1) | AAA AAG CAG GCT CCA T (SEQ ID NO: 2) |
| Total ADAR1 | TGC TGC TGA ATT CAA GTT GG (SEQ ID NO: 3) | TCG TTC TCC CCA ATC AAG AC (SEQ ID NO: 4) |
| CDKN1A | ATG AAA TTC ACC CCC TTT CC (SEQ ID NO: 5) | AGG TGA GGG GAC TCC AAA GT (SEQ ID NO: 6) |
| CDKN2A | ATA TGC CTT CCC CCA CTA CC (SEQ ID NO: 7) | CGT GAG TGC TCA CTC CAG AA (SEQ ID NO: 8) |
| MDM2 | TTC CCA GCC TAG GTT TCA GA (SEQ ID NO: 9) | AAC ACG GAG CTT GAG AGG AA (SEQ ID NO: 10) |
| pri-miR-26a | GCC CAA TGG CAT AGC AAG A (SEQ ID NO: 11) | GGC CAG TCA TGC TTA CAG TCA C (SEQ ID NO: 12) |
| pri-miR-155 | AGC TTT ATA ACC GCA TGT GCA TAC (SEQ ID NO: 13) | CAG ATT TCC CCT TCC TGG TTT (SEQ ID NO: 14) |

TABLE S2-continued

List of RT-qPCR primers.

| Transcript | FW primer (5'-3') | Rev primer (5'-3') |
|---|---|---|
| HPRT | TCA GGG ATT TGA ATC ATG TTT GTG (SEQ ID NO: 15) | CGA TGT CAA TAG GAC TCC AGA TG (SEQ ID NO: 16) |

Example 2: Enzymatic DNA and RNA Mutagenesis Promotes Pre-Leukemia Stem Cell Evolution This example demonstrates that methods and compositions as provided herein are effective and can be used to inhibit APOBEC3G (A3G) activity (to decrease DNA base editing), and/or ADAR1p150 (to decrease adenosine to inosine RNA editing) to eliminate or reduce numbers of pre-leukemia stem cells (pre-LSCs), and reduce or eliminate formation of leukemia stem cells (LCSs), and to treat a myeloproliferative disorder. This example demonstrates that malignant DNA and RNA editase activity of APOBEC3C and ADAR1p150 drives the clonal expansion of pre-LSC to self-renewing AML LSC and β-catenin activation.

While innate immune DNA and RNA base editing enzymes protect the human genome from retroviral integration, hyperactivation has been linked to cancer evolution and cancer stem cell generation. Here, we investigated DNA and RNA mutagenesis in myeloproliferative neoplasm pre-leukemia stem cell (pre-LSCs) evolution into LSCs in acute myeloid leukemia. Comparative hematopoietic stem cell and progenitor-enriched whole genome and whole transcriptome sequencing revealed overexpression of the cytidine-to-thymidine DNA base editing enzyme, APOBEC3C, and increased ADAR1p150-mediated adenosine-to-inosine RNA editing in pre-LSC. Pre-LSC evolution into LSC was characterized by RNA hyper-editing and upregulation of ADAR1p150, STAT3β and β-catenin. While lentiviral ADAR1p150 overexpression enhanced pre-LSC replating and engraftment commensurate with β-catenin activation, lentiviral ADAR1 p150 shRNA knockdown reduced activated β-catenin levels. Thus, early detection and targeted inhibition of enzymatic mutagenesis may represent a tractable pre-cancer stem cell eradication strategy.

Both APOBEC3 (anti-viral apolipoprotein B mRNA editing enzyme, catalytic polypeptide-like) and ADAR1 (adenosine deaminase acting on RNA1) are part of innate immune response and restrict retroviral replication and LINE element retro-transposition. Malignant activation of APOBEC3 and ADAR1 can occur in stem and progenitor cells which are vital for tissue maintenance. The resulted hyper-editing can introduce mutations in DNA or RNA level, respectively. Recent studies also indicate ADAR1 as a novel immunotherapy target since deletion of ADAR1 sensitizes cancer cells to PD-1 immune checkpoint blockade(I). However, the combinatorial role of DNA and RNA enzymatic mutagenesis in human cancer stem cell initiation and evolution had not been clearly defined and could help to elucidate early diagnostic and therapeutic strategies that obviate relapse.

Myeloproliferative neoplasms (MPNs) were the first malignancies found to harbor somatic mutations in human hematopoietic stem cells (HSCs) that promote clonal expansion of myeloid progenitors(2-14). These pre-leukemia stem cells (pre-LSCs) vary in their capacity to self-renew, resist therapy(15-18) and contribute to acute myeloid leukemia (AML) transformation(19, 20). In contrast to the concept of spontaneous mutation, it is recently shown that DNA and RNA editing enzymes could behave as drivers in mutagenesis. For example, cytosine to uracil (C-to-U read as C-to-T) mutation signatures of DNA editase APOBEC3 were shown in many malignancies(21). Moreover, activation of RNA editase ADAR1 converts adenosine to inosine (A-to-I read as A-to-G), which leads to hyper-editing in self-renewal and cell cycle transcripts that fuels LSC generation(22). Through the regulation of mRNA and miRNA stability, ADAR1 plays a pivotal role in embryonic development and stem cell regulation(22-25). Critical RNA-sequencing studies have shown that elevated levels of the ADAR1 editase activity has emerged as a dominant driver of cancer progression and therapeutic resistance(26). Specifically, the deregulation of ADAR1 promotes the transformation of chronic myeloid leukemia (CML) from chronic phase (CP) to a therapy resistant blast crisis (BC) phase. We have previously shown that inflammation-responsive ADAR1 heavily contributes to stem cell differentiation and self-renewal in CML disease progression(22).

In this study, we investigated the contribution of DNA and RNA editing to pre-leukemia stem cell (LSC) transformation into the leukemia stem cells (LSCs) that drive myeloproliferative neoplasms (MPN) progression to acute myeloid leukemia (AML). Whole genome sequencing (WGS) analyses of 43 peripheral blood CD34$^+$ samples and 44 saliva samples from 39 MPN patients and 4 non-MPN controls compared with whole transcriptome sequencing (RNA-seq) analyses of 113 FACS-purified hematopoietic stem cells and progenitors from 78 individuals, including 54 MPN and AML patients and 24 healthy young and aged individuals, revealed that pre-LSC commonly harbored mutations in adaptive and innate immune response genes (HLA, KIR) DNA replication and repair, JAK2 and WNT signaling, pre-mRNA splicing regulatory genes and higher rates of C-to-T transitions as well as APOBEC3C upregulation typified by clonal expansion. During MPN progression, increased expression of the inflammatory cytokine signals, coincided with activation of the cytokine responsive ADAR editing isoform, ADAR1 p150(25, 27-29). Comparative WGS and RNA-seq editome analyses revealed novel RNA editing sites and RNA editing signatures that distinguished MF and AML from normal young and aged progenitors. In summary, early detection of dynamic DNA and RNA mutational hierarchies as well as malignant RNA editing may inform pre-LSC eradication strategies.

Results—Example 2

Deregulated C-to-T Editing in MPN Pre-Leukemia Stem Cells

Figure 1A:
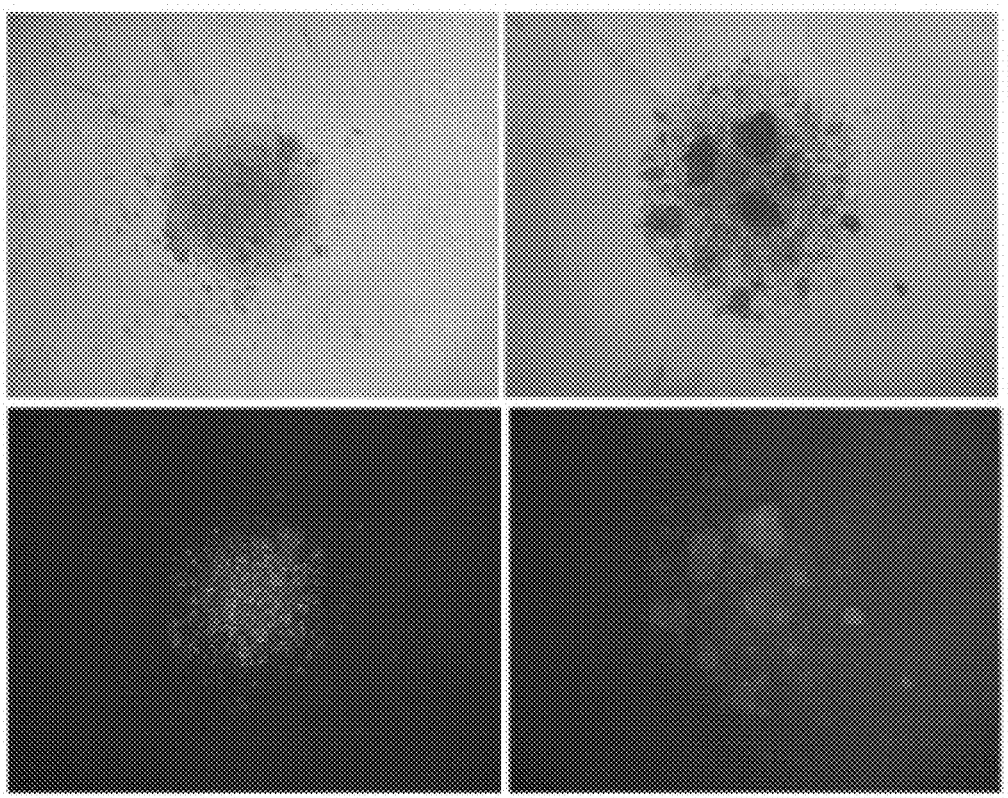
FIG. 1A-P illustrate how ADAR1 regulates cell cycle in normal hematopoiesis.
Figure 1B:
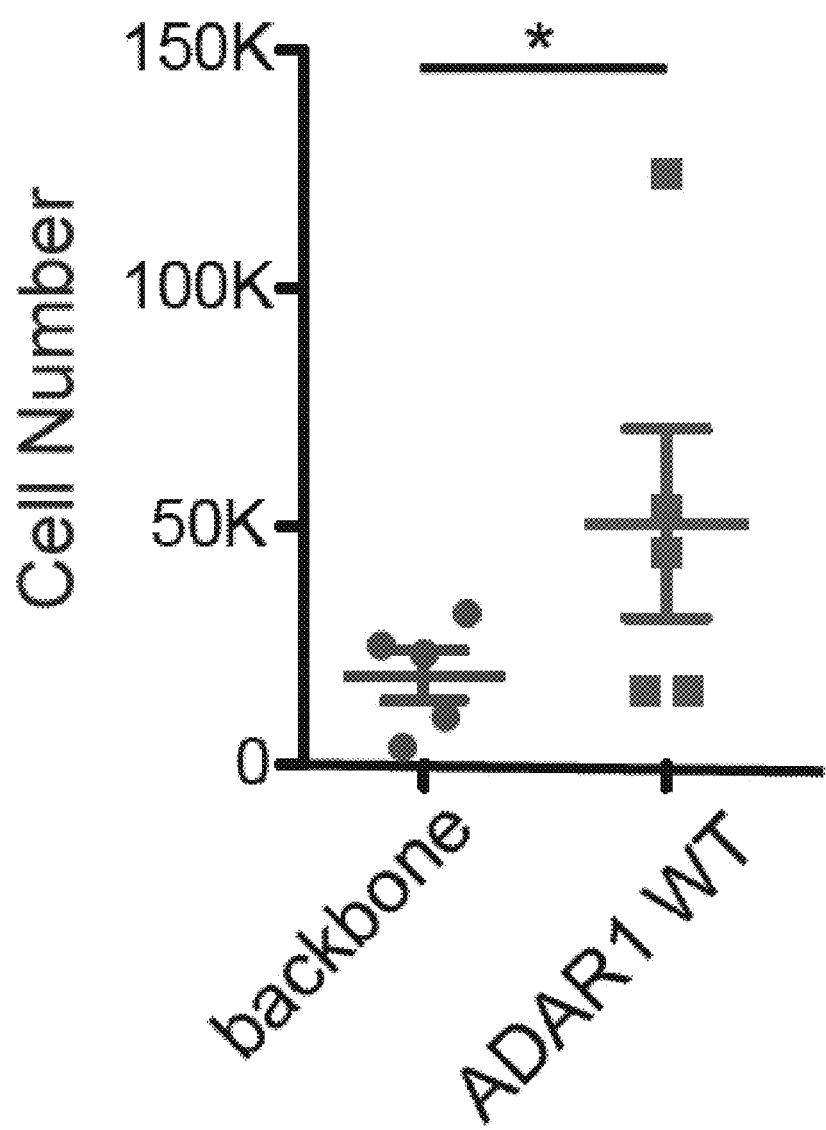
FIG. 1B-C graphically illustrate data showing accelerated cell expansion as observed by increased total cell number (FIG. 1B), stem cells (CD34$^+$ CD38$^-$Lin$^-$), and progenitors (CD34$^+$ CD38$^+$ Lin$^-$) (FIG. 1C)

To identify pre-LSC DNA mutational hierarchies, whole genome sequencing analysis (WGS) was performed on both peripheral blood samples (90× coverage) and saliva (30× coverage) from 37 individuals with various MPNs, including polycythemia vera (PV), essential thrombocythemia (ET), chronic myeloid leukemia (CML) and myelofibrosis (MF) as well as 4 non-MPN controls (including 1 CLL patient with a CALR SNP) (FIG. 13A, or FIG. 1a, Example 2). We performed single nucleotide variant, copy number variant and structural variant analyses on all samples, employing tumor-only somatic variant filtering on the peripheral blood samples and subtracting structural and copy number variants found in the four normal patients. We observed 62-428 (average 239) somatic single nucleotide variants, 135-221 (average 170) structural variants and 1-4 (average 1.7) copy number variants per patient in MPNs (FIG. 13B, or FIG. 1b, Example 2).

Figure 1C:
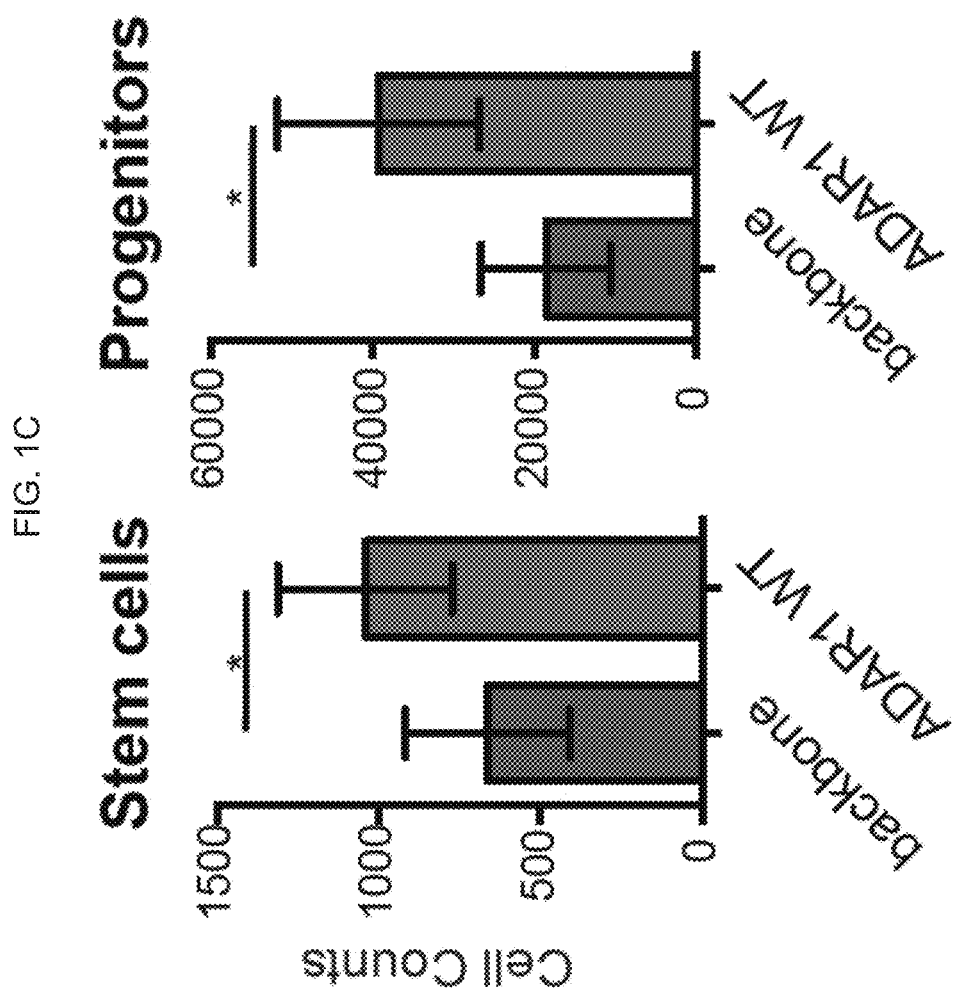

We examined the 69 known myeloid cancer genes (30) (driver mutations and copy-number changes) in peripheral blood WGS of MPN dataset and discovered that JAK2, CALR, ASKL1/3 and KMT2C are the most frequently mutated genes (FIG. 13B-C, or FIG. 1b-c, Example 2). Indeed, several patients with mutations in the 69 known myeloid cancer genes have either another malignancy or have progressed to sAML since the time of sample collection (FIG. 13C, or FIG. 1c, Example 2). We also examined non-MPN associated DNA mutations in MPN peripheral blood (FIG. 18A, or FIG. S1a, Example 2). Two genes, DAPK1 and RP1L1 were identified in high-risk patients, providing potential new biomarkers. Interestingly, we identified variants in several HLA-genes (HLA-DQB2, HLA-DQA2, HLA-DQB1) and killer-cell immunoglobulin receptors (KIR2DS4, KIR3DL2, KIR2DL4, AND KIR3DL1) in MPN WGS. This suggests that mutations of immune response genes and the corresponding dysfunction of immune system may contribute to LSC generation.

Since saliva may contain lymphocytes that harbor clonal mutations(19), we compared WGS mutations from saliva sample to peripheral blood sample in the same individual and identified several identical mutations, including JAK2 and ATM (FIG. 13C, FIG. 18B, or FIG. 1c and FIG. S1b, Example 2, respectively). This suggests saliva of MPN patients might provide a less invasive source of tissue to identify driver mutations.

Figure 1E:
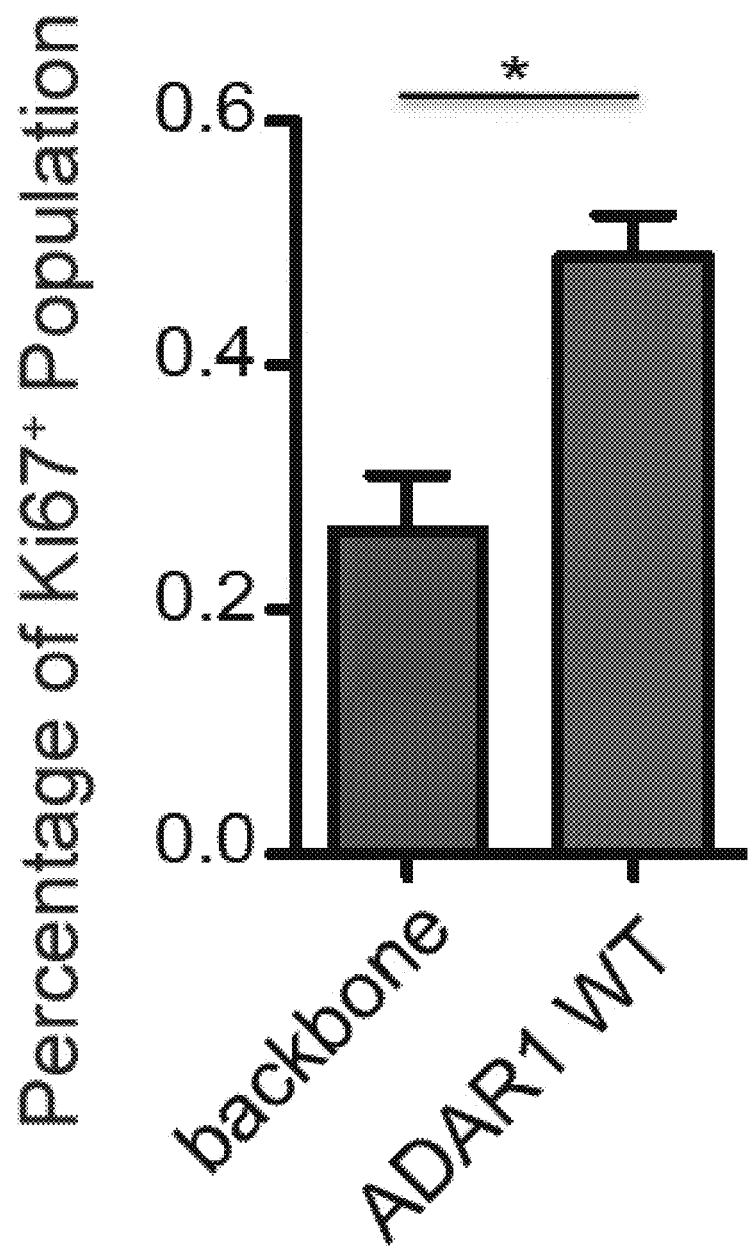
FIG. 1E graphically illustrates the percentage of Ki67+ cell population in the ADAR1 WT-expressing CD34$^+$ cells as shown in FIG. 1D, the backbone being the negative control.
Figure 1F:
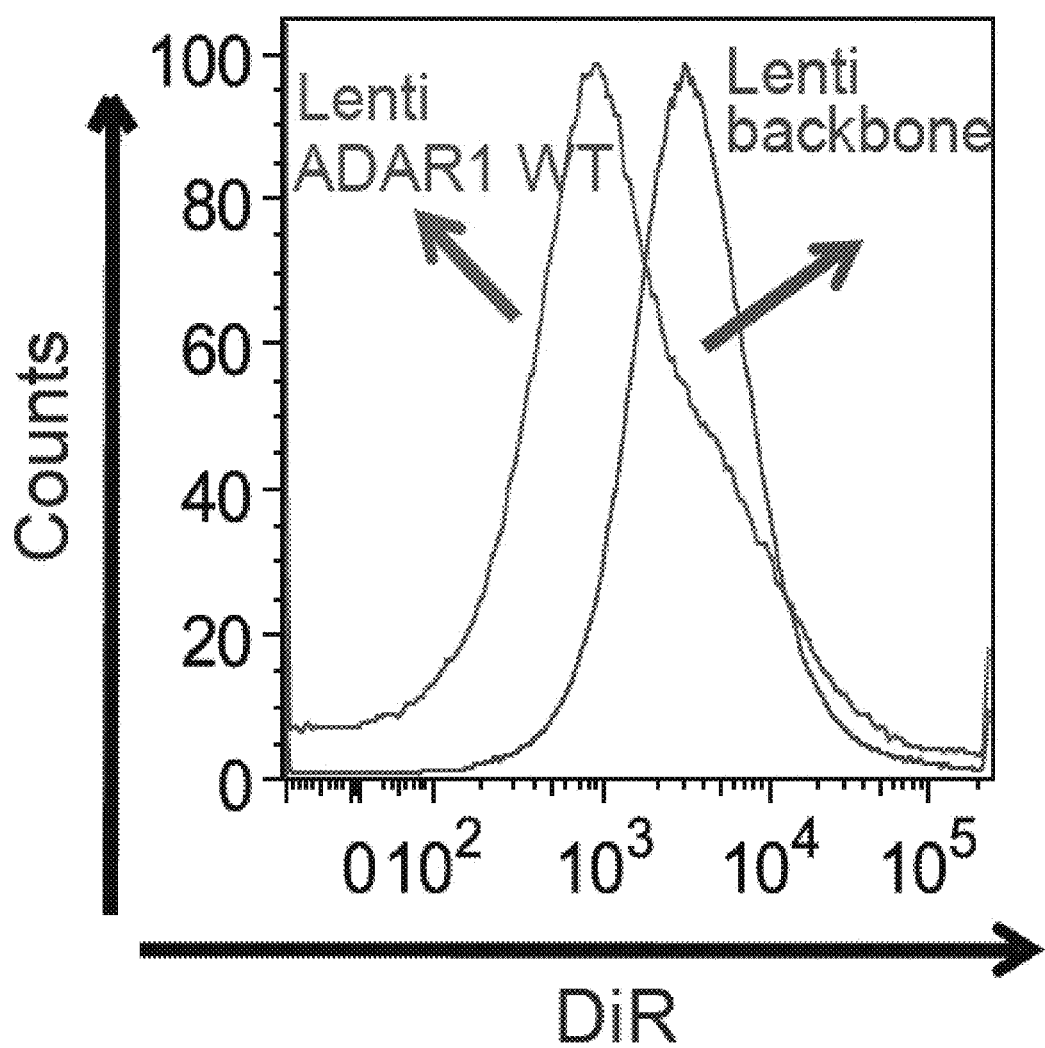
FIG. 1F graphically illustrates data showing that ADAR1 WT overexpression in cord blood CD34$^+$ cells induced accelerated loss of DiR signal compared with backbone control.
Figure 1G:
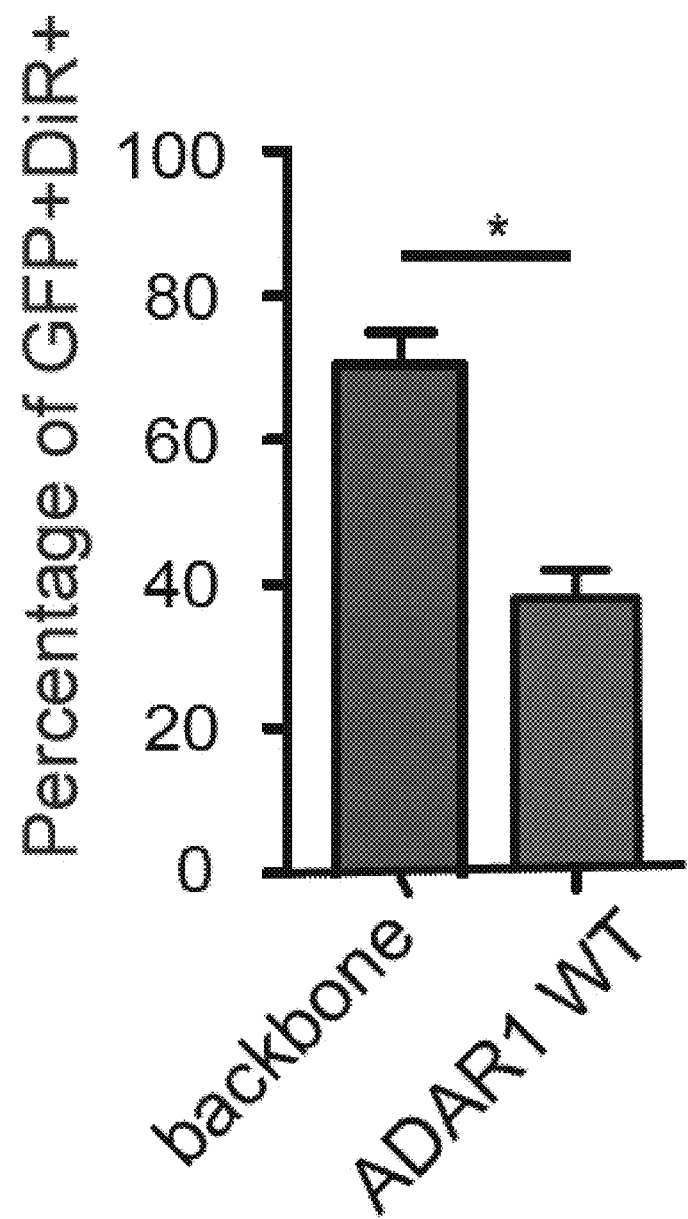
FIG. 1G graphically illustrates data from FIG. 1F, showing the percentage of Ki67+ cell population in the ADAR1 WT-expressing CD34$^+$ cells.
Figure 1H:
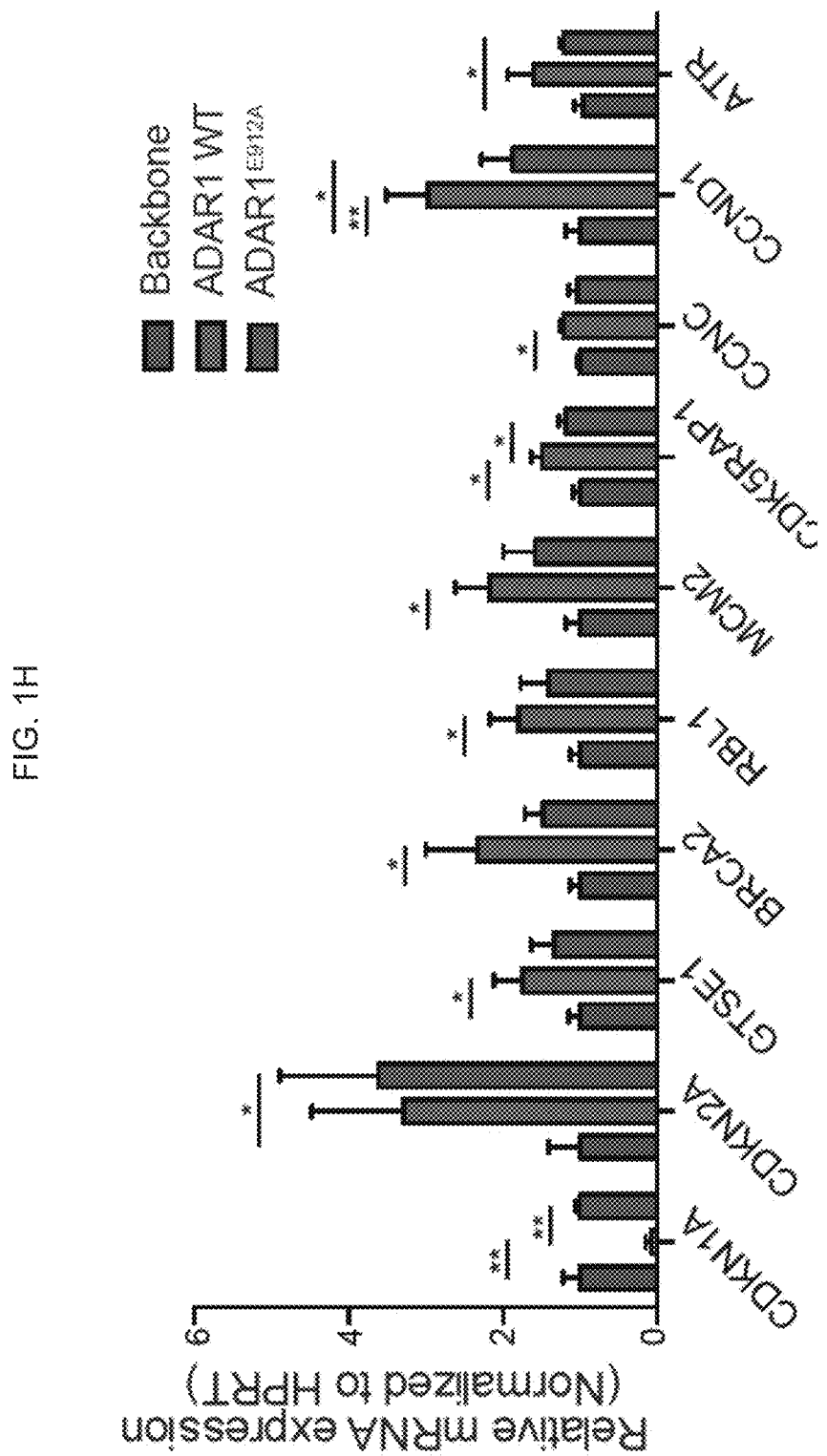
FIG. 1H graphically illustrates data showing that significant differential expressed cell cycle transcripts were determined by an RT-qPCR array of 84 transcripts on cord blood HSPC transduced with ADAR1 WT, ADAR1$^{E912A}$ inactive mutant, or lentiviral vector control.
Figure 1I:
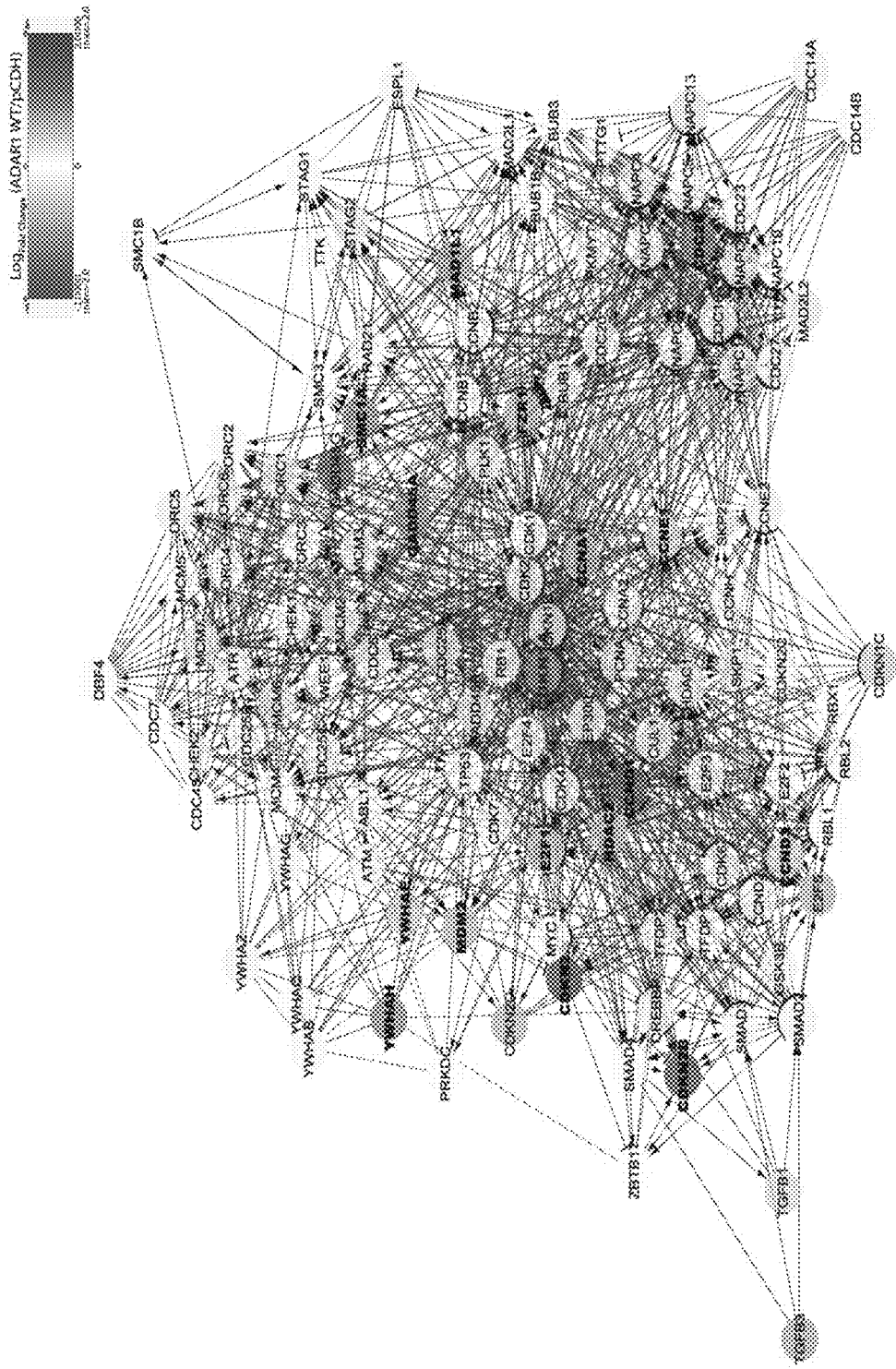
FIG. 1I schematically illustrates a cytoscape analysis of differentially expressed transcripts of KEGG Cell Cycle Pathway in ADAR1 WT-transduced cord blood versus lentiviral vector control by whole transcriptome RNA sequencing; the upper inset shows the log-fold change in ADAR1/pCDH.
Figure 1J:
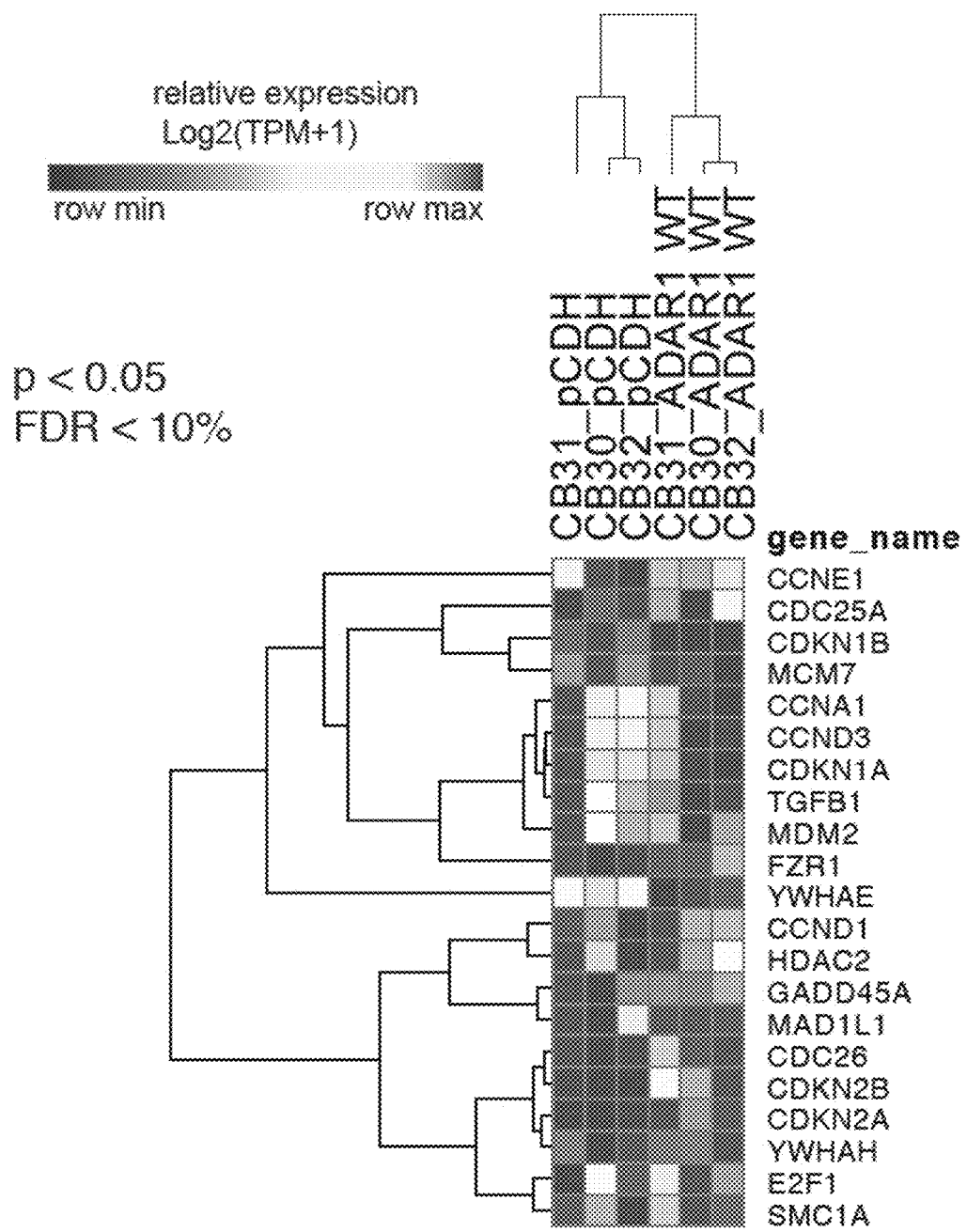
FIG. 1J schematically illustrates a heatmap showing an RNA-seq quantification on ADAR1 WT-transduced cord blood and lentiviral vector control for genes corresponding to the KEGG Cell Cycle Pathway, as visualized in the heatmap, with the inset showing relative expression log 2(TPM+1)
Figure 1L:
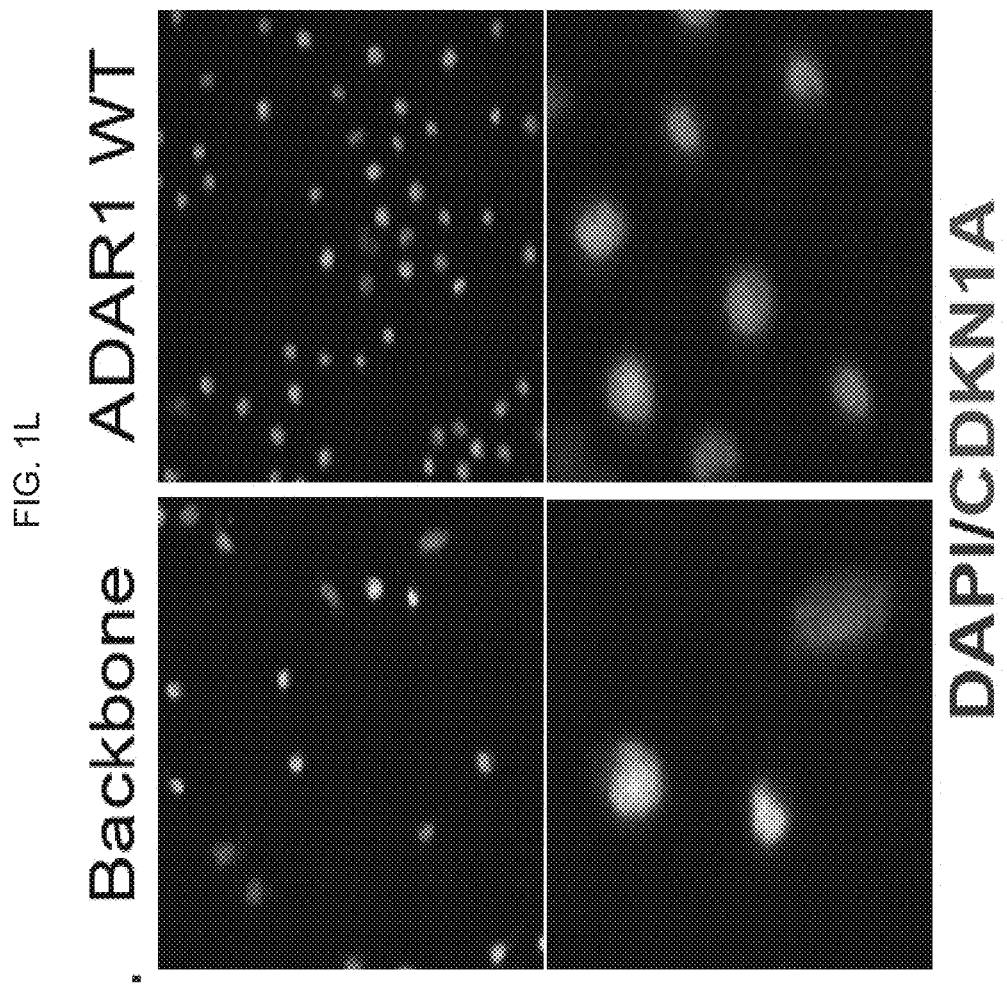
FIG. 1L illustrates an immunofluorescent image showing decreased CDKN1A protein expression in ADAR1 WT-expressing CD34$^+$ cells.
Figure 1M:
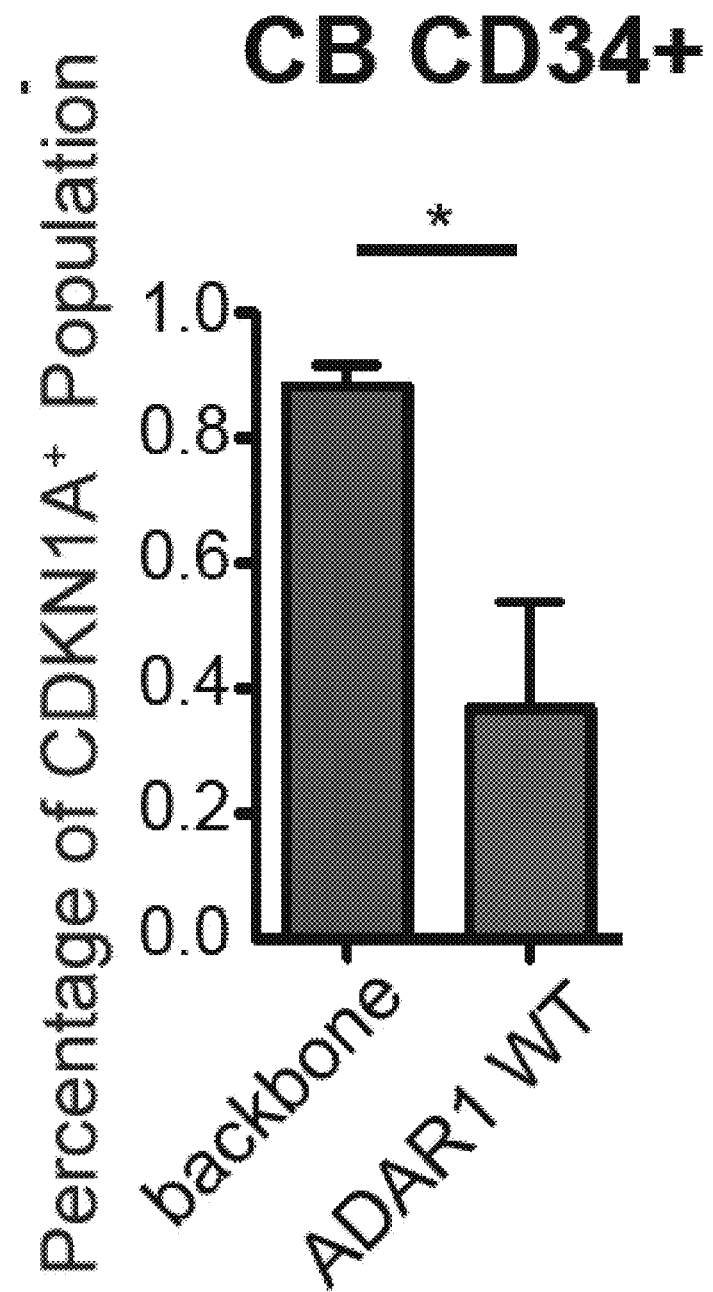
FIG. 1M graphically illustrates data from the immunofluorescent cells shown in FIG. 1L, showing the percentage of CDKN1A+ population in control backbone and in cord blood CD34+ ADAR1 wild type (WT) cells.
Figure 1N:
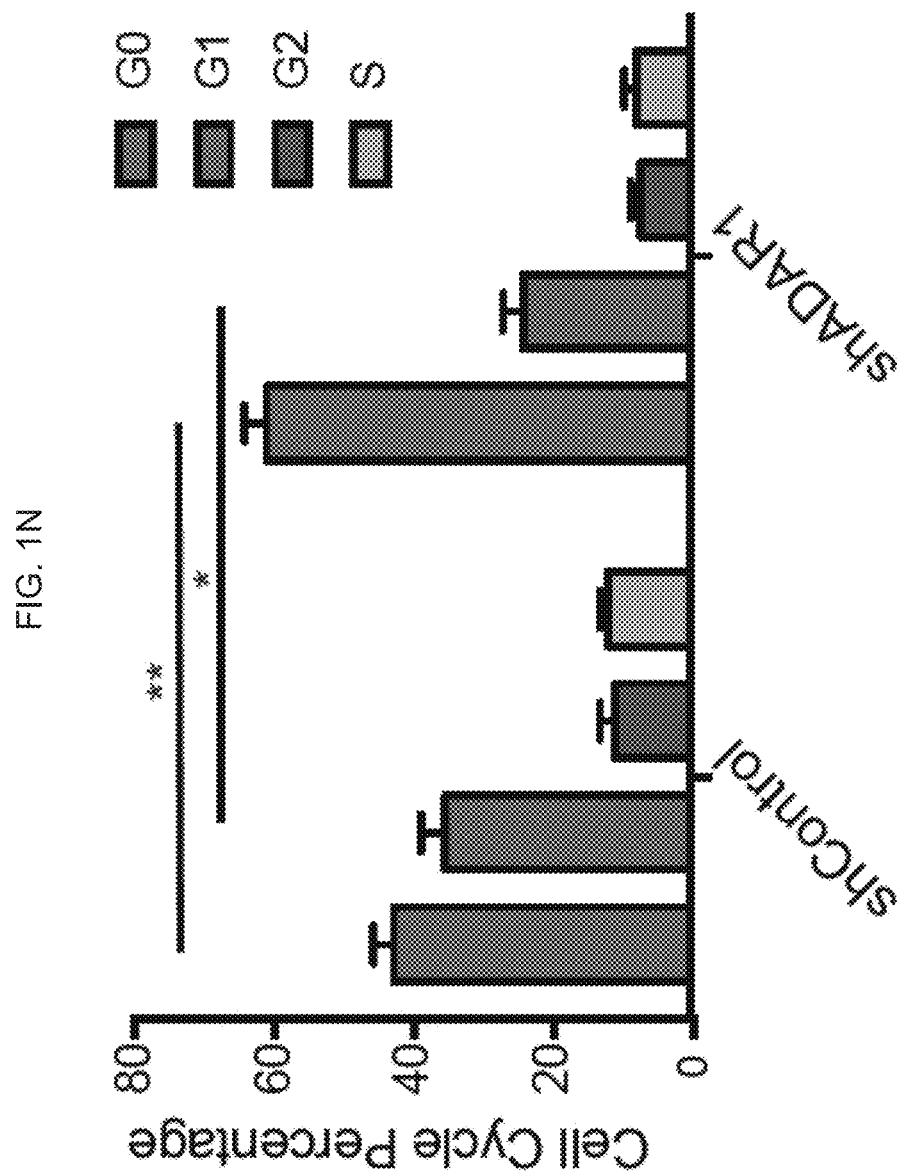
FIG. 1N graphically illustrates data showing that shRNA targeting ADAR1 reduced cell cycle acceleration and increased G$_0$ population of normal cord blood CD34$^+$ HSPC as measured by flow cytometry of Ki-67 and 7AAD.
Figure 1O:
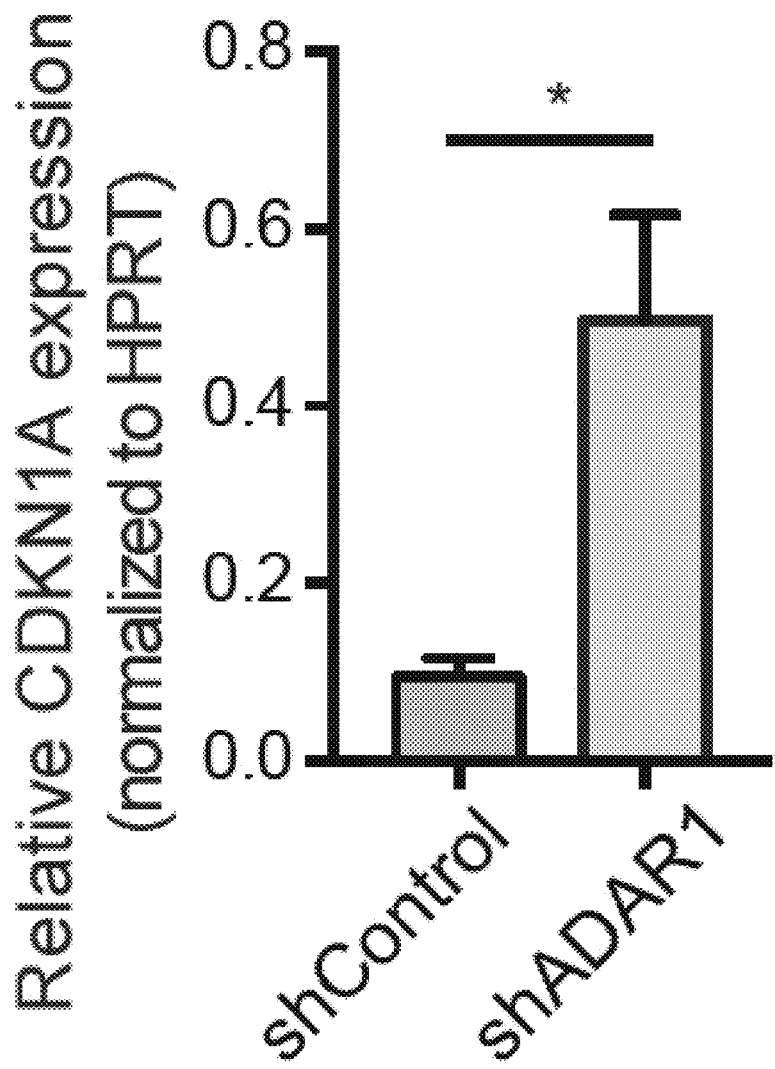
FIG. 1O graphically illustrates gene expression data from RT-qPCR, showing increased CDKN1A expression in cord blood CD34+ HSBC.
Figure 1P:
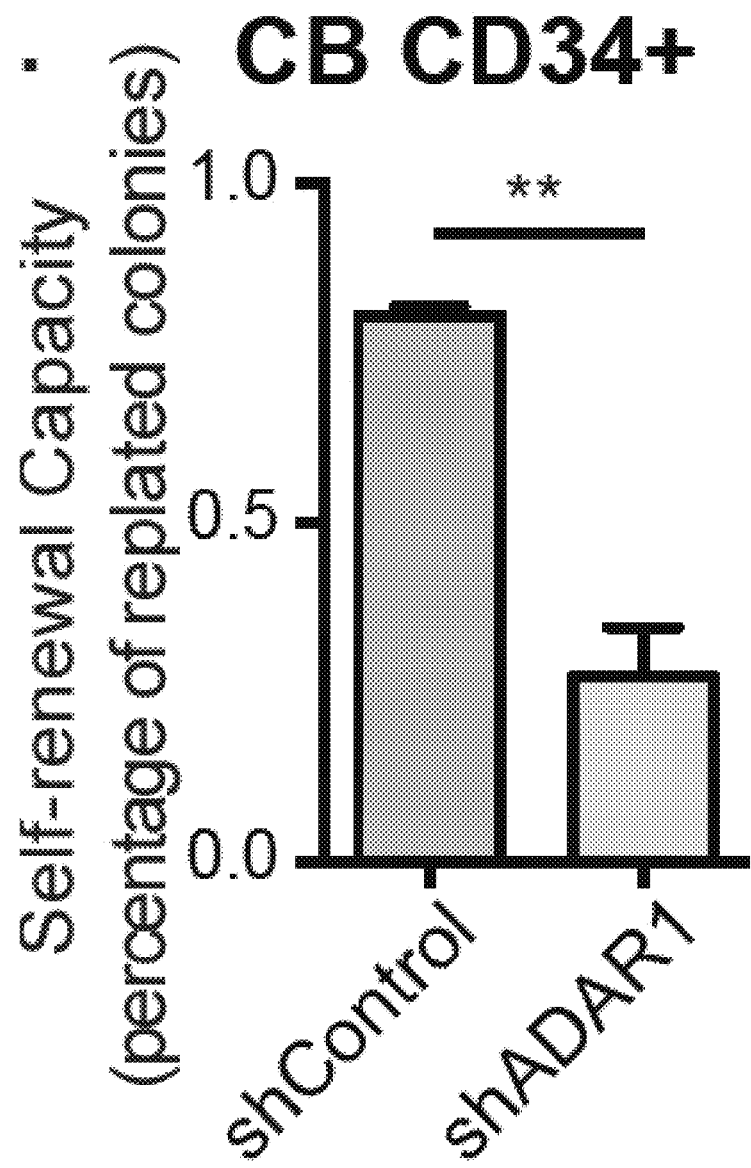

We were also interested in the types of DNA mutations associated with CD34$^+$ population of MPN patients. The most commonly observed mutations are C-to-T transitions (approximately 50%) in both peripheral blood and saliva samples; the second most common mutations are T-to-C changes (approximately 20%) (FIG. 18C-D, or FIG. S1c-d, Example 2). C-to-T mutations are a signature of Apolipoprotein B editing complex 3 (APOBEC3) family of DNA deaminases. This family of DNA deaminases plays a crucial role in the intrinsic response to retrovirus invasion by introducing mutations to viral genome thereby preventing viral production. There are seven APOBEC3 as a cluster in primates (APOBEC3A, APOBEC3B, APOBE3C, APOBEC3D, APOBEC3F, APOBEC3G, and APOBEC3H), likely due to the constant assaults from viral invasion. Therefore, we examined the expression of APOBEC3s in both progenitor and stem populations of MPN by RNA-seq (FIG. 13D, FIG. 18E-F, or FIG. 1d and S1e-f, of Example 2, respectively). This revealed that APOBEC3C is upregulated in the stem population of intermediate-risk (Int-MF) and high-risk myelofibrosis (HR-MF) samples, suggesting its role in leukemic transformation of malignant stem cells (FIG. 13D). Supporting our hypothesis, we observed a clonal expansion of cord blood CD34$^+$ HSPC upon APOBEC3C overexpression (FIG. 13E, or FIG. 1e, Example 2). Moreover, we observed increased stem cell population during transformation from MF to AML (FIG. 13F, or FIG. 1f, Example 2). It is interesting that APOBEC3B was reported as a driver of DNA mutagenesis in human cancers, but very little is known about APOBEC3C(21). Therefore, we report here for the first time that APOBEC3C is a molecular driver for pre-LSC transformation.

Inflammatory Cytokine Activation Promotes Malignant Transformation of MPN Pre-Leukemic Progenitors To further investigate these findings, whole transcriptome sequencing (RNA-seq) was performed on 113 FACS-purified stem cell (CD34$^+$CD38$^-$Lin$^-$) and progenitor (CD34$^+$CD38$^+$Lin$^-$) populations from 54 unique patients and 24 young and aged healthy controls (FIG. 13A, FIG. 19A, or FIG. 1a and FIG. S2a, Example 2).

A gene expression signature emerged that clearly distinguished MPN from normal samples (FIG. 14A, or FIG. 2a, Example 2). For the comparison of AML (non-normal, non-MPN) and MF, there were 678 differentially expressed genes in progenitors, with heatmaps of the top 25 genes showing more extreme expression (up or down) in the AML samples (FIG. 19C-D, or FIG. S2c-d, Example 2). Genes involved in regulation of inflammation, including CTSA, inflammatory cytokine receptor genes (ADGRE5 (CD97) and EFHD2), were upregulated in AML stem cells or progenitors relative to NIF, suggesting that deregulated inflammatory pathways may contribute to pre-LSC transformation to AML (FIG. 19B-C, or FIG. S2b-c, Example 2).

While MPN progenitors shared 2,894 common differentially expressed genes, MPN stem cells harbored only 24 common differentially expressed genes (FIG. 20A, or FIG. S3a, Example 2). A predominance of interferon- or inflammation-related transcripts were observed in MPN stem and progenitor cells relative to normal controls (FIG. 20B-E, or FIG. S3b-e, Example 2). For instance, IRF9 and IFITM1 were overexpressed in PV stem cells (FIG. 20B and FIG. 20D, or FIG. S3b and FIG. S3d, Example 2). In MF progenitors, expression of CSNK1G2, a WNT-β-catenin self-renewal pathway regulator, was elevated (FIG. 20C and FIG. 20E, or FIG. S3c and FIG. S3e, Example 2). In AML, stem and progenitor cells overexpressed IER2 and CSF1R, which have been associated with increased cytokine responsiveness and release of pro-inflammatory chemokines that promote invasion and metastasis (FIG. 20B-E, or FIG. S3b-e, Example 2).

We next performed Signaling Pathway Impact Analysis (SPIA) by comparing gene expression in normal aged progenitors and MPN pre-LSC progenitors (FIG. 14B, or FIG. 2b, Example 2). MPN and AML compared with age-matched healthy progenitors revealed activation of pathways involved in regulation of the chemokine signaling and transcriptional deregulation in cancer (FIG. 14B, or FIG. 2b, Example 2). Intriguingly, Epstein-Barr and Influenza A viral infection related pathways were upregulated in MPNs and AML compared with normal progenitors. With regard to Influenza A pathway activation in ET, PV and AML versus normal samples, approximately 60-70% of all genes in the pathway were differentially expressed (FIG. 14B, or FIG. 2b, Example 2). In conclusion, cytokine- and viral-driven pro-inflammatory signatures are associated with MPN initiation and pre-LSC progression in the rare stem cells and progenitors.

Isoform Switch Drives ADAR1 Activation in MPN Pre-LSC

Previously, we and other groups showed that spliceosome changes play an important role in MDS progression but splicing alterations during MPN pre-LSC transformation to AML had not been clearly elucidated(29). Unsupervised hierarchical clustering revealed that isoform expression patterns distinguished MPN from normal samples at the stem cell level but strikingly more at progenitor level (FIG. 14C, or FIG. 2c, Example 2). Indeed, compared with normal young and aged samples, MPN progenitors displayed a switch favoring expression of the inflammatory cytokine responsive ADAR1 p150 compared with the constitutively active ADAR1 p110 isoform regardless of previous therapy (FIG. 14D, or FIG. 2d, Example 2). Activation of ADAR1 p150 induced adenosine to inosine (A-to-I) RNA editing has been linked to therapeutic resistance and progression of many malignancies and cancer stem cell generation (24, 31). The isoform switch favoring p150 expression observed in all MPN pre-LSC might unmask a common pathway in cancer progression.

To investigate whether ADAR1-induced A-to-I RNA (i.e. epitranscriptomic) modifications contribute to acquisition and maintenance of stem cell properties(24), we performed SPIA analysis on differentially expressed genes from RNA-seq in cord blood progenitor or stem cells that were lentivirally transduced with ADAR1 WT or a deaminase inactive mutant(22) (FIG. 14E and FIG. 21A, or FIGS. 2e and S4a, respectively, Example 2). The results revealed several dysregulated KEGG pathways following ADAR1 WT and mutant overexpression. The two common pathways activated by ADAR1 WT overexpression in both stem and progenitor cells were pathways involved in cancer and viral carcinogenesis thereby mirroring viral pathway activation in ADAR1-overexpressing MPNs progenitors (FIG. 14B, FIG. 14E, and FIG. 21A, or FIG. 2b, FIGS. 2e and S4a, respectively, Example 2). Thus, inflammation, possibly linked to ADAR1 mediated viral activation, may contribute to MPN initiation and maintenance in the progenitor population.

Figure 14F:
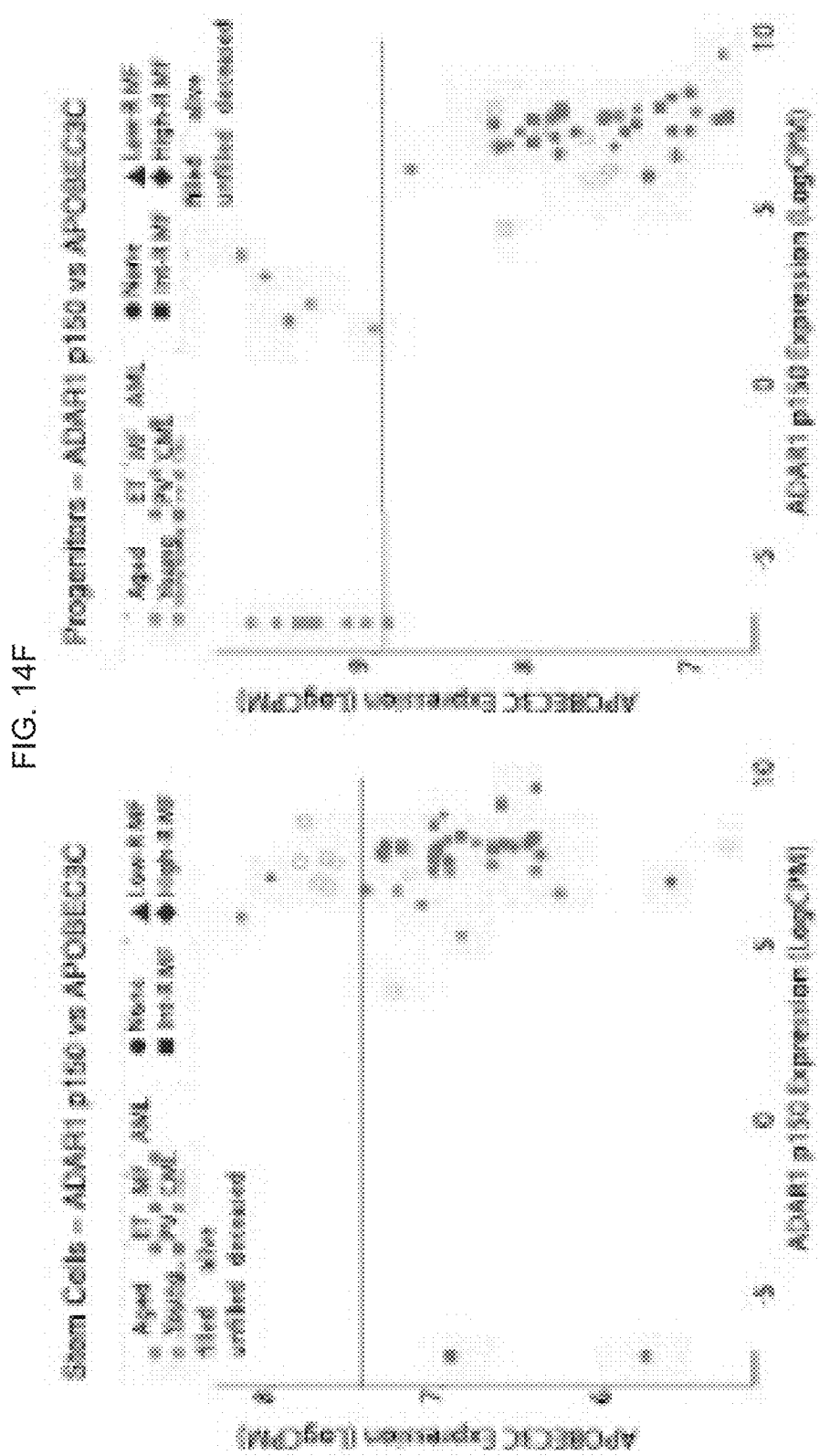

Activation of ADAR1 p150 induced A-to-I RNA editing has been linked to cancer stem cell generation and clonal expansion by enhancing self-renewal capacity of pre-LSC (24, 31). Therefore, we examine the relationship between DNA deaminase APOBEC3C and ADAR1 p150. To our surprise, we found a strong negative correlation (r=−0.81, p=6.9E-14) between ADAR1 p150 and APOBEC3C in MPN progenitor, suggesting p150 might suppress APOBEC3C directed C-to-T changes at the DNA level (FIG. 14F, or FIG. 2f, Example 2). Of the nine patients with high APOBEC3C and ADAR1p150 expression (pt #591, 616, 703, 560, 566, 567, 569, 576, and 666), six were deceased after the sample collection due to either progression or other causes (FIG. 14F, or FIG. 2f, Example 2, and Table S1). The low survival rate, combined with the clonal expansion observed with lentivirally overexpressed APOBEC3C (FIG. 14E, or FIG. 2E, Example 2), suggest APOBEC3C acts as a major source of DNA mutations in high-risk MPN pre-LSCs and can be used as a biomarker for survival.

Elevated Level of A-to-I RNA Editing Driven by ADAR1 p150 is Characteristic of MPN Pre-Leukemia Progenitors Since inflammatory cytokine-driven ADAR1 activation has been linked to cancer stem cell generation, we compared the overall A-to-I RNA editing activity, measured as the proportion of A-to-I RNA edits in both stem and progenitor cells, at different MPN stages and in AML (FIG. 15A, or FIG. 3a, Example 2). While no significant A-to-I editing changes were observed during normal aging, each MPN subtype possessed significantly elevated levels of RNA editing compared to normal aged controls (FIG. 15A, or FIG. 3a, Example 2). Moreover, ADAR1 p150 significantly correlated with editing activity in progenitors (r=0.62, p=1.3E-05), while a negative correlation was observed for either ADAR1 isoform in progenitors (r=−0.63, p=7.9E-06) (FIG. 15B and FIG. 21B, or FIG. 3b and FIG. S4b, respectively, Example 2).

To determine the frequency of RNA editing in different transcriptomic regions, we plotted the A-to-I editing changes (variant allele frequency; VAF) in young, aged, MPN and AML progenitors (FIG. 15C, or FIG. 3c, Example 2). Compared with normal young and aged bone marrow progenitors, MPN and AML progenitor harbored elevated RNA editing in bases that produced non-synonymous changes (FIG. 15D, or FIG. 3d, Example 2). Thus, ADAR1 induces RNA recoding events in MPN pre-LSC that persist following AML transformation.

Nonsynonymous A-to-I RNA Editing in MPN Stem and Progenitor Cells

Current RNA editing databases are primarily based on cell line or bulk tumor cell RNA sequencing data which may mask the cell type and cell context specific RNA editing events that trigger pre-LSC evolution into LSC. To identify novel RNA editing sites unique to pre-LSC, we analyzed RNA-seq variants from samples with matching WGS data. We also quantified nonsynonymous editing events using two known RNA editing databases(32, 33) (FIG. 15E, or FIG. 3e, Example 2). The data revealed a strikingly different editing pattern between normal control and MPN samples. There is a general trend of more recoding in MPN stem cells or progenitors than normal control. For example, CDK13 was edited in 84% of MPN samples but none of normal controls (FIG. 15E, or FIG. 3e, Example 2). Moreover, CDK13 expression was elevated in MPN stem (p<0.0001) and progenitor (p<0.0001) cells and CDK13 expression was also correlated with ADAR1 expression (FIG. 15F and FIG. 21C-D, or FIGS. 3f and S4c-d, respectively, of Example 2). Conversely, SUMF2 was only edited in normal controls and we observe no or reduced expression in MPN stem cells and progenitors (FIG. 15F and FIG. 21D, or FIGS. 3f and S4d, respectively, of Example 2). A-to-I RNA editing in CDK13 has been linked to worse prognosis in hepatocellular carcinoma (citation). Therefore, the nonsynonymous differentially RNA editing events will provide novel biomarkers for MPN pre-LSC generation and disease progression.

A-to-I RNA editing occurs predominantly in Alu repetitive elements since they give rise to stable double strand RNA structure (24). However, our dataset of the top 25 nonsynonymous editing events reveal that most recoding occurs in non-Alu regions, which suggest pre-LSC specific regulators might direct ADAR1 p150 activity in MPN stem cells and progenitors (FIG. 15E, or FIG. 3e, Example 2).

A-to-I RNA Editing Promotes Pre-LSC Evolution

Subsequently, we examined the expression of all 1295 differentially edited genes between MPN and normal aged controls (FIG. 16A, or FIG. 4a, Example 2). Hierarchical clustering of the gene expression values for differentially edited genes revealed that MPN samples clustered together compared with normal young and aged controls (FIG. 16A, or FIG. 4a, Example 2). Network analysis of the differentially edited genes propagated over the STRING(34) interactome and clustered with Louvain clustering revealed that in both AML and MF progenitors, A-to-I RNA edited transcripts were significantly enriched for genes involved in chromatin organization, cell cycle, as well as mRNA splicing (FIG. 16B-C, or FIG. 4b-c, Example 2). Additionally, progression from MF to AML was typified, at the progenitor level, by differential editing and expression of Hippo and Wnt signaling pathway and p53 pathway (FIG. 21E, or FIG. S4e, Example 2).

Interestingly, we observed STAT3 is differentially edited and has an increased expression in AML progenitors compared to normal counterparts (FIG. 16C, or FIG. 4c, Example 2). We have previously reported that JAK/STAT signaling pathway in CML LSC activates malignant A-to-I RNA editing in self-renewal genes and increases LSC self-renewal capacity (25). The direct editing of STAT3 suggests ADAR1 might augment the JAK/STAT signal further thereby enhancing LSC generation and disease progression.
A-to-I RNA Editing is Required for WNT-β-Catenin Activation in LSC Since RNA editing is associated with mRNA splicing in AML LSC, we decided to examine if ADAR1 activity is linked to differential expression of STAT3 isoforms. Alternative splicing in STAT3 exon 23 generate two isoforms, STAT3β and STAT3β (FIG. 17A, or FIG. 5a, Example 2). Previous report has shown that intronic RNA editing favors splicing toward STAT3β isoform (35). Indeed, we observed several AML samples have A-to-I RNA editing at these sites where only one normal aged (ABM) sample possess a RNA editing events (FIG. 17B, or FIG. 5b, Example 2). Interestingly, the expression of alternatively spliced STAT3β is elevated in all MPN progenitors compared to normal control, and increased in MF and sAML stem population as well (FIG. 17C, or FIG. 5c, Example 2). However, the expression of canonically spliced STAT3β isoform remains constant compared to normal controls (FIG. 22A, or FIG. S5a, Example 2). Moreover, we observed a strong correlation between ADAR1 p150 and STAT3β expression in both stem and progenitor populations (FIG. 17D and FIG. 22B, or FIGS. 5d and S5b, respectfully, of Example 2).

STAT3β has been linked to Wnt-β-catenin activity which is crucial for LSC generation. Therefore, we want to explore if ADAR1 is related to Wnt-β-catenin signaling activation in MPN pre-LSCs. Functionally, we performed a colony replating assay and determined that elevated ADAR1 expression in MF pre-LSC increases the self-renewal capacity of leukemia propagation cells (FIG. 17E, or FIG. 5e, Example 2). This is accompanied by activated β-catenin as observed in K562 cells stably transduced with ADAR1 WT (FIG. 17F, or FIG. 5f, Example 2). Moreover, ADAR1 knockdown mediated by shRNA inhibit β-catenin activation (FIG. 17G, or FIG. 5g, Example 2). Together, these data suggest that RNA recoding events are linked with pre-LSC generation and maintenance.

DISCUSSION

In addition to radiation-related mutagenesis and chemical carcinogenesis, cumulative data suggest that APOBEC3 DNA and ADAR1 RNA editing enzymes behave as enzymatic drivers of mutagenesis during human cancer evolution (3, 13, 14). Specifically, patterns of enzymatic deamination of cytosine to uracil (C-to-U read as C-to-T), induced by aberrant activation of primate-specific, antiviral DNA editase APOBEC3 family members, have been identified by whole exome sequencing in many human malignancies(7). Moreover, inflammatory cytokine induced hyper-activation of the antiviral RNA editase, ADAR1, in progenitors results in deamination of adenosine to inosine (A-to-I read as A-to-G) in self-renewal and cell cycle regulatory transcripts thereby fueling LSC generation(2, 6, 16, 65). Because innate immune editing enzymes are induced by cytosolic DNA, double stranded RNA or lentiviral transduction, they may also contribute to off-target DNA mutations and RNA alterations induced by CRISPR-Cas guided DNA base editing technologies as well as lentivirally delivered therapeutic gene correction strategies. The potential for induction of both genomic and epitranscriptomic instability provides a strong rationale for deciphering the oncogenic potential of combinatorial APOBEC3 and ADAR1 activation (66).

In this study, we focused on characterizing DNA and RNA mutations in MPN pre-leukemia progenitors to AML LSC. To investigate the role of malignant DNA and RNA deaminase activation in hematopoietic stem cells (HSCs) that promote clonal expansion of myeloid progenitors (2-14), we performed large scale whole genome sequencing and whole transcriptomic sequencing of the rare stem cells and progenitor populations in MPN and sAML. These rare populations are of great interest because the pre-LSCs vary in their capacity to self-renew, resist therapy (15-18) and contribute to sAML.

The most common mutations found in MPN pre-LSC are C-to-T changes driven by APOBEC3C at the stem cell level. The patients with high total C-to-T mutation loads are more likely to progress to sAML as well as lower survival rate. This suggest APOBEC3 activation in pre-LSC introduces additional C-to-T mutations fueling LSC transformation. Detection of APOBEC3 signature at stem cell level might provide a new class of biomarkers to predict patient progression.

Both ADAR1 and APOBEC3 play important roles in the intrinsic responses to retroviral invasion and also protect the human genome from retroelement integration. They also play additional roles in innate and adaptive immunity by controlling the response to inflammation signals. When comparing pre-LSC transcriptome RNA-seq to normal aged controls, we found the top activated pathways are viral infection pathways and chemokine signaling. This activation is also seen in normal progenitors overexpression ADAR1 WT. The most common viral signature is Epstein-Barr virus infection (ET, PV, and AML), which is capable of causing human oncogenesis. These data suggest viral invasion or host cell's response to viral invasion by RNA editing might play a role in pre-LSC transformation. The exact molecular mechanisms, whether it is direct viral integration or viral-induced genomic or transcriptomic damages of host cells, will need to be further explored.

The isoform switch favoring inflammation-responsive ADAR1p150 was observed during pre-LSC generation but not in normal stem cell aging. The resulting nonsynonymous RNA editing profiles are remarkably distinguished between normal controls and diseases phenotypes. For example, editing in CDK13, AZIN1, and WNK1 only presented in MPN samples, where SUMF2 is only edited in normal samples. The function of these editing events will need further studies. Moreover, ADAR1p150 activity determined either by detection of disease cell-specific RESSq-PCR(36) or a reporter system will provide a robust tool for LSC detection.

In summary, DNA and RNA mutational signatures demonstrate that pre-LSC genomic instability and predominance of splice site mutations; RNA splicing and inflammatory splice isoform deregulation; and inflammatory cytokine responsive RNA editome evolution may inform therapeutic strategies aimed at preventing AML transformation.

Figures—Example 2
FIG. 13A-F (or FIG. 1, Example 2)

FIG. 13A Sample Distribution in this study. Whole genome sequencing of 44 saliva samples was performed at 30× coverage. The samples were distributed among Polycythemia Vera (PV, n=5), Essential Thrombocythemia (ET, n=4), Myelofibrosis (MF, n=28), Chronic Myeloid Leukemia (CML, n=3) and non-MPN control individuals (n=4, including 3 healthy volunteers and 1 CLL with CALR SNP). In parallel, whole genome sequencing of 43 peripheral blood samples (90×) of a sample distribution of PV (n=6), ET (n=4), MF (n=26), CML (n=3) and non-MPN control individuals (n=4, including 1 CLL with CALR SNP). The somatic mutations were obtained from MPN patient samples (n=37) and non-MPN controls (healthy controls n=3 and CLL with CALR SNP n=1) with matching saliva and peripheral blood (n=41, shown in solid black). Whole transcriptomic sequencing (RNA-seq) was performed on 78 samples distributed as follows: PV (n=6), ET (n=2), MF (n=29), CML (n=5), AML (n=12), and non-MPN control individuals (n=24). These samples can further be broken down based on tissue of collection (peripheral blood or bone marrow) and cell types (stem cells and progenitor). In summary, from 54 unique subjects and 24 non-MPN controls we have 113 samples in the RNA sequencing cohort.

FIG. 13B Circos plot depicting somatic mutations, copy number variation and structural variation in Labels indicate the 69 genes(30). Circos plot track descriptions described in the figure.

FIG. 13C Mutated genes in 69 known MPN genes(30) in peripheral blood divided by MPN disease stage. Analyzed with GATK best practices workflow and variants were filtered to include the following: 1000 Genomes Project, ExAC, Gnomad allele frequencies<0.002, genes not present in normal control samples 780, 792, 795, variants in ClinVar not determined to be benign, loci with at least 10 reads. Color of alterations signifies the type of alteration: blue=copy number deletion, dark blue=structural variant deletion, orange=indel, green=single nucleotide variant. MPN disease stage depicted in colored bar at the bottom of the figure. *, patient deceased since sample collection; +, patient has another malignancy; &, patient progressed after sample collection, and &&, patient progressed to sAML after sample collection.

FIG. 13D Differential Expression of APOBEC3C mRNA in MPN stem population by RNA-seq.

FIG. 13E Brightfield image of cord blood CD34+ cells transduced with APOBEC3C.

FIG. 13F Comparison of HSC percentage in MPN samples by flow cytometry (CML n=4, PV n=3, ET n=2, MF n=23 and AML n=3).

FIG. 14A-F (or FIG. 2, Example 2):

FIG. 14A A heatmap based on normalized RNA-Seq expression for the top one percent of genes ranked by variance across all samples. Annotation for each sample is presented as a stack of colored bars representing Phenotype, cell type, source tissue, mutation status, and the treatment type (for MF samples only). Sample without a known JAK2 V617F SNP status are colored gray.

FIG. 14B Signaling Pathway Impact Analysis (SPIA) in ET, PV, MF and AML compared to ABM respectively. Listed are the top 5 activated pathways based on the NDE (number of genes dysregulated in sample set)/pSize (number of genes in pathway) in percent.

FIG. 14C Heatmap of normalized RNA-Seq expression of differentially expressed splicing isoforms for the top one percent of genes ranked by variance across all samples. Annotation for each sample is presented as a stack of colored bars representing Phenotype, cell type, source tissue, JAK2 V617F SNP status, and the treatment type. Sample without a known JAK2 V617F SNP status are colored gray.

FIG. 14D Ratio of ADAR1 isoforms (p150/p110) is analyzed in each MPN disease type using normalized RNA-Seq expression data from both stem cells and progenitor cells. The results of t-tests was determined between each phenotype and the aged bone marrow (ABM) normal control show that the ratio changes significantly in the disease progenitors but the not the young bone marrow (YBM) samples. (p<0.05=*; p<0.01=, p<0.005=*).

FIG. 14E Signaling Pathway Impact Analysis (SPIA) in cord blood lentivirally overexpressed with ADAR1 WT (top) and deamination deficient mutant ADAR1$^{E912A}$ (bottom) compared to pCDH backbone control (n=3). Listed are the top 6 activated pathways based on the NDE (number of genes in pathway)/pSize (number of genes dysregulated in sample set) in percent.

FIG. 14F Correlation of APOBEC3C with ADAR1 p150 isoform in stem cells and progenitors of aged bone marrow, young bone marrow, and MPN samples. The risk-group of MF patient is indicated.

FIG. 15A-F (or FIG. 3, Example 2)

FIG. 15A Violin plot of overall RNA editing frequency (VAF) by MPN subtype and young (YBM) and aged bone marrow (ABM) controls. The overall percentage of A-to-I RNA editing data is statistically significant elevated in PV, ET, MF, CML and AML primary patient samples compared to the normal ABM counterpart.

FIG. 15B Correlation of mean A-to-I RNA editing level to ADAR1 p150 isoform expression level in both stem cells (square) and progenitors (triangle). Each color represents a MPN disease stage.

FIG. 15C Box plots comparing RNA edit VAF of each MPN phenotype broken down by genomic region in progenitor population.

FIG. 15D Statistical comparison of RNA edit VAF of each MPN phenotype broken down by genomic region in progenitor population. The p-value values are derived from comparing the VAFs of each MPN stage and Aged Normal at each variant classification by the Kolmogorov Smirnov test.

FIG. 15E Top 25 ranked genes by occurrence of nonsynonymous RNA edit mutations broken down by known non Alu and Alu region, and novel non-Alu and Alu regions stratified by MPN phenotype, treatment and cell type.

FIG. 15F Normalized and Log 2 transformed RNA-Seq expression data for CDK13 and SUMF2 in the progenitor population plotted by MPN phenotype. The results of t-tests (ns=not significant; p<0.05=*; p<0.01=, p<0.005=*) between each phenotype and the Aged Bone Marrow (ABM) Normal group are shown.

FIG. 16A-C (or FIG. 4, Example 2)

FIG. 16A Heatmap based on gene expression z-scores of 1295 differentially edited genes.

FIG. 16B Network analysis of differentially edited genes between normal aged sample and MF. Out of the 834 significantly differentially edited genes, 690 were found in the interactome and used as seeds for network propagation on the STRING high confidence interactome. The most proximal genes in network space were identified (circles), and the subgraph composed of these seeds plus proximal genes is visualized using a modified spring-embedded layout algorithm. A graph-based modularity maximization clustering algorithm was used to identify groups of genes which were highly interconnected, and these clusters were used to modify the spring-embedded positions so that genes in the same cluster were pulled apart radially. Genes in each cluster were annotated with associated pathways identified by functional enrichment analysis, using the full gene subnetwork as the background gene list. Differential expression log fold change was mapped to the node color, with blue nodes significantly downregulated in MF compared to normal aged, and red nodes significantly upregulated in MF compared to normal aged. Gray nodes were not significantly differentially expressed (fdr<0.05).

FIG. 16C Network analysis of differentially edited genes between normal aged samples and AML. Out of the 757 significantly differentially edited genes, 642 were found in the interactome and used as seeds for network propagation on the STRING high confidence interactome. The most proximal genes in network space were identified (circles), and the subgraph composed of these seeds plus proximal genes is visualized using a modified spring-embedded layout algorithm. A graph-based modularity maximization clustering algorithm was used to identify groups of genes which were highly interconnected, and these clusters were used to modify the spring-embedded positions so that genes in the same cluster were pulled apart radially. Genes in each cluster were annotated with associated pathways identified by functional enrichment analysis, using the full gene subnetwork as the background gene list. Differential expression log fold change was mapped to the node color, with blue nodes significantly downregulated in AML compared to normal aged, and red nodes significantly upregulated in AML compared to normal aged. Gray nodes were not significantly differentially expressed (fdr<0.05).

FIG. 17A-G (or FIG. 5, Example 2)

FIG. 17A STAT3 isoforms generation by alternative splicing and stop codon.

FIG. 17B Known A-to-I RNA editing locations(35) in normal aged (ABM) and AML as determined by RNA-seq data.

FIG. 17C Expression STAT3β isoform in normal young (YBM), normal aged (ABM), and MPN stem cell and progenitor population using normalized RNA-Seq data. The results of t-tests was determined between each MPN phenotype and the aged bone marrow (ABM) normal control. (p<0.05=*).

FIG. 17D Correlation of STAT3β isoform with ADAR1 p150 isoform in progenitors of aged bone marrow (ABM), young bone marrow (YBM), and MPN samples. The risk-group of MF patient is indicated.

FIG. 17E Self-renewal capacity as measured by colony replating assay in MF CD34+ HSPC transduced pCDH backbone or ADAR1 WT.

FIG. 17F Beta-catenin activity was measured by flow cytometry in K562 BC CML cells stably transduced with pCDH lentiviral backbone or ADAR1 WT.

FIG. 17G Beta-catenin activity by flow cytometry in KG-1a cells with ADAR1 knockdown by shRNA. The shRNA is marked by GFP signal.

FIG. 18A-D (or FIG. S1, Example 2), Top DNA Mutations in MPN Peripheral Blood or Saliva Samples:

FIG. 18A Top mutations in MPN patients from peripheral blood including single nucleotide variants (SNVs), copy number variants (CNVs) and structural variants (SVs). MPN disease stage depicted in colored bar at the bottom of the figure. *, patient deceased since sample collection; +, patient has another malignancy; &, patient progressed after sample collection, and &&, patient progressed to sAML after sample collection. Color of alterations signifies the type of alteration depicted by Mutation Type legend. Fraction of C to T mutations colored according to percent in legend.

FIG. 18B Top mutations in MPN patients saliva including single nucleotide variants (SNVs), copy number variants (CNVs) and structural variants (SVs). MPN disease stage depicted in colored bar at the bottom of the figure. *, patient deceased since sample collection; +, patient has another malignancy; &, patient progressed after sample collection, and &&, patient progressed to sAML after sample collection. Color of alterations signifies the type of alteration depicted by Mutation Type legend. Fraction of C to T mutations colored according to percent in legend.

FIG. 18C Boxplot of the number of somatic mutations in peripheral blood or saliva broken down by nucleotide change and transitions/transversions. Both somatic and germline variants were included.

FIG. 18D Expression of APOBEC3 family genes in stem cells and progenitors of normal aged (ABM), normal young (YBM), MPN and AML progenitors.

FIG. 19A-C (or FIG. S2, Example 2): Different gene expression in purified MPN stem cells and progenitors:

FIG. 19A Gating strategy for FACS-purified stem cell (CD34$^+$CD38$^-$Lin$^-$) and progenitor (CD34$^+$CD38$^+$Lin$^-$) populations from 54 unique patients and 24 young and aged healthy controls;

FIG. 19B Heatmap shown of the top 25 differentially expressed genes in AML stem cells compared with MF stem cells (987 total DE genes);

FIG. 19C Heatmap shown of the top 25 differentially expressed genes in AML progenitors compared with MF progenitors (678 total DE genes).

FIG. 20A-E (or FIG. S3, Example 2), Top Unique Genes in MPN Stem Cells or Progenitors:

FIG. 20A Results for differential expression analysis of RNA-Seq data between patients with various phenotypes in stem and progenitor cells. The Venn diagram shows the overlap of significantly different genes (adjusted p-val<0.05) between the comparisons. *Adjusted Statistical significance values have been used;

FIG. 20B The top 10 statistically significant genes in the stem cell population are listed in table;

FIG. 20C The top 10 statistically significant genes in the progenitor cell population are listed in table;

FIG. 20D Volcano plot of stem cell population of MPN compared to ABM for genes with an adjusted p-value with 0.025 or less (PV, AML and CML), an adjusted p-value of 0.001 (MF);

FIG. 20E Volcano plot for the progenitor cell population of MPN compared to ABM for genes with an adjusted p-value of 0.001 or less (PV, MF and AML), and an adjusted p-value of 0.025 (CML and ET).

FIG. 21A-E (or FIG. S4, Example 2), A-to-I RNA Editing Between MPN Stage and Normal Aged Bone Marrow:

FIG. 21A Signaling Pathway Impact Analysis (SPIA) in cord blood stem cells lentivirally overexpressed with ADAR1 compared to pCDH backbone control (n=3). Listed are the top 6 activated pathways based on the NDE (number of genes in pathway)/pSize (number of genes dysregulated in sample set) in percent;

FIG. 21B Correlation of ADAR1 p110 isoform expression with mean A-to-I RNA editing in stem (square) or progenitor (triangle) population of each MPN subtype. Each color represent a MPN subtype;

FIG. 21C Correlation of CDK13 expression and ADAR1 expression in stem and progenitor population of MPN;

FIG. 21D Normalized and Log 2 transformed RNA-Seq expression data for CDK13 and SUMF2 in stem cells plotted by MPN phenotype. The results of t-tests (ns=not significant; p<0.05=*; p<0.01=, p<0.005=*) between each phenotype and the Aged Bone Marrow (ABM) Normal group are shown;

FIG. 21E Network analysis of differentially edited genes between MF and AML. Out of the 158 significantly differentially edited genes, 140 were found in the interactome and used as seeds for network propagation on the STRING high confidence interactome. The most proximal genes in network space were identified (circles), and the subgraph composed of these seeds plus proximal genes is visualized using a modified spring-embedded layout algorithm. A graph-based modularity maximization clustering algorithm was used to identify groups of genes which were highly interconnected, and these clusters were used to modify the spring-embedded positions so that genes in the same cluster were pulled apart radially. Genes in each cluster were annotated with associated pathways identified by functional enrichment analysis, using the full gene subnetwork as the background gene list. Differential expression log fold change was mapped to the node color, with blue nodes significantly downregulated in AML compared to MF, and red nodes significantly upregulated in AML compared to MF. Gray nodes were not significantly differentially expressed (fdr<0.05).

FIG. 22A-D (or FIG. S5, Example 2), A-to-I RNA Editing Between MPN Stage and Normal Aged Bone Marrow:

FIG. 22A Expression STAT3α isoform in normal young (YBM), normal aged (ABM), and MPN stem cells and progenitors using normalized RNA-Seq data;

FIG. 22B Correlation of STAT3β isoform with ADAR1 p150 isoform in stem cells of aged bone marrow (ABM), young bone marrow (YBM), and MPN samples. The risk-group of MF patient is indicated;

FIG. 22C Self-renewal capacity as measured by colony replating assay in MF CD34+ HSPC transduced pCDH backbone or ADAR1 E912A deaminase mutant;

FIG. 22D Beta-catenin activity was measured by flow cytometry in K562 BC CML cells stably transduced with pCDH lentiviral backbone or ADAR1 E912A mutant.

Materials and Methods—Example 2

Human Subjects

Primary Myeloproliferative Neoplasm patient samples were obtained from consenting patients at the University of California according the Institutional Review Board-approved protocols.

Patient Sample Processing and Preparation—DNA Sequencing

CD34+ cells: Peripheral blood mononuclear cells were isolated by Ficoll-Paque density centrifugation and cryopreserved in liquid nitrogen. CD34+ cells were selected from peripheral blood mononuclear cells from both MPN patients and normal controls by magnetic bead separation (MACS; Miltenyi, Bergisch Gladbach, Germany) as previously described(28) with minor modification using a different kit for magnetic bead separation: Catalog 130-100-453. DNA from the peripheral blood CD34+ population was extracted according to manufacturer recommendations using QIAamp DNA Blood Mini Kit (Qiagen, Catalog number 51104).

Saliva cells: Subjects abstained from eating at least 1 hour prior to saliva donation and rinsed their mouths with water to remove food residue immediately prior to saliva donation. Subjects then deposited 1 mL of saliva into the collection device, which was stabilized immediately afterwards (Biomatrica, Catalog number 97021-011A). Stabilized saliva was passed through 70-100 micron strainers to further remove food residues. DNA was extracted using the QIAamp DNA Blood Mini Kit (Qiagen, Catalog number 51104) described above with minor modifications. Both peripheral blood (90×) and saliva (30×) cell samples were sequenced on the Illumina HiSeq X sequencer using a 150-base paired-end single-index read format.

Patient Sample Processing and Preparation—RNA Sequencing

Mononuclear cells from peripheral blood and bone marrow were purified, cryopreserved, and enriched for CD34+ cells as described above. Enriched CD34+ fractions were stained with fluorescent antibodies against human CD45, CD34, CD38, Lineage markers (BD Pharmingen; CD2 PE-Cy5, 1:20, cat 555328, CD3 PE-Cy5, 1:20, cat 555334, CD4 PE-Cy5, 1:10, cat 555348, CD8 PE-Cy5, 1:50, cat 555368, CD14 PerCP-Cy5.5, 3:100, cat 550787, CD19 PE-Cy5, 1:50, cat 555414, CD20 PE-Cy5, 1:20, cat 555624, CD56 PE-Cy5, 1:10, cat 555517, CD45 APC, 1:50, cat 335790, CD34 BV421, 1:100, cat 562577, CD38 PE-Cy7, 1:50, cat 335790), and propidium iodide. Cells were FACS-purified using a FACS Aria II (Sanford Consortium Stem Cell Core Facility) into hematopoietic stem cell (Lin−CD45+CD34+CD38−) and progenitor (Lin−CD45+CD34+CD38+) populations directly into RLT lysis buffer (Qiagen) for RNA extraction followed by RNA-Seq (The Scripps Research Institute Next Generation Sequencing Core) on Illumina HiSeq platforms.

| Antibody | Supplier | Catalog Number | Clone | Lot |
|---|---|---|---|---|
| CD2 PE-Cy5 | BD Pharmingen | 555328 | RPA-2.10 | 6070653 |
| CD3 PE-Cy5 | BD Pharmingen | 555334 | UCHT1 | 5349958 |
| CD4 PE-Cy5 | BD Pharmingen | 555348 | RPA-T4 | 6036632 |
| CD8 PE-Cy5 | BD Pharmingen | 555368 | RPA-T8 | 5219728 |
| CD14 PerCP-Cy5.5 | BD Pharmingen | 550787 | M5E2 | 6070674 |
| CD19 PE-Cy5 | BD Pharmingen | 555414 | HIB19 | 6126777 |
| CD20 PE-Cy5 | BD Pharmingen | 555624 | 2H7 | 6126778 |
| CD56 PE-Cy5 | BD Pharmingen | 555517 | B159 | 7177552 |
| CD45 APC | Life Technologies | MHCD4505 | HI30 | 1966219A |
| CD34 BV421 | BD Pharmingen | 562577 | 581 | 7153978 |
| CD38 PE-Cy7 | BD Biosciences | 335790 | HB7 | 8002648 |

Bioinformatics Analysis

The analysis code and documentation for the computational analyses are available through Github™: https://github.com/ucsd-ccbb/MPN_atlas_methods.

RNA-Sequencing Read Preprocessing

RNA-Seq was performed on Illumina's NextSeq 500™ sequencer with 150 base pair (bp) paired-end reads. Sequencing data were de-multiplexed and output as fastq files using Illumina's bcl2fastg™ (v2.17).

RNA Editing Analysis

RNA reads were aligned using 2-pass alignment with STAR 2.5.2b 2-pass alignment. Alignment deduplication was performed with Picard MarkDuplicates™ followed for SortSam™. Alignments were then processed sequentially according to GATK best practices for calling RNA-Seq variants with tools SplitNCigarReads™ RealignerTargetCreator™, IndelRealigner™, BaseRecalibrator™, PrintReads™ Variants were called with HaplotypeCaller™ and filtered with VariantFiltration™ for FS<30, QD>2, QUAL>20. Mismatches in first 6 base pairs of each read were discarded. Alu sites were identified and kept from RepeatMasker™. Non-alu variants were further processed: We removed those in repetitive regions based on the RepeatMasker™ annotation. Intronic sites within 4 bp of splicing junctions were removed. Next, we filtered variants in homopolymer runs. All sites were then kept if there were a minimum of three alternative allele carrying reads and ten total reads and a minimum allele frequency of 0.10. We then identified known RNA editing sites according to RADAR and DARNED. To filter mismatches to ADAR specific RNA edits, we kept A to G variants in genes on the positive strand and T to C variants on the negative strand(30, 31, 33-35). Novel RNA editing sites were defined as RNA variants that were not present in the DNA. RNA edits were annotated with Oncotator and further filtered to remove sites that exist in ExAC, 1000 Genomes Project, and dbSNP. Sites were annotated with variant classification (3'UTR, 5'UTR, 5' Flank, Missense, Silent, Intron, IGR, RNA). Differential editing analysis was performed using a Chi-Square test compare the differences in editing in each gene for each variant classification (i.e. MDM2-3'UTR MF vs AN). Significance was set at p<0.05. The contingency table for each test was set up as follows:

|            | Condition 1              | Condition 2              |
|------------|--------------------------|--------------------------|
| Edited     | N sites                  | N sites                  |
| Not Edited | N possible sites – N sites | N possible sites – N sites |

N sites is the number of aggregated sites where N possible sites is the number of uniquely edited coordinates within a variant classification*number of samples. Genes with only intergenic differentially editing events were removed. To account for multiple testing, adjusted p-values were calculated using the Benjamini-Hochberg procedure and genes with events below an adjusted p-value of 0.05 were called significant and retained in the final lists.

Transcript and Gene Quantification and Differential Expression Quality control of the raw fastq files was performed using the software tool FastQC (Andrews, S. & Others. FastQC: a quality control tool for high throughput sequence data. (2010)). Sequencing reads were aligned to the human genome (hg19) using the STAR v2.5.1a aligner(36). Read quantification was performed with RSEM(37) v1.3.0 and GENCODE annotation (genocode.v19.annotation.gft). The R BioConductor packages edgeR™ (38) and limma (39) were used to implement the limma-voom (40) method for differential expression analysis. The experimental design was modeled upon disease and tissue type (~0+disease; ~0+tissue; ~0+disease+tissue). Significance was defined by using an adjusted p-value cut-off of 0.05 after multiple testing correction using a moderated t-statistic in Limma. Genes with an adjusted p-value of <0.05 (based on the moderated t-statistic using the Benjamini-Hochberg (BH) method for multiple testing correction [27]) were considered significantly differentially expressed (DE)(41). Functional enrichment of the differentially expressed genes was performed using Signaling Pathway Impact Analysis with the Bioconductor package SPIA(42).

Whole Genome Sequencing (WGS) Analysis

WGS analysis was performed on 82 samples, which included 41 peripheral blood and 41 saliva samples. We performed sequence alignment and variant calling using the GATK best practice pipeline implemented in cirrus-NGS (https://github.com/ucsd-ccbb/cirrus-ngs). The reference genomes were realigned to the human 1000 genomes v37 (43) which contains the autosomes, X, Y and MT but without haplotype sequence or EBV. BWA-mem v.0.7.12. (44) was used for mapping short reads against the human 1000 genomes v37. Subsequent processing was carried out with SAMtools™ v.1.1(45-48), Picard Tools v1.96, Genome Analysis Toolkit (GATK) v2.4-9(46), which consisted of the following steps: sorting and splitting of the BAM files, marking of duplicate reads, local realignment, indel realignment and recalibration of base quality scores, reads coverage file in bed format for each individual, germline and somatic variant calling.

Variant Annotation & Filtering Peripheral blood variants were annotated with Oncotator™ from a multisample VCF file. We filtered variants by the following strategy to obtain somatic variants from tumor only samples (https://www-.sciencedirect.com/science/article/pii/S1525157817305986#bib11): retained insertions, deletions, and nonsynonymous variants with ExAC, 1000 Genomes™, and gnomad population allele frequency<0.002. Variants with ClinVar™ clinical significance of "benign" were removed. We also removed variants present in three normal controls.

Structural Variant and Copy Number Analysis

SV2 was used to genotype structural variants, where the input were results from Lumpy and Manta SV™ callers and GATK SNVs. SVs were annotated and prioritized with SnpEff and Simple SV Annotation. SVs were subsequently filtered to exclude those present in 1000 Genomes Project, intergenic regions, and those with low or moderate impact. SVs present in the three normal controls were also removed from all samples. CNVkit was used to discover somatic copy number variants with the batch command and –m wgs parameter. The three normal controls were pooled together for use as a normal panel.

Network Analysis of Differentially Edited Genes

Significantly differentially edited genes were used as seeds for network propagation(52) on the STRING high confidence interactome(53) for three comparisons (AML vs MF, AML vs Aged Normal, MF vs Aged Normal).

The most proximal genes to the seed set were identified using a network propagation method, using degree-matched sampling to generate proximity z-scores for each gene in the network. Genes with a z-score>2 were retained in the network and used for visualization and downstream analysis. A graph-based modularity maximization clustering algorithm was used to identify groups of genes within the most proximal genes which were highly interconnected. Genes in the entire network and within each of these clusters were annotated with associated pathways identified by functional enrichment analysis, with the gprofiler tool(55) using the proximal gene set as the background gene list for enrichment of the clusters and the STRING interactome genes as the background for the entire network enrichment.

Network visualization and propagation was performed using Cytoscape(56) and VisJS2jupyter(57). The subgraph composed of the most proximal genes is visualized using a modified spring-embedded layout algorithm, modified by cluster membership, so that genes belonging to the same cluster are separated from other clusters. Differential expression log fold change was mapped to the node color, for the significantly differentially expressed genes (FDR<0.05) within the subgraph.

Lentiviral Overexpression

Lentiviral human wild-type and mutant ADAR1$^{E912A}$ (pCDH-EF1-T2A-copGFP) were produced according to published protocol(23). All lentivirus was tested by transduction of 293T cells and efficiency was assessed by qRT-PCR. Lentiviral transduction of primary patient samples was performed at a MOI of 100-200. The cells were cultured for 3-4 days in 96-well plate ($2\times10^5$-$5\times10^5$ cells per well) containing StemPro (Life Technologies) media supplemented with human IL-6, stem cell factor (SCF), Thrombopoietin (Tpo) and FLT-3 (all from R&D Systems)(23, 58-60). The transduced cells were collected for RNA extraction and complementary DNA was synthesized according to published methods(23, 58-60).

REFERENCES EXAMPLE 1

Abrahamsson, A. E., et al (2009). Glycogen synthase kinase 3beta missplicing contributes to leukemia stem cell generation. Proceedings of the National Academy of Sciences of the United States of America 106, 3925-3929.

Aken, B. L., et al. (2016). The Ensembl gene annotation system. Database (Oxford) 2016.

Batzer, M. A., and Deininger, P. L. (2002). Alu repeats and human genomic diversity. Nat Rev Genet 3, 370-379.

Chen, J., et al. (2016). The role of microRNA-26a in human cancer progression and clinical application. Tumour Biol 37, 7095-7108.

Chen, L., Li, Y., Lin, C. H., Chan, T. H., Chow, R. K., Song, Y., Liu, M., Yuan, Y. F., Fu, L., Kong, K. L., et al. (2013). Recoding RNA editing of AZIN1 predisposes to hepatocellular carcinoma. Nature medicine 19, 209-216.

Chou, C. H., et al. (2016). miRTarBase 2016: updates to the experimentally validated miRNA-target interactions database. Nucleic Acids Res 44, D239-247.

Chung, H., et al (2018). Human ADAR1 Prevents Endogenous RNA from Triggering Translational Shutdown. Cell 172, 811-824 e814.

Cox, D. B. T., Gootenberg, J. S., Abudayyeh, O. O., Franklin, B., Kellner, M. J., Joung, J., and Zhang, F. (2017). RNA editing with CRISPR-Cas13. Science.

Deininger, P. (2011). Alu elements: know the SINEs. Genome Biol 12, 236.

Dobin, A., Davis, C. A., Schlesinger, F., Drenkow, J., Zaleski, C., Jha, S., Batut, P., Chaisson, M., and Gingeras, T. R. (2013). STAR: ultrafast universal RNA-seq aligner. Bioinformatics 29, 15-21.

Fan, T., Jiang, S., Chung, N., Alikhan, A., Ni, C., Lee, C. C., and Hornyak, T. J. (2011). EZH2-dependent suppression of a cellular senescence phenotype in melanoma cells by inhibition of p21/CDKN1A expression. Mol Cancer Res 9, 418-429.

Fatica, A., and Fazi, F. (2013). MicroRNA-regulated pathways in hematological malignancies: how to avoid cells playing out of tune. Int J Mol Sci 14, 20930-20953.

Fu, X., et al. (2014). miR-26a enhances miRNA biogenesis by targeting Lin28B and Zcchc11 to suppress tumor growth and metastasis. Oncogene 33, 4296-4306.

Goff, D. J., et al. (2013). A Pan-BCL2 inhibitor renders bone-marrow-resident human leukemia stem cells sensitive to tyrosine kinase inhibition. Cell Stem Cell 12, 316-328.

Guo, Y., Dai, Y., Yu, H., Zhao, S., Samuels, D. C., and Shyr, Y. (2017). Improvements and impacts of GRCh38 human reference on high throughput sequencing data analysis. Genomics 109, 83-90.

Han, L., Diao, L., Yu, S., Xu, X., Li, J., Zhang, R., Yang, Y., Werner, H. M., Eterovic, A. K., Yuan, Y., et al. (2015). The Genomic Landscape and Clinical Relevance of A-to-I RNA Editing in Human Cancers. Cancer Cell 28, 515-528.

Hartner, J. C., et al. (2009). ADAR1 is essential for the maintenance of hematopoiesis and suppression of interferon signaling. Nat Immunol 10, 109-115.

Jamieson, C. H., et al. (2004). Granulocyte-macrophage progenitors as candidate leukemic stem cells in blast-crisis CML. N Engl J Med 351, 657-667.

Jeggari, A., et al. (2012). miRcode: a map of putative microRNA target sites in the long non-coding transcriptome. Bioinformatics 28, 2062-2063.

Jiang, Q., et al. (2017). RNA editing-dependent epitranscriptome diversity in cancer stem cells. Nat Rev Cancer 17, 381-392.

Jiang, Q., Crews, L. A., and Jamieson, C. H. (2013). ADAR1 promotes malignant progenitor reprogramming in chronic myeloid leukemia. Proceedings of the National Academy of Sciences of the United States of America 110, 1041-1046.

Jurka, J., and Smith, T. (1988). A fundamental division in the Alu family of repeated sequences. Proceedings of the National Academy of Sciences of the United States of America 85, 4775-4778.

Kaymaz, B. T., et al. (2015). Revealing genome-wide mRNA and microRNA expression patterns in leukemic cells highlighted "hsa-miR-2278" as a tumor suppressor for regain of chemotherapeutic imatinib response due to targeting STAT5A. Tumour Biol 36, 7915-7927.

Kiran, A., and Baranov, P. V. (2010). DARNED: a DAtabase of RNa EDiting in humans. Bioinformatics 26, 1772-1776.

Lechman, E. R., et al. (2016). miR-126 Regulates Distinct Self-Renewal Outcomes in Normal and Malignant Hematopoietic Stem Cells. Cancer Cell 29, 602-606.

Li, B., and Dewey, C. N. (2011). RSEM: accurate transcript quantification from RNA-Seq data with or without a reference genome. BMC Bioinformatics 12, 323.

Li, H., Handsaker, et al., and Genome Project Data Processing, S. (2009). The Sequence Alignment/Map format and SAMtools. Bioinformatics 25, 2078-2079.

Liddicoat, B. J., et al. (2015). RNA editing by ADAR1 prevents MDAS sensing of endogenous dsRNA as non-self. Science 349, 1115-1120.

Lu, J., et al. (2011). MiR-26a inhibits cell growth and tumorigenesis of nasopharyngeal carcinoma through repression of EZH2. Cancer Res 71, 225-233.

Mallela, A., and Nishikura, K. (2012). A-to-I editing of protein coding and noncoding RNAs. Crit Rev Biochem Mol Biol 47, 493-501.

Mannion, N. M., et al. (2014). The RNA-editing enzyme ADAR1 controls innate immune responses to RNA. Cell Rep 9, 1482-1494.

Marcu-Malina, V., Goldberg, S., Vax, E., Amariglio, N., Goldstein, I., and Rechavi, G. (2016). ADAR1 is vital for B cell lineage development in the mouse bone marrow. Oncotarget.

Margueron, R., Li, G., Sarma, K., Blais, A., Zavadil, J., Woodcock, C. L., Dynlacht, B. D., and Reinberg, D. (2008). Ezh1 and Ezh2 maintain repressive chromatin through different mechanisms. Mol Cell 32, 503-518.

Martin, M. (2011). Cutadapt Removes Adapter Sequences From High-Throughput Sequencing Reads. EMBnetjournal 17.

Matsumoto, A., Takeishi, S., Kanie, T., Susaki, E., Onoyama, I., Tateishi, Y., Nakayama, K., and Nakayama, K. I. (2011). p57 is required for quiescence and maintenance of adult hematopoietic stem cells. Cell Stem Cell 9, 262-271.

Mende, N., Kuchen, E. E., Lesche, M., Grinenko, T., Kokkaliaris, K. D., Hanenberg, H., Lindemann, D., Dahl, A., Platz, A., Hofer, T., et al. (2015). CCND1-CDK4-mediated cell cycle progression provides a competitive advantage for human hematopoietic stem cells in vivo. J Exp Med 212, 1171-1183.

Mortazavi, A., et al. (2008). Mapping and quantifying mammalian transcriptomes by RNA-Seq. Nat Methods 5, 621-628.

Neri, F., Zippo, A., Krepelova, A., Cherubini, A., Rocchigiani, M., and Oliviero, S. (2012). Myc regulates the transcription of the PRC2 gene to control the expression of developmental genes in embryonic stem cells. Mol Cell Biol 32, 840-851.

Nishikura, K. (2010). Functions and regulation of RNA editing by ADAR deaminases. Annu Rev Biochem 79, 321-349.

Nishikura, K. (2016). A-to-I editing of coding and non-coding RNAs by ADARs. Nat Rev Mol Cell Biol 17, 83-96.

Pawlyn, C., et al. (2017). Overexpression of EZH2 in multiple myeloma is associated with poor prognosis and dysregulation of cell cycle control. Blood Cancer J 7, e549.

Peng, X., Xu, X., Wang, Y., Hawke, D. H., Yu, S., Han, L., Zhou, Z., Mojumdar, K., Jeong, K. J., Labrie, M., et al. (2018). A-to-I RNA Editing Contributes to Proteomic Diversity in Cancer. Cancer Cell.

Picardi, E., and Pesole, G. (2013). REDItools: high-throughput RNA editing detection made easy. Bioinformatics 29, 1813-1814.

Qi, L., Chan, T. H., Tenen, D. G., and Chen, L. (2014). RNA editome imbalance in hepatocellular carcinoma. Cancer Res 74, 1301-1306.

Qin, Y. R., Qiao, J. J., Chan, T. H., Zhu, Y. H., Li, F. F., Liu, H., Fei, J., Li, Y., Guan, X. Y., and Chen, L. (2014). Adenosine-to-inosine RNA editing mediated by ADARs in esophageal squamous cell carcinoma. Cancer Res 74, 840-851.

Quinlan, A. R., and Hall, I. M. (2010). BEDTools: a flexible suite of utilities for comparing genomic features. Bioinformatics 26, 841-842.

Ramaswami, G., and Li, J. B. (2014). RADAR: a rigorously annotated database of A-to-I RNA editing. Nucleic Acids Res 42, D109-113.

Ramaswami, G., and Li, J. B. (2016). Identification of human RNA editing sites: A historical perspective. Methods.

Robinson, M. D., McCarthy, D. J., and Smyth, G. K. (2010). edgeR: a Bioconductor package for differential expression analysis of digital gene expression data. Bioinformatics 26, 139-140.

Salvatori, B., et al. (2011). Critical Role of c-Myc in Acute Myeloid Leukemia Involving Direct Regulation of miR-26a and Histone Methyltransferase EZH2. Genes Cancer 2, 585-592.

Sander, S., Bullinger, L., Klapproth, K., Fiedler, K., Kestler, H. A., Barth, T. F., Moller, P., Stilgenbauer, S., Pollack, J. R., and Wirth, T. (2008). MYC stimulates EZH2 expression by repression of its negative regulator miR-26a. Blood 112, 4202-4212.

Shah, S. P., et al. (2009). Mutational evolution in a lobular breast tumour profiled at single nucleotide resolution. Nature 461, 809-813.

Tan, M. H., Li, Q., Shanmugam, R., Piskol, R., Kohler, J., Young, A. N., Liu, K. I., Zhang, R., Ramaswami, G., Ariyoshi, K., et al. (2017). Dynamic landscape and regulation of RNA editing in mammals. Nature 550, 249-254.

Trotta, R., et al. (2003). BCR/ABL activates mdm2 mRNA translation via the La antigen. Cancer Cell 3, 145-160.

Vlachos, I. S., et al. (2015). DIANA-miRPath v3.0: deciphering microRNA function with experimental support. Nucleic Acids Research 43, W460-W466.

Wang, L., Wang, S., and Li, W. (2012). RSeQC: quality control of RNA-seq experiments. Bioinformatics 28, 2184-2185.

Wang, Q., Khillan, J., Gadue, P., and Nishikura, K. (2000). Requirement of the RNA editing deaminase ADAR1 gene for embryonic erythropoiesis. Science 290, 1765-1768.

Wojtowicz, E. E., et al. (2016). Ectopic miR-125a Expression Induces Long-Term Repopulating Stem Cell Capacity in Mouse and Human Hematopoietic Progenitors. Cell Stem Cell 19, 383-396.

Xia, K., et al. (2015). miR-411 regulated ITCH expression and promoted cell proliferation in human hepatocellular carcinoma cells. Biomed Pharmacother 70, 158-163.

Xie, H., et al. (2016). Chronic Myelogenous Leukemia—Initiating Cells Require Polycomb Group Protein EZH2. Cancer Discov 6, 1237-1247.

Yang, C. C., et al. (2017). ADAR1-mediated 3' UTR editing and expression control of antiapoptosis genes fine-tunes cellular apoptosis response. Cell Death Dis 8, e2833.

Yang, W., Chendrimada, T. P., Wang, Q., Higuchi, M., Seeburg, P. H., Shiekhattar, R., and Nishikura, K. (2006). Modulation of microRNA processing and expression through RNA editing by ADAR deaminases. Nat Struct Mol Biol 13, 13-21.

Zhang, L., et al. (2016a). Altered RNA editing in 3' UTR perturbs microRNA-mediated regulation of oncogenes and tumor-suppressors. Sci Rep 6, 23226.

Zhang, Y., et al. (2016b). miR-411-5p inhibits proliferation and metastasis of breast cancer cell via targeting GRB2. Biochem Biophys Res Commun 476, 607-613.

Zhao, H., et al. (2014). CrossMap: a versatile tool for coordinate conversion between genome assemblies. Bioinformatics 30, 1006-1007.

Zhao, R., et al. (2016a). Implications of Genetic and Epigenetic Alterations of CDKN2A (p16(INK4a)) in Cancer. EBioMedicine 8, 30-39.

Zhao, Z., et al. (2016b). miR-411 contributes the cell proliferation of lung cancer by targeting FOXO1. Tumour Biol 37, 5551-5560.

Zipeto, M. A., et al. (2016). ADAR1 Activation Drives Leukemia Stem Cell Self-Renewal by Impairing Let-7 Biogenesis. Cell Stem Cell.

Zipeto, M. A., Jiang, Q., Melese, E., and Jamieson, C. H. (2015). RNA rewriting, recoding, and rewiring in human disease. Trends Mol Med 21, 549-559.

REFERENCES EXAMPLE 2

1. J. J. Ishizuka et al., Loss of ADAR1 in tumours overcomes resistance to immune checkpoint blockade. *Nature* 565, 43-48 (2019).
2. G. Q. Daley, R. A. Van Etten, D. Baltimore, Induction of chronic myelogenous leukemia in mice by the P210bcr/abl gene of the Philadelphia chromosome. *Science* 247, 824-830 (1990).
3. J. W. Adamson, P. J. Fialkow, S. Murphy, J. F. Prchal, L. Steinmann, Polycythemia vera: stem-cell and probable clonal origin of the disease. *N Engl J Med* 295, 913-916 (1976).
4. D. Kozbor et al., Expression of a translocated c-abl gene in hybrids of mouse fibroblasts and chronic myelogenous leukaemia cells. *Nature* 319, 331-333 (1986).
5. E. J. Baxter et al., Acquired mutation of the tyrosine kinase JAK2 in human myeloproliferative disorders. *Lancet* 365, 1054-1061 (2005).
6. R. L. Levine et al., Activating mutation in the tyrosine kinase JAK2 in polycythemia vera, essential thrombocythemia, and myeloid metaplasia with myelofibrosis. *Cancer Cell* 7, 387-397 (2005).
7. C. James et al., A unique clonal JAK2 mutation leading to constitutive signalling causes polycythaemia vera. *Nature* 434, 1144-1148 (2005).

8. R. Kralovics et al., A gain-of-function mutation of JAK2 in myeloproliferative disorders. *N Engl J Med* 352, 1779-1790 (2005).
9. S. Anand et al., Effects of the JAK2 mutation on the hematopoietic stem and progenitor compartment in human myeloproliferative neoplasms. *Blood* 118, 177-181 (2011).
10. T. Klampfl et al., Somatic mutations of calreticulin in myeloproliferative neoplasms. *N Engl J Med* 369, 2379-2390 (2013).
11. J. Nangalia et al., Somatic CALR mutations in myeloproliferative neoplasms with nonmutated JAK2. *N Engl J Med* 369, 2391-2405 (2013).
12. T. Barbui et al., Philadelphia chromosome-negative classical myeloproliferative neoplasms: revised management recommendations from European LeukemiaNet. *Leukemia* 32, 1057-1069 (2018).
13. R. Rampal et al., Integrated genomic analysis illustrates the central role of JAK-STAT pathway activation in myeloproliferative neoplasm pathogenesis. *Blood* 123, e123-133 (2014).
14. H. Lee-Six et al., Population dynamics of normal human blood inferred from somatic mutations. *Nature*, (2018).
15. M. Kleppe et al., Dual Targeting of Oncogenic Activation and Inflammatory Signaling Increases Therapeutic Efficacy in Myeloproliferative Neoplasms. *Cancer Cell* 33, 29-43 e27 (2018).
16. M. L. Gishizky, J. Johnson-White, O. N. Witte, Efficient transplantation of BCR-ABL-induced chronic myelogenous leukemia-like syndrome in mice. *Proc Natl Acad Sci USA* 90, 3755-3759 (1993).
17. C. H. Jamieson et al., Granulocyte-macrophage progenitors as candidate leukemic stem cells in blast-crisis CML. *N Engl J Med* 351, 657-667 (2004).
18. D. J. Rossi, C. H. Jamieson, I. L. Weissman, Stems cells and the pathways to aging and cancer. *Cell* 132, 681-696 (2008).
19. L. I. Shlush et al., Identification of pre-leukaemic haematopoietic stem cells in acute leukaemia. *Nature* 506, 328-333 (2014).
20. R. A. Mesa et al., NCCN Guidelines Insights: Myeloproliferative Neoplasms, Version 2.2018. *J Natl Compr Canc Netw* 15, 1193-1207 (2017).
21. M. B. Burns, N. A. Temiz, R. S. Harris, Evidence for APOBEC3B mutagenesis in multiple human cancers. *Nat Genet* 45, 977-983 (2013).
22. Q. Jiang et al., Hyper-Editing of Cell-Cycle Regulatory and Tumor Suppressor RNA Promotes Malignant Progenitor Propagation. *Cancer Cell* 35, 81-94 e87 (2019).
23. J. C. Hartner, C. R. Walkley, J. Lu, S. H. Orkin, ADAR1 is essential for the maintenance of hematopoiesis and suppression of interferon signaling. *Nat Immunol* 10, 109-115 (2009).
24. Q. Jiang, L. A. Crews, F. Holm, C. H. M. Jamieson, RNA editing-dependent epitranscriptome diversity in cancer stem cells. *Nat Rev Cancer* 17, 381-392 (2017).
25. M. A. Zipeto et al., ADAR1 Activation Drives Leukemia Stem Cell Self-Renewal by Impairing Let-7 Biogenesis. *Cell Stem Cell*, (2016).
26. L. Han et al., The Genomic Landscape and Clinical Relevance of A-to-I RNA Editing in Human Cancers. *Cancer Cell* 28, 515-528 (2015).
27. L. Han et al., The Genomic Landscape and Clinical Relevance of A-to-I RNA Editing in Human Cancers. *Cancer Cell* 28, 515-528 (2015).
28. M. H. Tan et al., Dynamic landscape and regulation of RNA editing in mammals. *Nature* 550, 249-254 (2017).
29. L. A. Crews et al., RNA Splicing Modulation Selectively Impairs Leukemia Stem Cell Maintenance in Secondary Human AML. *Cell Stem Cell* 19, 599-612 (2016).
30. J. Grinfeld et al., Classification and Personalized Prognosis in Myeloproliferative Neoplasms. *N Engl J Med* 379, 1416-1430 (2018).
31. Q. Jiang et al., ADAR1 promotes malignant progenitor reprogramming in chronic myeloid leukemia. *Proc Natl Acad Sci USA* 110, 1041-1046 (2013).
32. A. Kiran, P. V. Baranov, DARNED: a DAtabase of RNa EDiting in humans. Bioinformatics 26, 1772-1776 (2010).
33. G. Ramaswami, J. B. Li, RADAR: a rigorously annotated database of A-to-I RNA editing. *Nucleic Acids Res* 42, D109-113 (2014).
34. D. Szklarczyk et al., The STRING database in 2017: quality-controlled protein-protein association networks, made broadly accessible. *Nucleic Acids Res* 45, D362-D368 (2017).
35. L. Goldberg, M. Abutbul-Amitai, G. Paret, Y. Nevo-Caspi, Alternative Splicing of STAT3 Is Affected by RNA Editing. *DNA Cell Biol* 36, 367-376 (2017).
36. L. A. Crews et al., An RNA editing fingerprint of cancer stem cell reprogramming. *J Transl Med* 13, 52 (2015).

A number of embodiments of the invention have been described. Nevertheless, it can be understood that various modifications may be made without departing from the spirit and scope of the invention. Accordingly, other embodiments are within the scope of the following claims.

What is claimed is:

1. A method for:
   treating or ameliorating a cancer in an individual in need thereof,
   inhibiting or slowing a leukemia progenitor cell propagation,
   inhibiting or slowing a blast crisis chronic myeloid leukemia progenitor propagation in an individual in need thereof,
   eliminating or reducing the numbers of pre-leukemia stem cells (pre-LSCs) in an individual in need thereof, reducing or eliminating the formation of leukemia stem cells (LCSs) in an individual in need thereof, or
   treating or ameliorating a myeloproliferative disorder in an individual in need thereof,
   the method comprising inhibiting the expression or activity of an ADAR1p150 protein, message (mRNA) or gene, by:
   (a) (i) providing or having provided:
      (1) an inhibitor of the expression or activity of an ADAR1p150 protein, message (mRNA) or gene, and
      (2) an miR-155 RNA molecule or a nucleic acid encoding an miR-155 RNA molecule; and
   (ii) administering or having administered to the individual in need thereof (1) the inhibitor and (2) the miR-155 RNA molecule, or expressing (1) the inhibitor or (2) the nucleic acid encoding the miR-155 RNA molecule, in a cancer cell, a leukemia cell, a leukemia stem cell (LSC) or a pre-leukemia cell stem cell (pre-LSC); or
   (b) administering or having administered to an individual in need thereof, or administering or expressing in a cancer cell, a leukemia cell, a leukemia stem cell (LSC) or a pre-leukemia cell stem cell (pre-LSC), an inhibitor of the expression or activity of an ADAR1p150 protein, message (mRNA) or gene and the miR-155 RNA molecule or the nucleic acid encoding the miR-155 RNA molecule.

2. The method of claim 1, wherein the inhibitor of the expression or activity of the ADAR1p150 protein, message (mRNA) or gene, comprises or is:
   (a) an miRNA; or
   (b) an antisense nucleotide sequence capable of inhibiting the expression or activity of the ADAR1p150 protein, message (mRNA) or gene.

3. The method of claim 1, wherein the individual in need thereof is a patient who has elevated RNA editing in a cancer promoter 3'UTR, or decreased RNA editing in a cancer suppressor 3'UTR, thus making the patient more susceptible to cancer progression or relapse, wherein the RNA editing is 3'UTR A-to-I RNA editing.

4. The method of claim 2, wherein the miRNA or antisense nucleotide sequence and/or the miR-155 RNA molecule or the nucleic acid encoding the miR-155 RNA molecule, is heterologous to the cancer cell, the leukemia cell (LC), the leukemia stem cell (LSC) or the pre leukemia stem cell (pre-LSC), and the heterologous miRNA or antisense nucleotide sequence and/or the nucleic acid encoding the miR-155 RNA molecule is operably contained within a vector or recombinant virus, and the vector or recombinant virus is placed inside or within the cancer or leukemia cell to express intracellularly the heterologous miRNA or antisense nucleotide sequence and/or the nucleic acid encoding the miR-155 RNA molecule.

5. The method of claim 1, wherein the inhibitor of the expression or activity of the ADAR1p150 protein, message (mRNA) or gene, and/or the miR-155 RNA molecule or the nucleic acid encoding the miR-155 RNA molecule, is formulated as a pharmaceutical composition.

6. The method of claim 1, wherein the cancer is a leukemia or a myeloproliferative disorder in the individual in need thereof.

7. The method of claim 1, wherein the inhibitor of the expression or activity of the ADAR1p150 protein, message (mRNA) or gene and/or the miR-155 RNA molecule or the nucleic acid encoding the miR-155 RNA molecule, is a heterologous inhibitor or heterologous miR-155 RNA molecule or heterologous nucleic acid encoding the miR-155 RNA molecule.

8. The method of claim 5, wherein the pharmaceutical composition is administered in vitro, ex vivo or in vivo, or is administered to an individual in need thereof.

9. The method of claim 5, wherein the pharmaceutical composition is formulated for administration intravenously (IV), parenterally, nasally, topically, orally, or by liposome or targeted or vessel-targeted nanoparticle delivery.

10. The method of claim 1, wherein the inhibitor of the ADAR1p150 protein, message (mRNA) or gene, comprises or is an inhibitor of transcription, translation or protein expression.

11. The method of claim 1, wherein the inhibitor of the ADAR1p150 protein, message (mRNA) or gene, comprises or is: a small molecule, a protein, an antibody, a monoclonal antibody, a nucleic acid, a lipid or a fat, a polysaccharide, an RNA or a DNA.

12. The method of claim 1, wherein the antisense nucleotide sequence capable of inhibiting the expression or activity of the ADAR1p150 protein, message (mRNA) or gene comprises an shRNA targeting ADAR1p150.

13. The method of claim 1, wherein the antisense nucleotide sequence capable of inhibiting the expression or activity of the ADAR1p150 protein, message (mRNA) or gene and/or the nucleic acid encoding the miR-155 RNA molecule, is contained in a lentivirus vector.

14. The method of claim 4, wherein the expression of the heterologous miRNA or antisense nucleotide sequence and/or the nucleic acid encoding the miR-155 RNA molecule, by the vector or recombinant virus is under control of an inducible promoter.

15. The method of claim 1, wherein the administering or having administered to an individual in need thereof:
    (a) the inhibitor of the expression or activity of an ADAR1p150 protein, message (mRNA) or gene; and,
    (b) the miR-155 RNA molecule or the nucleic acid encoding the miR-155 RNA molecule,
    treats or ameliorates the cancer in the individual in need thereof.

16. The method of claim 1, wherein the administering or having administered to an individual in need thereof:
    (a) the inhibitor of the expression or activity of an ADAR1p150 protein, message (mRNA) or gene; and,
    (b) the miR-155 RNA molecule or the nucleic acid encoding the miR-155 RNA molecule,
    inhibits or slows the leukemia progenitor cell propagation.

17. The method of claim 1, wherein the administering or having administered to an individual in need thereof:
    (a) the inhibitor of the expression or activity of an ADAR1p150 protein, message (mRNA) or gene; and,
    (b) the miR-155 RNA molecule or the nucleic acid encoding the miR-155 RNA molecule,
    inhibits or slows the blast crisis chronic myeloid leukemia progenitor propagation in the individual in need thereof.

18. The method of claim 1, wherein the administering or having administered to an individual in need thereof:
    (a) the inhibitor of the expression or activity of an ADAR1p150 protein, message (mRNA) or gene; and,
    (b) the miR-155 RNA molecule or the nucleic acid encoding the miR-155 RNA molecule,
    eliminates or reduces the numbers of pre-leukemia stem cells (pre-LSCs) in the individual in need thereof, reducing or eliminating the formation of leukemia stem cells (LCSs) in the individual in need thereof.

19. The method of claim 1, wherein the administering or having administered to an individual in need thereof:
    (a) the inhibitor of the expression or activity of an ADAR1p150 protein, message (mRNA) or gene; and,
    (b) the miR-155 RNA molecule or the nucleic acid encoding the miR-155 RNA molecule,
    treats or ameliorates the myeloproliferative disorder in the individual in need thereof.

\* \* \* \* \*